United States Patent
Kim et al.

(10) Patent No.: US 11,572,574 B2
(45) Date of Patent: Feb. 7, 2023

(54) ARTIFICIAL GENOME MANIPULATION FOR GENE EXPRESSION REGULATION

(71) Applicant: TOOLGEN INCORPORATED, Seoul (KR)

(72) Inventors: Seokjoong Kim, Seoul (KR); Dong Woo Song, Seoul (KR); Jae Young Lee, Seoul (KR); Jung Min Lee, Gyeongsangbuk-do (KR); Gyu-bon Cho, Seoul (KR); Hee Sook Bae, Gyeonggi-do (KR)

(73) Assignee: TOOLGEN INCORPORATED, Seoul (KR)

( * ) Notice: Subject to any disclaimer, the term of this patent is extended or adjusted under 35 U.S.C. 154(b) by 165 days.

(21) Appl. No.: 16/776,707

(22) Filed: Jan. 30, 2020

(65) Prior Publication Data
US 2020/0199617 A1 Jun. 25, 2020

Related U.S. Application Data

(63) Continuation-in-part of application No. PCT/KR2018/011424, filed on Sep. 27, 2018.

(60) Provisional application No. 62/799,169, filed on Jan. 31, 2019, provisional application No. 62/565,868, filed on Sep. 29, 2017, provisional application No. 62/564,478, filed on Sep. 28, 2017.

(51) Int. Cl.
| C07H 21/02 | (2006.01) |
| C07H 21/04 | (2006.01) |
| C12N 15/85 | (2006.01) |
| C12N 15/113 | (2010.01) |
| C12N 9/22 | (2006.01) |

(52) U.S. Cl.
CPC ............ *C12N 15/85* (2013.01); *C12N 9/22* (2013.01); *C12N 15/113* (2013.01); *C12N 2310/20* (2017.05)

(58) Field of Classification Search
CPC ..................... C12N 15/111; C12N 2310/20
See application file for complete search history.

(56) References Cited

U.S. PATENT DOCUMENTS

| 2014/0242664 A1 | 8/2014 | Zhang et al. |
| 2015/0071898 A1 | 3/2015 | Liu et al. |
| 2015/0284727 A1 | 10/2015 | Kim et al. |

FOREIGN PATENT DOCUMENTS

| EP | 3539980 A2 | 9/2019 |
| KR | 10-2015-0101446 A | 9/2015 |
| KR | 10-2015-0105633 A | 9/2015 |

(Continued)

OTHER PUBLICATIONS

Office Action of RU Patent Application No. 2020114785, dated Mar. 10, 2021.

(Continued)

*Primary Examiner* — Amy H Bowman
(74) *Attorney, Agent, or Firm* — Harness, Dickey & Pierce, P.L.C.

(57) ABSTRACT

The present invention relates to an expression control composition for controlling the expression of a duplicate gene or a method using the same. In addition, the present invention relates to a method of treating or improving a disease caused by gene duplication using the expression control composition for controlling the expression of a duplicate gene.

15 Claims, 45 Drawing Sheets

Specification includes a Sequence Listing.

| sgRNAs | Direction | Mismatch 0 | Mismatch 1 | Mismatch 2 | Indel ratio(%) |
|---|---|---|---|---|---|
| sgRNA_TATA_Sp#1 | - | 1 | 0 | 1 | 32.80 |
| sgRNA_TATA_Sp#2 | + | 1 | 0 | 0 | 42.00 |
| sgRNA_TATA_Sp#3 | + | 1 | 0 | 0 | 25.20 |
| sgRNA_TATA_Sp#4 | + | 1 | 0 | 2 | 59.10 |
| sgRNA_TATA_Sp#5 | + | 1 | 0 | 0 | 16.20 |
| sgRNA_TATA_Sp#6 | + | 1 | 0 | 1 | 30.30 |
| sgRNA_TATA_Sp#7 | - | 1 | 0 | 1 | 53.80 |
| sgRNA_TATA_Sp#8 | + | 1 | 0 | 0 | 7.30 |
| sgRNA_TATA_Sp#9 | - | 1 | 0 | 1 | 26.90 |
| sgRNA_TATA_Sp#10 | - | 1 | 0 | 1 | 15.90 |
| sgRNA_TATA_Sp#11 | - | 1 | 0 | 2 | 24.20 |
| sgRNA_TATA_Sp#12 | - | 1 | 0 | 2 | 38.20 |
| sgRNA_TATA_Sp#13 | - | 1 | 0 | 0 | 6.90 |
| sgRNA_TATA_Sp#14 | + | 1 | 0 | 1 | 62.00 |
| sgRNA_TATA_Sp#15 | + | 1 | 0 | 1 | 54.60 |
| sgRNA_TATA_Sp#16 | - | 1 | 0 | 1 | 32.50 |

(56) References Cited

FOREIGN PATENT DOCUMENTS

| | | | |
|---|---|---|---|
| KR | 10-2016-0050069 A | 5/2016 | |
| RU | 2015148637 A | 5/2017 | |
| WO | WO 2013/176772 A1 * | 11/2013 | ........... C12N 15/111 |
| WO | WO-2014-065596 A1 | 5/2014 | |
| WO | WO-2014-093712 A1 | 6/2014 | |
| WO | WO-2014-197748 A2 | 12/2014 | |
| WO | WO-2015-035162 A2 | 3/2015 | |
| WO | WO-2015/048577 A2 | 4/2015 | |
| WO | WO-2015-139139 A1 | 9/2015 | |
| WO | WO-2016-205613 A1 | 12/2016 | |
| WO | WO-2017/035416 A2 | 3/2017 | |
| WO | WO-2017/083852 A1 | 5/2017 | |
| WO | WO-2018-088694 A2 | 5/2018 | |
| WO | WO 2018/106782 A1 * | 6/2018 | ........... C12N 15/111 |
| WO | WO-2018/106782 A1 | 6/2018 | |

OTHER PUBLICATIONS

Search Report of RU Patent Application No. 2020114785, dated Mar. 10, 2021.
Office Action of CA Patent Application No. 3,077,153, dated Mar. 29, 2021.
Iobodin, B. et al., "Transcription Impacts the Efficiency of mRNA Translation via Co transcriptional N6-adenosine Methylation", Cell, 169(2), pp. 326-337.e12, Apr. 6, 2017.
Search Report of SG Patent Application No. 11202002130W, dated Apr. 20, 2021.
Written Opinion of SG Patent Application No. 11202002130W, dated Apr. 20, 2021.
"Pantera, Harrison, et al. ""A Genome Editing Approach to Studying Pmp22 Enhancer Functionality""FASEB Journal, vol. 30, No. Suppl. 1 [online] Apr. 1, 2016, pp. 584.2".
Kim H. and Kim S-J., A guide to genome engineering with programmable.
Office Action of JP Patent Application No. 2020-513755, dated May 18, 2021.
Rennoll, Sherri A. et al., Cancers, 2016, vol. 8, No. 52, pp. 1-15, doi:10.3390/cancers805005.
JBC, 1994, vol. 269, No. 41, pp. 25795-25808.
Supplementary Partial European Search Report of EP Patent Application No. 18862957.0, dated May 19, 2021.
"Luke A Gilbert et al.,""Genome-Scale CRISPR-Mediated Control of Gene Repression and Activation""Cell. Oct. 23, 2014;159(3):pp. 647-661".
Luke A Gilbert et al, "Genome-Scale CRISPR-Mediated Control of Gene Repression and Activation" Cell. Oct. 23, 2014, pp. 647-661.
Sabrina Mahalia Heman-Ackah et al, "Precision Modulation of Neurodegenerative Disease-Related Gene Expression in Human iPSC-Derived Neurons", Science Reports, vol. 6, Jun. 24, 2016.
Sabrina Mahalia Heman-Ackah et al, "Supplementary information to Precision Modulation of Neurodegenerative Disease-Related Gene Expression in Human iPSC-Derived Neurons", Nature. Jun. 24, 2016, pp. 1-14.
Ji-Su Lee et al: "Targeted PMP22 TATA-box editing by CRISPR/Cas9 reduces demyelinating neuropathy of Charcot-Marie-Tooth disease type 1A in mice", Nucleic Acids Research, vol. 48, Issue 1, Jan. 10, 2020, pp. 130-140, https://doi.org/10.1093/nar/gkz1070.
Wojtal D et al. "Spell Checking Nature: Versatility of CRISPR/Cas9 for Developing Treatments for Inherited Disorders", The American Journal of Human Genetics, 2016, vol. 98, pp. 90-101, the abstract, p. 94 the left column, the last paragraph, p. 95, the right column, paragraph 1, p. 97, the right column, paragraph 2, p. 98, the left column. Paragraph 2.
Office Action from corresponding Russian Patent Application No. 2020114785, dated Oct. 9, 2020.
International Search Report from corresponding PCT Application No. PCT/KR2018/011424, dated May 7, 2019.
Hamdan, H, et al.; "Control of Human PLP1 Expression Through Transcriptional Regulatory Elements and Alternatively Spliced Exons in Intron 1", American Society for Neurochemistry, 2015, pp. 1-12.
Hamdan, H., et al.; "The wmN1 Enhancer Region in Intron 1 Is Required for Expression of Human PLP1", Glia. Aug. 2018 ; 66(8): 1763-1774.
Meng, F., et al.; "Characterization of an Intronic Enhancer That Regulates Myelin Proteolipid Protein (Plp) Gene Expression in Oligodendrocytes", Journal of Neuroscience Research 82:346-356 (2005).
Tuason, M. C., et al,; "Separate Proteolipid Protein/DM20 Enhancers Serve Different Lineages and Stages of Development", The Journal of Neuroscience, Jul. 2, 2008 • 28(27):6895-6903.
Wight, P. A., et al.; "Effects of Intron 1 Sequences on Human PLP1 Expression: Implications for PLP1-Related Disorders", American Society for Neurochemistry, 2017, pp. 1-6.
Extended European Search Report from corresponding European Patent Application No. 18862957.0, dated Oct. 6, 2021.
Gilbert Luke A et al: "excerpt of table S2 of Genome-Scale CRISPR-Mediated Control of Gene Repression and Activation" Cell, Oct. 9, 2014 (Oct. 9, 2014), pp. 1-2.
Erming Wang et al.: "MicroRNA expression in mouse oligodendrocytes and regulation of proteolipid protein gene expression", Journal of Neuroscience Research, vol. 90, No. 9, Apr. 14, 2012 (Apr. 14, 2012), pp. 1701-1712.
Office Action from corresponding Japanese Patent Application No. 2020-513755, dated Mar. 1, 2022.
Fu, Y., et al.; "Improving CRISPR-Cas nuclease specificity using truncated guide RNAs", Nature Biotechnology, vol. 32, No. 3, Mar. 2014, pp. 279-284.
O'Connell, M. R., et al.; "Programmable RNA recognition and cleavage by CRISPR/Cas9", Nature, 2014, vol. 516, pp. 263-266.
Osaka, H., et al.; "Pathophysiology and emerging therapeutic strategy in Pelizaeus-Merzbacher disease", Expert Opinion on Orphan Drugs, 3; 12, pp. 1447-1459.
Notice of Allowance from corresponding Russian Patent Application No. 2020114785, dated Dec. 17, 2021.

* cited by examiner

FIG. 1

| sgRNAs | Direction | Mismatch 0 | Mismatch 1 | Mismatch 2 | Indel ratio(%) |
|---|---|---|---|---|---|
| sgRNA_TATA_Sp#1 | - | 1 | 0 | 1 | 32.80 |
| sgRNA_TATA_Sp#2 | + | 1 | 0 | 0 | 42.00 |
| sgRNA_TATA_Sp#3 | + | 1 | 0 | 0 | 25.20 |
| sgRNA_TATA_Sp#4 | + | 1 | 0 | 2 | 59.10 |
| sgRNA_TATA_Sp#5 | + | 1 | 0 | 0 | 16.20 |
| sgRNA_TATA_Sp#6 | + | 1 | 0 | 1 | 30.30 |
| sgRNA_TATA_Sp#7 | - | 1 | 0 | 1 | 53.80 |
| sgRNA_TATA_Sp#8 | + | 1 | 0 | 0 | 7.30 |
| sgRNA_TATA_Sp#9 | - | 1 | 0 | 1 | 26.90 |
| sgRNA_TATA_Sp#10 | - | 1 | 0 | 1 | 15.90 |
| sgRNA_TATA_Sp#11 | - | 1 | 0 | 2 | 24.20 |
| sgRNA_TATA_Sp#12 | - | 1 | 0 | 2 | 38.20 |
| sgRNA_TATA_Sp#13 | - | 1 | 0 | 0 | 6.90 |
| sgRNA_TATA_Sp#14 | + | 1 | 0 | 1 | 62.00 |
| sgRNA_TATA_Sp#15 | + | 1 | 0 | 1 | 54.60 |
| sgRNA_TATA_Sp#16 | - | 1 | 0 | 1 | 32.50 |

FIG. 2

| sgRNAs | Direction | Mismatch 0 | Mismatch 1 | Mismatch 2 | Indel ratio(%) |
|---|---|---|---|---|---|
| sgRNA_Enh_Sp#1 | - | 1 | 0 | 1 | 66.30 |
| sgRNA_Enh_Sp#2 | - | 1 | 0 | 0 | 18.80 |
| sgRNA_Enh_Sp#3 | - | 1 | 0 | 1 | 24.40 |
| sgRNA_Enh_Sp#4 | - | 1 | 0 | 0 | 44.00 |
| sgRNA_Enh_Sp#5 | - | 1 | 0 | 2 | 41.30 |
| sgRNA_Enh_Sp#6 | + | 1 | 0 | 1 | 8.60 |
| sgRNA_Enh_Sp#10 | - | 1 | 0 | 2 | 19.30 |
| sgRNA_Enh_Sp#11 | - | 1 | 0 | 2 | 21.90 |
| sgRNA_Enh_Sp#12 | - | 1 | 0 | 2 | 2.50 |
| sgRNA_Enh_Sp#13 | - | 1 | 0 | 1 | 12.80 |
| sgRNA_Enh_Sp#14 | - | 1 | 0 | 1 | 11.40 |
| sgRNA_Enh_Sp#15 | + | 1 | 0 | 1 | 21.80 |
| sgRNA_Enh_Sp#16 | + | 1 | 0 | 1 | 47.40 |

FIG. 3

| sgRNAs | Direction | Mismatch 0 | Mismatch 1 | Mismatch 2 | Indel ratio(%) |
|---|---|---|---|---|---|
| sgRNA_TATA_Cj#1 | + | 1 | 0 | 0 | 0.35 |
| sgRNA_TATA_Cj#2 | + | 1 | 0 | 0 | 0.07 |
| sgRNA_TATA_Cj#3 | + | 1 | 0 | 0 | 0.04 |
| sgRNA_TATA_Cj#4 | + | 1 | 0 | 1 | 3.80 |
| sgRNA_TATA_Cj#5 | + | 1 | 0 | 0 | 36.10 |
| sgRNA_TATA_Cj#6 | - | 1 | 0 | 0 | 0.02 |
| sgRNA_TATA_Cj#7 | + | 1 | 0 | 0 | 0.02 |
| sgRNA_TATA_Cj#8 | - | 1 | 0 | 0 | 0.06 |
| sgRNA_TATA_Cj#9 | - | 1 | 0 | 0 | 0.15 |
| sgRNA_TATA_Cj#10 | - | 1 | 0 | 0 | 13.10 |
| sgRNA_TATA_Cj#11 | - | 1 | 0 | 0 | 0.12 |

FIG. 4

| sgRNAs | Direction | Mismatch 0 | Mismatch 1 | Mismatch 2 | Indel ratio(%) |
|---|---|---|---|---|---|
| sgRNA_Enh_Cj#1 | + | 1 | 0 | 0 | 16.70 |
| sgRNA_Enh_Cj#2 | + | 1 | 0 | 0 | 0.07 |
| sgRNA_Enh_Cj#3 | - | 1 | 0 | 0 | 0 |
| sgRNA_Enh_Cj#4 | + | 1 | 0 | 0 | 1.18 |
| sgRNA_Enh_Cj#5 | - | 1 | 0 | 0 | 0.03 |
| sgRNA_Enh_Cj#6 | - | 1 | 0 | 0 | 0.05 |
| sgRNA_Enh_Cj#7 | - | 1 | 0 | 0 | 0.09 |
| sgRNA_Enh_Cj#8 | + | 1 | 0 | 0 | 0.28 |
| sgRNA_Enh_Cj#9 | - | 1 | 0 | 0 | 41.40 |
| sgRNA_Enh_Cj#10 | + | 1 | 0 | 0 | 0.45 |
| sgRNA_Enh_Cj#11 | - | 1 | 0 | 0 | 0.55 |
| sgRNA_Enh_Cj#12 | + | 1 | 0 | 0 | 2.83 |
| sgRNA_Enh_Cj#13 | + | 1 | 0 | 0 | 0.03 |

FIG. 5

| Name | sgRNAs | More than minimum frequency | Insertions | Deletions | Indel ratio(%) |
|---|---|---|---|---|---|
| TATA WT | | 26730 | 28 | 70 | 0.40 |
| TATA-1 | sgRNA_TATA_Sp#15 | 30466 | 3110 | 6357 | 31.10 |
| TATA-2 | sgRNA_TATA_Sp#12 | 9286 | 0 | 6929 | 74.60 |
| | sgRNA_TATA_Sp#14 | 5651 | 118 | 4972 | 90.10 |
| Enh WT | | 27917 | 0 | 11 | 0.00 |
| Enh-3 | sgRNA_Enh_Sp#1 | 32148 | 8744 | 10126 | 58.70 |
| Enh-4 | sgRNA_Enh_Sp#5 | 37486 | 23 | 30928 | 82.60 |
| | sgRNA_Enh_Sp#16 | 37277 | 69 | 35000 | 94.10 |
| Enh-5 | sgRNA_Enh_Sp#1 | 30576 | 2782 | 14544 | 56.70 |
| | sgRNA_Enh_Sp#4 | 30399 | 217 | 11894 | 39.80 |
| CDS-SP1 WT | | 35424 | 0 | 40 | 0.10 |
| CDS-SP1 | sgRNA_CDS_Sp#1 | 32206 | 4613 | 9077 | 42.50 |
| CDS-SP3 WT | | 21997 | 0 | 0 | 0.00 |
| CDS-SP3 | sgRNA_CDS_Sp#3 | 27511 | 3441 | 11877 | 55.70 |

FIG. 6

| sgRNAs | CDS-SP1 | | CDS-SP3 | |
| --- | --- | --- | --- | --- |
| | Reads | Ratio | Reads | Ratio |
| Total indels | 13690 | 1 | 15312 | 1 |
| 3N±1, 3N±2 | 10063 | 0.74 | 12795 | 0.84 |
| 3N±0 | 3627 | 0.26 | 2517 | 0.16 |

% Indel Reads

FIG. 15

| Indel | Local Sequence | Frequency (%) |
|---|---|---|
| WT | ACTGAAGCCAGACCAGGGCGTCTTTCCAGTTTATTCAGGGGCTGGTCCAATGCTGGGATATGTCATGGTGGCCTGAGAGGTTCTCAGCCTC | |
| -1 | ACTGAAGCCAGACCAGGGCGTCTTTCCAG-TTATTCAGGGGCTGGTCCAATGCTGGGATATGTCATGGCGGCCTGAGAGGTTCTCAGCCTC | 14.00 |
| -2 | ACTGAAGCCAGACCAGGGCGTCTTTCCAGTT--TTCAGGGGCTGGTCCAATGCTGGGATATGTCATGGTGGCCTGAGAGGTTCTCAGCCTC | 8.86 |
| +1 | ACTGAAGCCAGACCAGGGCGTCTTTCCAGTTTATTCAGGGGCTGGTCCAATGCTGGGATATGTCATGGCCTGAGAGGTTCTCAGCCTC | 3.84 |
| -3 | ACTGAAGCCAGACCAGGGCGTCTTTCCAGT---TTCAGGGGCTGGTCCAATGCTGGGATATGTCATGGCGGCCTGAGAGGTTCTCAGCCTC | 3.53 |
| -4 | ACTGAAGCCAGACCAGGGCGTCTTTCCAG----TTCAGGGGCTGGTCCAATGCTGGGATATGTCATGGCGGCCTGAGAGGTTCTCAGCCTC | 2.81 |

FIG. 16

| | Location | Position | Target sequence (5' to 3') | Gene |
|---|---|---|---|---|
| On-target | chr17 | 15265347 | GGACCAGCCCTGAATAAACTGG | hPMP22-TATA |
| Off1 | chr5 | 135488419 | GGACCAGCCaGAATAAACAAG | Intergenic |
| Off2 | chr8 | 140735957 | tGACCAGtCCaTGAATAAACCAG | PTK2 (Intron) |
| Off3 | chr12 | 14124312 | GGACCAGaCaCTGAATAtACCAG | Intergenic |
| Off4 | chr4 | 97775621 | GGACCAGCCaGAATAAAtTGG | STPG2 (Intron) |
| Off5 | chr5 | 26531145 | GGAtCAGCCCCaGAATAAAtTAG | Intergenic |
| Off6 | chr1 | 41780482 | GGAgCAtCCCaGAATAAACAAG | HIVEP3 (Intron) |
| Off7 | chr1 | 157564675 | GGAtCAGCgtCTGAATAAACAAG | Intergenic |
| Off8 | chr13 | 20254256 | aGACCAGCCCaGAAcAAACAAG | Intergenic |
| Off9 | chr15 | 100401183 | GtACgAGCCCTGAATAAAtAGG | CERS3 (Exon) |
| Off10 | chr6 | 26006396 | GGACCAGCAaaCaCTGAATAAACAAG | Intergenic |
| Off11 | chr20 | 10136908 | GcACCAGCCaCTGAATtAACAAG | SNAP25 (Intron) |
| Off12 | chrX | 7525146 | GtACCAGCCaCTGAAaAAACAAG | Intergenic |
| Off13 | chr18 | 1972251 | GaACCAGCCCCTGAttAgAACAAG | Intergenic |
| Off14 | chr18 | 77536261 | GtACCAGCCCTGAAaAAAACAAG | Intergenic |
| Off15 | chr11 | 30065750 | GtACCAGCCCCTGcAaAAACAAG | Intergenic |
| Off16 | chr11 | 30579429 | GcACCAGgCCtGAATAAACAAG | MPP2D2 (Intron) |
| Off17 | chr11 | 35726323 | GGcCCAGCCaCTGAgTAAACTAG | TRIM44 (Intron) |
| Off18 | chr11 | 112468286 | GGAattGCCCCTGAATAAACAAG | RP11-65M17.3 (Intron) |

FIG. 18

| | Location | Position | Target sequence (5' to 3') | Gene |
|---|---|---|---|---|
| On-target | chr17 | 15265347 | GGACCAGCCCTGAATAAAC*TGG* | hPMP22-TATA |
| Off1 | chr5 | 38420810 | GGgaacagCCCTGAATAAAC*CTG* | EGFLAM (Intron) |
| Off2 | chr7 | 28618099 | aGgaCCagCtCTGAATAAAC*AGG* | CREB5 (Intron) |
| Off3 | chr5 | 38420811 | GGAaCAGCCCTgaATAAAC*TGG* | EGFLAM (Intron) |
| Off4 | chr10 | 93462291 | GagttcAGCCCTGAATAAAC*AGG* | Intergenic |
| Off5 | chr3 | 78627344 | GGgaCCagCCCAGAATAAa*GGG* | Intergenic |
| Off6 | chr2 | 131586033 | aagCCAaCCCTGAATAAAC*AGG* | Intergenic |
| Off7 | chr18 | 56254369 | cacaCAGCCCTcAATAAAC*TGG* | ALPK2 (Intron) |
| Off8 | chr22 | 27477459 | GaggCAGCCCTGtATAAAC*TGG* | Intergenic |
| Off9 | chr6 | 91586787 | GacCagccCCCTGAATAAca*TGG* | Intergenic |

FIG. 22

| | Location | Position | Target sequence (5' to 3') | Gene |
|---|---|---|---|---|
| On-target | chr17 | 15265347 | GGACCAGCCCCTGAATAAAC*TGG* | hPMP22-TATA |
| Off1 | chr12 | 118558427 | GtACCAGCCCCTGAcaAAAC*AGG* | Intergenic |
| Off2 | chr1 | 74579514 | GGAgCAGCCCCggAATgAAC*AGG* | Zfp142 (Exon) |
| Off3 | chr13 | 50187695 | GGACCAGCCCCTGtATAccC*TGG* | Intergenic |
| Off4 | chr13 | 50319559 | GGACCAGCCCCTGtATAccC*TGG* | Intergenic |
| Off5 | chr13 | 50623450 | GGACCAGCCCCTGtATAccC*TGG* | Intergenic |
| Off6 | chr2 | 29191358 | GGcCCtgCCCTaAATAAAC*AGG* | Intergenic |
| Off7 | chr9 | 102823783 | GGAtCAGCCCaGAATAAcC*TGG* | Intergenic |
| Off8 | chrX | 101405421 | GGACtAGCCCCTGAgTAcAC*TGG* | Zmym3 (Exon) |

ARTIFICIAL GENOME MANIPULATION FOR GENE EXPRESSION REGULATION

CROSS-REFERENCE TO RELATED APPLICATIONS

This application is a continuation-in-part of PCT Application No. PCT/KR2018/011424, filed on Sep. 27, 2018, which claims benefit and priority to U.S. Application Nos. 62/564,478, filed on Sep. 28, 2017 and 62/565,868, filed on Sep. 29, 2017 and also claims priority to U.S. Application No. 62/799,169, filed on Jan. 31, 2019. The entire disclosures of the applications identified in this paragraph are incorporated herein by references.

FIELD

The present invention relates to an expression control composition for controlling the expression of a duplicate gene and a method using the same. More particularly, the present invention relates to an expression control composition which includes a guide nucleic acid capable of targeting the transcriptional regulatory region of a duplicate gene and a method of regulating the expression of a duplicate gene by artificially manipulating and/or modifying the transcriptional regulatory region of the duplicate gene using the expression control composition. In addition, the present invention relates to a method of treating or improving a disease caused by gene duplication using the expression control composition for regulating the expression of a duplicate gene.

BACKGROUND

Gene duplication is one of the errors generated in the genetic recombination of a chromosome, and a replication phenomenon of duplicating a partial region of the chromosome. Gene duplication is a type of mutation that is passed on to the next generation. Gene duplication, along with gene deletion occurring due to non-replication of a partial region of the chromosome, affects gene expression.

Gene duplication also causes a hereditary disease. Representatively, Charcot-Marie-Tooth (CMT) type 1A results from gene duplication occurring in a specific region of a chromosome, and the overexpression of a gene involved in the peripheral nerve development of hands and feet occurs due to gene duplication, and thus malformity of hands and feet is caused.

As such, it is important for a gene to be expressed at a suitable position and the right time for normal performance of biological processes such as cell proliferation, death, aging and differentiation. When a gene is improperly expressed at an inappropriate time and position, particularly, the abnormal gene expression caused by gene duplication may lead to a disease, and therefore, it is necessary to understand the mechanism of a molecule for controlling the expression of each gene, and it is important to identify a transcription regulatory factor associated with each gene. There are various transcription regulatory factors that can precisely control gene expression, for example, a promoter, a distal control element, and a transcription factor, an activator and coactivators, which are involved in the control of gene expression.

Gene expression may be controlled by the change in a transcription regulatory factor, and an abnormal change in transcription regulatory factor may cause the abnormal expression of a gene, thereby inducing a disease. Accordingly, the change in transcription regulatory factor may cause various diseases, or improve and treat diseases.

However, the current method of controlling a transcription regulatory factor only controls transient gene expression, and continuous gene expression regulation is difficult. For this reason, there is no fundamental treatment method for treating a disease caused by gene expression abnormalities or difficulties. Therefore, there is a demand for a method exhibiting a more continuous therapeutic effect by genetic editing or modification of a transcription regulatory factor.

Non-Patent Document

1. Hamdan, H., Kockara, N. T., Jolly, L. A., Haun, S., and Wight, P. A. (2015). Control of human PLP1 expression through transcriptional regulatory elements and alternatively spliced exons in intron 1. ASN Neuro 7.
2. Hamdan, H., Patyal, P., Kockara, N. T., and Wight, P. A. (2018). The wmN1 enhancer region in intron 1 is required for expression of human PLP1. Glia.
3. Meng, F., Zolova, O., Kokorina, N. A., Dobretsova, A., and Wight, P. A. (2005). Characterization of an intronic enhancer that regulates myelin proteolipid protein (Plp) gene expression in oligodendrocytes. J Neurosci Res 82, 346-356.
4. Tuason, M. C., Rastikerdar, A., Kuhlmann, T., Goujet-Zalc, C., Zalc, B., Dib, S., Friedman, H., and Peterson, A. (2008). Separate proteolipid protein/DM20 enhancers serve different lineages and stages of development. J Neurosci 28, 6895-6903.
5. Wight, P. A. (2017). Effects of Intron 1 Sequences on Human PLP1 Expression: Implications for PLP1-Related Disorders. ASN Neuro 9, 1759091417720583.

SUMMARY

The present invention relates to an expression control composition for controlling the expression of a duplicate gene present in the genome of a cell. More specifically, the present invention relates to an expression control composition including a guide nucleic acid capable of targeting the transcriptional regulatory region of a duplicate gene, and a method of controlling the expression of a duplicate gene by artificially manipulating and/or modifying the transcriptional regulatory region of the duplicate gene using the expression control composition. In addition, the present invention relates to a method of treating or improving a disease caused by gene duplication using the expression control composition for controlling the expression of a duplicate gene.

The present invention provides an expression control composition for controlling the expression of a duplicate gene present in the genome of a cell.

In one aspect, the expression control composition may comprise the following: a guide nucleic acid capable of targeting a target sequence present in a transcriptional regulatory region of a duplicate gene or a nucleic acid encoding the same; and one or more editor protein or a nucleic acid encoding the same.

The guide nucleic acid may include a guide domain capable of targeting the target sequence present in the transcriptional regulatory region of the duplicated gene.

Here, the guide domain may include a guide sequence capable of forming a complementary binding with a guide nucleic acid-binding sequence of the target sequence present in the transcriptional regulatory region of the duplicated gene.

Here, the guide domain may form a complementary binding with the guide nucleic acid-binding sequence of the target sequence in the transcriptional regulatory region of the duplicated gene.

Here, the complementary binding may include mismatching bindings of 0 to 5.

The guide nucleic acid may include one or more domains selected from the group consisting of a first complementary domain, a second complementary domain, a proximal domain and a tail domain.

The editor protein may be a CRISPR enzyme.

The guide nucleic acid and editor protein may form a guide nucleic acid-editor protein complex.

Here, the guide nucleic acid-editor protein complex may be formed by interacting with a partial nucleic acid of the guide nucleic acid and a partial amino acid of the editor protein.

The transcriptional regulatory region may be one or more regions selected from the group consisting of a promoter region, an enhancer region, a silencer region, an insulator region and a locus control region (LCR).

The target sequence may be a 10 to 25-nt (nucleotide) contiguous sequence located in the transcriptional regulatory region of the duplicate gene.

The target sequence may be a 10 to 25-nt contiguous sequence located in or adjacent to a promoter region of the duplicate gene.

Here, the target sequence may be a 10 to 25-nt contiguous sequence located in or adjacent to a core promoter region of the duplicate gene.

Here, the target sequence may be a 10 to 25-nt contiguous sequence including a TATA box region of the core promoter region of the duplicate gene or a 10 to 25-nt contiguous sequence located adjacent to the TATA box region.

Here, the target sequence may be a 10 to 25-nt contiguous sequence including all or a part of the 5'-TATA-3' (SEQ ID NO: 261) sequence present in the core promoter region of the duplicate gene.

Here, the target sequence may be a 10 to 25-nt contiguous sequence including all or a part of the 5'-TATAWAW-3' (W=A or T) (SEQ ID NO: 262) sequence present in the core promoter region of the duplicate gene.

Here, the target sequence may be a 10 to 25-nt contiguous sequence including all or a part of the 5'-TATAWAWR-3' (W=A or T, R=A or G) (SEQ ID NO: 263) sequence present in the core promoter region of the duplicate gene.

Here, the target sequence may be a 10 to 25-nt contiguous sequence including all or a part of a sequence selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence.

Here, the target sequence may be a 10 to 25-nt contiguous sequence located to 5' end or 3' end of a sequence selected from the group consisting of the 5'-TATA-3' (SEQ ID NO: 261) sequence, the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence.

The target sequence may be a 10 to 25-nt contiguous sequence located in an enhancer region of the duplicate gene.

The target sequence may be a 10 to 25-nt contiguous sequence located adjacent to an enhancer region of the duplicate gene.

The target sequence may be a 10 to 25-nt contiguous sequence located adjacent to 5' end and/or 3' end of PAM (proto-spacer-adjacent motif) sequence in a nucleic acid sequence of the transcriptional regulatory region of the duplicate gene.

Here, the PAM sequence may be determined according to the CRISPR enzyme.

The CRISPR enzyme may be a Cas9 protein or a Cpf1 protein.

Here, the Cas9 protein may be one or more Cas9 proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein and a *Neisseria meningitidis*-derived Cas9 protein.

The duplicate gene may be one or more genes selected from the group consisting of a PMP22 gene, a PLP1 gene, a MECP2 gene, a SOX3 gene, a RAI1 gene, a TBX1 gene, an ELN gene, a JAGGED1 gene, a NSD1 gene, a MMP23 gene, a LMB1 gene, a SNCA gene and an APP gene.

The duplicate gene may be an oncogene.

Here, the oncogene may be one or more genes selected from the group consisting of a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The cell may be a eukaryotic cell.

The eukaryotic cell may be a mammalian cell.

The guide nucleic acid and editor protein may be present in one or more vectors in a form of a nucleic acid sequence, respectively.

Here, the vector may be a plasmid or a viral vector.

Here, the viral vector may be one or more viral vectors selected from the group consisting of a retrovirus, a lentivirus, an adenovirus, an adeno-associated virus (AAV), a vaccinia virus, a poxvirus and a herpes simplex virus.

The expression control composition may include the guide nucleic acid and the editor protein in a form of the guide nucleic acid-editor protein complex.

The expression control composition may further comprise a donor.

In another aspect, the expression control composition may include the following:

i) a first guide nucleic acid capable of targeting a target sequence located upstream of the transcriptional regulatory region of a duplicate gene or a nucleic acid sequence encoding the same;

ii) a second guide nucleic acid capable of targeting a target sequence located downstream of the transcriptional regulatory region of a duplicate gene or a nucleic acid sequence encoding the same; and iii) one or more editor proteins or nucleic acid sequence(s) encoding the same.

The first guide nucleic acid may include a first guide domain capable of targeting a target sequence located upstream of the transcriptional regulatory region of a duplicate gene.

Here, the first guide domain may include a guide sequence capable of complementarily binding to a guide nucleic acid-binding sequence of the target sequence located upstream of the transcriptional regulatory region of a duplicate gene.

Here, the first guide domain may complementarily bind with the guide nucleic acid-binding sequence of the target sequence located upstream of the transcriptional regulatory region of a duplicate gene.

Here, the complementary binding may include 0 to 5 mismatches.

The second guide nucleic acid may include a second guide domain capable of targeting a target sequence located downstream of the transcriptional regulatory region of a duplicate gene.

Here, the second guide domain may include a guide sequence capable of complementarily binding to a guide nucleic acid-binding sequence of the target sequence located downstream of the transcriptional regulatory region of a duplicate gene.

Here, the second guide domain may complementarily bind with the guide nucleic acid-binding sequence of the target sequence located downstream of the transcriptional regulatory region of a duplicate gene.

Here, the complementary binding may include 0 to 5 mismatches.

The first guide nucleic acid and/or the second guide nucleic acid may include one or more domains selected from the group consisting of a first complementary domain, a linker domain, a second complementary domain, a proximal domain and a tail domain.

The first guide nucleic acid and/or second guide nucleic acid may target the transcriptional regulatory region of the same duplicate gene.

The editor protein may be a CRISPR enzyme.

The first guide nucleic acid and the editor protein may form a first guide nucleic acid-editor protein complex.

Here, the first guide nucleic acid-editor protein complex may be formed by interactions of a partial nucleic acid of the first guide nucleic acid and partial amino acids of the editor protein.

The second guide nucleic acid and the editor protein may form a second guide nucleic acid-editor protein complex.

Here, the second guide nucleic acid-editor protein complex may be formed by interactions of a partial nucleic acid of the second guide nucleic acid and partial amino acids of the editor protein.

The transcriptional regulatory region may be one or more regions selected form the group consisting of a promoter region, an enhancer region, a silencer region, an insulator region and a locus control region (LCR).

The target sequence may be a 10 to 25-nt contiguous sequence located upstream of the transcriptional regulatory region of a duplicate gene.

The target sequence may be a 10 to 25-nt contiguous sequence located upstream of the promoter region of a duplicate gene or a 10 to 25-nt contiguous sequence adjacent to the promoter region thereof.

The target sequence may be a 10 to 25-nt contiguous sequence located upstream of the enhancer region of a duplicate gene.

The target sequence may be a 10 to 25-nt contiguous sequence adjacent to the 5' end and/or 3' end of a protospacer-adjacent motif (PAM) sequence of a nucleic acid sequence located upstream of the transcriptional regulatory region of a duplicate gene.

The target sequence may be a 10 to 25-nt contiguous sequence located downstream of the transcriptional regulartory region of a duplicate gene.

The target sequence may be a 10 to 25-nt contiguous sequence located downstream of the promoter region of a duplicate gene or a 10 to 25-nt contiguous sequence adjacent to the promoter region thereof.

The target sequence may be a 10 to 25-nt contiguous sequence located downstream of the enhancer region of a duplicate gene.

The target sequence may be a 10 to 25-nt contiguous sequence adjacent to the 5' end and/or 3' end of a PAM sequence of the nucleic acid sequence located downstream of the transcriptional regulartory region of a duplicate gene.

Here, the PAM sequence may be determined according to a CRISPR enzyme.

The CRISPR enzyme may be a Cas9 or Cpf1 protein.

Here, the Cas9 protein may be one or more Cas9 proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein and a *Neisseria meningitidis*-derived Cas9 protein.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

The cell may be a eukaryotic cell.

The eukaryotic cell may be a mammalian cell.

Each of the first guide nucleic acid, the second guide nucleic acid and the editor protein may be present in one or more vectors in the form of a nucleic acid sequence.

Here, the vector may be a plasmid or viral vector.

Here, the viral vector may be one or more viral vectors selected from the group consisting of a retrovirus, a lentivirus, an adenovirus, an adeno-associated virus (AAV), a vaccinia virus, a poxvirus and a herpes simplex virus.

The expression control composition may include guide nucleic acids and editor proteins in the forms of a first guide nucleic acid-editor protein complex and a second guide nucleic acid-editor protein complex.

The expression control composition may further include a donor.

In another aspect, the expression control composition may include a guide nucleic acid for targeting a TATA-box or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a 10 to 25-nt contiguous sequence including the entire or a part of the 5'-UAUA-3' (SEQ ID NO: 374) sequence.

The guide sequence complementarily binding to the target sequence may be a 10 to 25-nt contiguous sequence including the entire or a part of the 5'-UAUAWAW-3' (W=A or U) (SEQ ID NO: 375) sequence, or may be a 10 to 25-nt contiguous sequence including the entire or a part of the 5'-WUWUAUA-3' (W=A or U) (SEQ ID NO: 376) sequence.

The guide sequence complementarily binding to the target sequence may be a 10 to 25-nt contiguous sequence including the entire or a part of the 5'-UAUAWAWR-3' (W=A or U, R=A or G) (SEQ ID NO: 377) sequence, or may be a 10 to 25-nt contiguous sequence including the entire or a part of the 5'-RWUWUAUA-3' (W=A or U, R=A or G) (SEQ ID NO: 378) sequence.

The guide sequence complementarily binding to the target sequence may be a 10 to 25-nt contiguous sequence including the entirety or a part of one or more sequences selected from the group consisting of the 5'-CAUAAAA-3' (SEQ ID NO: 379) sequence, the 5'-UAUAA-3' (SEQ ID NO: 380) sequence, the 5'-UAUAAAA-3' (SEQ ID NO: 381) sequence, the 5'-CAUAAAUA-3' (SEQ ID NO: 382) sequence, the 5'-UAUAUAA-3' (SEQ ID NO: 383) sequence, the 5'-UAUAUAUAUAUAUAA-3' (SEQ ID NO: 384) sequence, the 5'-UAUAUUAUA-3' (SEQ ID NO: 385) sequence, the 5'-UAUAAA-3' (SEQ ID NO: 386) sequence, the 5'-UAUAAAAUA-3' (SEQ ID NO: 387) sequence, the 5'-UAUAUA-3' (SEQ ID NO: 388) sequence, the 5'-GAUUAAAAA-3' (SEQ ID NO: 389) sequence, the 5'-UAUAAAAA-3' (SEQ ID NO: 390) sequence, the 5'-UUAUAA-3' (SEQ ID NO: 391) sequence, the 5'-UUUUAAAA-3' (SEQ ID NO: 392) sequence, the 5'-UC-UUUAAAA-3' (SEQ ID NO: 393) sequence, the 5'-GA-CAUUUAA-3' (SEQ ID NO: 394) sequence, the 5'-UGAUAUCAA-3' (SEQ ID NO: 395) sequence, the 5'-UAUAAAUA-3' (SEQ ID NO: 396) sequence, the 5'-UAUAAGA-3' (SEQ ID NO: 397) sequence, the 5'-AAUAAA-3' (SEQ ID NO: 398) sequence, the 5'-UUUAUA-3' (SEQ ID NO: 399) sequence, the 5'-CAUAAAAA-3' (SEQ ID NO: 400) sequence, the 5'-UAUACA-3' (SEQ ID NO: 401) sequence, the 5'-UUUAAGA-3' (SEQ ID NO: 402) sequence, the 5'-GAUAAAG-3' (SEQ ID NO: 403) sequence, the 5'-UAUAACA-3' (SEQ ID NO: 404) sequence, the 5'-UC-UUAUCUU-3' (SEQ ID NO: 405) sequence, the 5'-UU-GUACUUU-3' (SEQ ID NO: 406) sequence, the 5'-CAUAUAA-3' (SEQ ID NO: 407) sequence, the 5'-UAUAAAU-3' (SEQ ID NO: 408) sequence, the 5'-UAUAUAUAAAAAAAA-3' (SEQ ID NO: 409) sequence and 5'-CAUAAAUAAAAAAAAUUA-3' (SEQ ID NO: 410) sequence.

The guide sequence complementarily binding to the target sequence may be a 10 to 25-nt contiguous sequence including the entirety or a part of one or more sequences selected from the group consisting of the 5'-UUUUAUG-3' (SEQ ID NO: 411) sequence, the 5'-UUAUA-3' (SEQ ID NO: 412) sequence, the 5'-UUUUAUA-3' (SEQ ID NO: 413) sequence, the 5'-UAUUUAUG-3' (SEQ ID NO: 414) sequence, the 5'-UUAUAUA-3' (SEQ ID NO: 415) sequence, the 5'-UUAUAUAUAUAUAUA-3' (SEQ ID NO: 416) sequence, the 5'-UAUAAUAUA-3' (SEQ ID NO: 417) sequence, the 5'-UUUAUA-3' (SEQ ID NO: 418) sequence, the 5'-UAUUUUAUA-3' (SEQ ID NO: 419) sequence, the 5'-UUUUUAAUC-3' (SEQ ID NO: 420) sequence, the 5'-UUUUUAUA-3' (SEQ ID NO: 421) sequence, the 5'-UUUUAAAGA-3' (SEQ ID NO: 422) sequence, the 5'-UUAAAUGUC-3' (SEQ ID NO: 423) sequence, the 5'-UUGAUAUCA-3' (SEQ ID NO: 424) sequence, the 5'-UAUUUAUA-3' (SEQ ID NO: 425) sequence, the 5'-UC-UUAUA-3' (SEQ ID NO: 426) sequence, the 5'-UUUAUU-3' (SEQ ID NO: 427) sequence, the 5'-UAUAAA-3' (SEQ ID NO: 428) sequence, the 5'-UUUUUAUG-3' (SEQ ID NO: 429) sequence, the 5'-UGUAUA-3' (SEQ ID NO: 430) sequence, the 5'-UCUUAAA-3' (SEQ ID NO: 431) sequence, the 5'-CUUUAUC-3' (SEQ ID NO: 432) sequence, the 5'-UGUUAUA-3' (SEQ ID NO: 433) sequence, the 5'-AAGAUAAGA-3' (SEQ ID NO: 434) sequence, the 5'-AAAGUACAA-3' (SEQ ID NO: 435) sequence, the 5'-UUAUAUG-3' (SEQ ID NO: 436) sequence, the 5'-AUUUAUA-3' (SEQ ID NO: 437) sequence, the 5'-UUUUUUUAUAUAUA-3' (SEQ ID NO: 438) sequence and 5'-UAAUUUUUUUUAUUUAUG-3' (SEQ ID NO: 439) sequence.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The nucleic acid encoding the guide nucleic acid may be included in a vector.

Here, the vector may be a plasmid or a viral vector.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

In another aspect, the expression control composition may include the following: a guide nucleic acid for targeting a TATA-box or a nucleic acid encoding the same; and a CRISPR enzyme or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a nucleotide sequence including at least one sequence selected from the group consisting of SEQ ID NOs: 374 to 439.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The CRISPR enzyme may be a Cas9 protein or a Cpf1 protein.

Here, the Cas9 protein may be at least one selected from the group consisting of a *Streptococcus thermophiles*-derived Cas9 protein, a *Campylobacter jejuni*-derived Cas9 protein and a *Streptococcus pyogenes*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The present invention provides a method for controlling the expression of a duplicate gene present in the genome of a eukaryotic cell.

In one aspect, the method for controlling the expression of a duplicate gene present in the genome of a eukaryotic cell may comprise introducing an expression control composition into the eukaryotic cell.

The expression control composition may comprise the following:

a guide nucleic acid capable of targeting a target sequence present in a transcriptional regulatory region of a duplicate gene or a nucleic acid encoding the same; and one or more editor protein or a nucleic acid encoding the same.

The eukaryotic cell may be a mammalian cell.

The guide nucleic acid may include a guide domain capable of targeting the target sequence present in the transcriptional regulatory region of the duplicated gene.

Here, the guide domain may include a nucleotide sequence capable of forming a complementary binding with a guide nucleic acid-binding sequence of the target sequence present in the transcriptional regulatory region of the duplicated gene.

Here, the guide domain may form a complementary binding with the guide nucleic acid-binding sequence of the target sequence in the transcriptional regulatory region of the duplicated gene.

Here, the complementary binding may include mismatching bindings of 0 to 5.

The guide nucleic acid may include one or more domains selected from the group consisting of a first complementary domain, a second complementary domain, a proximal domain and a tail domain.

The editor protein may be a CRISPR enzyme.

The guide nucleic acid and editor protein may form a guide nucleic acid-editor protein complex.

Here, the guide nucleic acid-editor protein complex may be formed by interacting with a partial nucleic acid of the guide nucleic acid and a partial amino acid of the editor protein.

The expression control composition may include the guide nucleic acid and the editor protein in a form of the guide nucleic acid-editor protein complex.

The expression control composition may include one or more vector in which the guide nucleic acid and the editor protein is included in a form of nucleic acid respectively.

The introducing may be performed by one or more methods selected from electroporation, liposomes, plasmids, viral vectors, nanoparticles and a protein translocation domain (PTD) fusion protein method.

In another aspect, the method of controlling the expression of a duplicate gene present in the genome of a eukaryotic cell may include introducing an expression control composition into a eukaryotic cell.

The expression control composition may include the following:

i) a first guide nucleic acid capable of targeting a target sequence located upstream of the transcriptional regulartory region of a duplicate gene or a nucleic acid sequence encoding the same;

ii) a second guide nucleic acid capable of targeting a target sequence located downstream of the transcriptional regulartory region of a duplicate gene or a nucleic acid sequence encoding the same; and iii) one or more editor proteins or nucleic acid sequence(s) encoding the same.

The eukaryotic cell may be a mammalian cell.

The first guide nucleic acid may include a first guide domain capable of targeting a target sequence located upstream of the transcriptional regulartory region of a duplicate gene.

Here, the first guide domain may include a nucleotide sequence capable of complementarily binding to a guide nucleic acid-binding sequence of the target sequence located upstream of the transcriptional regulartory region of the duplicate gene.

Here, the first guide domain may complementarily bind with the guide nucleic acid-binding sequence of the target sequence located upstream of the transcriptional regulartory region of the duplicate gene.

Here, the complementary binding may include 0 to 5 mismatches.

The second guide nucleic acid may include a second guide domain capable of targeting a target sequence located downstream of the transcriptional regulartory region of a duplicate gene.

Here, the second guide domain may include a nucleotide sequence capable of complementarily binding to a guide nucleic acid-binding sequence of the target sequence located downstream of the transcriptional regulartory region of a duplicate gene.

Here, the second guide domain may complementarily bind with the guide nucleic acid-binding sequence of the target sequence located downstream of the transcriptional regulartory region of a duplicate gene.

Here, the complementary binding may include 0 to 5 mismatches.

The first guide nucleic acid and/or the second guide nucleic acid may include one or more domains selected from the group consisting of a first complementary domain, a linker domain, a second complementary domain, a proximal domain and a tail domain.

The editor protein may be a CRISPR enzyme.

The first guide nucleic acid and the editor protein may form a first guide nucleic acid-editor protein complex.

Here, the first guide nucleic acid-editor protein complex may be formed by interactions of a partial nucleic acid of the first guide nucleic acid and partial amino acids of the editor protein.

The second guide nucleic acid and the editor protein may form a second guide nucleic acid-editor protein complex.

Here, the second guide nucleic acid-editor protein complex may be formed by interactions of a partial nucleic acid of the second guide nucleic acid and partial amino acids of the editor protein.

The expression control composition may include the first guide nucleic acid, the second guide nucleic acid and the editor protein in the forms of a first guide nucleic acid-editor protein complex and a second guide nucleic acid-editor protein complex.

The expression control composition may include one or more vectors including the first guide nucleic acid, the second guide nucleic acid and the editor protein as respective nucleic acid sequences.

The introduction may be performed using one or more methods selected from electroporation, liposomes, plasmids, viral vectors, nanoparticles and a protein translocation domain (PTD) fusion protein.

In another aspect, the method of controlling the expression of a duplicate gene present in the genome of a eukaryotic cell may include introducing an expression control composition into a eukaryotic cell.

The expression control composition may include the following: a guide nucleic acid for targeting a TATA-box or a nucleic acid encoding the same; and a CRISPR enzyme or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a nucleotide sequence including at least one sequence selected from the group consisting of SEQ ID NOs: 374 to 439.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The CRISPR enzyme may be a Cas9 protein or a Cpf1 protein.

Here, the Cas9 protein may be at least one selected from the group consisting of a *Streptococcus pyogenes*-derived Cas9 protein, a *Campylobacter jejuni*-derived Cas9 protein and a *Streptococcus thermophiles*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The introducing of the expression control composition may be performed by one or more methods selected from electroporation, liposomes, plasmids, viral vectors, nanoparticles and a protein translocation domain (PTD) fusion protein method.

In still another aspect, the method of controlling the expression of a duplicate gene present in the genome of a eukaryotic cell may include introducing an expression control composition into a eukaryotic cell.

The expression control composition may include the following:

a guide nucleic acid for targeting a transcriptional regulatory region of the duplicate gene or a nucleic acid encoding the same; and a CRISPR enzyme or a nucleic acid encoding the same.

The duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene, an APP gene, a MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene and an AKT2 gene.

The transcriptional regulatory region may be a promoter or an enhancer.

The guide nucleic acid may comprise a guide sequence complementarily binding with a target sequence present in the transcriptional regulatory region.

The guide sequence may be a sequence of 10 to 25 contiguous nucleotides.

The guide sequence complementarily binding to the target sequence may be a nucleotide sequence including at least one sequence selected from the group consisting of SEQ ID NOs: 440 to 581.

The guide nucleic acid may comprise a nucleotide sequence including or more sequences selected from the group consisting of SEQ ID NOs: 296 to 309, SEQ ID NO: 328 and SEQ ID NO: 329, or a nucleotide sequence having 80% or more homologous therewith.

The guide nucleic acid may be a single guide RNA.

The CRISPR enzyme may be a Cas9 protein or a Cpf1 protein.

Here, the Cas9 protein may be at least one selected from the group consisting of a *Streptococcus pyogenes*-derived Cas9 protein, a *Campylobacter jejuni*-derived Cas9 protein and a *Streptococcus thermophilus*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The introducing of the expression control composition may be performed by one or more methods selected from electroporation, liposomes, plasmids, viral vectors, nanoparticles and a protein translocation domain (PTD) fusion protein method.

The present invention provides a method for treating a gene duplication disease.

In one aspect, the method for treating a gene duplication disease may comprise administration of an expression control composition into a subject to be treated.

The expression control composition may comprise the following:

a guide nucleic acid capable of targeting a target sequence present in a transcriptional regulatory region of a duplicate gene or a nucleic acid encoding the same; and one or more editor protein or a nucleic acid encoding the same.

The guide nucleic acid may include a guide domain capable of targeting the target sequence present in the transcriptional regulatory region of the duplicated gene.

Here, the guide domain may include a nucleotide sequence capable of forming a complementary binding with a guide nucleic acid-binding sequence of the target sequence present in the transcriptional regulatory region of the duplicated gene.

Here, the guide domain may form a complementary binding with the guide nucleic acid-binding sequence of the target sequence in the transcriptional regulatory region of the duplicated gene.

Here, the complementary binding may include mismatching bindings of 0 to 5.

The guide nucleic acid may include one or more domains selected from the group consisting of a first complementary domain, a second complementary domain, a proximal domain and a tail domain.

The editor protein may be a CRISPR enzyme.

The guide nucleic acid and editor protein may form a guide nucleic acid-editor protein complex.

Here, the guide nucleic acid-editor protein complex may be formed by interacting with a partial nucleic acid of the guide nucleic acid and a partial amino acid of the editor protein.

The gene duplication disease may be Charcot-Marie-Tooth 1A (CMT1A), Dejerine-Sottas disease (DSD), Congenital Hypomyelination Neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), Velocardiofacial syndrome (VCFS), Williams Beuren syndrome (WBS), Alagille syndrome (AS), Growth retardation syndrome, Premature closure cranial sutures, Autosomal dominant leukodystrophy (ADLD), Parkinson disease or Alzheimer disease.

The gene duplication disease may be a cancer caused by an oncogene duplication.

Here, the cancer caused by an oncogene duplication may be Breast cancer, Cervical cancer, Colorectal cancer, Esophageal cancer, Gastric cancer, Glioblastoma, Head and neck cancer, Hepatocellular cancer, Neuroblastoma, Ovarian cancer, Sarcoma or Small cell lung cancer.

The subject to be treated may be a mammal including a human, a monkey, a mouse and a rat.

The administration may be performed by injection, transfusion, implantation or transplantation.

In another aspect, the method of treating a gene duplication disease may include administering an expression control composition into a subject to be treat.

The expression control composition may include the following:

i) a first guide nucleic acid capable of targeting a target sequence located upstream of the transcriptional regulartory region of a duplicate gene or a nucleic acid sequence encoding the same;

ii) a second guide nucleic acid capable of targeting a target sequence located downstream of the transcriptional regulartory region of a duplicate gene or a nucleic acid sequence encoding the same; and iii) one or more editor proteins or nucleic acid sequence(s) encoding the same.

The first guide nucleic acid may include a first guide domain capable of targeting a target sequence located upstream of the transcriptional regulartory region of a duplicate gene.

Here, the first guide domain may include a nucleotide sequence capable of complementarily binding to a guide nucleic acid-binding sequence of the target sequence located upstream of the transcriptional regulartory region of a duplicate gene.

Here, the first guide domain may complementarily bind with the guide nucleic acid-binding sequence of the target sequence located upstream of the transcriptional regulartory region of a duplicate gene.

Here, the complementary binding may include 0 to 5 mismatches.

The second guide nucleic acid may include a second guide domain capable of targeting a target sequence located downstream of the transcriptional regulartory region of a duplicate gene.

Here, the second guide domain may include a nucleotide sequence capable of complementarily binding to a guide nucleic acid-binding sequence of the target sequence located downstream of the transcriptional regulartory region of a duplicate gene.

Here, the second guide domain may complementarily bind with the guide nucleic acid-binding sequence of the target sequence located downstream of the transcriptional regulartory region of a duplicate gene.

Here, the complementary binding may include 0 to 5 mismatches.

The first guide nucleic acid and/or the second guide nucleic acid may include one or more domains selected from the group consisting of a first complementary domain, a linker domain, a second complementary domain, a proximal domain and a tail domain.

The editor protein may be a CRISPR enzyme.

The first guide nucleic acid, the second guide nucleic acid and the editor protein may form a first guide nucleic acid-editor protein complex and a second guide nucleic acid-editor protein complex.

Here, the first guide nucleic acid-editor protein complex may be formed by interactions of a partial nucleic acid of the first guide nucleic acid and partial amino acids of the editor protein.

Here, the second guide nucleic acid-editor protein complex may be formed by interactions of a partial nucleic acid of the second guide nucleic acid and partial amino acids of the editor protein.

The gene duplication disease may be Charcot-Marie-Tooth Type 1A (CMT1A), Dejerine-Sottas disease (DSD), congenital hypomyelination neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), velocardiofacial syndrome (VCFS), Williams Beuren syndrome (WBS), Alagille syndrome (AS), growth retardation syndrome, premature closure cranial sutures, autosomal dominant leukodystrophy (ADLD), Parkinson's disease or Alzheimer's disease.

The subject to be treat may be a mammal including a human, a monkey, a mouse and a rat.

The administration may be performed by injection, transfusion, implantation or transplantation.

In another aspect, the method of treating a gene duplication disease may include administering an expression control composition into a subject to be treat.

The expression control composition may include the following: a guide nucleic acid for targeting a TATA-box or a nucleic acid encoding the same; and a CRISPR enzyme or a nucleic acid encoding the same.

The TATA-box may be present in a promoter of a duplicate gene.

The guide nucleic acid may comprise a guide sequence complementarily binding with a target sequence.

The guide sequence may be a sequence of 10 to 25 contiguous nucleotides.

The guide sequence complementarily binding to the target sequence may be a nucleotide sequence including at least one sequence selected from the group consisting of SEQ ID NOs: 374 to 439.

The guide nucleic acid may be a single guide RNA.

The CRISPR enzyme may be a Cas9 protein or a Cpf1 protein.

Here, the Cas9 protein may be at least one selected from the group consisting of a *Streptococcus pyogenes*-derived Cas9 protein, a *Campylobacter jejuni*-derived Cas9 protein and a *Streptococcus thermophilus*-derived Cas9 protein.

The composition may include the guide nucleic acid and the CRISPR enzyme in a form of a guide nucleic acid-CRISPR enzyme complex.

The composition may be in a form of a vector including the nucleic acid encoding the guide nucleic acid and the CRISPR enzyme, respectively.

Here, the vector may be a plasmid or a viral vector.

The gene duplication disease may be Charcot-Marie-Tooth 1A (CMT1A), Dejerine-Sottas disease (DSD), Congenital Hypomyelination Neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), Velocardiofacial syndrome (VCFS), Williams Beuren syndrome (WBS), Alagille syndrome (AS), Growth retardation syndrome, Premature closure cranial sutures, Autosomal dominant leukodystrophy (ADLD), Parkinson disease or Alzheimer disease.

The gene duplication disease may be a cancer caused by an oncogene duplication.

Here, the cancer caused by an oncogene duplication may be Breast cancer, Cervical cancer, Colorectal cancer, Esophageal cancer, Gastric cancer, Glioblastoma, Head and neck cancer, Hepatocellular cancer, Neuroblastoma, Ovarian cancer, Sarcoma or Small cell lung cancer.

The subject to be treated may be a mammal including a human, a monkey, a mouse and a rat.

The administration may be performed by injection, transfusion, implantation or transplantation.

The present invention can control the expression of a duplication gene by an expression control composition. More specifically, the expression of the duplication gene can be controlled by artificially manipulating and/or modifying the transcriptional regulatory region of a duplicate gene by using the expression control composition including a guide nucleic acid capable of targeting the transcriptional regulatory region of the duplicate gene. A disease caused by gene duplication can also be improved or treated using the expression control composition for controlling the expression of the duplicate gene.

BRIEF DESCRIPTION OF THE DRAWINGS

FIG. 1 illustrates an indel frequency (%) of TATA-box due to SpCas9-sgRNA-mediated gene manipulation.

FIG. 2 illustrates an indel frequency (%) of enhancer due to SpCas9-sgRNA-mediated gene manipulation.

FIG. 3 illustrates an indel frequency (%) of TATA-box due to CjCas9-sgRNA-mediated gene manipulation.

FIG. 4 illustrates an indel frequency (%) of enhancer due to CjCas9-sgRNA-mediated gene manipulation.

FIG. 5 illustrates gene manipulation effects by SpCas9-sgRNA targeting regulatory elements of a human PMP22 gene in Schwann-like cells.

FIG. 6 illustrates Frameshift mutation ratios induced by the SpCas9-sgRNAs targeting CDS of human PMP22.

FIG. 15 illustrates indel patterns with a high frequency by PMP22-TATA RNP in off-targets and on-targets found through an in silico off-target analysis by target deep sequencing in human primary Schwann cells. The local sequence of WT is a SEQ ID NO: 592, and the local sequences including indels are SEQ ID NOs: 593 to 597 (Indel-1 to -4 order).

FIG. 16 shows off-target sites found through an in silico off-target analysis. The on-target sequence is a SEQ ID NO: 598, and the off-target sequences are SEQ ID NOs: 599 to 616 (Off1 to Off18 order).

FIG. 18 illustrates off-target sites appearing by the Dig-enome-seq among off-target sites found through an in silico off-target analysis. The on-target sequence is a SEQ ID NO: 598, and the off-target sequences are SEQ ID NOs: 617 to 625 (Off1 to Off9 order).

FIG. 22 illustrates off-target sites of PMP22-TATA sgRNA in a mouse genome by an in silico analysis. The on-target sequence is a SEQ ID NO: 598, and the off-target sequences are SEQ ID NOs: 626 to 633 (Off1 to Off8 order).

DETAILED DESCRIPTION

Figure 7:
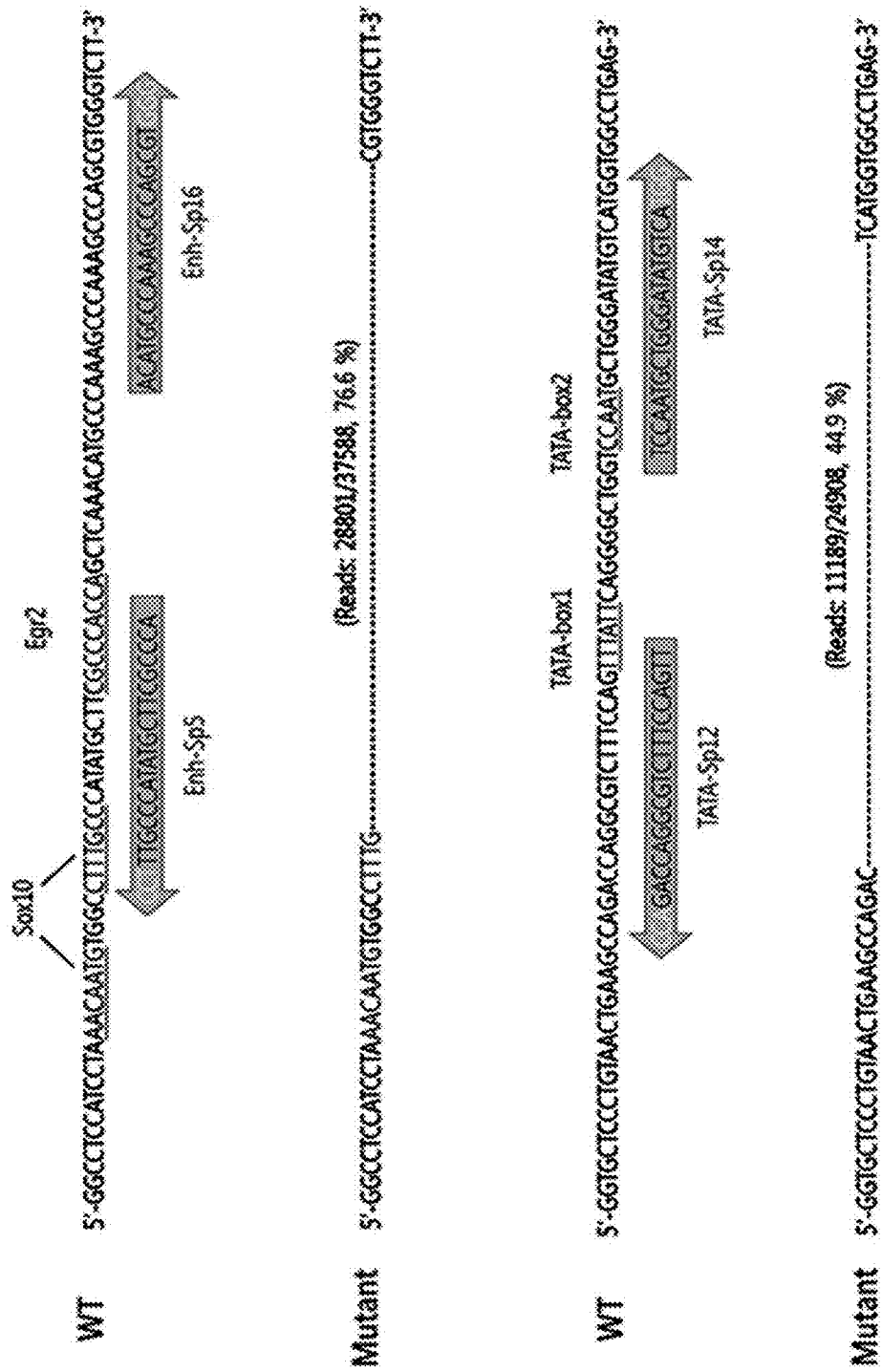
FIG. 7 illustrates Deletions of a small part of human PMP22 by the treatments of the dual sgRNAs. The WT sequence including sequences for Sox10 and Egr2 is a SEQ ID NO: 582, and the mutant sequence deleted a part thereof is a SEQ ID NO: 583. The target sequences for the Enh-Sp5 and the Enh-Sp16 are SEQ ID NOs: 584 and 585. In addition, the WT sequence including TATA-boxes is a SEQ ID NO: 586, and the mutant sequence deleted a part thereof is a SEQ ID NO: 587. The target sequences for the TATA-Sp12 and the TATA-Sp14 are SEQ ID NOs: 588 and 589.

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limitive.

One Aspect Disclosed in the Specification Relates to an Expression Control Composition.

The expression control composition is a composition for controlling the expression of a duplicate gene by gene duplication.

The "gene duplication" means that two or more identical genes are present in a genome. The gene duplication also include having two or more parts of the same gene in a genome. For example, the gene duplication may mean to be present two or more full-length A genes in a genome, or one full-length A gene and one or more parts, for example, exon 1, of the A gene in a genome. For example, the gene duplication may mean to be present two full-length B genes and one or more parts, for example, exon 1 and exon 2, of the B gene in a genome. The type of gene duplication may vary, and the gene duplication includes duplications (that is, two or more) of a full-length gene and/or a partial sequence of the gene in a genome.

In addition, the gene duplication includes a replication phenomenon of duplicating a partial region of a chromosome, which occurs during the genetic recombination of the chromosome. Such gene duplication is a type of gene mutation, and is passed on to the next generation. The gene duplication affects gene expression along with gene deletion which occurs because a partial region of a gene is not replicated.

Here, an object of gene duplication, that is, a gene that is present in a number of two or more is referred to as a "duplicate gene (duplication gene)".

The duplicate gene may be a gene increased in total copy number in a genome due to gene duplication.

The duplicate gene may be a mutant gene in which only a partial region is duplicated due to gene duplication. Here, the mutant gene may be a gene in which one or more nucleotide sequences in the whole sequence of the gene are duplicated. Alternatively, the mutant gene may be a gene in which a partial nucleic acid fragment of the gene is duplicated due to gene duplication. Here, the nucleic acid fragment may have a nucleotide sequence of 50 bp or more.

The gene duplication includes whole genome duplication.

The gene duplication includes target gene duplication. Here, the target gene duplication is a type of gene duplication in which, in the differentiation and adaptation of a new species to environmental changes, a related gene is amplified or disappears to be suitable for a specific environment, and most replications are done by transposons.

The gene duplication includes ectopic recombination. Here, the ectopic recombination occurs according to the degree of repeat sequences between two chromosomes because of replication resulting from unequal crossover during meiosis of homologous chromosomes. Duplication at the crossover point and reciprocal deletion arise. The ectopic recombination is mediated by a typical repetitive genetic element such as a transposable element, and results in replication caused by recombination.

The gene duplication includes replication slippage. Here, the replication slippage is replication of a short genetic sequence due to an error during DNA replication, and occurs when a DNA polymerase is incorrectly attached to a denatured DNA strand, and the DNA strand is replicated again. The replication slippage is also frequently mediated by a repetitive genetic element.

The gene duplication includes retrotransposition. Here, the retrotransposition is replication mediated by a retrovirus or retroelement invading cells, in which reverse transcription of a gene is performed to form a retrogene, and due to the recombination of retrogenes, gene replication is performed. The retrotransposition is mediated by a genetic element such as a retrotransposable element.

The gene duplication may increase the expression of mRNA transcribed from a duplicate gene. Here, the expression of the transcribed mRNA may be increased compared to a state in which gene duplication does not occur.

The gene duplication may increase the expression of a protein encoded by a duplicate gene. Here, the expression of the protein may be increased compared to a state in which gene duplication does not occur.

The gene duplication may cause a dysfunction of a protein encoded by a duplicate gene.

Here, the dysfunction may be an overfunction, a suppressed function and a third function of the protein.

The gene duplication may cause a gene duplication disease.

The "gene duplication disease" is a disease caused by gene duplication, and includes all diseases or disorders causing a genetic abnormality by abnormal amplification of a duplicate gene, and inducing pathological characteristics by a protein overexpressed or abnormally produced thereby. Here, the "pathological characteristics" refers to changes at a cellular level of an organism, and tissue, organ and individual levels due to a disease.

The gene duplication disease may be Charcot-Marie-Tooth Type 1A (CMT1A), Dejerine-Sottas disease (DSD), congenital hypomyelination neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), velocardiofacial syndrome (VCFS), Williams Beuren syndrome (WBS), Alagille syndrome (AS), growth retardation syndrome, premature closure cranial sutures, autosomal dominant leukodystrophy (ADLD), Parkinson's disease or Alzheimer's disease.

The gene duplication disease may be a cancer caused by oncogene duplication.

Here, the cancer may be breast cancer, cervical cancer, colorectal cancer, esophageal cancer, gastric cancer, glioblastoma, head and neck cancer, hepatocellular cancer, neuroblastoma, ovarian cancer, sarcoma or small cell lung cancer.

The gene duplication disease may be a disease caused by duplication of a PMP22 gene, a PLP1 gene, an MECP2 gene, a SOX3 gene, a RAI1 gene, a TBX1 gene, an ELN gene, a JAGGED1 gene, a NSD1 gene, a MMP23 gene, a LMB1 gene, a SNCA gene or an APP gene.

The gene duplication disease may be a disease caused by duplication of an MYC gene, an ERBB2 (HER2) gene, a CCND1 (Cyclin D1) gene, a FGFR1 gene, a FGFR2 gene, a HRAS gene, a KRAS gene, a MYB gene, a MDM2 gene, a CCNE (Cyclin E) gene, a MET gene, a CDK4 gene, an ERBB1 gene, a MYCN gene or an AKT2 gene.

The gene duplication disease may be a disease caused by an abnormal increase in the expression of transcribed mRNA of a duplicate gene.

The gene duplication disease may be a disease caused by an abnormal increase in the expression of a protein encoded by a duplicate gene.

The expression control composition may be used in the control of the expression of mRNA produced by transcription of a duplicate gene.

The expression control composition may be used in the control of the expression of a protein encoded by a duplicate gene.

The expression control composition may be used for artificial modification or manipulation of a duplicate gene.

Here, the "artificially modification or manipulation (artificially modified, manipulated or engineered)" refers to an artificially modified state, rather than a naturally-occurring state. Hereinafter, an unnaturally, artificially modified or manipulated duplicate gene may be used interchangeably with an artificial duplicate gene.

The "expression control system" is the term including all phenomena occurring due to the control of the expression of an artificially manipulated duplicate gene, and all materials, compositions, methods and uses directly or indirectly involved in the expression control system.

The expression control composition may be used for artificial manipulation or modification of the transcriptional regulatory region of the duplicate gene.

Here, the "transcriptional regulatory region (transcription control region)" is a region controlling an overall process of synthesizing RNA based on DNA of a gene, and includes all regions which interact with a transcription factor in a DNA sequence of a gene and/or a proximal DNA sequence of a gene. Here, the transcription factor is a protein that, when activated, binds to a specific region of DNA, that is, a response element close to a gene, thereby promoting or inhibiting gene expression, and the response element is included in the transcriptional regulatory region. The types and positions of the transcriptional regulatory region may vary according to a gene, and even in the same species, there may be a difference in nucleic acid sequences between individuals.

The transcriptional regulatory region may be a promoter, an enhancer, a silencer, an insulator and/or a locus control region (LCR).

The promoter may be a core promoter, a proximal promoter and/or a distal promoter.

Here, the core promoter may include a transcription start site (TSS), an RNA polymerase-binding site, a transcription factor-binding site and/or a TATA box.

The TATA box may be a region located 25 base pairs upstream of an initiation site used to initiate the transcription of Rpb4/Rbp7.

The TATA box may be a region located 30 base pairs upstream of the TSS.

The TATA box may be a region located 40 to 100 base pairs upstream of the TSS.

For example, the TATA box may be a region including a 5'-TATA(A/T)A(A/T)-3' sequence present in a promoter and/or a core promoter. Alternatively, the TATA box may be a region including a 5'-TATA(A/T)A(A/T)(A/G)-3' sequence present in a promoter and/or a core promoter.

For example, the TATA box may be a region including one or more sequences selected form the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence, which are present in a promoter and/or a core promoter.

For example, the TATA box may be a region in which a TATA-binding protein (TBP) present in a promoter and/or a core promoter binds.

Here, the proximal promoter may include a region 1 to 300-bp upstream of the TSS, a CpG site and/or a specific transcription factor-binding site.

The enhancer may include an enhancer-box (E-box).

The insulator may be a region that inhibits an interaction between an enhancer and a promoter or prevents the expansion of suppressed chromatin.

The locus control region (LCR) may be a region in which numerous cis-acting factors such as an enhancer, a silencer, an insulator, MAR, and SAR are present.

As One Aspect Disclosed in the Specification, the Expression Control Composition May Include a Guide Nucleic Acid.

The expression control composition may include a guide nucleic acid targeting a duplicate gene or a nucleic acid sequence encoding the same.

The "guide nucleic acid" refers to a nucleotide sequence that recognizes a target nucleic acid, gene or chromosome, and interacts with an editor protein. Here, the guide nucleic acid may complementarily bind to a partial nucleotide sequence in the target nucleic acid, gene or chromosome. In addition, a partial nucleotide sequence of the guide nucleic acid may interact with some amino acids of the editor protein, thereby forming a guide nucleic acid-editor protein complex.

The guide nucleic acid may perform a function to induce a guide nucleic acid-editor protein complex to be located in a target region of a target nucleic acid, gene or chromosome.

The guide nucleic acid may be present in the form of DNA, RNA or a DNA/RNA hybrid, and may have a nucleic acid sequence of 5 to 150 nt.

The guide nucleic acid may have one continuous nucleic acid sequence.

For example, the one continuous nucleic acid sequence may be $(N)_m$, where N represents A, T, C or G, or A, U, C or G, and m is an integer of 1 to 150.

The guide nucleic acid may have two or more continuous nucleic acid sequences.

For example, the two or more continuous nucleic acid sequences may be $(N)_m$ and $(N)_o$, where N represents A, T, C or G, or A, U, C or G, m and o are an integer of 1 to 150, and m and o may be the same as or different from each other.

The guide nucleic acid may include one or more domains.

The domains may be, but are not limited to, a guide domain, a first complementary domain, a linker domain, a second complementary domain, a proximal domain, or a tail domain.

Here, one guide nucleic acid may have two or more functional domains. Here, the two or more functional domains may be different from each other. For one example, one guide nucleic acid may have a guide domain and a first complementary domain. For another example, one guide nucleic acid may have a second complementary domain, a proximal domain and a tail domain. For still another example, one guide nucleic acid may have a guide domain, a first complementary domain, a second complementary domain, a proximal domain and a tail domain. Alternatively, the two or more functional domains included in one guide nucleic acid may be the same as each other. For one example, one guide nucleic acid may have two or more proximal domains. For another example, one guide nucleic acid may have two or more tail domains. However, the description that the functional domains included in one guide nucleic acid are the same domains does not mean that the sequences of the two functional domains are the same. Even if the sequences are different, the two functional domain can be the same domain when perform functionally the same function.

The functional domain will be described in detail below.

i) Guide Domain

The term "guide domain" is a domain capable of complementary binding with partial sequence of either strand of a double strand of a nucleic acid in a transcriptional regulatory region of a target gene, and acts for specific interaction with a nucleic acid in a transcriptional regulatory region of a target gene. For example, the guide domain may perform a function to induce a guide nucleic acid-editor protein complex to be located to a specific nucleotide sequence in a nucleic acid of a transcriptional regulatory region of a target gene.

The guide domain may be a sequence of 10 to 35 nucleotides.

In an example, the guide domain may be a sequence of 10 to 35, 15 to 35, 20 to 35, 25 to 35 or 30 to 35 nucleotides.

In another example, the guide domain may be a sequence of 10 to 15, 15 to 20, 20 to 25, 25 to 30 or 30 to 35 nucleotides.

The guide domain may have a guide sequence.

The term "guide sequence" is a nucleotide sequence complementary to partial sequence of either strand of a double strand of a nucleic acid in a transcriptional regulatory region of a target gene. Here, the guide sequence may be a nucleotide sequence having at least 50%, 55%, 60%, 65%, 70%, 75%, 80%, 85%, 90%, 95% or more complementarity or complete complementarity.

The guide sequence may be a sequence of 10 to 25 nucleotides.

In an example, the guide sequence may be a sequence of 10 to 25, 15 to 25 or 20 to 25 nucleotides.

In another example, the guide sequence may be a sequence of 10 to 15, 15 to 20 or 20 to 25 nucleotides.

In addition, the guide domain may further include an additional nucleotide sequence.

The additional nucleotide sequence may be utilized to improve or degrade the function of the guide domain.

The additional nucleotide sequence may be utilized to improve or degrade the function of the guide sequence.

The additional nucleotide sequence may be a sequence of 1 to 10 nucleotides.

In one example, the additional nucleotide sequence may be a sequence of 2 to 10, 4 to 10, 6 to 10 or 8 to 10 nucleotides.

In another example, the additional nucleotide sequence may be a sequence of 1 to 3, 3 to 6 or 7 to 10 nucleotides.

In one embodiment, the additional nucleotide sequence may be a sequence of 1, 2, 3, 4, 5, 6, 7, 8, 9 or 10 nucleotides.

For example, the additional nucleotide sequence may be one nucleotide sequence G (guanine), or two nucleotide sequence GG.

The additional nucleotide sequence may be located at the 5' end of the guide sequence.

The additional nucleotide sequence may be located at the 3' end of the guide sequence.

ii) First Complementary Domain

The term "first complementary domain" is a domain including a nucleotide sequence complementary to a second complementary domain to be described in below, and has enough complementarity so as to form a double strand with the second complementary domain. For example, the first complementary domain may be a nucleotide sequence having at least 50%, 55%, 60%, 65%, 70%, 75%, 80%, 85%, 90%, 95% or more complementarity or complete complementarity to a second complementary domain.

The first complementary domain may form a double strand with a second complementary domain by a complementary binding. Here, the formed double strand may act to form a guide nucleic acid-editor protein complex by interacting with some amino acids of the editor protein.

The first complementary domain may be a sequence of 5 to 35 nucleotides.

In an example, the first complementary domain may be a sequence of 5 to 35, 10 to 35, 15 to 35, 20 to 35, 25 to 35, or 30 to 35 nucleotides.

In another example, the first complementary domain may be a sequence of 1 to 5, 5 to 10, 10 to 15, 15 to 20, 20 to 25, 25 to 30 or 30 to 35 nucleotides.

iii) Linker Domain

The term "linker domain" is a nucleotide sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a sequence of 1 to 30 nucleotides.

In one example, the linker domain may be a sequence of 1 to 5, 5 to 10, 10 to 15, 15 to 20, 20 to 25, or 25 to 30 nucleotides.

In another example, the linker domain may be a sequence of 1 to 30, 5 to 30, 10 to 30, 15 to 30, 20 to 30, or 25 to 30 nucleotides.

iv) Second Complementary Domain

The term "second complementary domain" is a domain including a nucleotide sequence complementary to the first complementary domain described above, and has enough complementarity so as to form a double strand with the first complementary domain. For example, the second complementary domain may be a nucleotide sequence having at least 50%, 55%, 60%, 65%, 70%, 75%, 80%, 85%, 90%, 95% or more complementarity or complete complementarity to a first complementary domain.

The second complementary domain may form a double strand with a first complementary domain by a complementary binding. Here, the formed double strand may act to form a guide nucleic acid-editor protein complex by interacting with some amino acids of the editor protein. The second complementary domain may have a nucleotide sequence complementary to a first complementary domain, and a nucleotide sequence having no complementarity to the first complementary domain, for example, a nucleotide sequence not forming a double strand with the first complementary domain, and may have a longer base sequence than the first complementary domain.

The second complementary domain may be a sequence of 5 to 35 nucleotides.

In an example, the second complementary domain may be a sequence of 5 to 35, 10 to 35, 15 to 35, 20 to 35, 25 to 35, or 30 to 35 nucleotides.

In another example, the second complementary domain may be a sequence of 1 to 5, 5 to 10, 10 to 15, 15 to 20, 20 to 25, 25 to 30 or 30 to 35 nucleotides.

v) Proximal Domain

The term "proximal domain" is a nucleotide sequence located adjacent to a second complementary domain.

The proximal domain may have a complementary nucleotide sequence therein, and may be formed in a double strand due to a complementary nucleotide sequence.

The proximal domain may be a sequence of 1 to 20 nucleotides.

In one example, the proximal domain may be a sequence of 1 to 20, 5 to 20, 10 to 20 or 15 to 20 nucleotide.

In another example, the proximal domain may be a sequence of 1 to 5, 5 to 10, 10 to 15 or 15 to 20 nucleotides.

vi) Tail Domain

The term "tail domain" is a nucleotide sequence located at one or more ends of the both ends of the guide nucleic acid.

The tail domain may have a complementary nucleotide sequence therein, and may be formed in a double strand due to a complementary nucleotide sequence.

The tail domain may be a sequence of 1 to 50 nucleotides.

In an example, the tail domain may be a sequence of 5 to 50, 10 to 50, 15 to 50, 20 to 50, 25 to 50, 30 to 50, 35 to 50, 40 to 50, or 45 to 50 nucleotides.

In another example, the tail domain may be a sequence of 1 to 5, 5 to 10, 10 to 15, 15 to 20, 20 to 25, 25 to 30, 30 to 35, 35 to 40, 40 to 45, or 45 to 50 nucleotides.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP).

The guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

In One Exemplary Embodiment Disclosed in the Specification, the Guide Nucleic Acid May be a gRNA.

The term "gRNA" refers to a RNA capable of specifically targeting a gRNA-CRISPR enzyme complex, that is, a CRISPR complex, with respect to a nucleic acid in a transcriptional regulatory region of a target gene. In addition, the gRNA is a RNA specific to the nucleic acid in the transcriptional regulatory region of the target gene, which may bind to a CRISPR enzyme and guide the CRISPR enzyme to the transcriptional regulatory region of the target gene.

The gRNA may include multiple domains. Due to each domain, interactions may occur in a three-dimensional structure or active form of a gRNA strand, or between these strands.

The gRNA may be called single-stranded gRNA (single RNA molecule, single gRNA or sgRNA); or double-stranded gRNA (including more than one, generally, two discrete RNA molecules).

In one exemplary embodiment, the single-stranded gRNA may include a guide domain, that is, a domain including a guide sequence capable of forming a complementary bond with a nucleic acid in a transcriptional regulatory region of a target gene; a first complementary domain; a linker domain; a second complementary domain, which is a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a nucleic acid in a transcriptional regulatory region of a target gene and a first complementary domain; and a second strand which includes a second complementary domain, which is a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a nucleic acid in a transcriptional regulatory region of a target gene; a first complementary domain; a second complementary domain, and a domain having a sequence complementary to the first complementary domain sequence, thereby forming a double-stranded nucleic acid with the first complementary domain in the 5' to 3' direction.

Here, the first complementary domain may have homology with a natural first complementary domain, or may be derived from a natural first complementary domain. In addition, the first complementary domain may have a difference in the nucleotide sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Staphylococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUUAGAGCUA-3' (SEQ ID NO: 296) or a nucleotide sequence having partial, that is, at least 50% or more, or complete homology with 5'-GUUUUAGAGCUA-3' (SEQ ID NO: 296). Here, the first complementary domain may further include $(X)_n$, resulting in 5'-GUUUUAGAGCUA$(X)_n$-3' (SEQ ID NO: 296). The X may be selected from the group consisting of bases A, T, U and G, and the n may represent the number of nucleotides, which is an integer of 5 to 15. Here, the $(X)_n$ may be n repeats of the same nucleotide, or a mixture of n nucleotides of A, T, U and G.

In another embodiment, when the first complementary domain is the first complementary domain of *Campylobacter jejuni* or a first complementary domain derived therefrom, the first complementary domain may be 5'-GUUUUAGUCCCUUUUUAAAUUUCUU-3' (SEQ ID NO: 297), or a nucleotide sequence having partial, that is, at least 50% or more, or complete homology with 5'-GUUUUAGUCCCUUUUUAAAUUUCUU-3' (SEQ ID NO: 297). Here, the first complementary domain may further include $(X)_n$, resulting in 5'-GUUUUAGUCCCUUUUUAAAUUUCUU$(X)_n$-3' (SEQ ID NO: 297). The X may be selected from the group consisting of nucleotides A, T, U and G, and the n may represent the number of nucleotides, which is an integer of 5 to 15. Here, the $(X)_n$ may represent n repeats of the same nucleotide, or a mixture of n nucleotides of A, T, U and G.

In another embodiment, the first complementary domain may have partial, that is, at least 50% or more, or complete homology with a first complementary domain of *Parcubacteria bacterium* (GWC2011_GWC2_44_17), *Lachnospiraceae bacterium* (MC2017), *Butyrivibrio proteoclasiicus*, *Peregrinibacteria bacterium* (GW2011_GWA_33_10), *Acidaminococcus* sp. (BV3L6), *Porphyromonas macacae*, *Lachnospiraceae bacterium* (ND2006), *Porphyromonas crevioricanis*, *Prevotella disiens*, *Moraxella bovoculi* (237), *Smiihella* sp. (SC_KO8D17), *Leptospira inadai*, *Lachnospiraceae bacterium* (MA2020), *Francisella novicida* (U112), *Candidatus Methanoplasma termitum* or *Eubacterium eligens*, or a first complementary domain derived therefrom.

For example, when the first complementary domain is the first complementary domain of *Parcubacteria bacterium* or a first complementary domain derived therefrom, the first complementary domain may be 5'-UUUGUAGAU-3' (SEQ ID NO: 298), or a nucleotide sequence having partial, that is, at least 50% or more homology with 5'-UUUGUAGAU-3' (SEQ ID NO: 298). Here, the first complementary domain may further include $(X)_n$, resulting in 5'-$(X)_n$UUUGUAGAU-3' (SEQ ID NO: 298). The X may be selected from the group consisting of nucleotides A, T, U and G, and the n may represent the number of nucleotides, which is an integer of 1 to 5. Here, the $(X)_n$ may represent n repeats of the same nucleotide, or a mixture of n nucleotides of A, T, U and G.

Here, the linker domain may be a nucleotide sequence connecting a first complementary domain with a second complementary domain.

The linker domain may form a covalent or non-covalent bonding with a first complementary domain and a second complementary domain, respectively.

The linker domain may connect the first complementary domain with the second complementary domain covalently or non-covalently.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding.

The linker domain may be used to produce single-stranded gRNA by being connected with crRNA and tracrRNA of double-stranded gRNA or connecting the crRNA with the tracrRNA by covalent or non-covalent bonding.

Here, the second complementary domain may have homology with a natural second complementary domain, or may be derived from the natural second complementary domain. In addition, the second complementary domain may have a difference in nucleotide sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus pyogenes*, *Campylobacter jejuni*, *Streptococcus thermophilus*, *Staphylococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-<u>UAGCAAGU UAAAA</u>U-3' (SEQ ID NO: 299), or a nucleotide sequence having partial, that is, at least 50% or more homology with 5'-<u>UAGCAAGUUAAAA</u>U-3' (SEQ ID NO: 299) (a nucleotide sequence forming a double strand with the first complementary domain is underlined). Here, the second complementary domain may further include $(X)_n$ and/or $(X)_m$, resulting in 5'-$(X)_n$ <u>UAGCAAGUUAAAA</u>U$(X)_m$-3' (SEQ ID NO: 299). The X may be selected from the group consisting of nucleotides A, T, U and G, and each of the n and m may represent the number of nucleotides, in which the n may be an integer of 1 to 15, and the m may be an integer of 1 to 6. Here, the $(X)_n$ may represent n repeats of the same nucleotide, or a mixture of n nucleotides of A, T, U and G. In addition, $(X)_m$ may represent m repeats of the same nucleotide, or a mixture of m nucleotides of A, T, U and G.

In another example, when the second complementary domain is the second complementary domain of *Campylobacter jejuni* or a second complementary domain derived therefrom, the second complementary domain may be 5'-<u>AAGAAAUUUAAAAAGGGACUAAAA</u>U-3' (SEQ ID NO: 300), or a nucleotide sequence having partial, that is, at least 50% or more homology with 5'-<u>AAGAAAUUUAAAAAGGGACUAAAA</u>U-3' (SEQ ID NO: 300) (a nucleotide sequence forming a double strand with the first complementary domain is underlined). Here, the second complementary domain may further include $(X)_n$ and/or $(X)_m$, resulting in 5'-$(X)_n$ <u>AAGAAAUUUAAAAAGGGACUAAAA</u>U$(X)_m$-3' (SEQ ID NO: 300). The X may be selected from the group consisting of nucleotides A, T, U and G, and each of the n and m may represent the number of nucleotides, in which the n may be an integer of 1 to 15, and the m may be an integer of 1 to 6. Here, $(X)_n$ may represent n repeats of the same nucleotide, or a mixture of n nucleotides of A, T, U and G.

In addition, $(X)_m$ may represent m repeats of the same nucleotide, or a mixture of m nucleotides of A, T, U and G.

In another embodiment, the second complementary domain may have partial, that is, at least 50% or more, or complete homology with a second complementary domain of *Parcubacteria bacterium* (GWC2011_GWC2_44_17), *Lachnospiraceae bacterium* (MC2017), *Butyrivibrio proteoclasiicus*, *Peregrinibacteria bacterium* (GW2011_GWA_33_10), *Acidaminococcus* sp. (BV3L6), *Porphyromonas macacae*, *Lachnospiraceae bacterium* (ND2006), *Porphyromonas crevioricanis*, *Prevotella disiens*, *Moraxella bovoculi* (237), *Smiihella* sp. (SC_KO8D17), *Leptospira inadai*, *Lachnospiraceae bacterium* (MA2020), *Francisella novicida* (U112), *Candidatus Methanoplasma termitum* or *Eubacterium eligens*, or a second complementary domain derived therefrom.

For example, when the second complementary domain is a second complementary domain of *Parcubacteria bacterium* or a second complementary domain derived therefrom, the second complementary domain may be 5'-AAAUUUCUACU-3' (SEQ ID NO: 301), or a nucleotide sequence having partial, that is, at least 50% or more homology with 5'-AAAUUUCUACU-3' (SEQ ID NO: 301) (a nucleotide sequence forming a double strand with the first complementary domain is underlined). Here, the second complementary domain may further include $(X)_n$ and/or $(X)_m$, resulting in 5'-$(X)_n$AAAUUUCUACU$(X)_m$-3' (SEQ ID NO: 301). The X may be selected from the group consisting of nucleotides A, T, U and G, and each of the n and m may represent the number of nucleotides, in which the n may be an integer of 1 to 10, and the m may be an integer of 1 to 6. Here, the $(X)_n$ may represent n repeats of the same nucleotide, or a mixture of n nucleotides of A, T, U and G. In addition, the $(X)_m$ may represent m repeats of the same nucleotide, or a mixture of m nucleotides of A, T, U and G.

Here, the first complementary domain and the second complementary domain may complementarily bind to each other.

The first complementary domain and the second complementary domain may form a double strand by the complementary binding.

The formed double strand may interact with a CRISPR enzyme.

Optionally, the first complementary domain may include an additional nucleotide sequence that does not complementarily bind to a second complementary domain of a second strand.

Here, the additional nucleotide sequence may be a sequence of 1 to 15 nucleotides. For example, the additional nucleotide sequence may be a sequence of 1 to 5, 5 to 10 or 10 to 15 nucleotides.

Here, the proximal domain may be a domain located at the 3'end direction of the second complementary domain.

The proximal domain may have homology with a natural proximal domain, or may be derived from the natural proximal domain. In addition, the proximal domain may have a difference in nucleotide sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes*, *Campylobacter jejuni*, *Streptococcus thermophilus*, *Staphylococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGC-UAGUCCG-3' (SEQ ID NO: 302), or a nucleotide sequence having partial, that is, at least 50% or more homology with 5'-AAGGCUAGUCCG-3' (SEQ ID NO: 302). Here, the proximal domain may further include $(X)_n$, resulting in 5'-AAGGCUAGUCCG$(X)_n$-3' (SEQ ID NO: 302). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides of A, T, U and G.

In yet another example, when the proximal domain is a proximal domain of *Campylobacter jejuni* or a proximal domain derived therefrom, the proximal domain may be 5'-AAAGAGUUUGC-3' (SEQ ID NO: 303), or a nucleotide sequence having at least 50% or more homology with 5'-AAAGAGUUUGC-3' (SEQ ID NO: 303). Here, the proximal domain may further include $(X)_n$, resulting in 5'-AAAGAGUUUGC$(X)_n$-3' (SEQ ID NO: 303). The X may be selected from the group consisting of nucleotides A, T, U and G, and the n may represent the number of nucleotides, which is an integer of 1 to 40. Here, the $(X)_n$ may represent n repeats of the same nucleotide, or a mixture of n nucleotides of A, T, U and G.

Here, the tail domain is a domain which is able to be selectively added to the 3' end of single-stranded gRNA or the first or second strand of double-stranded gRNA.

The tail domain may have homology with a natural tail domain, or may be derived from the natural tail domain. In addition, the tail domain may have a difference in nucleotide sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes*, *Campylobacter jejuni*, *Streptococcus thermophilus*, *Staphylococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3' (SEQ ID NO: 304), or a nucleotide sequence having partial, that is, at least 50% or more homology with 5'-UUAUCAAC-UUGAAAAAGUGGCACCGAGUCGGUGC-3' (SEQ ID NO: 304). Here, the tail domain may further include $(X)_n$, resulting in 5'-UUAUCAAC-UUGAAAAAGUGGCACCGAGUCGGUGC$(X)_n$-3' (SEQ ID NO: 304). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3' (SEQ ID NO: 305), or a nucleotide sequence having partial, that is, at least 50% or more homology with 5'-GGGACUCUGCGGGGUUA-CAAUCCCCUAAAACCGCUUUU-3' (SEQ ID NO: 305). Here, the tail domain may further include $(X)_n$, resulting in 5'-GGGACUCUGCGGGGUUACAAUCCCC- UAAAACCGCUUUU(X)$_n$-3' (SEQ ID NO: 305). The X may be selected from the group consisting of nucleotides A, T, U and G, and the n may represent the number of nucleotides, which is an integer of 1 to 15. Here, the (X)$_n$ may represent n repeats of the same nucleotide, or a mixture of n nucleotides of A, T, U and G.

In another embodiment, the tail domain may include a 1 to 10-nt sequence at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

The gRNA may include a plurality of domains as described above, and therefore, the length of the nucleic acid sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or double-stranded gRNA (including more than one, generally two discrete RNA molecules).

Double-Stranded gRNA

The double-stranded gRNA consists of a first strand and a second strand.

Here, the first strand may consist of

5'-[guide domain]-[first complementary domain]-3', and the second strand may consist of 5'-[second complementary domain]-[proximal domain]-3' or 5'-[second complementary domain]-[proximal domain]-[tail domain]-3'.

Here, the first strand may be referred to as crRNA, and the second strand may be referred to as tracrRNA.

Here, the first strand and the second strand may optionally include an additional nucleotide sequence.

In one example, the first strand may be

5'-(N$_{target}$)-(Q)$_m$-3'; or

5'-(X)$_a$-(N$_{target}$)-(X)$_b$-(Q)$_m$-(X)$_c$-3'.

Here, the N$_{target}$ is a nucleotide sequence complementary to partial sequence of either strand of a double strand of a nucleic acid in a transcriptional regulatory region of a target gene, and a nucleotide sequence region which may be changed according to a target sequence on a nucleic acid in a transcriptional regulatory region of a target gene.

Here, the (Q)$_m$ is a nucleotide sequence including a first complementary domain, which is able to form a complementary bond with the second complementary domain of the second strand. The (Q)$_m$ may be a sequence having partial or complete homology with the first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Streptococcus pyogenes* or a *Streptococcus pyogenes*-derived first complementary domain, the (Q)$_m$ may be 5'-GUUUUAGAGCUA-3' (SEQ ID NO: 296), or a nucleotide sequence having at least 50% or more homology with 5'-GUUUUAGAGCUA-3' (SEQ ID NO: 296).

In another example, when the first complementary domain has partial or complete homology with a first complementary domain of *Campylobacter jejuni* or a *Campylobacter jejuni*-derived first complementary domain, the (Q)$_m$ may be 5'-GUUUUAGUCCC-UUUUUAAAUUUCUU-3' (SEQ ID NO: 297), or a nucleotide sequence having at least 50% or more homology with 5'-GUUUUAGUCCCUUUUUAAAUUUCUU-3' (SEQ ID NO: 297).

In still another example, when the first complementary domain has partial or complete homology with a first complementary domain of *Streptococcus thermophilus* or a *Streptococcus thermophilus*-derived first complementary domain, the (Q)$_m$ may be 5'-GUUUUAGAGCUGUGUU-GUUUCG-3' (SEQ ID NO: 306), or a nucleotide sequence having at least 50% or more homology with 5'-GUUUUA-GAGCUGUGUUGUUUCG-3' (SEQ ID NO: 306).

In addition, each of the (X)$_a$, (X)$_b$ and (X)$_c$ is selectively an additional nucleotide sequence, where the X may be each independently selected from the group consisting of A, U, C and G, and each of the a, b and c may be the number of nucleotides, which is 0 or an integer of 1 to 20.

In one exemplary embodiment, the second strand may be

5'-(Z)$_h$-(P)$_k$-3'; or 5'-(X)$_d$-(Z)$_h$-(X)$_e$-(P)$_k$-(X)$_f$-3'.

In another embodiment, the second strand may be

5'-(Z)$_h$-(P)$_k$-(F)$_i$-3'; or 5'-(X)$_d$-(Z)$_h$-(X)$_e$-(P)$_k$-(X)$_f$-(F)$_i$-3'.

Here, the (Z)$_h$ is a nucleotide sequence including a second complementary domain, which is able to form a complementary bond with the first complementary domain of the first strand. The (Z)$_h$ may be a sequence having partial or complete homology with the second complementary domain of a species existing in nature, and the nucleotide sequence of the second complementary domain may be modified according to the species of origin. The Z may be each independently selected from the group consisting of A, U, C and G, and the h may be the number of nucleotides, which is an integer of 5 to 50.

For example, when the second complementary domain has partial or complete homology with a second complementary domain of *Streptococcus pyogenes* or a second complementary domain derived therefrom, the (Z)$_h$ may be 5'-UAGCAAGUUAAAAU-3' (SEQ ID NO: 299), or a nucleotide sequence having at least 50% or more homology with 5'-UAGCAAGUUAAAAU-3' (SEQ ID NO: 299).

In another example, when the second complementary domain has partial or complete homology with a second complementary domain of *Campylobacter jejuni* or a second complementary domain derived therefrom, the (Z)$_h$ may be 5'-AAGAAAUUUAAAAAGGGACUAAAAU-3' (SEQ ID NO: 300), or a nucleotide sequence having at least 50% or more homology with 5'-AAGAAAUUUAAAAAGGGAC-UAAAAU-3' (SEQ ID NO: 300).

In still another example, when the second complementary domain has partial or complete homology with a second complementary domain of *Streptococcus thermophilus* or a second complementary domain derived therefrom, the (Z)$_h$ may be 5'-CGAAACAACACAGCGAGUUAAAAU-3' (SEQ ID NO: 307), or a nucleotide sequence having at least 50% or more homology with 5'-CGAAACAACACAGCGAGUUAAAAU-3' (SEQ ID NO: 307).

The (P)$_k$ is a nucleotide sequence including a proximal domain, which may have partial or complete homology with a proximal domain of a species existing in nature, and the nucleotide sequence of the proximal domain may be modified according to the species of origin. The P may be each independently selected from the group consisting of A, U, C and G, and the k may be the number of nucleotides, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3' (SEQ ID NO: 302), or a nucleotide sequence having at least 50% or more homology with 5'-AAGGCUAGUCCG-3' (SEQ ID NO: 302).

In another example, when the proximal domain has partial or complete homology with a proximal domain of *Campylobacter jejuni* or a proximal domain derived therefrom, the $(P)_k$ may be 5'-AAAGAGUUUGC-3' (SEQ ID NO: 303), or a nucleotide sequence having at least 50% or more homology with 5'-AAAGAGUUUGC-3' (SEQ ID NO: 303).

In still another example, when the proximal domain has partial or complete homology with a proximal domain of *Streptococcus thermophilus* or a proximal domain derived therefrom, the $(P)_k$ may be 5'-AAGGCUUAGUCCG-3' (SEQ ID NO: 308), or a nucleotide sequence having at least 50% or more homology with 5'-AAGGCUUAGUCCG-3' (SEQ ID NO: 308).

The $(F)_i$ may be a nucleotide sequence including a tail domain, and having partial or complete homology with a tail domain of a species existing in nature, and the nucleotide sequence of the tail domain may be modified according to the species of origin. The F may be each independently selected from the group consisting of A, U, C and G, and the i may be the number of nucleotides, which is an integer of 1 to 50.

For example, when the tail domain has partial or complete homology with a tail domain of *Streptococcus pyogenes* or a tail domain derived therefrom, the $(F)_i$ may be 5'-UUAUCAACUUGAAAAAGUGGCACCGAGUCGGUGC-3' (SEQ ID NO: 304), or a nucleotide sequence having at least 50% or more homology with 5'-UUAUCAACUUGAAAAAGUGGCACCGAGUCGGUGC-3' (SEQ ID NO: 304).

In another example, when the tail domain has partial or complete homology with a tail domain of *Campylobacter jejuni* or a tail domain derived therefrom, the $(F)_i$ may be 5'-GGGACUCUGCGGGGUUACAAUCCCC-UAAAACCGCUUUU-3' (SEQ ID NO: 305), or a nucleotide sequence having at least 50% or more homology with 5'-GGGACUCUGCGGGGUUACAAUCCCC-UAAAACCGCUUUU-3' (SEQ ID NO: 305).

In still another example, when the tail domain has partial or complete homology with a tail domain of *Streptococcus thermophilus* or a tail domain derived therefrom, the $(F)_i$ may be 5'-UACUCAACUUGAAAAG-GUGGCACCGAUUCGGUGUUUUU-3' (SEQ ID NO: 309), or a nucleotide sequence having at least 50% or more homology with 5'-UACUCAACUUGAAAAG-GUGGCACCGAUUCGGUGUUUUU-3' (SEQ ID NO: 309).

In addition, the $(F)_i$ may include a sequence of 1 to 10 nucleotides at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

In addition, the $(X)_d$, $(X)_e$ and $(X)_f$ may be nucleotide sequences selectively added, where the X may be each independently selected from the group consisting of A, U, C and G, and each of the d, e and f may be the number of nucleotides, which is 0 or an integer of 1 to 20.

Single-Stranded gRNA

Single-stranded gRNA may be classified into a first single-stranded gRNA and a second single-stranded gRNA.

First Single-Stranded gRNA

First single-stranded gRNA is single-stranded gRNA in which a first strand or a second strand of the double-stranded gRNA is linked by a linker domain.

Specifically, the single-stranded gRNA may consist of

5'-[guide domain]-[first complementary domain]-[linker domain]-[second complementary domain]-3', 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3'.

The first single-stranded gRNA may selectively include an additional nucleotide sequence.

In one exemplary embodiment, the first single-stranded gRNA may be

5'-$(N_{target})$-$(Q)_m$-$(L)_j$-$(Z)_h$-3';
5'-$(N_{target})$-$(Q)_m$-$(L)_j$-$(Z)_h$-$(P)_k$-3'; or
5'-$(N_{target})$-$(Q)_m$-$(L)_j$-$(Z)_h$-$(P)_k$-$(F)_i$-3'.

In another embodiment, the single-stranded gRNA may be

5-$(X)_a$-$(N_{target})$-$(X)_b$-$(Q)_m$-$(X)_c$-$(L)_j$-$(X)_d$-$(Z)_h$-$(X)_e$-3';
5-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-3'; or
5-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-$(F)_i$-3'.

Here, the $N_{target}$ is a nucleotide sequence complementary to partial sequence of either strand of a double strand of a nucleic acid in a transcriptional regulatory region of a target gene, and a nucleotide sequence region capable of being changed according to a target sequence on a transcriptional regulatory region of a target gene.

The $(Q)_m$ includes a nucleotide sequence including the first complementary domain, which is able to form a complementary bond with a second complementary domain. The $(Q)_m$ may be a sequence having partial or complete homology with a first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Streptococcus pyogenes* or a first complementary domain derived therefrom, the $(Q)_m$ may be 5'-GUUUUA-GAGCUA-3' (SEQ ID NO: 296), or a nucleotide sequence having at least 50% or more homology with 5'-GUUUUA-GAGCUA-3' (SEQ ID NO: 296).

In another example, when the first complementary domain has partial or complete homology with a first complementary domain of *Campylobacter jejuni* or a first complementary domain derived therefrom, the $(Q)_m$ may be 5'-GUUUUAGUCCCUUUUUAAAUUUCUU-3' (SEQ ID NO: 297), or a nucleotide sequence having at least 50% or more homology with 5'-GUUUUAGUCCC-UUUUUAAAUUUCUU-3' (SEQ ID NO: 297).

In still another example, when the first complementary domain has partial or complete homology with a first complementary domain of *Streptococcus thermophilus* or a first complementary domain derived therefrom, the $(Q)_m$ may be 5'-GUUUUAGAGCUGUGUUGUUUCG-3' (SEQ ID NO: 306), or a nucleotide sequence having at least 50% or more homology with 5'-GUUUUAGAGCUGUGUU-GUUUCG-3' (SEQ ID NO: 306).

In addition, the $(L)_j$ is a nucleotide sequence including the linker domain, and connecting the first complementary domain with the second complementary domain, thereby producing single-stranded gRNA. Here, the L may be each independently selected from the group consisting of A, U, C and G, and the j may be the number of nucleotides, which is an integer of 1 to 30.

The $(Z)_h$ is a nucleotide sequence including the second complementary domain, and includes a nucleotide sequence capable of complementary binding with the first complementary domain. The $(Z)_h$ may be a sequence having partial or complete homology with the second complementary domain of a species existing in nature, and the nucleotide sequence of the second complementary domain may be changed according to the species of origin. The Z may be each independently selected from the group consisting of A, U, C and G, and the h is the number of nucleotides, which may be an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3' (SEQ ID NO: 299), or a nucleotide sequence having at least 50% or more homology with 5'-UAGCAAGUUAAAAU-3' (SEQ ID NO: 299).

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3' (SEQ ID NO: 300), or a nucleotide sequence having at least 50% or more homology with 5'-AAGAAAUUUAAAAAGGGAC-UAAAAU-3' (SEQ ID NO: 300).

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3' (SEQ ID NO: 307), or a nucleotide sequence having at least 50% or more homology with 5'-CGAAACAACACAGCGAGUUAAAAU-3' (SEQ ID NO: 307).

The $(P)_k$ is a nucleotide sequence including a proximal domain, which may have partial or complete homology with a proximal domain of a species existing in nature, and the nucleotide sequence of the proximal domain may be modified according to the species of origin. The P may be each independently selected from the group consisting of A, U, C and G, and the k may be the number of nucleotides, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3' (SEQ ID NO: 302), or a nucleotide sequence having at least 50% or more homology with 5'-AAGGCUAGUCCG-3' (SEQ ID NO: 302).

In another example, when the proximal domain has partial or complete homology with a proximal domain of *Campylobacter jejuni* or a proximal domain derived therefrom, the $(P)_k$ may be 5'-AAAGAGUUUGC-3' (SEQ ID NO: 303), or a nucleotide sequence having at least 50% or more homology with 5'-AAAGAGUUUGC-3' (SEQ ID NO: 303).

In still another example, when the proximal domain has partial or complete homology with a proximal domain of *Streptococcus thermophilus* or a proximal domain derived therefrom, the $(P)_k$ may be 5'-AAGGCUUAGUCCG-3' (SEQ ID NO: 308), or a nucleotide sequence having at least 50% or more homology with 5'-AAGGCUUAGUCCG-3' (SEQ ID NO: 308).

The $(F)_i$ may be a nucleotide sequence including a tail domain, and having partial or complete homology with a tail domain of a species existing in nature, and the nucleotide sequence of the tail domain may be modified according to the species of origin. The F may be each independently selected from the group consisting of A, U, C and G, and the i may be the number of nucleotides, which is an integer of 1 to 50.

For example, when the tail domain has partial or complete homology with a tail domain of *Streptococcus pyogenes* or a tail domain derived therefrom, the $(F)_i$ may be 5'-UUAU-CAACUUGAAAAAGUGGCACCGAGUCGGUGC-3' (SEQ ID NO: 304), or a nucleotide sequence having at least 50% or more homology with 5'-UUAUCAAC-UUGAAAAAGUGGCACCGAGUCGGUGC-3' (SEQ ID NO: 304).

In another example, when the tail domain has partial or complete homology with a tail domain of *Campylobacter jejuni* or a tail domain derived therefrom, the $(F)_i$ may be 5'-GGGACUCUGCGGGGUUACAAUCCCC-UAAAACCGCUUUU-3' (SEQ ID NO: 305), or a nucleotide sequence having at least 50% or more homology with 5'-GGGACUCUGCGGGGUUACAAUCCCC-UAAAACCGCUUUU-3' (SEQ ID NO: 305).

In still another example, when the tail domain has partial or complete homology with a tail domain of *Streptococcus thermophilus* or a tail domain derived therefrom, the $(F)_i$ may be 5'-UACUCAACUUGAAAAG-GUGGCACCGAUUCGGUGUUUUU-3' (SEQ ID NO: 309), or a nucleotide sequence having at least 50% or more homology with 5'-UACUCAACUUGAAAAG-GUGGCACCGAUUCGGUGUUUUU-3' (SEQ ID NO: 309).

In addition, the $(F)_i$ may include a sequence of 1 to 10 nucleotides at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

In addition, the $(X)_a$, $(X)_b$, $(X)_c$, $(X)_d$, $(X)_e$ and $(X)_f$ may be nucleotide sequences selectively added, where the X may be each independently selected from the group consisting of A, U, C and G, and each of the a, b, c, d, e and f may be the number of nucleotides, which is 0 or an integer of 1 to 20.

Second Single-Stranded gRNA

Second single-stranded gRNA may be single-stranded gRNA consisting of a guide domain, a first complementary domain and a second complementary domain.

Here, the second single-stranded gRNA may consist of:

5'-[second complementary domain]-[first complementary domain]-[guide domain]-3'; or 5'-[second complementary domain]-[linker domain]-[first complementary domain]-[guide domain]-3'.

The second single-stranded gRNA may selectively include an additional nucleotide sequence.

In one exemplary embodiment, the second single-stranded gRNA may be

5'-$(Z)_h$-$(Q)_m$-$(N_{target})$-3'; or

5'-$(X)_a$-$(Z)_h$-$(X)_b$-$(Q)_m$-$(X)_c$-$(N_{target})$-3'.

In another embodiment, the single-stranded gRNA may be

5-$(Z)_h$-$(L)_j$-$(Q)_m$-$(N_{target})$-3'; or

5'-$(X)_a$-$(Z)_h$-$(L)_j$-$(Q)_m$-$(X)_c$-$(N_{target})$-3'.

Here, the $N_{target}$ is a nucleotide sequence complementary to partial sequence of either strand of a double strand of a nucleic acid in a transcriptional regulatory region of a target gene, and a nucleotide sequence region capable of being changed according to a target sequence on a transcriptional regulatory region of a target gene. The $(Q)_m$ is a nucleotide sequence including the first complementary domain, and includes a nucleotide sequence capable of complementary binding with a second complementary domain. The $(Q)_m$ may be a sequence having partial or complete homology with the first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of Parcubacteria bacterium or a first complementary domain derived therefrom, the $(Q)_m$ may be 5'-UUUGUAGAU-3' (SEQ ID NO: 298), or a nucleotide sequence having at least 50% or more homology with 5'-UUUGUAGAU-3' (SEQ ID NO: 298).

The $(Z)_h$ is a nucleotide sequence including a second complementary domain, and includes a nucleotide sequence capable of complementary binding with a second complementary domain. The $(Z)_h$ may be a sequence having partial or complete homology with the second complementary domain of a species existing in nature, and the nucleotide sequence of the second complementary domain may be modified according to the species of origin. The Z may be each independently selected from the group consisting of A, U, C and G, and the h may be the number of nucleotides, which is an integer of 5 to 50.

For example, when the second complementary domain has partial or complete homology with a second complementary domain of Parcubacteria bacterium or a Parcubacteria bacterium-derived second complementary domain, the $(Z)_h$ may be 5'-AAAUUUCUACU-3' (SEQ ID NO: 301), or a nucleotide sequence having at least 50% or more homology with 5'-AAAUUUCUACU-3' (SEQ ID NO: 301).

In addition, the $(L)_j$ is a nucleotide sequence including the linker domain, which connects the first complementary domain with the second complementary domain. Here, the L may be each independently selected from the group consisting of A, U, C and G, and the j may be the number of nucleotides, which is an integer of 1 to 30.

In addition, each of the $(X)_a$, $(X)_b$ and $(X)_c$ is selectively an additional nucleotide sequence, where the X may be each independently selected from the group consisting of A, U, C and G, and the a, b and c may be the number of nucleotides, which is 0 or an integer of 1 to 20.

In One Exemplary Embodiment of the Specification, the Guide Nucleic Acid May be gRNA Complementarily Binding to a Target Sequence in the Transcriptional Regulatory Region of a Duplicate Gene.

The "target sequence" refers to a nucleotide sequence present in the transcriptional regulartory region of a target gene or nucleotide sequence(s) located upstream and/or downstream of the transcriptional regulartory region of a target gene, and particularly, a partial nucleotide sequence in a target region in the transcriptional regulartory region of a target gene or a partial nucleotide sequence in a target region located upstream and/or downstream of the transcriptional regulartory region of a target gene, and here, the "target region" may be a region that can be modified by a guide nucleic acid-editor protein in the transcriptional regulartory region of a target gene or a region that can be modified by a guide nucleic acid-editor protein located upstream and/or downstream of the transcriptional regulartory region of a target gene.

Hereinafter, the target sequence may be used to refer to both of two types of nucleotide sequence information. For example, in the case of a target gene, the target sequence may refer to the nucleotide sequence information of a transcribed strand of target gene DNA, or the nucleotide sequence information of a non-transcribed strand.

For example, the target sequence may refer to a partial nucleotide sequence (transcribed strand), that is, 5'-ATCATTGGCAGACTAGTTCG-3' (SEQ ID NO: 310), in the target region of target gene A, and a nucleotide sequence complementary thereto (non-transcribed strand), that is, 5'-CGAACTAGTCTGCCAATGAT-3' (SEQ ID NO: 311).

The target sequence may be a 5 to 50-nt sequence.

In one exemplary embodiment, the target sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The target sequence includes a guide nucleic acid-binding sequence or a guide nucleic acid-non binding sequence.

The "guide nucleic acid-binding sequence" is a nucleotide sequence having partial or complete complementarity with a guide sequence included in the guide domain of the guide nucleic acid, and may be complementarily bonded with the guide sequence included in the guide domain of the guide nucleic acid. The target sequence and guide nucleic acid-binding sequence may be a nucleotide sequence that may vary according to a target to be genetically engineered or edited depending on the transcriptional regulatory region of the target gene, and may be designed in various ways according to a nucleic acid sequence in the transcriptional regulatory region of the target gene.

The "guide nucleic acid-non binding sequence" is a nucleotide sequence having partial or complete homology with a guide sequence included in the guide domain of the guide nucleic acid, and may not be complementarily bonded with the guide sequence included in the guide domain of the guide nucleic acid. In addition, the guide nucleic acid-non binding sequence may be a nucleotide sequence having complementarity with the guide nucleic acid-binding sequence, and may be complementarily bonded with the guide nucleic acid-binding sequence.

The guide nucleic acid-binding sequence may be a partial nucleotide sequence of the target sequence, and one nucleotide sequence of two nucleotide sequences having different sequence order to each other included in the target sequence, that is, one of the two nucleotide sequences capable of complementary binding to each other. Here, the guide nucleic acid-non binding sequence may be a nucleotide sequence other than the guide nucleic acid-binding sequence of the target sequence.

For example, when a partial nucleotide sequence, that is, 5'-ATCATTGGCAGACTAGTTCG-3' (SEQ ID NO: 310), of a target region in the transcriptional regulatory region of the target gene A, and a nucleotide sequence, that is, 5'-CGAACTAGTCTGCCAATGAT-3' (SEQ ID NO: 311), which is complementary thereto, are used as target sequences, the guide nucleic acid-binding sequence may be one of the two target sequences, that is, 5'-ATCATTGGCA-GACTAGTTCG-3' (SEQ ID NO: 310) or 5'-CGAACTAGTCTGCCAATGAT-3' (SEQ ID NO: 311). Here, when the guide nucleic acid-binding sequence is 5'-ATCATTGGCAGACTAGTTCG-3' (SEQ ID NO: 310), the guide nucleic acid-non binding sequence may be 5'-CGAACTAGTCTGCCAATGAT-3' (SEQ ID NO: 311), or when the guide nucleic acid-binding sequence is 5'-CGAACTAGTCTGCCAATGAT-3' (SEQ ID NO: 311), the guide nucleic acid-non binding sequence may be 5'-ATCATTGGCAGACTAGTTCG-3' (SEQ ID NO: 310).

The guide nucleic acid-binding sequence may be one of the target sequences, that is, a nucleotide sequence which is the same as a transcribed strand and a nucleotide sequence which is the same as a non-transcribed strand. Here, the guide nucleic acid-non binding sequence may be a nucleotide sequence other than the guide nucleic acid-binding sequence of the target sequences, that is, one selected from a nucleotide sequence which is the same as a transcribed strand and a nucleotide sequence which is the same as a non-transcribed strand.

The guide nucleic acid-binding sequence may have the same length as the target sequence.

The guide nucleic acid-non binding sequence may have the same length as the target sequence or the guide nucleic acid-binding sequence.

The guide nucleic acid-binding sequence may be a 5 to 50-nt sequence.

In one exemplary embodiment, the guide nucleic acid-binding sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The guide nucleic acid-non binding sequence may be a 5 to 50-nt sequence.

In one exemplary embodiment, the guide nucleic acid-nonbinding sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The guide nucleic acid-binding sequence may partially or completely complementarily bind to the guide sequence included in the guide domain of the guide nucleic acid, and the length of the guide nucleic acid-binding sequence may be the same as that of the guide sequence.

The guide nucleic acid-binding sequence may be a nucleotide sequence complementary to the guide sequence included in the guide domain of the guide nucleic acid, and for example, a nucleotide sequence which has at least 70%, 75%, 80%, 85%, 90%, 95% or more complementarity or complete complementarity.

As an example, the guide nucleic acid-binding sequence may have or include a 1 to 8-nt sequence which is not complementary to the guide sequence included in the guide domain of the guide nucleic acid.

The guide nucleic acid-non binding sequence may have partial or complete homology with the guide sequence included in the guide domain of the guide nucleic acid, and the length of the guide nucleic acid-non binding sequence may be the same as that of the guide sequence.

The guide nucleic acid-non binding sequence may be a nucleotide sequence having homology with the guide sequence included in the guide domain of the guide nucleic acid, and for example, a nucleotide sequence which has at least 70%, 75%, 80%, 85%, 90%, 95% or more homology or complete homology.

In one example, the guide nucleic acid-non binding sequence may have or include a 1 to 8-nt sequence which is not homologous to the guide sequence included in the guide domain of the guide nucleic acid.

The guide nucleic acid-non binding sequence may complementarily bind with the guide nucleic acid-binding sequence, and the guide nucleic acid-non binding sequence may have the same length as the guide nucleic acid-binding sequence.

The guide nucleic acid-non binding sequence may be a nucleotide sequence complementary to the guide nucleic acid-binding sequence, and for example, a nucleotide sequence having at least 90%, 95% or more complementarity or complete complementarity.

In one example, the guide nucleic acid-non binding sequence may have or include a 1 to 2-nt sequence which is not complementary to the guide nucleic acid-binding sequence.

In addition, the guide nucleic acid-binding sequence may be a nucleotide sequence located near a nucleotide sequence recognized by an editor protein.

In one example, the guide nucleic acid-binding sequence may be a consecutive 5 to 50-nt sequence located adjacent to the 5' end and/or 3' end of a nucleotide sequence recognized by an editor protein.

In addition, the guide nucleic acid-non binding sequence may be a nucleotide sequence located near a nucleotide sequence recognized by an editor protein.

In one example, the guide nucleic acid-non binding sequence may be a 5 to 50-nt contiguous sequence located adjacent to the 5' end and/or 3' end of a nucleotide sequence recognized by an editor protein.

The "targeting" refers to complementary binding with the guide nucleic acid-binding sequence of the target sequence present in the transcriptional regulatory region of a target gene. Here, the complementary binding may be 100% completely complementary binding, or 70% or more and less than 100%, incomplete complementary binding. Therefore, the "targeting gRNA" refers to gRNA complementarily binding to the guide nucleic acid-binding sequence of the target sequence present in the transcriptional regulatory region of a target gene.

The target gene disclosed in the specification may be a duplicate gene.

The target gene disclosed in the specification may be a PMP22 gene, a PLP1 gene, an MECP2 gene, a SOX3 gene, a RAI1 gene, a TBX1 gene, an ELN gene, a JAGGED1 gene, an NSD1 gene, an MMP23 gene, an LMB1 gene, a SNCA gene and/or an APP gene.

The target gene disclosed in the specification may be an oncogene.

Here, the oncogene may be an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and/or an AKT2 gene.

In an exemplary embodiment, the target sequence disclosed in the specification may be a 10 to 35-nt contiguous sequence located in the promoter region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene,␣an HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in the core promoter region of a duplicate gene.

For example, the target sequence may be a 10 to 25-nt contiguous sequence located in a region including or near TTS of a duplicate gene.

For example, the target sequence may be a 10 to 25-nt contiguous sequence located in a region including or near the RNA polymerase-binding region of a duplicate gene.

For example, the target sequence may be a 10 to 25-nt contiguous sequence located in a region including or near the transcription factor-binding region of a duplicate gene.

For example, the target sequence may be a 10 to 25-nt contiguous sequence located in a region including or near the TATA box of a duplicate gene.

For example, the target sequence may be a 10 to 25-nt contiguous sequence including all or a part of the 5'-TATA-3' (SEQ ID NO: 261) sequence present in the core promoter region of the duplicate gene.

Here, the guide sequence complementarily binding to the target sequence may be a 10 to 25-nt contiguous sequence including the entire or a part of the 5'-UAUA-3' (SEQ ID NO: 374) sequence.

For example, the target sequence may be a 10 to 25-nt contiguous sequence including all or a part of the 5'-TATAWAW-3' (W=A or T) (SEQ ID NO: 262) sequence present in the core promoter region of the duplicate gene.

Here, the guide sequence complementarily binding to the target sequence may be a 10 to 25-nt contiguous sequence including the entire or a part of the 5'-UAUAWAW-3' (W=A or U) (SEQ ID NO: 375) sequence, or may be a 10 to 25-nt contiguous sequence including the entire or a part of the 5'-WUWUAUA-3' (W=A or U) (SEQ ID NO: 376) sequence.

For example, the target sequence may be a 10 to 25-nt contiguous sequence including all or a part of the 5'-TATAWAWR-3' (W=A or T, R=A or G) (SEQ ID NO: 263) sequence present in the core promoter region of the duplicate gene.

Here, the guide sequence complementarily binding to the target sequence may be a 10 to 25-nt contiguous sequence including the entire or a part of the 5'-UAUAWAWR-3' (W=A or U, R=A or G) (SEQ ID NO: 377) sequence, or may be a 10 to 25-nt contiguous sequence including the entire or a part of the 5'-RWUWUAUA-3' (W=A or U, R=A or G) (SEQ ID NO: 378) sequence.

For example, the target sequence may be a 10 to 25-nt contiguous sequence including the entirety or a part of one or more sequences selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence, which are present in the core promoter region of a duplicate gene.

Here, the guide sequence complementarily binding to the target sequence may be a 10 to 25-nt contiguous sequence including the entirety or a part of one or more sequences selected from the group consisting of the 5'-CAUAAAA-3' (SEQ ID NO: 379) sequence, the 5'-UAUAA-3' (SEQ ID NO: 380) sequence, the 5'-UAUAAAA-3' (SEQ ID NO: 381) sequence, the 5'-CAUAAAUA-3' (SEQ ID NO: 382) sequence, the 5'-UAUAUAA-3' (SEQ ID NO: 383) sequence, the 5'-UAUAUAUAUAUAUAA-3' (SEQ ID NO: 384) sequence, the 5'-UAUAUUAUA-3' (SEQ ID NO: 385) sequence, the 5'-UAUAAA-3' (SEQ ID NO: 386) sequence, the 5'-UAUAAAAUA-3' (SEQ ID NO: 387) sequence, the 5'-UAUAUA-3' (SEQ ID NO: 388) sequence, the 5'-GAUUAAAAA-3' (SEQ ID NO: 389) sequence, the 5'-UAUAAAAA-3' (SEQ ID NO: 390) sequence, the 5'-UUAUAA-3' (SEQ ID NO: 391) sequence, the 5'-UUUUAAAA-3' (SEQ ID NO: 392) sequence, the 5'-UCUUUAAAA-3' (SEQ ID NO: 393) sequence, the 5'-GACAUUUAA-3' (SEQ ID NO: 394) sequence, the 5'-UGAUAUCAA-3' (SEQ ID NO: 395) sequence, the 5'-UAUAAAUA-3' (SEQ ID NO: 396) sequence, the 5'-UAUAAGA-3' (SEQ ID NO: 397) sequence, the 5'-AAUAAA-3' (SEQ ID NO: 398) sequence, the 5'-UUUAUA-3' (SEQ ID NO: 399) sequence, the 5'-CAUAAAAA-3' (SEQ ID NO: 400) sequence, the 5'-UAUACA-3' (SEQ ID NO: 401) sequence, the 5'-UUUAAGA-3' (SEQ ID NO: 402) sequence, the 5'-GAUAAAG-3' (SEQ ID NO: 403) sequence, the 5'-UAUAACA-3' (SEQ ID NO: 404) sequence, the 5'-UCUUAUCUU-3' (SEQ ID NO: 405) sequence, the 5'-UUGUACUUU-3' (SEQ ID NO: 406) sequence, the 5'-CAUAUAA-3' (SEQ ID NO: 407) sequence, the 5'-UAUAAAU-3' (SEQ ID NO: 408) sequence, the 5'-UAUAUAUAAAAAAAA-3' (SEQ ID NO: 409) sequence and 5'-CAUAAAUAAAAAAAAUUA-3' (SEQ ID NO: 410) sequence.

Alternatively, the guide sequence complementarily binding to the target sequence may be a 10 to 25-nt contiguous sequence including the entirety or a part of one or more sequences selected from the group consisting of the 5'-UUUUAUG-3' (SEQ ID NO: 411) sequence, the 5'-UUAUA-3' (SEQ ID NO: 412) sequence, the 5'-UUUUAUA-3' (SEQ ID NO: 413) sequence, the 5'-UAUUUAUG-3' (SEQ ID NO: 414) sequence, the 5'-UUAUAUA-3' (SEQ ID NO: 415) sequence, the 5'-UUAUAUAUAUAUAUA-3' (SEQ ID NO: 416) sequence, the 5'-UAUAAUAUA-3' (SEQ ID NO: 417) sequence, the 5'-UUUAUA-3' (SEQ ID NO: 418) sequence, the 5'-UAUUUUAUA-3' (SEQ ID NO: 419) sequence, the 5'-UUUUUAAUC-3' (SEQ ID NO: 420) sequence, the 5'-UUUUUAUA-3' (SEQ ID NO: 421) sequence, the 5'-UUUUAAAGA-3' (SEQ ID NO: 422) sequence, the 5'-UUAAAUGUC-3' (SEQ ID NO: 423) sequence, the 5'-UUGAUAUCA-3' (SEQ ID NO: 424) sequence, the 5'-UAUUUAUA-3' (SEQ ID NO: 425) sequence, the 5'-UCUUAUA-3' (SEQ ID NO: 426) sequence, the 5'-UUUAUU-3' (SEQ ID NO: 427) sequence, the 5'-UAUAAA-3' (SEQ ID NO: 428) sequence, the 5'-UUUUUAUG-3' (SEQ ID NO: 429) sequence, the 5'-UGUAUA-3' (SEQ ID NO: 430) sequence, the 5'-UCUUAAA-3' (SEQ ID NO: 431) sequence, the 5'-CUUUAUC-3' (SEQ ID NO: 432) sequence, the 5'-UGUUAUA-3' (SEQ ID NO: 433) sequence, the 5'-AAGAUAAGA-3' (SEQ ID NO: 434) sequence, the 5'-AAAGUACAA-3' (SEQ ID NO: 435) sequence, the 5'-UUAUAUG-3' (SEQ ID NO: 436) sequence, the 5'-AUUUAUA-3' (SEQ ID NO: 437) sequence, the 5'-UUUUUUUUAUAUAUA-3' (SEQ ID NO: 438) sequence and 5'-UAAUUUUUUUUAUUUAUG-3' (SEQ ID NO: 439) sequence.

For example, the target sequence may be a 10 to 25-nt contiguous sequence, which includes the entire or a part of a TATA-binding protein (TBP)-binding nucleic acid sequence, which is present in the core promoter region of a duplicate gene.

In another example, the target sequence may be a 10 to 25-nt contiguous sequence located in the proximal promoter region of a duplicate gene.

For example, the target sequence may be a 10 to 25-nt contiguous sequence located in a 1 to 300 bp upstream region of the TSS of a duplicate gene.

In still another example, the target sequence may be a 10 to 25-nt contiguous sequence located in the distal promoter region of a duplicate gene.

The target sequence disclosed in the specification may be a 10 to 35-nt contiguous sequence located in the enhancer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

For example, the target sequence may be a 10 to 25-nt contiguous sequence located in a region including or near the enhancer-box (E-box) of a duplicate gene.

For example, the target sequence may be a 10 to 35-nt contiguous sequence located in the enhancer region present in an intron of a duplicate gene.

The target sequence disclosed in the specification may be a 10 to 35-nt contiguous sequence located in the insulator region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected form the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located in the silencer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located in the locus control region (LCR) of a duplicate gene.

Here, the duplicate gene may be one or more genes selected from a group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located upstream of the promoter region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located upstream of the core promoter region of a duplicate gene.

For example, the target sequence may be a 10 to 25-nt contiguous sequence including TSS of a duplicate gene or located upstream of the region close to the TSS.

For example, the target sequence may be a 10 to 25-nt contiguous sequence including an RNA polymerase-binding site of a duplicate gene or located upstream of the region close to the RNA polymerase-binding site.

For example, the target sequence may be a 10 to 25-nt contiguous sequence including a transcription factor-binding site of a duplicate gene or located upstream of the region close to the transcription factor-binding site.

For example, the target sequence may be a 10 to 25-nt contiguous sequence including a TATA box of a duplicate gene or located upstream of the region close to the TATA box.

For example, the target sequence may be a 10 to 25-nt contiguous sequence located upstream of a region including the 5'-TATA-3' (SEQ ID NO: 261) sequence present in the core promoter region of the duplicate gene.

For example, the target sequence may be a 10 to 25-nt contiguous sequence located upstream of a region including the 5'-TATAWAW-3' (W=A or T) (SEQ ID NO: 262) sequence present in the core promoter region of a duplicate gene.

For example, the target sequence may be a 10 to 25-nt contiguous sequence located upstream of a region including the 5'-TATAWAWR-3' (W=A or T, R=A or G) (SEQ ID NO: 263) sequence present in the core promoter region of a duplicate gene.

For example, the target sequence may be a 10 to 25-nt contiguous sequence located upstream of a region including one or more sequences selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTATCTT-3' (SEQ ID NO: 290) sequence, the 5'-TTGTACTTT-3' (SEQ ID NO: 291) sequence, the 5'-CATATA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAAATTA-3' (SEQ ID NO: 295) sequence, which are present in the core promoter region of a duplicate gene.

For example, the target sequence may be a 10 to 25-nt contiguous sequence located upstream of a region including a nucleic acid sequence binding to a TATA-binding protein (TBP) present in the core promoter region of a duplicate gene.

In another example, the target sequence may be a 10 to 25-nt contiguous sequence located upstream of the proximal promoter region of a duplicate gene.

For example, the target sequence may be a 10 to 25-nt contiguous sequence located upstream of the 1 to 300 bp upstream region of TSS of a duplicate gene.

In still another example, the target sequence may be a 10 to 25-nt contiguous sequence located upstream of the distal promoter region of a duplicate gene.

The target sequence disclosed in the specification may be a 10 to 35-nt contiguous sequence located downstream of the promoter region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located downstream of the core promoter region of a duplicate gene.

For example, the target sequence may be a 10 to 25-nt contiguous sequence including TSS of a duplicate gene or located downstream of the region close to the TSS.

For example, the target sequence may be a 10 to 25-nt contiguous sequence including an RNA polymerase-binding site of a duplicate gene or located downstream of the region close to the RNA polymerase-binding site.

For example, the target sequence may be a 10 to 25-nt contiguous sequence including a transcription factor-binding site of a duplicate gene or located downstream of the region close to the transcription factor-binding site.

For example, the target sequence may be a 10 to 25-nt contiguous sequence including a TATA box of a duplicate gene or located downstream of the region close to the TATA box.

For example, the target sequence may be a 10 to 25-nt contiguous sequence located downstream of a region including the 5'-TATA-3' (SEQ ID NO: 261) sequence present in the core promoter region of the duplicate gene.

For example, the target sequence may be a 10 to 25-nt contiguous sequence located downstream of a region including the 5'-TATAWAW-3' (W=A or T) (SEQ ID NO: 262) sequence present in the core promoter region of a duplicate gene.

For example, the target sequence may be a 10 to 25-nt contiguous sequence located downstream of a region including the 5'-TATAWAWR-3' (W=A or T, R=A or G) (SEQ ID NO: 263) sequence present in the core promoter region of a duplicate gene.

For example, the target sequence may be a 10 to 25-nt contiguous sequence located downstream of a region including one or more sequences selected from the group consisting of the 5'-CATAAAA-3' (SEQ ID NO: 264) sequence, the 5'-TATAA-3' (SEQ ID NO: 265) sequence, the 5'-TATAAAA-3' (SEQ ID NO: 266) sequence, the 5'-CATAAATA-3' (SEQ ID NO: 267) sequence, the 5'-TATATAA-3' (SEQ ID NO: 268) sequence, the 5'-TATATATATATATAA-3' (SEQ ID NO: 269) sequence, the 5'-TATATTATA-3' (SEQ ID NO: 270) sequence, the 5'-TATAAA-3' (SEQ ID NO: 271) sequence, the 5'-TATAAAATA-3' (SEQ ID NO: 272) sequence, the 5'-TATATA-3' (SEQ ID NO: 273) sequence, the 5'-GATTAAAAA-3' (SEQ ID NO: 274) sequence, the 5'-TATAAAAA-3' (SEQ ID NO: 275) sequence, the 5'-TTATAA-3' (SEQ ID NO: 276) sequence, the 5'-TTTTAAAA-3' (SEQ ID NO: 277) sequence, the 5'-TCTTTAAAAA-3' (SEQ ID NO: 278) sequence, the 5'-GACATTTAA-3' (SEQ ID NO: 279) sequence, the 5'-TGATATCAA-3' (SEQ ID NO: 280) sequence, the 5'-TATAAATA-3' (SEQ ID NO: 281) sequence, the 5'-TATAAGA-3' (SEQ ID NO: 282) sequence, the 5'-AATAAA-3' (SEQ ID NO: 283) sequence, the 5'-TTTATA-3' (SEQ ID NO: 284) sequence, the 5'-CATAAAAA-3' (SEQ ID NO: 285) sequence, the 5'-TATACA-3' (SEQ ID NO: 286) sequence, the 5'-TTTAAGA-3' (SEQ ID NO: 287) sequence, the 5'-GATAAAG-3' (SEQ ID NO: 288) sequence, the 5'-TATAACA-3' (SEQ ID NO: 289) sequence, the 5'-TCTTTATCTT-3' (SEQ ID NO: 290) sequence, the 5'-TTGTACTTT-3' (SEQ ID NO: 291) sequence, the 5'-CATATAA-3' (SEQ ID NO: 292) sequence, the 5'-TATAAAT-3' (SEQ ID NO: 293) sequence, the 5'-TATATATAAAAAAAA-3' (SEQ ID NO: 294) sequence and 5'-CATAAATAAAAAAATTA-3' (SEQ ID NO: 295) sequence, which are present in the core promoter region of a duplicate gene.

For example, the target sequence may be a 10 to 25-nt contiguous sequence located downstream of a region including a nucleic acid sequence binding to a TATA-binding protein (TBP) present in the core promoter region of a duplicate gene.

In another example, the target sequence may be a 10 to 25-nt contiguous sequence located downstream of the proximal promoter region of a duplicate gene.

For example, the target sequence may be a 10 to 25-nt contiguous sequence located downstream of the 1 to 300 bp downstream region of TSS of a duplicate gene.

In still another example, the target sequence may be a 10 to 25-nt contiguous sequence located downstream of the distal promoter region of a duplicate gene.

The target sequence disclosed in the specification may be a 10 to 35-nt contiguous sequence located upstream of an enhancer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

For example, the target sequence may be a 10 to 25-nt contiguous sequence including an enhancer-box (E-box) of a duplicate gene or located upstream of the region closed to the enhancer-box.

For example, the target sequence may be a 10 to 35-nt contiguous sequence located upstream of an enhancer region present in an intron of a duplicate gene.

The target sequence disclosed in the specification may be a 10 to 35-nt contiguous sequence located downstream of an enhancer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

For example, the target sequence may be a 10 to 25-nt contiguous sequence including an enhancer-box (E-box) of a duplicate gene or located downstream of the region closed to the enhancer-box.

For example, the target sequence may be a 10 to 35-nt contiguous sequence located downstream of an enhancer region present in an intron of a duplicate gene.

The target sequence disclosed in the specification may be a 10 to 35-nt contiguous sequence located upstream of an insulator region pf a duplicate gene.

The target sequence disclosed in the specification may be a 10 to 35-nt contiguous sequence located downstream of an insulator region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located upstream of a silencer region of a duplicate gene.

The target sequence disclosed in the specification may be a 10 to 35-nt contiguous sequence located downstream of a silencer region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence located upstream of a locus control region (LCR) of a duplicate gene.

The target sequence disclosed in the specification may be a 10 to 35-nt contiguous sequence located downstream of a LCR of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

The target sequence disclosed in the specification may be a 10 to 35-nt contiguous sequence, which is adjacent to the 5' end and/or 3' end of a proto-spacer-adjacent motif (PAM) sequence located in the transcriptional regulatory region of a duplicate gene.

The target sequence disclosed in the specification may be a 10 to 35-nt contiguous sequence adjacent to the 5' end and/or 3' end of a PAM sequence located upstream of the transcriptional regulartory region of a duplicate gene.

The target sequence disclosed in the specification may be a 10 to 35-nt contiguous sequence adjacent to the 5' end and/or 3' end of a PAM sequence located downstream of the transcriptional regulartory region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

Here, the transcriptional regulatory region of a duplicate gene may be the promoter, enhancer, silencer, insulator or locus control region (LCR) of a duplicate gene.

The "proto-spacer-adjacent motif (PAM) sequence" is a nucleotide sequence that can be recognized by an editor protein. Here, the PAM sequence may have different nucleotide sequences according to the type of the editor protein and an editor protein-derived species.

Here, the PAM sequence may be, for example, one or more sequences of the following sequences (described in a 5' to 3' direction).

NGG (N is A, T, C or G);

NNNNRYAC (N is each independently A, T, C or G, R is A or G, and Y is C or T);

NNAGAAW (N is each independently A, T, C or G, and W is A or T);

NNNNGATT (N is each independently A, T, C or G);

NNGRR(T) (N is each independently A, T, C or G, and R is A or G); and

TTN (N is A, T, C or G).

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one exemplary embodiment, when the PAM sequence recognized by the editor protein is 5'-NGG-3', 5'-NAG-3' and/or 5'-NGA-3' (N=A, T, G or C; or A, U, G or C), the target sequence may be a 10 to 25-nt contiguous sequence located adjacent to the 5' end and/or 3' end of the 5'-NGG-3', 5'-NAG-3' and/or 5'-NGA-3' (N=A, T, G or C; or A, U, G or C) sequence(s) in the transcriptional regularatory region of a duplicate gene, or upstream or downstream of the transcriptional regularatory region of a duplicate gene. For example, when the duplicate gene is PMP22, the transcriptional regularatory region may be a promoter, and the promoter may be a P1 promoter, a P2 promoter or both of the promoters. Here, when the PAM sequence recognized by the editor protein is 5'-NGG-3', 5'-NAG-3' and/or 5'-NGA-3' (N=A, T, G or C; or A, U, G or C), the target sequence may be a 10 to 25-nt contiguous sequence located adjacent to the 5' end and/or 3' end of the 5'-NGG-3', 5'-NAG-3' and/or 5'-NGA-3' (N=A, T, G or C; or A, U, G or C) sequence in the promoter (a P1 promoter, a P2 promoter or both of the promoters) of a PMP22 gene, or upstream or downstream of the promoter (a P1 promoter, a P2 promoter or both of the promoters) of a PMP22 gene.

In another exemplary embodiment, when the PAM sequence recognized by the editor protein is 5'-NGGNG-3' and/or 5'-NNAGAAW-3' (W=A or T, N=A, T, G or C; or A, U, G or C), the target sequence may be a 10 to 25-nt contiguous sequence located adjacent to the 5' end and/or 3' end of the 5'-NGGNG-3' and/or 5'-NNAGAAW-3' (W=A or T, N=A, T, G or C; or A, U, G or C) sequence in the transcriptional regularatory region of a duplicate gene, or upstream or downstream of the transcriptional regularatory region of a duplicate gene.

In still another exemplary embodiment, when the PAM sequence recognized by the editor protein is 5'-NNNN-GATT-3' and/or 5'-NNNGCTT-3' (N=A, T, G or C; or A, U, G or C), the target sequence may be a 10 to 25-nt contiguous sequence located adjacent to the 5' end and/or 3' end of the 5'-NNNNGATT-3' and/or 5'-NNNGCTT-3' (N=A, T, G or C; or A, U, G or C) sequence in the transcriptional regularatory region of a duplicate gene, upstream or downstream of the transcriptional regularatory region of a duplicate gene.

In one exemplary embodiment, when the PAM sequence recognized by the editor protein is 5'-NNNVRYAC-3' (V=G, C or A; R=A or G, Y=C or T, N=A, T, G or C; or A, U, G or C), the target sequence may be a 10 to 25-nt contiguous sequence located adjacent to the 5' end and/or 3' end of the 5'-NNNVRYAC-3' (V=G, C or A; R=A or G, Y=C or T, N=A, T, G or C; or A, U, G or C) sequence in the transcriptional regulartory region of a duplicate gene, or upstream or downstream of the transcriptional regulartory region of a duplicate gene.

In another exemplary embodiment, when the PAM sequence recognized by the editor protein is 5'-NAAR-3' (R=A or G, N=A, T, G or C; or A, U, G or C), the target sequence may be a 10 to 25-nt contiguous sequence located adjacent to the 5' end and/or 3' end of the 5'-NAAR-3'(R=A or G, N=A, T, G or C; or A, U, G or C) sequence in the transcriptional regularatory region of a duplicate gene, or upstream or downstream of the transcriptional regularatory region of a duplicate gene.

In still another exemplary embodiment, when the PAM sequence recognized by the editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence located adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the transcriptional regulartory region of a duplicate gene, or upstream or downstream of the transcriptional regulartory region of a duplicate gene.

In one exemplary embodiment, when the PAM sequence recognized by the editor protein is 5'-TTN-3' (N=A, T, G or C; or A, U, G or C), the target sequence may be a 10 to 25-nt contiguous sequence located adjacent to the 5' end and/or 3' end of the 5'-TTN-3' (N=A, T, G or C; or A, U, G or C) sequence in the transcriptional regulartory region of a duplicate gene, or upstream or downstream of the transcriptional regulartory region of a duplicate gene.

Hereinafter, examples of target sequences that can be used in an exemplary embodiment disclosed in the specification are listed in Tables 1, 2, 3, 4, 5, 6, 7, 8 and 9. The target sequences disclosed in Tables 1, 2, 3, 4, 5, 6, 7, 8 and 9 are non-guide nucleic acid-binding sequences, and complementary sequences thereof, which are guide nucleic acid-binding sequences, may be predicted from the sequences listed in the tables. In addition, gRNAs shown in Tables 1, 2, 3, 4, 5 and 6 were named Sp for SpCas9 and Cj for CjCas9 according to an editor protein.

TABLE 1

Target sequences of human PMP22 gene for SpCas9

| gRNA | No. | Target (5' to 3') | SEQ ID NO |
|---|---|---|---|
| hPMP22-TATA-Sp#1 | 1 | GGACCAGCCCCTGAATAAAC | SEQ ID NO: 1 |
| hPMP22-TATA-Sp#2 | 2 | GGCGTCTTTCCAGTTTATTC | SEQ ID NO: 2 |
| hPMP22-TATA-Sp#3 | 3 | GCGTCTTTCCAGTTTATTCA | SEQ ID NO: 3 |
| hPMP22-TATA-Sp#4 | 4 | CGTCTTTCCAGTTTATTCAG | SEQ ID NO: 4 |
| hPMP22-TATA-Sp#5 | 5 | TTCAGGGGCTGGTCCAATGC | SEQ ID NO: 5 |
| hPMP22-TATA-Sp#6 | 6 | TCAGGGGCTGGTCCAATGCT | SEQ ID NO: 6 |
| hPMP22-TATA-Sp#7 | 7 | ACCATGACATATCCCAGCAT | SEQ ID NO: 7 |
| hPMP22-TATA-Sp#8 | 8 | TTTCCAGTTTATTCAGGGGC | SEQ ID NO: 8 |

TABLE 1-continued

Target sequences of human PMP22 gene for SpCas9

| gRNA | No. | Target (5' to 3') | SEQ ID NO |
|---|---|---|---|
| hPMP22-TATA-Sp#9 | 9 | CAGTTACAGGGAGCACCACC | SEQ ID NO: 9 |
| hPMP22-TATA-Sp#10 | 10 | CTGGTCTGGCTTCAGTTACA | SEQ ID NO: 10 |
| hPMP22-TATA-Sp#11 | 11 | CCTGGTCTGGCTTCAGTTAC | SEQ ID NO: 11 |
| hPMP22-TATA-Sp#12 | 12 | AACTGGAAAGACGCCTGGTC | SEQ ID NO: 12 |
| hPMP22-TATA-Sp#13 | 13 | GAATAAACTGGAAAGACGCC | SEQ ID NO: 13 |
| hPMP22-TATA-Sp#14 | 14 | TCCAATGCTGGGATATGTCA | SEQ ID NO: 14 |
| hPMP22-TATA-Sp#15 | 15 | AATGCTGGGATATGTCATGG | SEQ ID NO: 15 |
| hPMP22-TATA-Sp#16 | 16 | ATAGAGGCTGAGAACCTCTC | SEQ ID NO: 16 |
| hPMP22-Enh-Sp#1 | 17 | TTGGGCATGTTTGAGCTGGT | SEQ ID NO: 17 |
| hPMP22-Enh-Sp#2 | 18 | TTTGGGCATGTTTGAGCTGG | SEQ ID NO: 18 |
| hPMP22-Enh-Sp#3 | 19 | GAGCTGGTGGGCGAAGCATA | SEQ ID NO: 19 |
| hPMP22-Enh-Sp#4 | 20 | AGCTGGTGGGCGAAGCATAT | SEQ ID NO: 20 |
| hPMP22-Enh-Sp#5 | 21 | TGGGCGAAGCATATGGGCAA | SEQ ID NO: 21 |
| hPMP22-Enh-Sp#6 | 22 | GGCCTCCATCCTAAACAATG | SEQ ID NO: 22 |
| hPMP22-Enh-Sp#10 | 23 | GGGTTGGGAGGTTTGGGCGT | SEQ ID NO: 23 |
| hPMP22-Enh-Sp#11 | 24 | AGGTTTGGGCGTGGGAGTCC | SEQ ID NO: 24 |
| hPMP22-Enh-Sp#12 | 25 | TTCAGAGACTCAGCTATTT | SEQ ID NO: 25 |
| hPMP22-Enh-Sp#13 | 26 | GGCCACATTGTTTAGGATG | SEQ ID NO: 26 |
| hPMP22-Enh-Sp#14 | 27 | GGCTTTGGGCATGTTTGAG | SEQ ID NO: 27 |
| hPMP22-Enh-Sp#15 | 28 | AACATGCCCAAAGCCCAGC | SEQ ID NO: 28 |
| hPMP22-Enh-Sp#16 | 29 | ACATGCCCAAAGCCCAGCG | SEQ ID NO: 29 |
| hPMP22-CDS-Sp#1 | 30 | CGATGATACTCAGCAACAGG | SEQ ID NO: 30 |
| hPMP22-CDS-Sp#3 | 31 | ATGGACACGCAACTGATCTC | SEQ ID NO: 31 |

TABLE 2

Target sequences of human PMP22 gene for CjCas9

| gRNA | No. | Target (5' to 3') | SEQ ID NO |
|---|---|---|---|
| hPMP22-TATA-Cj#1 | 1 | GCCCTCTGAATCTCCAGTCAAT | SEQ ID NO: 32 |
| hPMP22-TATA-Cj#2 | 2 | AATCTCCAGTCAATTCCAACAC | SEQ ID NO: 33 |
| hPMP22-TATA-Cj#3 | 3 | AATTAGGCAATTCTTGTAAAGC | SEQ ID NO: 34 |
| hPMP22-TATA-Cj#4 | 4 | TTAGGCAATTCTTGTAAAGCAT | SEQ ID NO: 35 |
| hPMP22-TATA-Cj#5 | 5 | AAAGCATAGGCACACATCACCC | SEQ ID NO: 36 |
| hPMP22-TATA-Cj#6 | 6 | GCCTGGTCTGGCTTCAGTTACA | SEQ ID NO: 37 |
| hPMP22-TATA-Cj#7 | 7 | GTGTCCAACTTTGTTTGCTTTC | SEQ ID NO: 38 |
| hPMP22-TATA-Cj#8 | 8 | GTATTCTGGAAAGCAAACAAAG | SEQ ID NO: 39 |
| hPMP22-TATA-Cj#9 | 9 | CAGTCTTGGCATCACAGGCTTC | SEQ ID NO: 40 |
| hPMP22-TATA-Cj#10 | 10 | GGACCTCTTGGCTATTACACAG | SEQ ID NO: 41 |

TABLE 2-continued

Target sequences of human PMP22 gene for CjCas9

| gRNA | No. | Target (5' to 3') | SEQ ID NO |
|---|---|---|---|
| hPMP22-TATA-Cj#11 | 11 | GGAGCCAGTGGGACCTCTTGGC | SEQ ID NO: 42 |
| hPMP22-Enh-Cj#1 | 12 | TAAATCACAGAGGCAAAGAGTT | SEQ ID NO: 43 |
| hPMP22-Enh-Cj#2 | 13 | TTGCATAGTGCTAGACTGTTTT | SEQ ID NO: 44 |
| hPMP22-Enh-Cj#3 | 14 | GGGTCATGTGTTTTGAAAACAG | SEQ ID NO: 45 |
| hPMP22-Enh-Cj#4 | 15 | CCCAAACCTCCCAACCCACAAC | SEQ ID NO: 46 |
| hPMP22-Enh-Cj#5 | 16 | ACTCAGCTATTTCTGGAATGAC | SEQ ID NO: 47 |
| hPMP22-Enh-Cj#6 | 17 | TCATCGCCTTTGTGAGCTCCAT | SEQ ID NO: 48 |
| hPMP22-Enh-Cj#7 | 18 | CAGACACAGGCTTTGCTCTAGC | SEQ ID NO: 49 |
| hPMP22-Enh-Cj#8 | 19 | CAAAGCCTGTGTCTGGCCACTA | SEQ ID NO: 50 |
| hPMP22-Enh-Cj#9 | 20 | AGCAGTTTGTGCCCACTAGTGG | SEQ ID NO: 51 |
| hPMP22-Enh-Cj#10 | 21 | ATGTCAAGGTATTCCAGCTAAC | SEQ ID NO: 52 |
| hPMP22-Enh-Cj#11 | 22 | GAATAACTGTATCAAAGTTAGC | SEQ ID NO: 53 |
| hPMP22-Enh-Cj#12 | 23 | TTCCTAATTAAGAGGCTTTGTG | SEQ ID NO: 54 |
| hPMP22-Enh-Cj#13 | 24 | GAGCTAGTTTGTCAGGGTCTAG | SEQ ID NO: 55 |

TABLE 3

Target sequences of human PLP1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-TATA-Sp-01 | 1 | GACTTTGGGAGCTAATATCTAGG | SEQ ID NO: 56 | + | 1 | 0 | 0 | - |
| hPLP1-wMN1-Sp-01 | 2 | CCCTTTCATCTTCCCATTCGTGG | SEQ ID NO: 57 | + | 1 | 0 | 0 | Up |
| hPLP1-wMN1-Sp-02 | 3 | CCTTTCATCTTCCCATTCGTGGG | SEQ ID NO: 58 | + | 1 | 0 | 0 | Up |
| hPLP1-wMN1-Sp-03 | 4 | CCCACGAATGGGAAGATGAAAGG | SEQ ID NO: 59 | - | 1 | 0 | 0 | Up |
| hPLP1-wMN1-Sp-04 | 5 | CATCTTCCCATTCGTGGGCAAGG | SEQ ID NO: 60 | + | 1 | 0 | 0 | Up |
| hPLP1-wMN1-Sp-05 | 6 | TCTCCACCTTGCCCACGAATGGG | SEQ ID NO: 61 | - | 1 | 0 | 0 | Up |
| hPLP1-wMN1-Sp-06 | 7 | GTCTCCACCTTGCCCACGAATGG | SEQ ID NO: 62 | - | 1 | 0 | 0 | Up |
| hPLP1-wMN1-Sp-07 | 8 | CCCAATGCTTGCACATAAATTGG | SEQ ID NO: 63 | + | 1 | 0 | 0 | Up |
| hPLP1-wMN1-Sp-08 | 9 | CCAATTTATGTGCAAGCATTGGG | SEQ ID NO: 64 | - | 1 | 0 | 0 | Up |

TABLE 3-continued

Target sequences of human PLP1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Sp-09 | 10 | TCCAATTTATGTGCAAGCATTGG | SEQ ID NO: 65 | − | 1 | 0 | 0 | Up |
| hPLP1-wMN1-Sp-10 | 11 | TGTGCGCGTCTGAAGAGGAGTGG | SEQ ID NO: 66 | + | 1 | 0 | 0 | Up |
| hPLP1-wMN1-Sp-11 | 12 | GTGCGCGTCTGAAGAGGAGTGGG | SEQ ID NO: 67 | + | 1 | 0 | 0 | Up |
| hPLP1-wMN1-Sp-12 | 13 | TGCGCGTCTGAAGAGGAGTGGGG | SEQ ID NO: 68 | + | 1 | 0 | 0 | Up |
| hPLP1-wMN1-Sp-13 | 14 | TAGTCCAGATGCTGTTGCCGTGG | SEQ ID NO: 69 | + | 1 | 0 | 0 | Up |
| hPLP1-wMN1-Sp-14 | 15 | ATTACCACGGCAACAGCATCTGG | SEQ ID NO: 70 | − | 1 | 0 | 0 | Up |
| hPLP1-wMN1-Sp-15 | 16 | GACACGATTTAGTATTACCACGG | SEQ ID NO: 71 | − | 1 | 0 | 0 | Up |
| hPLP1-wMN1-Sp-16 | 17 | CTAAATCGTGTCCAAAGAGGAGG | SEQ ID NO: 72 | + | 1 | 0 | 0 | Up |
| hPLP1-wMN1-Sp-17 | 18 | AGGAATCTCAGCCTCCTCTTTGG | SEQ ID NO: 73 | − | 1 | 0 | 0 | Up |
| hPLP1-wMN1-Sp-18 | 19 | GTGGACAAGGTTAACTAAAAAGG | SEQ ID NO: 74 | − | 1 | 0 | 0 | Up |
| hPLP1-wMN1-Sp-19 | 20 | ATAGTCAAATCATGTGGACAAGG | SEQ ID NO: 75 | − | 1 | 0 | 0 | Up |
| hPLP1-wMN1-Sp-20 | 21 | TGCTGGATAGTCAAATCATGTGG | SEQ ID NO: 76 | − | 1 | 0 | 0 | Up |
| hPLP1-wMN1-Sp-21 | 22 | ACATGATTTGACTATCCAGCAGG | SEQ ID NO: 77 | + | 1 | 0 | 0 | Up |
| hPLP1-wMN1-Sp-22 | 23 | ATTTGACTATCCAGCAGGCTTGG | SEQ ID NO: 78 | + | 1 | 0 | 0 | Up |
| hPLP1-wMN1-Sp-23 | 24 | GTCCCGAAGTCTCTGGGGCCTGG | SEQ ID NO: 79 | − | 1 | 0 | 0 | Up |
| hPLP1-wMN1-Sp-24 | 25 | AAAACAGTCCCGAAGTCTCTGGG | SEQ ID NO: 80 | − | 1 | 0 | 0 | Up |
| hPLP1-wMN1-Sp-25 | 26 | GAAAACAGTGCCGAAGTCTCTGG | SEQ ID NO: 81 | − | 1 | 0 | 0 | Up |
| hPLP1-wMN1-Sp-26 | 27 | TATATACCACATTCAAGTGCTGG | SEQ ID NO: 82 | − | 1 | 0 | 0 | Up |

TABLE 3-continued

Target sequences of human PLP1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Sp-27 | 28 | TGGATATAACGAAGTTGTGTGGG | SEQ ID NO: 83 | - | 1 | 0 | 0 | Down |
| hPLP1-wMN1-Sp-28 | 29 | ATGGATATAACGAAGTTGTGTGG | SEQ ID NO: 84 | - | 1 | 0 | 0 | Down |
| hPLP1-wMN1-Sp-29 | 30 | ATATGTTTGTTCACCCCAACAGG | SEQ ID NO: 85 | + | 1 | 0 | 0 | Down |
| hPLP1-wMN1-Sp-30 | 31 | GAAAACTTGAAATCCTGTTGGGG | SEQ ID NO: 86 | - | 1 | 0 | 0 | Down |
| hPLP1-wMN1-Sp-31 | 32 | TAGACATTAGGAGAAACAGAAGG | SEQ ID NO: 87 | - | 1 | 0 | 0 | Down |
| hPLP1-wMN1-Sp-32 | 33 | CTAGCAGTGACATAGACATTAGG | SEQ ID NO: 88 | - | 1 | 0 | 0 | Down |
| hPLP1-wMN1-Sp-33 | 34 | AGCCACCTGACTTTGATGAAAGG | SEQ ID NO: 89 | - | 1 | 0 | 0 | Down |
| hPLP1-wMN1-Sp-34 | 35 | TGAGAAATGTTATTACTATATGG | SEQ ID NO: 90 | + | 1 | 0 | 0 | Down |
| hPLP1-wMN1-Sp-35 | 36 | AGACTGCGAGATGAGAGAGTTGG | SEQ ID NO: 91 | - | 1 | 0 | 0 | Down |
| hPLP1-wMN1-Sp-36 | 37 | CTCGCAGTCTGTACTTAGACTGG | SEQ ID NO: 92 | + | 1 | 0 | 0 | Down |
| hPLP1-wMN1-Sp-37 | 38 | AATGTCTCTTGAGAGAGCCAAGG | SEQ ID NO: 93 | + | 1 | 0 | 0 | Down |

TABLE 4

Target sequences of human PLP1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Cj-01 | 1 | ATGGAAGATGAAAGGGAAGTAACTGGTAC | SEQ ID NO: 94 | - | 1 | 0 | 0 | Up |
| hPLP1-wMN1-Cj-02 | 2 | ACTTTGATTGTTAAAACTTATCCTTGGCAC | SEQ ID NO: 95 | - | 1 | 0 | 0 | Up |
| hPLP1-wMN1-Cj-03 | 3 | AGTCCTACCTCAGCTTCCCAATGCTTGCAC | SEQ ID NO: 96 | + | 1 | 0 | 0 | Up |
| hPLP1-wMN1-Cj-04 | 4 | CAATGCTTGCACATAAATTGGAATGTGTAC | SEQ ID NO: 97 | + | 1 | 0 | 0 | Up |
| hPLP1-wMN1-Cj-05 | 5 | ACACAGAGAGAGACAGAATGAATGATGTAC | SEQ ID NO: 98 | - | 1 | 0 | 0 | Up |

TABLE 4-continued

Target sequences of human PLP1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| hPLP1-wMN1-Cj-06 | 6 | TCCTCTTCAGACGCGCACACACACACAC | SEQ ID NO: 99 | - | 1 | 0 | 0 | Up |
| hPLP1-wMN1-Cj-07 | 7 | ACTCCTCTTCAGACGCGCACACACACAC | SEQ ID NO: 100 | - | 1 | 0 | 0 | Up |
| hPLP1-wMN1-Cj-08 | 8 | CCACTCCTCTTCAGACGCGCACACACAC | SEQ ID NO: 101 | - | 1 | 0 | 0 | Up |
| hPLP1-wMN1-Cj-09 | 9 | CCCCACTCCTCTTCAGACGCGCACACAC | SEQ ID NO: 102 | - | 1 | 0 | 0 | Up |
| hPLP1-wMN1-Cj-10 | 10 | CTCCCCACTCCTCTTCAGACGCGCACAC | SEQ ID NO: 103 | - | 1 | 0 | 0 | Up |
| hPLP1-wMN1-Cj-11 | 11 | TACTCCCCACTCCTCTTCAGACGCGCAC | SEQ ID NO: 104 | - | 1 | 0 | 0 | Up |
| hPLP1-wMN1-Cj-12 | 12 | TATACTCCCCACTCCTCTTCAGACGCGCAC | SEQ ID NO: 105 | - | 1 | 0 | 0 | Up |
| hPLP1-wMN1-Cj-13 | 13 | ACAGCATCTGGACTATCTTGTTTCCTATAC | SEQ ID NO: 106 | - | 1 | 0 | 0 | Up |
| hPLP1-wMN1-Cj-14 | 14 | ATAGTCCAGATGCTGTTGCCGTGGTAATAC | SEQ ID NO: 107 | + | 1 | 0 | 0 | Up |
| hPLP1-wMN1-Cj-15 | 15 | AAAAGGAATCTCAGCCTCCTCTTTGGACAC | SEQ ID NO: 108 | - | 1 | 0 | 0 | Up |
| hPLP1-wMN1-Cj-16 | 16 | TGTCACTGCTAGTGTGCTTAATTCTTGTAC | SEQ ID NO: 109 | + | 1 | 0 | 0 | Down |
| hPLP1-wMN1-Cj-17 | 17 | ATGTGAATTCAGTACAAGAATTAAGCACAC | SEQ ID NO: 110 | - | 1 | 0 | 0 | Down |
| hPLP1-wMN1-Cj-18 | 18 | TTATGTGAATTCAGTACAAGAATTAAGCAC | SEQ ID NO: 111 | - | 1 | 0 | 0 | Down |
| hPLP1-wMN1-Cj-19 | 19 | CTTTCATTTCTGTTTATGTGAATTCAGTAC | SEQ ID NO: 112 | - | 1 | 0 | 0 | Down |
| hPLP1-wMN1-Cj-20 | 20 | TTCACATAAACAGAAATGAAAGAAAAACAC | SEQ ID NO: 113 | + | 1 | 0 | 0 | Down |
| hPLP1-wMN1-Cj-21 | 21 | ATGCCAACTCTCTCATCTCGCAGTCTGTAC | SEQ ID NO: 114 | + | 1 | 0 | 0 | Down |
| hPLP1-wMN1-Cj-22 | 22 | GAGACATTCTCACATTTCCAGTCTAAGTAC | SEQ ID NO: 115 | - | 1 | 0 | 0 | Down |

TABLE 5

Target sequences of mouse Plp1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-TATA-Sp-01 | 1 | TGTTTGGTAGTATAGTAAGTAGG | SEQ ID NO: 116 | + | 1 | 0 | 1 | — |
| mPlp1-wMN1-Sp-01 | 2 | GGTCTAGAAAAGATCAAGCCAGG | SEQ ID NO: 117 | + | 1 | 0 | 0 | Up |
| mPlp1-wMN1-Sp-02 | 3 | GCCAGGACTGTGACCTGATAAGG | SEQ ID NO: 118 | + | 1 | 0 | 0 | Up |
| mPlp1-wMN1-Sp-03 | 4 | TCACCTTCACACTTTAACCAAGG | SEQ ID NO: 119 | + | 1 | 0 | 0 | Up |
| mPlp1-wMN1-Sp-04 | 5 | CAAGGTTGAGACAATGTTCCAGG | SEQ ID NO: 120 | + | 1 | 0 | 0 | Up |
| mPlp1-wMN1-Sp-05 | 6 | CCAATTCATGTGCAAACATTTGG | SEQ ID NO: 121 | − | 1 | 0 | 0 | Up |
| mPlp1-wMN1-Sp-06 | 7 | CATCACAGTTTATACTTAGCTGG | SEQ ID NO: 122 | + | 1 | 0 | 0 | Down |
| mPlp1-wMN1-Sp-07 | 8 | ATCACAGTTTATACTTAGCTGGG | SEQ ID NO: 123 | + | 1 | 0 | 0 | Down |
| mPlp1-wMN1-Sp-08 | 9 | GGAATACCTCAGGCTCAACAGG | SEQ ID NO: 124 | − | 1 | 0 | 0 | Down |
| mPlp1-wMN1-Sp-09 | 10 | TCTCTGTTTCGGAATACCTCAGG | SEQ ID NO: 125 | − | 1 | 0 | 0 | Down |
| mPlp1-wMN1-Sp-10 | 11 | CTGTCGACTACTTTGATGAAAGG | SEQ ID NO: 126 | + | 1 | 0 | 0 | Down |
| mPlp1-wMN1-Sp-11 | 12 | TGAACCAAGATGATTATTTGTGG | SEQ ID NO: 127 | − | 1 | 0 | 1 | Up |
| mPlp1-wMN1-Sp-12 | 13 | ATCTTGGTTCATAGAAATTTGGG | SEQ ID NO: 128 | + | 1 | 0 | 1 | Up |
| mPlp1-wMN1-Sp-13 | 14 | AGCCTTGCATGGCAGAGCTTGG | SEQ ID NO: 129 | − | 1 | 0 | 1 | Up |
| mPlp1-wMN1-Sp-14 | 15 | ACACTTTAACCAAGGAAAGAGGG | SEQ ID NO: 130 | + | 1 | 0 | 1 | Up |
| mPlp1-wMN1-Sp-15 | 16 | TACCAGATCCCCTCTTTCCTTGG | SEQ ID NO: 131 | − | 1 | 0 | 1 | Up |
| mPlp1-wMN1-Sp-16 | 17 | CATTTGGAGGCCAAAATACAAGG | SEQ ID NO: 132 | − | 1 | 0 | 1 | Up |
| mPlp1-wMN1-Sp-17 | 18 | CCAAATGTTTGCACATGAATTGG | SEQ ID NO: 133 | + | 1 | 0 | 1 | Up |
| mPlp1-wMN1-Sp-18 | 19 | AGTCCAGATGCTGTCCCTGAAGG | SEQ ID NO: 134 | + | 1 | 0 | 1 | Up |

TABLE 5-continued

Target sequences of mouse Plp1 gene for SpCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-wMN1-Sp-19 | 20 | CGCAAGCCATTCAAACACAAAG | SEQ ID NO: 135 | + | 1 | 0 | 1 | Down |
| mPlp1-wMN1-Sp-20 | 21 | TCAAACCCTGTTGAGCCTGAGG | SEQ ID NO: 136 | + | 1 | 0 | 1 | Down |
| mPlp1-wMN1-Sp-21 | 22 | CGGAATACCTCAGGCTCAACAG | SEQ ID NO: 137 | - | 1 | 0 | 1 | Down |
| mPlp1-wMN1-Sp-22 | 23 | GTCAAAATGTGAATTCTAACAGG | SEQ ID NO: 138 | - | 1 | 0 | 1 | Down |
| mPlp1-wMN1-Sp-23 | 24 | TTATCTATTCTATTAGAGCTCGG | SEQ ID NO: 139 | - | 1 | 0 | 0 | Down |
| mPlp1-wMN1-Sp-24 | 25 | ATCAAGTAATGAAATGGACAAGG | SEQ ID NO: 140 | - | 1 | 0 | 1 | Down |
| mPlp1-wMN1-Sp-25 | 26 | CTCCCACTGCCTTATTAGCAG | SEQ ID NO: 141 | - | 1 | 0 | 0 | Up |
| mPlp1-wMN1-Sp-26 | 27 | AGAGCTCAAATGGGTTCTAAAG | SEQ ID NO: 142 | - | 1 | 0 | 0 | Up |
| mPlp1-wMN1-Sp-27 | 28 | ACCACATTCAAGAGCTCAAATG | SEQ ID NO: 143 | - | 1 | 0 | 0 | Up |
| mPlp1-wMN1-Sp-28 | 29 | TTACAGATTGGTTACACTTGGGG | SEQ ID NO: 144 | + | 1 | 0 | 0 | Down |
| mPlp1-wMN1-Sp-29 | 30 | ATCACTGCTGCTACTACTTATGG | SEQ ID NO: 145 | - | 1 | 0 | 0 | Up |
| mPlp1-wMN1-Sp-30 | 31 | ATACCTGCCTAATAAGGCAGTGG | SEQ ID NO: 146 | + | 1 | 0 | 0 | Up |
| mPlp1-wMN1-Sp-31 | 32 | GATCAGGAGAGTCAGTGGGATG | SEQ ID NO: 147 | + | 1 | 0 | 1 | Down |
| mPlp1-wMN1-Sp-32 | 33 | CTATTGTGAGTCTCAGATTAAGG | SEQ ID NO: 148 | - | 1 | 0 | 1 | Down |
| mPlp1-wMN1-Sp-33 | 34 | TATTACAGATTGGTTACACTTGG | SEQ ID NO: 149 | + | 1 | 0 | 1 | Down |
| mPlp1-wMN1-Sp-34 | 35 | ATTACAGATTGGTTACACTTGGG | SEQ ID NO: 150 | + | 1 | 0 | 1 | Down |
| mPlp1-wMN1-Sp-35 | 36 | TACAGATTGGTTACACTTGGGGG | SEQ ID NO: 151 | + | 1 | 0 | 1 | Down |
| mPlp1-wMN1-Sp-36 | 37 | ACAGATTGGTTACACTTGGGGGG | SEQ ID NO: 152 | + | 1 | 0 | 1 | Down |

TABLE 6

Target sequences of mouse Plp1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-TATA-Cj-01 | 1 | CTACTTACTATACTACCAAACACACCGCAC | SEQ ID NO: 153 | - | 1 | 0 | 0 | — |
| mPlp1-TATA-Cj-02 | 2 | AAAGCCTACTTACTATACTACCAAACACAC | SEQ ID NO: 154 | - | 1 | 0 | 0 | — |
| mPlp1-TATA-Cj-03 | 3 | CAAAGCCTACTTACTATACTACCAAACAC | SEQ ID NO: 155 | - | 1 | 0 | 0 | — |
| mPlp1-TATA-Cj-04 | 4 | GGGTCTGAATCAAAAGCCTACTTACTATAC | SEQ ID NO: 156 | - | 1 | 0 | 0 | — |
| mPlp1-wMN1-Cj-01 | 5 | AGAGTGGGATTCTACAAGTCACCTTCACAC | SEQ ID NO: 157 | + | 1 | 0 | 0 | Up |
| mPlp1-wMN1-Cj-02 | 6 | GGAAAGAGGGGATCTGGTAGCATAAAGTAC | SEQ ID NO: 158 | + | 1 | 0 | 0 | Up |
| mPlp1-wMN1-Cj-03 | 7 | GGGATCTGGTAGCATAAAGTACAGCTACAC | SEQ ID NO: 159 | + | 1 | 0 | 0 | Up |
| mPlp1-wMN1-Cj-04 | 8 | ATCTGTCACTAGCGACAAGTGTAGCTGTAC | SEQ ID NO: 160 | - | 1 | 0 | 0 | Up |
| mPlp1-wMN1-Cj-05 | 9 | TCATGTGCAAACATTTGGAGGCCAAAATAC | SEQ ID NO: 161 | - | 1 | 0 | 0 | Up |
| mPlp1-wMN1-Cj-06 | 10 | GACATACAGAGAGGGGCGGAGAGAAATAC | SEQ ID NO: 162 | - | 1 | 0 | 0 | Up |
| mPlp1-wMN1-Cj-07 | 11 | ATACTGACGCCATCACATCACAGTTTATAC | SEQ ID NO: 163 | + | 1 | 0 | 0 | Down |
| mPlp1-wMN1-Cj-08 | 12 | TAAAACTATAAGCTCTCTGTTTCGGAATAC | SEQ ID NO: 164 | - | 1 | 0 | 0 | Down |
| mPlp1-wMN1-Cj-09 | 13 | TCATCAAAGTAGTCGACAGTCAAAGCATAC | SEQ ID NO: 165 | - | 1 | 0 | 0 | Down |
| mPlp1-wMN1-Cj-10 | 14 | TGAATTCTAACAGGAAAACTCAGAACATAC | SEQ ID NO: 166 | - | 1 | 0 | 0 | Down |
| mPlp1-wMN1-Cj-11 | 15 | ACTGCTGCTACTACTTATGGTGACTAGTAC | SEQ ID NO: 167 | - | 1 | 0 | 0 | Up |
| mPlp1-wMN1-Cj-12 | 16 | AGTCACCATAAGTAGTAGCAGAGTGATAC | SEQ ID NO: 168 | + | 1 | 0 | 0 | Up |
| mPlp1-wMN1-Cj-13 | 17 | CATAAGTAGTAGCAGCAGTGATACTAATAC | SEQ ID NO: 169 | + | 1 | 0 | 0 | Up |
| mPlp1-wMN1-Cj-14 | 18 | TTGAATGGCTTGCGAACAAAGATTAAACAC | SEQ ID NO: 170 | - | 1 | 0 | 0 | Down |
| mPlp1-wMN1-Cj-15 | 19 | TTAATCTTTGTTCGCAAGCCATTCAAACAC | SEQ ID NO: 171 | + | 1 | 0 | 0 | Down |

TABLE 6-continued

Target sequences of mouse Plp1 gene for CjCas9

| sgRNA | No. | Target with PAM (5' to 3') | SEQ ID NO | Direction | Mismatch 0 | Mismatch 1 | Mismatch 2 | location |
|---|---|---|---|---|---|---|---|---|
| mPlp1-wMN1-Cj-16 | 20 | TTGCTGCATCTCTAACGTGAACTCTAACAC | SEQ ID NO: 172 | - | 1 | 0 | 0 | Down |
| mPlp1-wMN1-Cj-17 | 21 | TTCACGTTAGAGATGCAGCAAAGTCTATAC | SEQ ID NO: 173 | + | 1 | 0 | 0 | Down |
| mPlp1-wMN1-Cj-18 | 22 | TGGAAGCAACTCTAAATCACCACCCGATAC | SEQ ID NO: 174 | - | 1 | 0 | 0 | Down |
| mPlp1-wMN1-Cj-19 | 23 | TTCCAAAGTTCTGTCACCCAGTAAAAACAC | SEQ ID NO: 175 | + | 1 | 0 | 0 | Down |
| mPlp1-wMN1-Cj-20 | 24 | TTCAAGAGCTCAAATGGGTTCTAAAGGCAC | SEQ ID NO: 176 | - | 1 | 0 | 0 | Up |
| mPlp1-wMN1-Cj-21 | 25 | TTGAATGTGGTATAAGTGCTAATATCATAC | SEQ ID NO: 177 | + | 1 | 0 | 0 | Up |
| mPlp1-wMN1-Cj-22 | 26 | GTATAAGTGCTAATATCATACAGGAAACAC | SEQ ID NO: 178 | + | 1 | 0 | 0 | Up |
| mPlp1-wMN1-Cj-23 | 27 | GTGTTTCCTGTATGATATTAGCACTTATAC | SEQ ID NO: 179 | - | 1 | 0 | 0 | Up |
| mPlp1-wMN1-Cj-24 | 28 | GACTTTGTGTTTCCTGTATGATATTAGCAC | SEQ ID NO: 180 | - | 1 | 0 | 0 | Up |
| mPlp1-wMN1-Cj-25 | 29 | AAAACAATTATCAGGCAGTGACAGAGACAC | SEQ ID NO: 181 | - | 1 | 0 | 0 | Down |
| mPlp1-wMN1-Cj-26 | 30 | CCAAGATACTAGAGTAGCTGTGACTGGCAC | SEQ ID NO: 182 | - | 1 | 0 | 0 | Down |
| mPlp1-wMN1-Cj-27 | 31 | GGCCTATAGCCATTCAAATGGCCAAGATAC | SEQ ID NO: 183 | - | 1 | 0 | 0 | Down |
| mPlp1-wMN1-Cj-28 | 32 | GTCCCATCTCCCTAAGTCTCGAATCTGCAC | SEQ ID NO: 184 | - | 1 | 0 | 0 | Down |

TABLE 7

Target sequences of human P1 promoter for SpCas9

| No. | Target with PAM (5' to 3') | SEQ ID NO | Mismatch 0 | Mismatch 1 | Mismatch 2 |
|---|---|---|---|---|---|
| 1 | AGTTACAGGGAGCACCACCAGGG | SEQ ID NO: 330 | 1 | 0 | 0 |
| 2 | CAGTTACAGGGAGCACCACCAGG | SEQ ID NO: 331 | 1 | 0 | 0 |
| 3 | CTGGTCTGGCTTCAGTTACAGGG | SEQ ID NO: 332 | 1 | 0 | 0 |
| 4 | CCTGGTCTGGCTTCAGTTACAGG | SEQ ID NO: 333 | 1 | 0 | 0 |

TABLE 7-continued

Target sequences of human P1 promoter for SpCas9

| No. | Target with PAM (5' to 3') | SEQ ID NO | Mismatch 0 | Mismatch 1 | Mismatch 2 |
|---|---|---|---|---|---|
| 5 | CCTGGTCTGGCTTCAGTTACAGG | SEQ ID NO: 334 | 1 | 0 | 0 |
| 6 | TCTGCAGAATTCACTGGGAGGGG | SEQ ID NO: 335 | 1 | 0 | 0 |
| 7 | CTCTGCAGAATTCACTGGGAGGG | SEQ ID NO: 336 | 1 | 0 | 0 |
| 8 | TCTCTGCAGAATTCACTGGGAGG | SEQ ID NO: 337 | 1 | 0 | 0 |
| 9 | TAATCTCTGCAGAATTCACTGGG | SEQ ID NO: 338 | 1 | 0 | 0 |
| 10 | TTAATCTCTGCAGAATTCACTGG | SEQ ID NO: 339 | 1 | 0 | 0 |

TABLE 8

Target sequences of human P1 promoter for CjCas9

| No. | Target with PAM (5' to 3') | SEQ ID NO | Mismatch 0 | Mismatch 1 | Mismatch 2 |
|---|---|---|---|---|---|
| 1 | GCCTGGTCTGGCTTCAGTTACAGGGAGCAC | SEQ ID NO: 340 | 1 | 0 | 0 |
| 2 | GTGTCCAACTTTGTTTGCTTTCCAGAATAC | SEQ ID NO: 341 | 1 | 0 | 0 |
| 3 | GTATTCTGGAAAGCAAACAAAGTTGGACAC | SEQ ID NO: 342 | 1 | 0 | 0 |
| 4 | CAGTCTTGGCATCACAGGCTTCAGGCATAC | SEQ ID NO: 343 | 1 | 0 | 0 |
| 5 | GGACCTCTTGGCTATTACACAGGTTGGCAC | SEQ ID NO: 344 | 1 | 0 | 0 |
| 6 | GGAGCCAGTGGGACCTCTTGGCTATTACAC | SEQ ID NO: 345 | 1 | 0 | 0 |
| 7 | CCCAGTGAATTCTGCAGAGATTAAATATAC | SEQ ID NO: 346 | 1 | 0 | 0 |
| 8 | GGAAGGATCTGTGTCTACAGTGTTACATAC | SEQ ID NO: 347 | 1 | 0 | 0 |
| 9 | TTACCTGCACGTATGTAACACTGTAGACAC | SEQ ID NO: 348 | 1 | 0 | 0 |
| 10 | AAATAAAACTTACCTGCACGTATGTAACAC | SEQ ID NO: 349 | 1 | 0 | 0 |
| 11 | AAGTTTATTTAAAATAAAACTTACCTGCAC | SEQ ID NO: 350 | 1 | 0 | 0 |
| 12 | AAAGCATAGGCACACATCACCCAGAGGCAC | SEQ ID NO: 351 | 1 | 0 | 0 |
| 13 | TTAGGCAATTCTTGTAAAGCATAGGCACAC | SEQ ID NO: 352 | 1 | 0 | 0 |
| 14 | AATTAGGCAATTCTTGTAAAGCATAGGCAC | SEQ ID NO: 353 | 1 | 0 | 0 |
| 15 | AATCTCCAGTCAATTCCAACACAAATGCAC | SEQ ID NO: 354 | 1 | 0 | 0 |

TABLE 8-continued

Target sequences of human P1 promoter for CjCas9

| No. | Target with PAM (5' to 3') | SEQ ID NO | Mismatch 0 | Mismatch 1 | Mismatch 2 |
|---|---|---|---|---|---|
| 16 | GCCCTCTGAATCTCCAGT CAATTCCAACAC | SEQ ID NO: 355 | 1 | 0 | 0 |
| 17 | TATATCCTTGGTTAAAAGG TGGATATATAC | SEQ ID NO: 356 | 1 | 0 | 0 |

TABLE 9

Target sequences of mouse P1 promoter for CjCas9

| No. | Target with PAM (5' to 3') | SEQ ID NO | Mismatch 0 | Mismatch 1 | Mismatch 2 |
|---|---|---|---|---|---|
| 1 | CTCTTGGGATCACTCTAT CCTGGAAGATAC | SEQ ID NO: 357 | 1 | 0 | 0 |
| 2 | CTTGGGATCACTCTATCC TGGAAGATACAC | SEQ ID NO: 358 | 1 | 0 | 0 |
| 3 | TCTATCCTGGAAGATACA CAAGCTGGACAC | SEQ ID NO: 359 | 1 | 0 | 0 |
| 4 | GAGACATCCAAGTGGAG GAAGGGGTTACAC | SEQ ID NO: 360 | 1 | 0 | 0 |
| 5 | CTCTATAAAGCACACCCT ACCCAGAGATAC | SEQ ID NO: 361 | 1 | 0 | 0 |
| 6 | ACAAAAACTGAGCCACTC TATAAAGCACAC | SEQ ID NO: 362 | 1 | 0 | 0 |
| 7 | GGACAAAAACTGAGCCAC TCTATAAAGCAC | SEQ ID NO: 363 | 1 | 0 | 0 |

Hereinafter, examples of guide sequences that can be used in an exemplary embodiment disclosed in the specification are listed in Tables 10, 11, 12, 13, 14 and 15. In addition, gRNAs shown in Tables 10, 11, 12, 13, 14 and 15 were named Sp for SpCas9 and Cj for CjCas9 according to an editor protein.

TABLE 10

Guide sequences of gRNA for targeting human PMP22 gene

| gRNA | Guide Sequence (5' to 3') | SEQ ID NO |
|---|---|---|
| hPMP22-TATA-Sp#1 | GGACCAGCCCCUGAAUAAAC | SEQ ID NO: 440 |
| hPMP22-TATA-Sp#2 | GGCGUCUUUCCAGUUUAUUC | SEQ ID NO: 441 |
| hPMP22-TATA-Sp#3 | GCGUCUUUCCAGUUUAUUCA | SEQ ID NO: 442 |
| hPMP22-TATA-Sp#4 | CGUCUUUCCAGUUUAUUCAG | SEQ ID NO: 443 |
| hPMP22-TATA-Sp#5 | UUCAGGGGCUGGUCCAAUGC | SEQ ID NO: 444 |
| hPMP22-TATA-Sp#6 | UCAGGGGCUGGUCCAAUGCU | SEQ ID NO: 445 |
| hPMP22-TATA-Sp#7 | ACCAUGACAUAUCCCAGCAU | SEQ ID NO: 446 |
| hPMP22-TATA-Sp#8 | UUUCCAGUUUAUUCAGGGGC | SEQ ID NO: 447 |
| hPMP22-TATA-Sp#9 | CAGUUACAGGGAGCACCACC | SEQ ID NO: 448 |
| hPMP22-TATA-Sp#10 | CUGGUCUGGCUUCAGUUACA | SEQ ID NO: 449 |
| hPMP22-TATA-Sp#11 | CCUGGUCUGGCUUCAGUUAC | SEQ ID NO: 450 |
| hPMP22-TATA-Sp#12 | AACUGGAAAGACGCCUGGUC | SEQ ID NO: 451 |

TABLE 10-continued

Guide sequences of gRNA for targeting human PMP22 gene

| gRNA | Guide Sequence (5' to 3') | SEQ ID NO |
|---|---|---|
| hPMP22-TATA-Sp#13 | GAAUAAACUGGAAAGACGCC | SEQ ID NO: 452 |
| hPMP22-TATA-Sp#14 | UCCAAUGCUGGGAUAUGUCA | SEQ ID NO: 453 |
| hPMP22-TATA-Sp#15 | AAUGCUGGGAUAUGUCAUGG | SEQ ID NO: 454 |
| hPMP22-TATA-Sp#16 | AUAGAGGCUGAGAACCUCUC | SEQ ID NO: 455 |
| hPMP22-Enh-Sp#1 | UUGGGCAUGUUUGAGCUGGU | SEQ ID NO: 456 |
| hPMP22-Enh-Sp#2 | UUUGGGCAUGUUUGAGCUGG | SEQ ID NO: 457 |
| hPMP22-Enh-Sp#3 | GAGCUGGUGGGCGAAGCAUA | SEQ ID NO: 458 |
| hPMP22-Enh-Sp#4 | AGCUGGUGGGCGAAGCAUAU | SEQ ID NO: 459 |
| hPMP22-Enh-Sp#5 | UGGGCGAAGCAUAUGGGCAA | SEQ ID NO: 460 |
| hPMP22-Enh-Sp#6 | GGCCUCCAUCCUAAACAAUG | SEQ ID NO: 461 |
| hPMP22-Enh-Sp#10 | GGGUUGGGAGGUUUGGGCGU | SEQ ID NO: 462 |
| hPMP22-Enh-Sp#11 | AGGUUUGGGCGUGGGAGUCC | SEQ ID NO: 463 |
| hPMP22-Enh-Sp#12 | UUCAGAGACUCAGCUAUUU | SEQ ID NO: 464 |
| hPMP22-Enh-Sp#13 | GGCCACAUUGUUUAGGAUG | SEQ ID NO: 465 |
| hPMP22-Enh-Sp#14 | GGCUUUGGGCAUGUUUGAG | SEQ ID NO: 466 |
| hPMP22-Enh-Sp#15 | AACAUGCCCAAAGCCCAGC | SEQ ID NO: 467 |
| hPMP22-Enh-Sp#16 | ACAUGCCCAAAGCCCAGCG | SEQ ID NO: 468 |
| hPMP22-CDS-Sp#1 | CGAUGAUACUCAGCAACAGG | SEQ ID NO: 469 |
| hPMP22-CDS-Sp#3 | AUGGACACGCAACUGAUCUC | SEQ ID NO: 470 |

TABLE 11

Guide sequences of gRNA for targeting human PMP22 gene

| gRNA | Guide Sequence (5' to 3') | SEQ ID NO |
|---|---|---|
| hPMP22-TATA-Cj#1 | GCCCUCUGAAUCUCCAGUCAAU | SEQ ID NO: 471 |
| hPMP22-TATA-Cj#2 | AAUCUCCAGUCAAUUCCAACAC | SEQ ID NO: 472 |
| hPMP22-TATA-Cj#3 | AAUUAGGCAAUUCUUGUAAAGC | SEQ ID NO: 473 |
| hPMP22-TATA-Cj#4 | UUAGGCAAUUCUUGUAAAGCAU | SEQ ID NO: 474 |
| hPMP22-TATA-Cj#5 | AAAGCAUAGGCACACAUCACCC | SEQ ID NO: 475 |
| hPMP22-TATA-Cj#6 | GCCUGGUCUGGCUUCAGUUACA | SEQ ID NO: 476 |
| hPMP22-TATA-Cj#7 | GUGUCCAACUUUGUUUGCUUUC | SEQ ID NO: 477 |
| hPMP22-TATA-Cj#8 | GUAUUCUGGAAAGCAAACAAAG | SEQ ID NO: 478 |
| hPMP22-TATA-Cj#9 | CAGUCUUGGCAUCACAGGCUUC | SEQ ID NO: 479 |
| hPMP22-TATA-Cj#10 | GGACCUCUUGGCUAUUACACAG | SEQ ID NO: 480 |
| hPMP22-TATA-Cj#11 | GGAGCCAGUGGGACCUCUUGGC | SEQ ID NO: 481 |
| hPMP22-Enh-Cj#1 | UAAAUCACAGAGGCAAAGAGUU | SEQ ID NO: 482 |
| hPMP22-Enh-Cj#2 | UUGCAUAGUGCUAGACUGUUUU | SEQ ID NO: 483 |
| hPMP22-Enh-Cj#3 | GGGUCAUGUGUUUUGAAAACAG | SEQ ID NO: 484 |

TABLE 11-continued

Guide sequences of gRNA for targeting human PMP22 gene

| gRNA | Guide Sequence (5' to 3') | SEQ ID NO |
|---|---|---|
| hPMP22-Enh-Cj#4 | CCCAAACCUCCCAACCCACAAC | SEQ ID NO: 485 |
| hPMP22-Enh-Cj#5 | ACUCAGCUAUUUCUGGAAUGAC | SEQ ID NO: 486 |
| hPMP22-Enh-Cj#6 | UCAUCGCCUUUGUGAGCUCCAU | SEQ ID NO: 487 |
| hPMP22-Enh-Cj#7 | CAGACACAGGCUUUGCUCUAGC | SEQ ID NO: 488 |
| hPMP22-Enh-Cj#8 | CAAAGCCUGUGUCUGGCCACUA | SEQ ID NO: 489 |
| hPMP22-Enh-Cj#9 | AGCAGUUUGUGCCCACUAGUGG | SEQ ID NO: 490 |
| hPMP22-Enh-Cj#10 | AUGUCAAGGUAUUCCAGCUAAC | SEQ ID NO: 491 |
| hPMP22-Enh-Cj#11 | GAAUAACUGUAUCAAAGUUAGC | SEQ ID NO: 492 |
| hPMP22-Enh-Cj#12 | UUCCUAAUUAAGAGGCUUUGUG | SEQ ID NO: 493 |
| hPMP22-Enh-Cj#13 | GAGCUAGUUUGUCAGGGUCUAG | SEQ ID NO: 494 |

TABLE 12

Guide sequences of gRNA for targeting human PLP1 gene

| gRNA | Guide Sequence (5' to 3') | SEQ ID NO |
|---|---|---|
| hPLP1-TATA-Sp-01 | GACUUUGGGAGCUAAUAUCU | SEQ ID NO: 495 |
| hPLP1-wMN1-Sp-01 | CCCUUUCAUCUUCCCAUUCG | SEQ ID NO: 496 |
| hPLP1-wMN1-Sp-02 | CCUUUCAUCUUCCCAUUCGU | SEQ ID NO: 497 |
| hPLP1-wMN1-Sp-03 | CCCACGAAUGGGAAGAUGAA | SEQ ID NO: 498 |
| hPLP1-wMN1-Sp-04 | CAUCUUCCCAUUCGUGGGCA | SEQ ID NO: 499 |
| hPLP1-wMN1-Sp-05 | UCUCCACCUUGCCCACGAAU | SEQ ID NO: 500 |
| hPLP1-wMN1-Sp-06 | GUCUCCACCUUGCCCACGAA | SEQ ID NO: 501 |
| hPLP1-wMN1-Sp-07 | CCCAAUGCUUGCACAUAAAU | SEQ ID NO: 502 |
| hPLP1-wMN1-Sp-08 | CCAAUUUAUGUGCAAGCAUU | SEQ ID NO: 503 |
| hPLP1-wMN1-Sp-09 | UCCAAUUUAUGUGCAAGCAU | SEQ ID NO: 504 |
| hPLP1-wMN1-Sp-10 | UGUGCGCGUCUGAAGAGGAG | SEQ ID NO: 505 |
| hPLP1-wMN1-Sp-11 | GUGCGCGUCUGAAGAGGAGU | SEQ ID NO: 506 |
| hPLP1-wMN1-Sp-12 | UGCGCGUCUGAAGAGGAGUG | SEQ ID NO: 507 |
| hPLP1-wMN1-Sp-13 | UAGUCCAGAUGCUGUUGCCG | SEQ ID NO: 508 |
| hPLP1-wMN1-Sp-14 | AUUACCACGGCAACAGCAUC | SEQ ID NO: 509 |
| hPLP1-wMN1-Sp-15 | GACACGAUUUAGUAUUACCA | SEQ ID NO: 510 |
| hPLP1-wMN1-Sp-16 | CUAAAUCGUGUCCAAAGAGG | SEQ ID NO: 511 |
| hPLP1-wMN1-Sp-17 | AGGAAUCUCAGCCUCCUCUU | SEQ ID NO: 512 |
| hPLP1-wMN1-Sp-18 | GUGGACAAGGUUAACUAAAA | SEQ ID NO: 513 |
| hPLP1-wMN1-Sp-19 | AUAGUCAAAUCAUGUGGACA | SEQ ID NO: 514 |
| hPLP1-wMN1-Sp-20 | UGCUGGAUAGUCAAAUCAUG | SEQ ID NO: 515 |
| hPLP1-wMN1-Sp-21 | ACAUGAUUUGACUAUCCAGC | SEQ ID NO: 516 |
| hPLP1-wMN1-Sp-22 | AUUUGACUAUCCAGCAGGCU | SEQ ID NO: 517 |

TABLE 12-continued

Guide sequences of gRNA for targeting human PLP1 gene

| gRNA | Guide Sequence (5' to 3') | SEQ ID NO |
|---|---|---|
| hPLP1-wMN1-Sp-23 | GUCCCGAAGUCUCUGGGGCC | SEQ ID NO: 518 |
| hPLP1-wMN1-Sp-24 | AAAACAGUCCCGAAGUCUCU | SEQ ID NO: 519 |
| hPLP1-wMN1-Sp-25 | GAAAACAGUCCCGAAGUCUC | SEQ ID NO: 520 |
| hPLP1-wMN1-Sp-26 | UAUAUACCACAUUCAAGUGC | SEQ ID NO: 521 |
| hPLP1-wMN1-Sp-27 | UGGAUAUAACGAAGUUGUGU | SEQ ID NO: 522 |
| hPLP1-wMN1-Sp-28 | AUGGAUAUAACGAAGUUGUG | SEQ ID NO: 523 |
| hPLP1-wMN1-Sp-29 | AUAUGUUUGUUCACCCCAAC | SEQ ID NO: 524 |
| hPLP1-wMN1-Sp-30 | GAAAACUUGAAAUCCUGUUG | SEQ ID NO: 525 |
| hPLP1-wMN1-Sp-31 | UAGACAUUAGGAGAAACAGA | SEQ ID NO: 526 |
| hPLP1-wMN1-Sp-32 | CUAGCAGUGACAUAGACAUU | SEQ ID NO: 527 |
| hPLP1-wMN1-Sp-33 | AGCCACCUGACUUUGAUGAA | SEQ ID NO: 528 |
| hPLP1-wMN1-Sp-34 | UGAGAAAUGUUAUUACUAUA | SEQ ID NO: 529 |
| hPLP1-wMN1-Sp-35 | AGACUGCGAGAUGAGAGAGU | SEQ ID NO: 530 |
| hPLP1-wMN1-Sp-36 | CUCGCAGUCUGUACUUAGAC | SEQ ID NO: 531 |
| hPLP1-wMN1-Sp-37 | AAUGUCUCUUGAGAGAGCCA | SEQ ID NO: 532 |

TABLE 13

Guide sequences of gRNA for targeting human PLP1 gene

| gRNA | Guide Sequence (5' to 3') | SEQ ID NO |
|---|---|---|
| hPLP1-wMN1-Cj-01 | AUGGGAAGAUGAAAGGGAAGUA | SEQ ID NO: 533 |
| hPLP1-wMN1-Cj-02 | ACUUUGAUUGUUAAAACUUAUC | SEQ ID NO: 534 |
| hPLP1-wMN1-Cj-03 | AGUCCUACCUCAGCUUCCCAAU | SEQ ID NO: 535 |
| hPLP1-wMN1-Cj-04 | CAAUGCUUGCACAUAAAUUGGA | SEQ ID NO: 536 |
| hPLP1-wMN1-Cj-05 | ACACAGAGAGAGACAGAAUGAA | SEQ ID NO: 537 |
| hPLP1-wMN1-Cj-06 | UCCUCUUCAGACGCGCACACAC | SEQ ID NO: 538 |
| hPLP1-wMN1-Cj-07 | ACUCCUCUUCAGACGCGCACAC | SEQ ID NO: 539 |
| hPLP1-wMN1-Cj-08 | CCACUCCUCUUCAGACGCGCAC | SEQ ID NO: 540 |
| hPLP1-wMN1-Cj-09 | CCCCACUCCUCUUCAGACGCGC | SEQ ID NO: 541 |
| hPLP1-wMN1-Cj-10 | CUCCCCACUCCUCUUCAGACGC | SEQ ID NO: 542 |
| hPLP1-wMN1-Cj-11 | UACUCCCCACUCCUCUUCAGAC | SEQ ID NO: 543 |
| hPLP1-wMN1-Cj-12 | UAUACUCCCCACUCCUCUUCAG | SEQ ID NO: 544 |
| hPLP1-wMN1-Cj-13 | ACAGCAUCUGGACUAUCUUGUU | SEQ ID NO: 545 |
| hPLP1-wMN1-Cj-14 | AUAGUCCAGAUGCUGUUGCCGU | SEQ ID NO: 546 |
| hPLP1-wMN1-Cj-15 | AAAAGGAAUCUCAGCCUCCUCU | SEQ ID NO: 547 |
| hPLP1-wMN1-Cj-16 | UGUCACUGCUAGUGUGCUUAAU | SEQ ID NO: 548 |
| hPLP1-wMN1-Cj-17 | AUGUGAAUUCAGUACAAGAAUU | SEQ ID NO: 549 |
| hPLP1-wMN1-Cj-18 | UUAUGUGAAUUCAGUACAAGAA | SEQ ID NO: 550 |

TABLE 13-continued

Guide sequences of gRNA for targeting human PLP1 gene

| gRNA | Guide Sequence (5' to 3') | SEQ ID NO |
|---|---|---|
| hPLP1-wMN1-Cj-19 | CUUUCAUUUCUGUUUAUGUGAA | SEQ ID NO: 551 |
| hPLP1-wMN1-Cj-20 | UUCACAUAAACAGAAAUGAAAG | SEQ ID NO: 552 |
| hPLP1-wMN1-Cj-21 | AUGCCAACUCUCUCAUCUCGCA | SEQ ID NO: 553 |
| hPLP1-wMN1-Cj-22 | GAGACAUUCUCACAUUUCCAGU | SEQ ID NO: 554 |

TABLE 14

Guide sequences of gRNA for targeting human P1 promoter

| gRNA | Guide Sequence (5' to 3') | SEQ ID NO |
|---|---|---|
| hPMP22-P1-Sp-01 | AGUUACAGGGAGCACCACCA | SEQ ID NO: 555 |
| hPMP22-P1-Sp-02 | CAGUUACAGGGAGCACCACC | SEQ ID NO: 556 |
| hPMP22-P1-Sp-03 | CUGGUCUGGCUUCAGUUACA | SEQ ID NO: 557 |
| hPMP22-P1-Sp-04 | CCUGGUCUGGCUUCAGUUAC | SEQ ID NO: 558 |
| hPMP22-P1-Sp-05 | CCUGGUCUGGCUUCAGUUAC | SEQ ID NO: 559 |
| hPMP22-P1-Sp-06 | UCUGCAGAAUUCACUGGGAG | SEQ ID NO: 560 |
| hPMP22-P1-Sp-07 | CUCUGCAGAAUUCACUGGGA | SEQ ID NO: 561 |
| hPMP22-P1-Sp-08 | UCUCUGCAGAAUUCACUGGG | SEQ ID NO: 562 |
| hPMP22-P1-Sp-09 | UAAUCUCUGCAGAAUUCACU | SEQ ID NO: 563 |
| hPMP22-P1-Sp-10 | UUAAUCUCUGCAGAAUUCAC | SEQ ID NO: 564 |

TABLE 15

Guide sequences of gRNA for targeting human P1 promoter

| gRNA | Guide Sequence (5' to 3') | SEQ ID NO |
|---|---|---|
| hPMP22-P1-Cj-01 | GCCUGGUCUGGCUUCAGUUACA | SEQ ID NO: 565 |
| hPMP22-P1-Cj-02 | GUGUCCAACUUUGUUUGCUUUC | SEQ ID NO: 566 |
| hPMP22-P1-Cj-03 | GUAUUCUGGAAAGCAAACAAAG | SEQ ID NO: 567 |
| hPMP22-P1-Cj-04 | CAGUCUUGGCAUCACAGGCUUC | SEQ ID NO: 568 |
| hPMP22-P1-Cj-05 | GGACCUCUUGGCUAUUACACAG | SEQ ID NO: 569 |
| hPMP22-P1-Cj-06 | GGAGCCAGUGGGACCUCUUGGC | SEQ ID NO: 570 |
| hPMP22-P1-Cj-07 | CCCAGUGAAUUCUGCAGAGAUU | SEQ ID NO: 571 |
| hPMP22-P1-Cj-08 | GGAAGGAUCUGUGUCUACAGUG | SEQ ID NO: 572 |
| hPMP22-P1-Cj-09 | UUACCUGCACGUAUGUAACACU | SEQ ID NO: 573 |
| hPMP22-P1-Cj-10 | AAAUAAAACUUACCUGCACGUA | SEQ ID NO: 574 |
| hPMP22-P1-Cj-11 | AAGUUUAUUUAAAAUAAAACUU | SEQ ID NO: 575 |
| hPMP22-P1-Cj-12 | AAAGCAUAGGCACACAUCACCC | SEQ ID NO: 576 |
| hPMP22-P1-Cj-13 | UUAGGCAAUUCUUGUAAAGCAU | SEQ ID NO: 577 |
| hPMP22-P1-Cj-14 | AAUUAGGCAAUUCUUGUAAAGC | SEQ ID NO: 578 |

TABLE 15-continued

Guide sequences of gRNA for targeting human P1 promoter

| gRNA | Guide Sequence (5' to 3') | SEQ ID NO |
|---|---|---|
| hPMP22-P1-Cj-15 | AAUCUCCAGUCAAUUCCAACAC | SEQ ID NO: 579 |
| hPMP22-P1-Cj-16 | GCCCUCUGAAUCUCCAGUCAAU | SEQ ID NO: 580 |
| hPMP22-P1-Cj-17 | UAUAUCCUUGGUUAAAAGGUGG | SEQ ID NO: 581 |

As One Aspect Disclosed in the Specification, the Expression Control Composition May Include a Guide Nucleic Acid and an Editor Protein.

In one exemplary embodiment, the expression control composition may include the following:

(a) a guide nucleic acid capable of targeting a target sequence located in the transcriptional regulatory region of a duplicate gene or a nucleic acid sequence encoding the same; and (b) one or more editor proteins or a nucleic acid sequence(s) encoding the same.

A description related to the duplicate gene is as described above.

A description related to the transcriptional regulatory region is as described above.

A description related to the target sequence is as described above.

In another exemplary embodiment, the expression control composition may include the following:

i) a first guide nucleic acid capable of targeting a target sequence located upstream of the transcriptional regulartory region of a duplicate gene or a nucleic acid sequence encoding the same;

ii) a second guide nucleic acid capable of targeting a target sequence located downstream of the transcriptional regulartory region of a duplicate gene or a nucleic acid sequence encoding the same; and iii) one or more editor proteins or nucleic acid sequence(s) encoding the same.

A description of the duplicate gene is as described above.

A description of the transcriptional regulartory region is as described above.

A description of the target sequence is as described above.

The expression control composition may include a guide nucleic acid-editor protein complex.

The term "guide nucleic acid-editor protein complex" refers to a complex formed through the interaction between a guide nucleic acid and an editor protein.

A description related to the guide nucleic acid is as described above.

The term "editor protein" refers to a peptide, polypeptide or protein which is able to directly bind to or interact with, without direct binding to, a nucleic acid.

Here, the nucleic acid may be a nucleic acid included in a target nucleic acid, gene or chromosome.

Here, the nucleic acid may be a guide nucleic acid.

The editor protein may be an enzyme.

Here, the term "enzyme" refers to a polypeptide or protein that contains a domain capable of cleaving a nucleic acid, gene or chromosome.

The enzyme may be a nuclease or restriction enzyme.

The editor protein may include a complete active enzyme.

Here, the "complete active enzyme" refers to an enzyme having the same function as the nucleic acid, gene or chromosome cleavage function of a wild-type enzyme. For example, the wild-type enzyme that cleaves double-stranded DNA may be a complete active enzyme that entirely cleaves double-stranded DNA. As another example, when the wild-type enzyme cleaving double-stranded DNA undergoes a deletion or substitution of a partial sequence of an amino acids sequence due to artificial engineering, the artificially engineered enzyme variant cleaves double-stranded DNA like the wild-type enzyme, the artificially engineered enzyme variant may be a complete active enzyme.

In addition, the complete active enzyme may include an enzyme having an improved function, compared to the wild-type enzyme. For example, a specific modified or manipulated form of the wild-type enzyme cleaving double-stranded DNA may have a complete enzyme activity, which is greater than the wild-type enzyme, that is, an increased activity of cleaving double-stranded DNA.

The editor protein may include an incomplete or partially active enzyme.

Here, the "incomplete or partially active enzyme" refers to an enzyme having some of the nucleic acid, gene or chromosome cleavage function of the wild-type enzyme. For example, a specific modified or manipulated form of the wild-type enzyme that cleaves double-stranded DNA may be a form having a first function or a form having a second function. Here, the first function is a function of cleaving the first strand of double-stranded DNA, and the second function may be a function of cleaving the second strand of double-stranded DNA. Here, the enzyme with the first function or the enzyme with the second function may be an incomplete or partially active enzyme.

The editor protein may include an inactive enzyme.

Here, the "inactive enzyme" refers to an enzyme in which the nucleic acid, gene or chromosome cleavage function of the wild-type enzyme is entirely inactivated. For example, a specific modified or manipulated form of the wild-type enzyme may be a form in which both of the first and second functions are lost, that is, both of the first function of cleaving the first strand of double-stranded DNA and the second function of cleaving the second strand thereof are lost. Here, the enzyme in which all of the first and second functions are lost may be inactive enzyme.

The editor protein may be a fusion protein.

Here, the term "fusion protein" refers to a protein produced by fusing an enzyme with an additional domain, peptide, polypeptide or protein.

The additional domain, peptide, polypeptide or protein may be a functional domain, peptide, polypeptide or protein, which has a function the same as or different from the enzyme.

The fusion protein may be a form in which the functional domain, peptide, polypeptide or protein is added to one or more of the amino end of an enzyme or the proximity thereof; the carboxyl end of the enzyme or the proximity thereof; the middle part of the enzyme; or a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase. The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucuronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV (SEQ ID NO: 312); NLS derived from nucleoplasmin (e.g., nucleoplasmin bipartite NLS with a sequence KRPAATKKAGQAKKKK (SEQ ID NO: 313)); c-myc NLS with an amino acid sequence PAAKRVKLD (SEQ ID NO: 314) or RQRRNELKRSP (SEQ ID NO: 315); hRNPA1 M9 NLS with a sequence NQSSNFGPMKGGNFG-GRSSGPYGGGGQYFAKPRNQGGY (SEQ ID NO: 316); an importin-α-derived IBB domain sequence RMRIZFKNKGKDTAELRRRRVEVSVELRKAKKD-EQILKRRNV (SEQ ID NO: 317); myoma T protein sequences VSRKRPRP (SEQ ID NO: 318) and PPKKARED (SEQ ID NO: 319); human p53 sequence PQPKKKPL (SEQ ID NO: 320); a mouse c-abl IV sequence SALIKKKKKMAP (SEQ ID NO: 321); influenza virus NS1 sequences DRLRR (SEQ ID NO: 322) and PKQKKRK (SEQ ID NO: 323); a hepatitis virus-δ antigen sequence RKLKKKIKKL (SEQ ID NO: 324); a mouse Mx1 protein sequence REKKKFLKRR (SEQ ID NO: 325); a human poly(ADP-ribose) polymerase sequence KRKGDEVDGVDEVAKKKSKK (SEQ ID NO: 326); or steroid hormone receptor (human) glucocorticoid sequence RKCLQAGMNLEARKTKK (SEQ ID NO: 327), but the present invention is not limited thereto.

The additional domain, peptide, polypeptide or protein may be a non-functional domain, peptide, polypeptide or protein that does not perform a specific function. Here, the non-functional domain, peptide, polypeptide or protein may be a domain, peptide, polypeptide or protein that does not affect the enzyme function.

The fusion protein may be a form in which the non-functional domain, peptide, polypeptide or protein is added to one or more of the amino end of an enzyme or the proximity thereof; the carboxyl end of the enzyme or the proximity thereof; the middle part of the enzyme; or a combination thereof.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

Alternatively, the modification may be substitution, removal, addition of some nucleotides in the nucleotide sequence encoding the editor protein, or a combination thereof.

In addition, optionally, the expression control composition may further include a donor having a desired specific nucleotide sequence, which is to be inserted, or a nucleic acid sequence encoding the same.

Here, the nucleic acid sequence to be inserted may be a partial nucleotide sequence in the transcriptional regulatory region of the duplicate gene.

Here, the nucleic acid sequence to be inserted may be a nucleic acid sequence used to introduce a mutation into the transcriptional regulatory region of the duplication gene. Here, the mutation may be a mutation that interferes with the transcription of a duplicate gene.

The term "donor" refers to a nucleotide sequence that helps homologous recombination (HR)-based repair of a damaged gene or nucleic acid.

The donor may be a double- or single-stranded nucleic acid.

The donor may be present in a linear or circular shape.

The donor may include a nucleotide sequence having homology with a nucleic acid in the transcriptional regulatory region of a target gene.

For example, the donor may include a nucleotide sequence having homology with each of nucleotide sequences at a location into which a specific nucleotide sequence is to be inserted, for example, upstream (left) and downstream (right) of a damaged nucleic acid. Here, the specific nucleotide sequence to be inserted may be located between a nucleotide sequence having homology with a nucleotide sequence downstream of the damaged nucleic acid and a nucleotide sequence having homology with a nucleotide sequence upstream of the damaged nucleic acid. Here, the nucleotide sequence having homology may have at least 50%, 55%, 60%, 65%, 70%, 75%, 80%, 85%, 90% or 95% or more homology or complete homology.

The donor may include a specific nucleic acid sequence.

Here, the specific nucleic acid sequence may be a partial nucleotide sequence of a target gene or a similar nucleotide sequence thereto. The partial nucleotide sequence of the target gene may include, for example, a normal nucleic acid sequence in which a mutation for editing a target gene having a mutation is edited. Alternatively, the partial similar nucleotide sequence of a target gene may include a mutation-induced nucleic acid sequence in which a part of the partial normal nucleic acid sequence of a target gene for mutating the normal target gene is modified.

Here, the specific nucleic acid sequence may be an exogenous nucleic acid sequence. For example, the exogenous nucleic acid sequence may be an exogenous gene desired to be expressed in cells having a target gene.

Here, the specific nucleic acid sequence may be a nucleic acid sequence desired to be expressed in cells having a target gene. For example, the specific nucleic acid sequence may be a specific gene expressed in cells having a target gene, and in this case, the specific gene may be increased in copy number in cells due to an expression control composition having the donor, and thus highly expressed.

Optionally, the donor may include an additional nucleotide sequence. Here, the additional nucleotide sequence may serve to increase the stability of the donor, the efficiency of insertion into a target, or homologous recombination efficiency.

For example, the additional nucleotide sequence may be an A and T nucleotide-rich nucleic acid sequence, that is, an A-T rich domain. For example, the additional nucleotide sequence may be a scaffold/matrix attachment region (SMAR).

The guide nucleic acid, editor protein or guide nucleic acid-editor protein complex disclosed in the specification may be delivered or introduced into a subject in various ways.

Here, the term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including a target gene or chromosome of a guide nucleic acid-editor protein complex.

The organism may be an animal, animal tissue or an animal cell.

The organism may be a human, human tissue or a human cell.

The tissue may be eyeball, skin, liver, kidney, heart, lung, brain, muscle tissue, or blood.

The cell may be a fibroblast, a Schwann cell, a nerve cell, an oligodendrocyte, a myoblast, a glial cell, a macrophage, an immune cell, a hepatocyte, a retinal pigment epithelial cell, a cancer cell or a stem cell.

The specimen or sample may be acquired from an organism including a target gene or chromosome and may be saliva, blood, retinal tissue, brain tissue, a Schwann cell, an oligodendrocyte, a myoblast, a fibroblast, a neuron, a glial cell, a macrophage, a hepatocyte, an immune cell, a cancer cell, or a stem cell.

Preferably, the subject may be an organism including a duplicate gene. Here, the subject may be an organism in which a duplicate gene is in a gene duplication state.

The guide nucleic acid, editor protein or guide nucleic acid-editor protein complex may be delivered or introduced into a subject in the form of DNA, RNA or a mixed form.

Here, the guide nucleic acid and/or editor protein may be delivered or introduced into a subject in the form of DNA, RNA or a mixed form by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

In one exemplary embodiment, the nucleic acid sequence encoding the guide nucleic acid and/or editor protein may be delivered or introduced into a subject by a vector.

The vector may include a nucleic acid sequence encoding a guide nucleic acid and/or editor protein.

In one example, the vector may simultaneously include nucleic acid sequences, which encode the guide nucleic acid and the editor protein, respectively.

In another example, the vector may include the nucleic acid sequence encoding the guide nucleic acid.

As an example, domains included in the guide nucleic acid may be contained all in one vector, or may be divided and then contained in different vectors.

In another example, the vector may include the nucleic acid sequence encoding the editor protein.

As an example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant lentivirus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

In another exemplary embodiment, the nucleic acid sequence encoding the guide nucleic acid and/or editor protein may be delivered or introduced into a subject by a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, gene gun, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

In one example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

In a certain embodiment, the non-vector may be delivered using a lipid shell.

In a certain embodiment, the non-vector may be delivered using an exosome. The exosome is an endogenous nanovesicle for transferring a protein and RNA, which can deliver RNA to the brain and another target organ.

In a certain embodiment, the non-vector may be delivered using a liposome. The liposome is a spherical vesicle structure which is composed of single or multiple lamellar lipid bilayers surrounding internal aqueous compartments and an external, lipophilic phospholipid bilayer which is relatively non-transparent. While the liposome may be made from several different types of lipids; phospholipids are most generally used to produce the liposome as a drug carrier.

In addition, the composition for delivery of the non-vector may be include other additives.

The editor protein may be delivered or introduced into a subject in the form of a peptide, polypeptide or protein.

The editor protein may be delivered or introduced into a subject in the form of a peptide, polypeptide or protein by a method known in the art.

The peptide, polypeptide or protein form may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

The guide nucleic acid and the editor protein may be delivered or introduced into a subject in the form of mixing a nucleic acid and a protein.

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

The guide nucleic acid-editor protein complex disclosed in the specification may modify a target nucleic acid, gene or chromosome.

For example, the guide nucleic acid-editor protein complex induces a modification in the sequence of a target nucleic acid, gene or chromosome. As a result, a protein expressed by the target nucleic acid, gene or chromosome may be modified in structure and/or function, or the expression of the protein may be controlled or inhibited.

The guide nucleic acid-editor protein complex may act at the DNA, RNA, gene or chromosome level.

In one example, the guide nucleic acid-editor protein complex may manipulate or modify the transcriptional regulatory region of a target gene to control (e.g., suppress, inhibit, reduce, increase or promote) the expression of a protein encoded by a target gene, or express a protein whose activity is controlled (e.g., suppressed, inhibited, reduced, increased or promoted) or modified.

The guide nucleic acid-editor protein complex may act at the transcription and translation stage of a gene.

In one example, the guide nucleic acid-editor protein complex may promote or inhibit the transcription of a target gene, thereby controlling (e.g., suppressing, inhibiting, reducing, increasing or promoting) the expression of a protein encoded by the target gene.

In another example, the guide nucleic acid-editor protein complex may promote or inhibit the translation of a target gene, thereby controlling (e.g., suppressing, inhibiting, reducing, increasing or promoting) the expression of a protein encoded by the target gene.

In One Exemplary Embodiment Disclosed in the Specification, the Expression Control Composition May Include gRNA and a CRISPR Enzyme.

In one example, the expression control composition may include the following:

(a) a gRNA that can target a target sequence located in the transcriptional regulatory region of a duplicate gene or a nucleic acid sequence encoding the same; and (b) one or more CRISPR enzymes or a nucleic acid sequence(s) encoding the same.

A description related to the duplicate gene is as described above.

A description related to the transcriptional regulatory region is as described above.

A description related to the target sequence is as described above.

In another example, the expression control composition may include:

i) a first guide nucleic acid capable of targeting a target sequence located upstream of the transcriptional regulartory region of a duplicate gene or a nucleic acid sequence encoding the same;

ii) a second guide nucleic acid capable of targeting a target sequence located downstream of the transcriptional regulartory region of a duplicate gene or a nucleic acid sequence encoding the same; and iii) one or more editor proteins or nucleic acid sequence(s) encoding the same.

A description of the duplicate gene is as described above.

A description of the transcriptional regulartory region is as described above.

A description of the target sequence is as described above.

The expression control composition may include a gRNA-CRISPR enzyme complex.

The term "gRNA-CRISPR enzyme complex" refers to a complex formed by the interaction between gRNA and a CRISPR enzyme.

A description related to the gRNA is as described above.

The term "CRISPR enzyme" is a main protein component of a CRISPR-Cas system, and forms a complex with gRNA, resulting in the CRISPR-Cas system.

The CRISPR enzyme may be a nucleic acid having a sequence encoding the CRISPR enzyme or a polypeptide (or a protein).

The CRISPR enzyme may be a Type II CRISPR enzyme.

The crystal structure of the type II CRISPR enzyme was determined according to studies on two or more types of natural microbial type II CRISPR enzyme molecules (Jinek et al., Science, 343(6176):1247997, 2014) and studies on Streptococcus pyogenes Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes a RuvC domain, an HNH domain and a PAM-interaction (PI) domain. Here, the RuvC domain encompasses RuvC-like domains, and the HNH domain encompasses HNH-like domains.

Here, the RuvC domain shares structural similarity with members of the microorganism family existing in nature having the type II CRISPR enzyme, and cleaves a single strand, for example, a non-complementary strand of a nucleic acid in the transcriptional regulatory region of a target gene, that is, a strand not forming a complementary bond with gRNA. The RuvC domain is sometimes referred to as a RuvCI domain, RuvCII domain or RuvCIII domain in the art, and generally called an RuvC I, RuvCII or RuvCIII.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs.

The PI domain recognizes a specific nucleotide sequence in the transcriptional regulatory region of a target gene, that is, a protospacer adjacent motif (PAM), or interacts with PAM. Here, the PAM may vary according to the origin of a Type II CRISPR enzyme. For example, when the CRISPR enzyme is SpCas9, the PAM may be 5'-NGG-3', and when the CRISPR enzyme is Streptococcus thermophilus Cas9 (StCas9), the PAM may be 5'-NNAGAAW-3' (W=A or T), when the CRISPR enzyme is Neisseria meningiditis Cas9 (NmCas9), the PAM may be 5'-NNNNGATT-3', and when the CRISPR enzyme is Campylobacter jejuni Cas9 (CjCas9), the PAM may be 5'-NNNVRYAC-3' (V=G or C or A, R=A or G, Y=C or T), herein, N is A, T, G or C; or A, U, G or C). However, while it is generally understood that PAM is determined according to the origin of the above-described enzyme, as the study of a mutant of an enzyme derived from the corresponding origin progresses, the PAM may be changed.

The Type II CRISPR enzyme may be Cas9.

The Cas9 may be derived from various microorganisms such as Streptococcus pyogenes, Streptococcus thermophilus, Streptococcus sp., Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas sp., Crocosphaera watsonii, Cyanothece sp., Microcystis aeruginosa, Synechococcus sp., Acetohalobium arabaticum, Ammonifex degensii, Caldicelulosiruptor bescii, Candidatus desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus and Acaryochloris marina.

The Cas9 is an enzyme which binds to gRNA so as to cleave or modify a target sequence or position on the transcriptional regulatory region of a target gene, and may consist of an HNH domain capable of cleaving a nucleic acid strand forming a complementary bond with gRNA, an RuvC domain capable of cleaving a nucleic acid strand forming a non-complementary bond with gRNA, an REC domain interacting the target and a PI domain recognizing a PAM. Hiroshi Nishimasu et al. (2014) Cell 156:935-949 may be referenced for specific structural characteristics of Cas9.

The Cas9 may be isolated from a microorganism existing in nature or non-naturally produced by a recombinant or synthetic method.

In addition, the CRISPR enzyme may be a Type V CRISPR enzyme.

The type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a nucleic acid in the transcriptional regulatory region of a target gene is dependent on the PAM sequence.

The PAM sequence may be a sequence present in the transcriptional regulatory region of a target gene, and recognized by the PI domain of a Type V CRISPR enzyme. The PAM sequence may have different sequences according to the origin of the Type V CRISPR enzyme. That is, each species has a specifically recognizable PAM sequence. For example, the PAM sequence recognized by Cpf1 may be 5'-TTN-3' (N is A, T, C or G). While it has been generally understood that PAM is determined according to the origin of the above-described enzyme, as the study of mutants of the enzyme derived from the corresponding origin progresses, the PAM may be changed.

The Type V CRISPR enzyme may be Cpf1.

The Cpf1 may be derived from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacillus, Methylobacterium* or *Acidaminococcus*.

The Cpf1 may consist of a RuvC-like domain corresponding to the RuvC domain of Cas9, a Nuc domain instead of the HNH domain of Cas9, an REC and WED domains recognizing a target, and a PI domain recognizing PAM. For specific structural characteristics of Cpf1, Takashi Yamano et al. (2016) Cell 165:949-962 may be referenced.

The Cpf1 may be isolated from a microorganism existing in nature or non-naturally produced by a recombinant or synthetic method.

The CRISPR enzyme may be a nuclease or restriction enzyme having a function of cleaving a double-stranded nucleic acid in the transcriptional regulatory region of a target gene.

The CRISPR enzyme may be a complete active CRISPR enzyme.

The term "complete active" refers to a state in which an enzyme has the same function as that of a wild-type CRISPR enzyme, and the CRISPR enzyme in such a state is named a complete active CRISPR enzyme. Here, the "function of the wild-type CRISPR enzyme" refers to a state in which an enzyme has functions of cleaving double-stranded DNA, that is, the first function of cleaving the first strand of double-stranded DNA and a second function of cleaving the second strand of double-stranded DNA.

The complete active CRISPR enzyme may be a wild-type CRISPR enzyme that cleaves double-stranded DNA.

The complete active CRISPR enzyme may be a CRISPR enzyme variant formed by modifying or manipulating the wild-type CRISPR enzyme that cleaves double-stranded DNA.

The CRISPR enzyme variant may be an enzyme in which one or more amino acids of the amino acid sequence of the wild-type CRISPR enzyme are substituted with other amino acids, or one or more amino acids are removed.

The CRISPR enzyme variant may be an enzyme in which one or more amino acids are added to the amino acid sequence of the wild-type CRISPR enzyme. Here, the location of the added amino acids may be the N-end, the C-end or the amino acid sequence of the wild-type enzyme.

The CRISPR enzyme variant may be a complete active enzyme with an improved function compared to the wild-type CRISPR enzyme.

For example, a specifically modified or manipulated form of the wild-type CRISPR enzyme, that is, the CRISPR enzyme variant may cleave double-stranded DNA while not binding to the double-stranded DNA to be cleaved or maintaining a certain distance therefrom. In this case, the modified or manipulated form may be a complete active CRISPR enzyme with an improved functional activity, compared to the wild-type CRISPR enzyme.

The CRISPR enzyme variant may be a complete active CRISPR enzyme with a reduced function, compared to the wild-type CRISPR enzyme.

For example, the specific modified or manipulated form of the wild-type CRISPR enzyme, that is, the CRISPR enzyme variant may cleave double-stranded DNA while very close to the double-stranded DNA to be cleaved or forming a specific bond therewith. Here, the specific bond may be, for example, a bond between an amino acid at a specific region of the CRISPR enzyme and a DNA sequence at the cleavage location. In this case, the modified or manipulated form may be a complete active CRISPR enzyme with a reduced functional activity, compared to the wild-type CRISPR enzyme.

The CRISPR enzyme may be an incomplete or partially active CRISPR enzyme.

The term "incomplete or partially active" refers to a state in which an enzyme has one selected from the functions of the wild-type CRISPR enzyme, that is, a first function of cleaving the first strand of double-stranded DNA and a second function of cleaving the second strand of double-stranded DNA. The CRISPR enzyme in this state is named an incomplete or partially active CRISPR enzyme. In addition, the incomplete or partially active CRISPR enzyme may be referred to as a nickase.

The term "nickase" refers to a CRISPR enzyme manipulated or modified to cleave only one strand of the double strand of a nucleic acid in the transcriptional regulatory region of a target gene, and the nickase has nuclease activity of cleaving a single strand, for example, a strand that is complementary or non-complementary to gRNA of a nucleic acid in the transcriptional regulatory region of a target gene. Therefore, to cleave the double strand, nuclease activity of the two nickases is needed.

The nickase may have nuclease activity by the RuvC domain. That is, the nickase may not include nuclease activity of the HNH domain, and to this end, the HNH domain may be manipulated or modified.

In one example, when the CRISPR enzyme is a Type II CRISPR enzyme, the nickase may be a Type II CRISPR enzyme including a modified HNH domain.

For example, provided that the Type II CRISPR enzyme is a wild-type SpCas9, the nickase may be a SpCas9 variant in which nuclease activity of the HNH domain is inactivated by mutation that the $840^{th}$ amino acid in the amino acid sequence of the wild-type SpCas9 is mutated from histidine to alanine. Since the nickase produced thereby, that is, the SpCas9 variant has nuclease activity of the RuvC domain, it is able to cleave a strand which is a non-complementary strand of a nucleic acid in the transcriptional regulatory region of a target gene, that is, a strand not forming a complementary bond with gRNA.

For another example, provided that the Type II CRISPR enzyme is a wild-type CjCas9, the nickase may be a CjCas9 variant in which nuclease activity of the HNH domain is inactivated by mutation that the 559$^{th}$ amino acid in the amino acid sequence of the wild-type CjCas9 is mutated from histidine to alanine. Since the nickase produced thereby, that is, the CjCas9 variant has nuclease activity of the RuvC domain, it is able to cleave a strand which is a non-complementary strand of a nucleic acid in the transcriptional regulatory region of a target gene, that is, a strand not forming a complementary bond with gRNA.

In addition, the nickase may have nuclease activity by the HNH domain of a CRISPR enzyme. That is, the nickase may not include the nuclease activity of the RuvC domain, and to this end, the RuvC domain may be manipulated or modified.

In one example, when the CRISPR enzyme is a Type II CRISPR enzyme, the nickase may be a Type II CRISPR enzyme including a modified RuvC domain.

For example, provided that the Type II CRISPR enzyme is a wild-type SpCas9, the nickase may be a SpCas9 variant in which nuclease activity of the RuvC domain is inactivated by mutation that the 10$^{th}$ amino acid in the amino acid sequence of the wild-type SpCas9 is mutated from aspartic acid to alanine. Since the nickase produced thereby, that is the SpCas9 variant has nuclease activity of the HNH domain, it is able to cleave a strand which is a complementary strand of a nucleic acid in the transcriptional regulatory region of a target gene, that is, a strand forming a complementary bond with gRNA.

For another example, provided that the Type II CRISPR enzyme is a wild-type CjCas9, the nickase may be a CjCas9 variant in which nuclease activity of the RuvC domain is inactivated by mutation that the 8$^{th}$ amino acid in the amino acid sequence of the wild-type CjCas9 is mutated from aspartic acid to alanine. Since the nickase produced thereby, that is, the CjCas9 variant has nuclease activity of the HNH domain, it is able to cleave a strand which is a complementary strand of a nucleic acid in the transcriptional regulatory region of a target gene, that is, a strand forming a complementary bond with gRNA.

The CRISPR enzyme may be an inactive CRISPR enzyme.

The term "inactive" refers to a state in which both of the functions of the wild-type CRISPR enzyme, that is, the first function of cleaving the first strand of double-stranded DNA and the second function of cleaving the second strand of double-stranded DNA are lost. The CRISPR enzyme in such a state is named an inactive CRISPR enzyme.

The inactive CRISPR enzyme may have nuclease inactivity due to variations in the domain having nuclease activity of a wild-type CRISPR enzyme.

The inactive CRISPR enzyme may have nuclease inactivity due to variations in a RuvC domain and an HNH domain. That is, the inactive CRISPR enzyme may not have nuclease activity generated by the RuvC domain and HNH domain of the CRISPR enzyme, and to this end, the RuvC domain and the HNH domain may be manipulated or modified.

In one example, when the CRISPR enzyme is a Type II CRISPR enzyme, the inactive CRISPR enzyme may be a Type II CRISPR enzyme having a modified RuvC domain and HNH domain.

For example, when the Type II CRISPR enzyme is a wild-type SpCas9, the inactive CRISPR enzyme may be a SpCas9 variant in which the nuclease activities of the RuvC domain and the HNH domain are inactivated by mutations of both aspartic acid 10 and histidine 840 in the amino acid sequence of the wild-type SpCas9 to alanine. Here, since, in the produced inactive CRISPR enzyme, that is, the SpCas9 variant, the nuclease activities of the RuvC domain and the HNH domain are inactivated, a double-stranded nucleic acid in the transcriptional regulatory region of a target gene may be entirely cleaved.

In another example, when the Type II CRISPR enzyme is a wild-type CjCas9, the inactive CRISPR enzyme may be a CjCas9 variant in which the nuclease activities of the RuvC domain and the HNH domain are inactivated by mutations of both aspartic acid 8 and histidine 559 in the amino acid sequence of the wild-type CjCas9 to alanine. Here, since, in the produced inactive CRISPR enzyme, that is, the CjCas9 variant, the nuclease activities of the RuvC domain and HNH domain are inactivated, a double-stranded nucleic acid in the transcriptional regulatory region of a target gene may not be entirely cleaved.

The CRISPR enzyme may have helicase activity, that is, an ability to anneal the helix structure of the double-stranded nucleic acid, in addition to the above-described nuclease activity.

In addition, the CRISPR enzyme may be modified to complete activate, incomplete or partially activate, or inactivate the helicase activity.

The CRISPR enzyme may be a CRISPR enzyme variant produced by artificially manipulating or modifying the wild-type CRISPR enzyme.

The CRISPR enzyme variant may be an artificially manipulated or modified CRISPR enzyme variant for modifying the functions of the wild-type CRISPR enzyme, that is, the first function of cleaving the first strand of double-stranded DNA and/or the second function of cleaving the second strand of double-stranded DNA.

For example, the CRISPR enzyme variant may be a form in which the first function of the functions of the wild-type CRISPR enzyme is lost.

Alternatively, the CRISPR enzyme variant may be a form in which the second function of the functions of the wild-type CRISPR enzyme is lost.

For example, the CRISPR enzyme variant may be a form in which both of the functions of the wild-type CRISPR enzyme, that is, the first function and the second function, are lost.

The CRISPR enzyme variant may form a gRNA-CRISPR enzyme complex by interactions with gRNA.

The CRISPR enzyme variant may be an artificially manipulated or modified CRISPR enzyme variant for modifying a function of interacting with gRNA of the wild-type CRISPR enzyme.

For example, the CRISPR enzyme variant may be a form having reduced interactions with gRNA, compared to the wild-type CRISPR enzyme.

Alternatively, the CRISPR enzyme variant may be a form having increased interactions with gRNA, compared to the wild-type CRISPR enzyme.

For example, the CRISPR enzyme variant may be a form having the first function of the wild-type CRISPR enzyme and reduced interactions with gRNA.

Alternatively, the CRISPR enzyme variant may be a form having the first function of the wild-type CRISPR enzyme and increased interactions with gRNA.

For example, the CRISPR enzyme variant may be a form having the second function of the wild-type CRISPR enzyme and reduced interactions with gRNA.

Alternatively, the CRISPR enzyme variant may be a form having the second function of the wild-type CRISPR enzyme and increased interactions with gRNA.

For example, the CRISPR enzyme variant may be a form not having the first and second functions of the wild-type CRISPR enzyme, and having reduced interactions with gRNA.

Alternatively, the CRISPR enzyme variant may be a form not having the first and second functions of the wild-type CRISPR enzyme and having increased interactions with gRNA.

Here, according to the interaction strength between gRNA and the CRISPR enzyme variant, various gRNA-CRISPR enzyme complexes may be formed, and according to the CRISPR enzyme variant, there may be a difference in function of approaching or cleaving the target sequence.

For example, the gRNA-CRISPR enzyme complex formed by a CRISPR enzyme variant having reduced interactions with gRNA may cleave a double or single strand of a target sequence only when very close to or localized to the target sequence completely complementarily bind to gRNA.

The CRISPR enzyme variant may be in a form in which at least one amino acid of the amino acid sequence of the wild-type CRISPR enzyme is modified.

As an example, the CRISPR enzyme variant may be in a form in which at least one amino acid of the amino acid sequence of the wild-type CRISPR enzyme is substituted.

As another example, the CRISPR enzyme variant may be in a form in which at least one amino acid of the amino acid sequence of the wild-type CRISPR enzyme is deleted.

As still another example, the CRISPR enzyme variant may be in a form in which at least one amino acid of the amino acid sequence of the wild-type CRISPR enzyme is added.

In one example, the CRISPR enzyme variant may be in a form in which at least one amino acid of the amino acid sequence of the wild-type CRISPR enzyme is substituted, deleted and/or added.

In addition, optionally, the CRISPR enzyme variant may further include a functional domain, in addition to the original functions of the wild-type CRISPR enzyme, that is, the first function of cleaving the first strand of double-stranded DNA and the second function of cleaving the second strand thereof. Here, the CRISPR enzyme variant may have an additional function, in addition to the original functions of the wild-type CRISPR enzyme.

The functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

The functional domain may be a deaminase.

For example, cytidine deaminase may be further included as a functional domain to an incomplete or partially-active CRISPR enzyme. In one exemplary embodiment, a fusion protein may be produced by adding a cytidine deaminase, for example, apolipoprotein B editing complex 1 (APOBEC1) to a SpCas9 nickase. The [SpCas9 nickase]-[APOBEC1] formed as described above may be used in nucleotide editing of C to T or U, or nucleotide editing of G to A.

In another example, adenine deaminase may be further included as a functional domain to the incomplete or partially-active CRISPR enzyme. In one exemplary embodiment, a fusion protein may be produced by adding adenine deaminases, for example, TadA variants, ADAR2 variants or ADAT2 variants to a SpCas9 nickase. The [SpCas9 nickase]-[TadA variant], [SpCas9 nickase]-[ADAR2 variant] or [SpCas9 nickase]-[ADAT2 variant] formed as described above may be used in nucleotide editing of A to G, or nucleotide editing of T to C, because the fusion protein modifies nucleotide A to inosine, the modified inosine is recognized as nucleotide G by a polymerase, thereby substantially exhibiting nucleotide editing of A to G.

The functional domain may be a nuclear localization sequence or signal (NLS) or a nuclear export sequence or signal (NES).

In one example, the CRISPR enzyme may include one or more NLSs. Here, one or more NLSs may be included at an N-terminus of a CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 312); NLS from nucleoplasmin (e.g., nucleoplasmin bipartite NLS having the sequence KRPAATKKAGQAKKKK (SEQ ID NO: 313)); c-myc NLS having the amino acid sequence PAAKRVKLD (SEQ ID NO: 314) or RQRR-NELKRSP (SEQ ID NO: 315); hRNPA1 M9 NLS having the sequence NQSSNFGPMKGGNFG-GRSSGPYGGGGQYFAKPRNQGGY (SEQ ID NO: 316); the sequence RMRIZFKNKGKDTAELRRRRVEVS-VELRKAKKDEQILKRRNV (SEQ ID NO: 317) of the IBB domain from importin-α; the sequences VSRKRPRP (SEQ ID NO: 318) and PPKKARED (SEQ ID NO: 319) of a myoma T protein; the sequence PQPKKKPL (SEQ ID NO: 320) of human p53; the sequence SALIKKKKKMAP (SEQ ID NO: 321) of mouse c-abl IV; the sequences DRLRR (SEQ ID NO: 322) and PKQKKRK (SEQ ID NO: 323) of influenza virus NS1; the sequence RKLKKKIKKL (SEQ ID NO: 324) of a hepatitis delta virus antigen; the sequence REKKKFLKRR (SEQ ID NO: 325) of a mouse Mx1 protein; the sequence KRKGDEVDGVDEVAKKKSKK (SEQ ID NO: 326) of a human poly (ADP-ribose) polymerase; or the NLS sequence RKCLQAGMNLEARKTKK (SEQ ID NO: 327), derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

The split-type CRISPR enzyme may be a complete, incomplete or partially active enzyme or inactive enzyme.

For example, when the CRISPR enzyme is a SpCas9, the SpCas9 may be divided into two parts between the residue 656, tyrosine, and the residue 657, threonine, thereby generating split SpCas9.

The split-type CRISPR enzyme may selectively include an additional domain, peptide, polypeptide or protein for reconstitution.

The additional domain, peptide, polypeptide or protein for reconstitution may be assembled for formation of the split-type CRISPR enzyme to be structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, when the CRISPR enzyme is a SpCas9, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycine is present, thereby producing a reconstituted CRISPR enzyme.

The CRISPR enzyme or CRISPR enzyme variant disclosed in the specification may be a polypeptide, protein or nucleic acid having a sequence encoding the same, and may be codon-optimized for a subject to introduce the CRISPR enzyme or CRISPR enzyme variant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized for optimal gene expression in a given organism based on codon optimization.

The gRNA, CRISPR enzyme or gRNA-CRISPR enzyme complex disclosed in the specification may be delivered or introduced into a subject by various delivering methods and various forms.

The subject related description is as described above.

In one exemplary embodiment, a nucleic acid sequence encoding the gRNA and/or CRISPR enzyme may be delivered or introduced into a subject by a vector.

The vector may include the nucleic acid sequence encoding the gRNA and/or CRISPR enzyme.

In one example, the vector may simultaneously include the nucleic acid sequences encoding the gRNA and the CRISPR enzyme.

In another example, the vector may include the nucleic acid sequence encoding the gRNA.

For example, domains contained in the gRNA may be contained in one vector, or may be divided and then contained in different vectors.

In another example, the vector may include the nucleic acid sequence encoding the CRISPR enzyme.

For example, in the case of the CRISPR enzyme, the nucleic acid sequence encoding the CRISPR enzyme may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding the gRNA and/or CRISPR enzyme).

For example, a promoter useful for the gRNA may be a H1, EF-1a, tRNA or U6 promoter. For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus. The virus may be a retrovirus, a lentivirus, an adenovirus, adeno-associated virus (AAV), vaccinia virus, a poxvirus or a herpes simplex virus, but the present invention is not limited thereto.

In one example, a nucleic acid sequence encoding gRNA and/or a CRISPR enzyme may be delivered or introduced by a recombinant lentivirus.

In another example, a nucleic acid sequence encoding gRNA and/or a CRISPR enzyme may be delivered or introduced by a recombinant adenovirus. In still another example, a nucleic acid sequence encoding gRNA and/or a CRISPR enzyme may be delivered or introduced by recombinant AAV. In yet another example, a nucleic acid sequence encoding gRNA and/or a CRISPR enzyme may be delivered or introduced by one or more hybrids of hybrid viruses, for example, the viruses described herein.

In one exemplary embodiment, the gRNA-CRISPR enzyme complex may be delivered or introduced into a subject.

For example, the gRNA may be present in the form of DNA, RNA or a mixture thereof. The CRISPR enzyme may be present in the form of a peptide, polypeptide or protein.

In one example, the gRNA and CRISPR enzyme may be delivered or introduced into a subject in the form of a gRNA-CRISPR enzyme complex including RNA-type gRNA and a protein-type CRISPR, that is, a ribonucleoprotein (RNP).

The gRNA-CRISPR enzyme complex may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The gRNA-CRISPR Enzyme Complex Disclosed in the Specification May be Used for Artificial Manipulation or Modification, or Deletion of the Transcriptional Regulartory Region of a Target Gene, that is, a Duplicate Gene.

The transcriptional regulatory region of a target gene may be manipulated or modified using the above-described gRNA-CRISPR enzyme complex, that is, the CRISPR complex. Here, the manipulation or modification of the transcriptional regulatory region of a target gene may include both of i) cleaving or damaging of the transcriptional regulatory region of a target gene and ii) repairing of the damaged transcriptional regulatory region.

The i) cleaving or damaging of the transcriptional regulatory region of the target gene may be cleavage or damage of the transcriptional regulatory region of the target gene using the CRISPR complex, and particularly, cleavage or damage of a target sequence of the transcriptional regulatory region The target sequence nay become a target of the gRNA-CRISPR enzyme complex, and the target sequence may or may not include a PAM sequence recognized by the CRISPR enzyme. Such a target sequence may provide a critical standard to one who is involved in the designing of gRNA.

The target sequence may be specifically recognized by gRNA of the gRNA-CRISPR enzyme complex, and therefore, the gRNA-CRISPR enzyme complex may be located near the recognized target sequence.

The "cleavage" at a target site refers to the breakage of a covalent backbone of a polynucleotide. The cleavage includes enzymatic or chemical hydrolysis of a phosphodiester bond, but the present invention is not limited thereto. Other than this, the cleavage may be performed by various methods. Both of single strand cleavage and double strand cleavage are possible, wherein the double strand cleavage may result from two distinct single strand cleavages. The double strand cleavage may produce a blunt end or a staggered end (or a sticky end).

In one example, the cleavage or damage of the transcriptional regulatory region of a target gene using the CRISPR complex may be the entire cleavage or damage of the double strand of a target sequence.

In one exemplary embodiment, when the CRISPR enzyme is a wild-type SpCas9, the double strand of a target sequence forming a complementary bond with gRNA may be completely cleaved by the CRISPR complex.

In another exemplary embodiment, when the CRISPR enzymes are SpCas9 nickase (D10A) and SpCas9 nickase (H840A), the two single strands of a target sequence forming a complementary bond with gRNA may be respectively cleaved by the each CRISPR complex. That is, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In another example, the cleavage or damage of the transcriptional regulatory region of a target gene using the CRISPR complex may be the cleavage or damage of only a single strand of the double strand of a target sequence. Here, the single strand may be a guide nucleic acid-binding sequence of the target sequence complementarily binding to gRNA, that is, a complementary single strand, or a non-guide nucleic acid-binding sequence not complementarily binding to gRNA, that is, a non-complementary single strand with gRNA.

In one exemplary embodiment, when the CRISPR enzyme is a SpCas9 nickase (D10A), the CRISPR complex may cleave the guide nucleic acid-binding sequence of a target sequence complementarily binding to gRNA, that is, a complementary single strand, by a SpCas9 nickase (D10A), and may not cleave a non-guide nucleic acid-binding sequence not complementarily binding to gRNA, that is, a non-complementary single strand with gRNA.

In another exemplary embodiment, when the CRISPR enzyme is a SpCas9 nickase (H840A), the CRISPR complex may cleave the non-guide nucleic acid-binding sequence of a target sequence not complementarily binding to gRNA, that is, a non-complementary single strand with gRNA by a SpCas9 nickase (H840A), and may not cleave the guide nucleic acid-binding sequence of a target sequence complementarily binding to gRNA, that is, a complementary single strand.

In still another example, the cleavage or damage of the transcriptional regulatory region of a target gene using the CRISPR complex may be partial removal of a nucleic acid fragment.

In one exemplary embodiment, when the CRISPR complexes consist of wild-type SpCas9 and two gRNAs having different target sequences, a double strand of a target sequence forming a complementary bond with the first gRNA may be cleaved, and a double strand of a target sequence forming a complementary bond with the second gRNA may be cleaved, resulting in the removal of nucleic acid fragments by the first and second gRNAs and SpCas9.

For example, when two CRISPR complexes consist of two gRNAs complementarily binding to different target sequences, such as one gRNA complementarily binding to a target sequence present upstream of an enhancer and the other gRNA complementarily binding to a target sequence present downstream of the enhancer, and wild-type SpCas9, the double strand of the target sequence present upstream of the enhancer complementarily binding to the first gRNA may be cleaved, and the double strand of the target sequence present downstream of the enhancer complementarily binding to the second gRNA may be cleaved, thereby removing a nucleic acid fragment, that is, an enhancer region by the first gRNA, the second gRNA and SpCas9.

In still another example, the transcriptional regulartory region of a target gene may be removed using the CRISPR complex.

In one exemplary embodiment, when the CRISPR complex consists of two gRNAs complementarily binding to different target sequences and wild-type SpCas9, a double strand of the target sequence capable of complementarily binding to first gRNA (e.g., the target sequence located upstream of the promoter of a target gene) may be cleaved, and a double strand of the target sequence capable of complementarily binding to second gRNA (e.g., the target sequence located downstream of the promoter of a target gene) may be cleaved, thereby a nucleic acid fragment or a specific region (e.g., the promoter of a target sequence) may be removed using the first gRNA, the second gRNA and SpCas9.

For example, when each of two CRISPR complexes consist of two gRNAs complementarily binding to different target sequences, for example, first gRNA complementarily binding to a target sequence present upstream of a promoter controlling the transcription of a duplicate gene (e.g., PMP22 gene) and second gRNA complementarily binding to a target sequence present downstream of the promoter, and wild-type SpCas9, a double strand of the target sequence present upstream of the promoter complementarily binding to the first gRNA may be cleaved, and a double strand of the target sequence present downstream of the promoter complementarily binding to the second gRNA may be cleaved, thereby removing a nucleic acid fragment, that is, a promoter region, using the first gRNA, the second gRNA and SpCas9.

For example, when each of two CRISPR complexes consist of two gRNAs complementarily binding to different target sequences, for example, first gRNA complementarily binding to a target sequence present upstream of an enhancer controlling the transcription of a duplicate gene (e.g., PMP22 gene) and second gRNA complementarily binding to a target sequence present downstream of the enhancer, and wild-type SpCas9, the double strand of the target sequence present upstream of the enhancer complementarily binding to the first gRNA may be cleaved, and the double strand of the target sequence present downstream of the enhancer complementarily binding to the second gRNA may be cleaved, thereby removing a nucleic acid fragment, that is, an enhancer region, using the first gRNA, the second gRNA and SpCas9.

The ii) repairing of the damaged transcriptional regulatory region may be repairing or restoring performed through non-homologous end joining (NHEJ) and homology-directed repair (HDR).

The non-homologous end joining (NHEJ) is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because mutation in a significant functional domain is probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a target gene in which the expression is controlled by the transcriptional regulatory region targeted by the CRISPR complex may be performed using such NHEJ. A double strand or two single strands of the transcriptional regulatory region of a target gene may be cleaved using the CRISPR enzyme such as Cas9 or Cpf1, and the broken double strand or two single strands may have indels through the NHEJ, thereby inducing specific knockout of the target gene in which the expression is controlled by the transcriptional regulatory region.

In one example, the double strand of the transcriptional regulatory region of a target gene may be cleaved using the CRISPR complex, and various indels (insertions and deletions) may be generated at a repaired region by repairing through NHEJ.

The term "indel" refers to a variation formed by inserting or deleting a partial nucleotide into/from the nucleotide sequence of DNA. Indels may be introduced into the target sequence during repair by HDR or NHEJ, when the gRNA-CRISPR enzyme complex, as described above, cleaves a target sequence in the transcriptional regulatory region of a target gene.

The homology directed repairing (HDR) is a correction method without an error, which uses a homologous sequence as a template to repair or restore the damaged transcriptional regulatory region, and generally, to repair or restoration broken DNA, that is, to restore innate information of cells, the broken DNA is repaired using information of a complementary nucleotide sequence which is not modified or information of a sister chromatid. The most common type of HDR is homologous recombination (HR). HDR is a repair or restore method usually occurring in the S or G2/M phase of actively dividing cells.

To repair or restore damaged DNA using HDR, rather than using a complementary nucleotide sequence or sister chromatin of the cells, a DNA template artificially synthesized using information of a complementary nucleotide sequence or homologous nucleotide sequence, that is, a nucleic acid template including a complementary nucleotide sequence or homologous nucleotide sequence may be provided to the cells, thereby repairing the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be a nucleic acid sequence or nucleic acid fragment for correcting the transcriptional regulatory region of the target gene modified by a mutation to a normal gene, or a gene or nucleic acid to be expressed in cells, but the present invention is not limited thereto.

In one example, a double or single strand of the transcriptional regulatory region of a target gene acid may be cleaved using the CRISPR complex, a nucleic acid template including a nucleotide sequence complementary to a nucleotide sequence adjacent to the cleavage site may be provided to cells, and the cleaved nucleotide sequence of the transcriptional regulatory region of the target gene may be repaired or restored through HDR.

Here, the nucleic acid template including the complementary nucleotide sequence may have a complementary nucleotide sequence of the broken DNA, that is, a cleaved double or single strand, and further include a nucleic acid sequence or nucleic acid fragment to be inserted into the broken DNA. An additional nucleic acid sequence or nucleic acid fragment may be inserted into the broken DNA, that is, a cleaved site of the transcriptional regulatory region of the target gene using the nucleic acid template including the complementary nucleotide sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting the transcriptional regulatory region of a target gene modified by a mutation to a normal gene or a gene or nucleic acid to be expressed in cells. The complementary nucleotide sequence may be a nucleotide sequence having complementary bonds with broken DNA, that is, right and left nucleotide sequences of the cleaved double or single strand of the transcriptional regulatory region of the target gene. Alternatively, the complementary nucleotide sequence may be a nucleotide sequence having complementary bonds with broken DNA, that is, 3' and 5' ends of the cleaved double or single strand of the transcriptional regulatory region of the target gene. The complementary nucleotide sequence may be a 15 to 3000-nt sequence, a length or size of the complementary nucleotide sequence may be suitably designed according to a size of the nucleic acid template or the transcriptional regulatory region of the target gene. Here, the nucleic acid template may be a double- or single-stranded nucleic acid, and may be linear or circular, but the present invention is not limited thereto.

In another example, a double- or single-strand of the transcriptional regulatory region of a target gene is cleaved using the CRISPR complex, a nucleic acid template including a homologous nucleotide sequence with a nucleotide sequence adjacent to a cleavage site is provided to cells, and the cleaved nucleotide sequence of the transcriptional regulatory region of the target gene may be repaired or restored by HDR.

Here, the nucleic acid template including the homologous nucleotide sequence may have a homologous nucleotide sequence of the broken DNA, that is, a cleaved double- or single-strand, and further include a nucleic acid sequence or nucleic acid fragment to be inserted into the broken DNA. An additional nucleic acid sequence or nucleic acid fragment may be inserted into broken DNA, that is, a cleaved site of the transcriptional regulatory region of a target gene using the nucleic acid template including a homologous nucleotide sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting the transcriptional regulatory region of a target gene or nucleic acid modified by a mutation to a normal gene, or a gene or nucleic acid to be expressed in cells. The homologous nucleotide sequence may be a nucleotide sequence having homology with the broken DNA, that is, the right and left nucleotide sequence of the cleaved double-strand of the transcriptional regulatory region. Alternatively, the complementary nucleotide sequence may be a nucleotide sequence having homology with broken DNA, that is, the 3' and 5' ends of a cleaved double or single strand of the transcriptional regulatory region. The homologous nucleotide sequence may be a 15 to 3000-nt sequence, and a length or size of the homologous nucleotide sequence may be suitably designed according to a size of the nucleic acid template or the transcriptional regulatory region of a target gene. Here, the nucleic acid template may be a double- or single-stranded nucleic acid, and may be linear or circular, but the present invention is not limited thereto.

Other than the NHEJ and HDR, there are various methods for repairing or restoring a damaged transcriptional regulatory region. For example, the method of repairing or restoring a damaged transcriptional regulatory region may be single-strand annealing, single-strand break repair, mismatch repair, nucleotide cleavage repair or a method using the nucleotide cleavage repair.

The single-strand annealing (SSA) is a method of repairing double strand breaks between two repeat sequences present in a target nucleic acid, and generally uses a repeat sequence of more than 30 nucleotides. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

The SSA, similar to HDR, utilizes a complementary sequence, that is, a complementary repeat sequence, and in contrast, does not requires a nucleic acid template for modifying or correcting a target nucleic acid sequence.

Single strand breaks in a genome are repaired through a separate mechanism, single-strand break repair (SSBR), from the above-described repair mechanisms. In the case of single-strand DNA breaks, PARP1 and/or PARP2 recognizes the breaks and recruits a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing is generally involved in repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a single nucleotide. After DNA gap filling, a DNA ligase promotes end joining.

The mismatch repair (MMR) works on mismatched DNA nucleotides. Each of an MSH2/6 or MSH2/3 complex has ATPase activity and thus plays an important role in recognizing a mismatch and initiating a repair, and the MSH2/6 primarily recognizes nucleotide-nucleotide mismatches and identifies one or two nucleotide mismatches, but the MSH2/3 primarily recognizes a larger mismatch.

The base excision repair (BER) is a repair method which is active throughout the entire cell cycle, and used to remove a small non-helix-distorting base damaged region from the genome. In the damaged DNA, damaged nucleotides are removed by cleaving an N-glycoside bond joining a nucleotide to the phosphate-deoxyribose backbone, and then the phosphodiester backbone is cleaved, thereby generating breaks in single-strand DNA. The broken single strand ends formed thereby were removed, a gap generated due to the removed single strand is filled with a new complementary nucleotide, and then an end of the newly-filled complementary nucleotide is ligated with the backbone by a DNA ligase, resulting in repair of the damaged DNA.

The nucleotide excision repair (NER) is an excision mechanism important for removing large helix-distorting damage from DNA, and when the damage is recognized, a short single-strand DNA segment containing the damaged region is removed, resulting in a single strand gap of 22 to 30 nucleotides. The generated gap is filled with a new complementary nucleotide, and an end of the newly filled complementary nucleotide is ligated with the backbone by a DNA ligase, resulting in the repair of the damaged DNA.

Effects of artificially manipulating the transcriptional regulatory region of a target gene by the gRNA-CRISPR enzyme complex may be largely knockout (knock-out), knockdown, knockin (knock-in) and increased expression.

The term "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when the transcriptional regulatory region of a target gene is edited using the gRNA-CRISPR enzyme complex, that is, the CRISPR complex, the transcriptional regulatory region of the target gene may be cleaved using the CRISPR complex. The transcriptional regulatory region damaged using the CRISPR complex may be repaired by NHEJ. In the damaged transcriptional regulatory region, an indel is generated by NHEJ and thus the damaged transcriptional regulatory region is inactivated, thereby inducing target gene or chromosome-specific knockout.

In another example, when the transcriptional regulatory region of a target gene is edited using the gRNA-CRISPR enzyme complex, that is, the CRISPR complex and a donor, the transcriptional regulatory region of the target gene may be cleaved using the CRISPR complex. The transcriptional regulatory region damaged using the CRISPR complex may be repaired by HDR using a donor. Here, the donor includes a homologous nucleotide sequence and a nucleotide sequence desired to be inserted. Here, the number of nucleotide sequences to be inserted may vary according to an insertion location or purpose. When the damaged transcriptional regulatory region is repaired using a donor, a nucleotide sequence to be inserted is inserted into the damaged nucleotide sequence region, and therefore, the transcriptional regulatory region may be inactivated, thereby inducing target gene or chromosome-specific knockout.

The term "knockdown" refers to a decrease in transcription and/or translation of a target gene or nucleic acid or the expression of a target protein. The onset of a disease may be prevented or a disease may be treated by regulating the overexpression of a gene or protein through the knockdown.

For example, when the transcriptional regulatory region of a target gene edited using the gRNA-CRISPR enzyme complex, that is, the CRISPR complex, the transcriptional regulatory region of the target gene may be cleaved using the CRISPR complex. The transcriptional regulatory region damaged using the CRISPR complex may be repaired by NHEJ. In the damaged transcriptional regulatory region, an indel is generated by NHEJ and thus the damaged transcriptional regulatory region is inactivated, thereby inducing target gene or chromosome-specific knockdown.

In another example, when the transcriptional regulartory region, for example, a promoter, of a target gene is deleted using two gRNA-CRISPR enzyme complexes, that is, two CRISPR complexes, a target sequence present upstream of the promoter and a target sequence present downstream of the promoter may be cleaved using the two CRISPR complexes. The promoter region cleaved by the two CRISPR complexes may be deleted, a cleaved end upstream of the cleaved promoter and a cleaved end downstream of the cleaved promoter may be repaired, and through this, the promoter is lost, resulting in inhibition of the transcription of a target gene or chromosome and induction of specific knockdown.

In another example, when the transcriptional regulatory region of a target gene is edited using the gRNA-CRISPR enzyme complex, that is, the CRISPR complex and a donor, the transcriptional regulatory region of the target gene may be cleaved using the CRISPR complex. The transcriptional regulatory region damaged using the CRISPR complex may be repaired by HDR using a donor. Here, the donor includes a homologous nucleotide sequence and a nucleotide sequence desired to be inserted. Here, the number of the nucleotide sequences to be inserted may vary according to an insertion location or purpose. When the damaged transcriptional regulatory region is repaired using a donor, a nucleotide sequence to be inserted is inserted into the damaged nucleotide sequence region, and therefore, the transcriptional regulatory region may be inactivated, thereby inducing target gene or chromosome-specific knockdown.

For example, when the transcriptional regulatory region of a target gene is edited using a gRNA-CRISPR inactive enzyme-transcription inhibitory activity domain complex, that is, a CRISPR-inactive complex including a transcription inhibitory activity domain, the CRISPR-inactive complex may specifically bind to the transcriptional regulatory region of the target gene, and the activity of the transcriptional regulatory region is inhibited by the transcription inhibitory activity domain included in the CRISPR-inactive complex, thereby inducing knockdown in which the expression of a target gene or chromosome is inhibited.

The term "knockin" refers to insertion of a specific nucleic acid or gene into a target gene or nucleic acid, and here, the "specific nucleic acid or gene" refers to a gene or nucleic acid of interest to be inserted or expressed. A mutant gene triggering a disease may be utilized in disease treatment by correction to normal or insertion of a normal gene to induce expression of the normal gene through the knockin.

In addition, the knockin may further need a donor.

For example, when a target gene or nucleic acid is edited using the gRNA-CRISPR enzyme complex, that is, the CRISPR complex and a donor, the target gene or nucleic acid may be cleaved using the CRISPR complex. The target gene or nucleic acid damaged using the CRISPR complex may be repaired by HDR using a donor. Here, the donor may include a specific nucleic acid or gene, and may be used to insert a specific nucleic acid or gene into the damaged gene or chromosome. Here, the inserted specific nucleic acid or gene may induce the expression of a protein.

The "increased expression" refers to an increase in the transcription and/or translation of a target gene or nucleic acid or the expression of a target protein, compared to before artificially manipulation. A disease may be prevented or treated by controlling the expression of an underexpressed or non-expressed gene or protein.

For example, when the transcriptional regulatory region of a target gene is edited using the gRNA-CRISPR enzyme complex, that is, the CRISPR complex, the transcriptional regulatory region of the target gene may be cleaved using the CRISPR complex. The transcriptional regulatory region damaged using the CRISPR complex may be repaired by NHEJ. In the damaged transcriptional regulatory region, an indel is generated by NHEJ, thereby increasing the activity of the transcriptional regulatory region and inducing the expression of a normal target gene or chromosome.

In One Exemplary Embodiment Disclosed in the Specification, the gRNA-CRISPR Enzyme Complex May Add an Artificial Manipulation or Modification to the Transcriptional Regulartory Region of a Duplicate Gene and/or a Region Adjacent to the Transcriptional Regulartory Region.

The gRNA-CRISPR enzyme complex may specifically recognize a target sequence in the transcriptional regulatory region of a duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The target sequence may be specifically recognized by gRNA of the gRNA-CRISPR enzyme complex, and therefore, the gRNA-CRISPR enzyme complex may be located near the recognized target sequence.

The target sequence may be a site or region in which an artificial modification occurs in the transcriptional regulatory region of a duplicate gene.

The target sequence may be a site or region in which an artificial modification occurs in the transcriptional regulartory region of a duplicate gene, or upstream and/or downstream of the transcriptional regulartory region.

A description of the target sequence is as described above.

In one exemplary embodiment, the target sequence may be one or more nucleotide sequences selected from the nucleotide sequences shown in Tables 1 to 9.

The gRNA-CRISPR enzyme complex may consist of a gRNA and a CRISPR enzyme.

The gRNA may include a guide domain capable of partially or completely complementarily binding to the guide nucleic acid-binding sequence of the target sequence in the transcriptional regulatory region of a duplicate gene.

The gRNA may include a guide domain capable of partially or completely complementarily binding with the guide nucleic acid-binding sequence of a target sequence located in the transcriptional regulartory region of a duplicate gene or in the region adjacent to the transcriptional regulartory region thereof.

The guide domain may be at least 70%, 75%, 80%, 85%, 90%, 95% or more complementary, or completely complementary to the guide nucleic acid-binding sequence.

The guide domain may include a nucleotide sequence complementary to the guide nucleic acid-binding sequence of the target sequence located in the transcriptional regulartory region of a duplicate gene or a region adjacent to the transcriptional regulartory region. Here, the complementary nucleotide sequence may include 0 to 5, 0 to 4, 0 to 3, or 0 to 2 mismatches.

The guide domain may include a guide sequence complementary to the guide nucleic acid-binding sequence of the target sequence located in the transcriptional regulartory region of a duplicate gene or a region adjacent to the transcriptional regulartory region.

In one exemplary embodiment, the guide sequence may be one or more nucleotide sequences selected from the nucleotide sequences shown in Tables 10 to 15.

The gRNA may include one or more domains selected from the group consisting of a first complementary domain, a linker domain, a second complementary domain, a proximal domain and a tail domain.

The CRISPR enzyme may be one or more selected from the group consisting of a Streptococcus pyogenes-derived Cas9 protein, a Campylobacter jejuni-derived Cas9 protein, a Streptococcus thermophilus-derived Cas9 protein, a Staphylococcus aureus-derived Cas9 protein, a Neisseria meningitidis-derived Cas9 protein and a Cpf1 protein. In one example, the editor protein may be a Campylobacter jejuni-derived Cas9 protein or a Staphylococcus aureus-derived Cas9 protein.

The gRNA-CRISPR enzyme complex may add various artificial manipulations or modifications to the transcriptional regulartory region of a duplicate gene and/or a region adjacent to the transcriptional regulartory region.

The artificially manipulated or modified transcriptional regulartory region of a duplicate gene and/or region adjacent to the transcriptional regulartory region may have one or more of the following modifications to a 1 to 50-bp contiguous nucleotide sequence located in a target sequence or adjacent to the 5' end and/or 3' end of the target sequence:

i) deletion of one or more nucleotides, ii) substitution of one or more nucleotides to nucleotides different from a wild-type gene, iii) insertion of one or more nucleotides, or iv) a combination of two or more selected from i) to iii).

For example, the artificially manipulated or modified transcriptional regulatory region of a duplicate gene may include deletion of one or more nucleotides in the 1b to 50-bp contiguous nucleotide sequence region located in a target sequence or adjacent to the 5' end and/or 3' end of the target sequence. In one example, the deleted nucleotides may be 1, 2, 3, 4 or 5 consecutive or non-consecutive base pairs. In another example, the deleted nucleotides may be a nucleotide fragment consisting of 2-bp or more consecutive nucleotides. Here, the nucleotide fragment may be 2 to 5, 6 to 10, 11 to 15, 16 to 20, 21 to 25, 26 to 30, 31 to 35, 36 to 40, 41 to 45, or 46 to 50 base pairs. In still another example, the deleted nucleotide may be two or more nucleotide fragments. Here, the two or more nucleotide fragments may be nucleotide fragments each having a non-consecutive nucleotide sequence, that is, one or more nucleotide sequence gaps, and may have two or more deletion sites due to the two or more deleted nucleotide fragments.

Alternatively, for example, the artificially manipulated or modified transcriptional regulatory region of a duplicate gene may include insertion of one or more nucleotides in the 1b to 50-bp contiguous nucleotide sequence region located in a target sequence or adjacent to the 5' end and/or 3' end of the target sequence. In one example, the inserted nucleotide may be 1, 2, 3, 4, or 5 consecutive base pairs. In another example, the inserted nucleotide may be a nucleotide fragment consisting of 5 or more consecutive base pairs. Here, the nucleotide fragment may be 5 to 10, 11 to 50, 50 to 100, 100 to 200, 200 to 300, 300 to 400, 400 to 500, 500 to 750, or 750 to 1000 base pairs. In still another example, the inserted nucleotides may be a partial or entire nucleotide sequence of a specific gene. Here, the specific gene may be a gene input from the outside, which is not included in a subject, such as human cells, with a duplication gene. Alternatively, the specific gene may be a gene included in a subject, such as human cells, with a duplication gene, for example, a gene present in the genome of a human cell.

Alternatively, for example, the artificially manipulated or modified transcriptional regulatory region of a duplicate gene may include the deletion and insertion of one or more nucleotides from/in a 1 to 50-bp contiguous nucleotide sequence region located in a target sequence or adjacent to the 5' end and/or 3' end of the target sequence. In one example, the deleted nucleotides may be 1, 2, 3, 4 or 5 consecutive or non-consecutive base pairs. Here, the inserted nucleotides may be 1, 2, 3, 4 or 5 base pairs; a nucleotide fragment; or a partial or entire nucleotide sequence of a specific gene, and the deletion and insertion may sequentially or simultaneously occur. Here, the inserted nucleotide fragment may be 5 to 10, 11 to 50, 50 to 100, 100 to 200, 200 to 300, 300 to 400, 400 to 500, 500 to 750, or 750 to 1000 base pairs. Here, the specific gene may be a gene input from the outside of a subject, such as human cells, with a duplication gene. Alternatively, the specific gene may be a gene included in a subject, such as human cells, with a duplication gene, for example, a gene present in the genome of a human cell. In another example, the deleted nucleotide may be a nucleotide fragment consisting of 2 base pairs or more. Here, the deleted nucleotide fragment may be 2 to 5, 6 to 10, 11 to 15, 16 to 20, 21 to 25, 26 to 30, 31 to 35, 36 to 40, 41 to 45, or 46 to 50 base pairs. Here, the inserted nucleotide may be 1, 2, 3, 4 or 5 base pairs; a nucleotide fragment; or a partial or entire nucleotide sequence of a specific gene, and the deletion and insertion may sequentially or simultaneously occur. In still another example, the deleted nucleotides may be two or more nucleotide fragments. Here, the inserted nucleotides may be 1, 2, 3, 4 or 5 base pairs; a nucleotide fragment; or a partial or entire nucleotide sequence of a specific gene, and the deletion and insertion may sequentially or simultaneously occur. In addition, the insertion may occur in a part or all of the deleted two or more sites.

The gRNA-CRISPR enzyme complex may add a variety of artificial manipulations or modifications to the transcriptional regulatory region of a duplicate gene according to the types of gRNA and a CRISPR enzyme.

In one example, when the CRISPR enzyme is a SpCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NGG-3' (N is A, T, G or C) PAM sequence present in a target region:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In another example, when the CRISPR enzyme is a CjCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNNNRYAC-3' (N is each independently A, T, C or G, R is A or G, and Y is C or T) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In still another example, when the CRISPR enzyme is a StCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNAGAAW-3' (N is each independently A, T, C or G, and W is A or T) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In one example, when the CRISPR enzyme is a NmCas9 protein, the artificially manipulated or modified transcriptional regulatory region of a duplicate gene may one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNNNGATT-3' (N is each independently A, T, C or G) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In another example, when the CRISPR enzyme is a SaCas9 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-NNGRR(T)-3' (refers to a sequence in which N is each independently A, T, C or G, R is A or G, and (T) is arbitrarily included) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

In still another example, when the CRISPR enzyme is a Cpf1 protein, the artificially manipulated or modified transcriptional regulatory region of a duplicate gene may include one or more of the following modifications in a 1 to 50-bp, 1 to 40-bp, 1 to 30-bp, or preferably, 1 to 25-bp contiguous nucleotide sequence region, which is located adjacent to the 5' end and/or 3' end of a 5'-TTN-3' (N is A, T, C or G) PAM sequence present in a target sequence:
  i) deletion of one or more nucleotides,
  ii) substitution of one or more nucleotides to nucleotides different from the wild-type gene,
  iii) insertion of one or more nucleotides, or
  iv) a combination of two or more selected from i) to iii).

The effect of artificially manipulating the transcriptional regulatory region of a duplicate gene by the gRNA-CRISPR enzyme complex may be knockout.

The expression of a protein encoded by a duplicate gene by the gRNA-CRISPR enzyme complex may be inhibited.

The effect of artificially manipulating the transcriptional regulatory region of a duplicate gene by the gRNA-CRISPR enzyme complex may be knockdown.

The expression of a protein encoded by a duplicate gene by the gRNA-CRISPR enzyme complex may be reduced.

The effect of artificially manipulating the transcriptional regulatory region of a duplicate gene by the gRNA-CRISPR enzyme complex may be knockin.

Here, the knockin effect may be induced by the gRNA-CRISPR enzyme complex and a donor additionally including an exogeneous nucleotide sequence or gene.

The effect of artificially manipulating the transcriptional regulatory region of a duplicate gene by the gRNA-CRISPR enzyme complex and the donor may be induced by expressing a peptide or protein encoded by the exogeneous nucleotide sequence or gene.

Here, the knockin effect may be induced by the gRNA-CRISPR enzyme complex and the donor including a nucleotide sequence desired to be inserted.

In One Exemplary Embodiment Disclosed in the Specification, the gRNA-CRISPR Enzyme Complex May Add an Artificial Manipulation or Modification to Delete the Transcriptional Regulartory Region of a Duplicate Gene.

The gRNA-CRISPR enzyme complex may specifically recognize a target sequence located upstream and/or downstream of the transcriptional regulartory region of a duplicate gene.

Here, the gRNA-CRISPR enzyme complex may include two types of gRNA-CRISPR enzyme complexes.

One of the two types of gRNA-CRISPR enzyme complexes may be a first gRNA-CRISPR enzyme complex specifically recognizing a target sequence located upstream of the transcriptional regulartory region of a duplicate gene.

The other one of the two types of gRNA-CRISPR enzyme complexes may be a second gRNA-CRISPR enzyme complex specifically recognizing a target sequence located downstream of the transcriptional regulartory region of the duplicate gene.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The target sequence may be specifically recognized by gRNA of the gRNA-CRISPR enzyme complex, and therefore, the gRNA-CRISPR enzyme complex may be located near the recognized target sequence.

The target sequence may be a site or region in which artificial cleavage occurs by the gRNA-CRISPR enzyme complex(es) located upstream and/or downstream of the transcriptional regulartory region of the duplicate gene.

A description of the target sequence is as described above.

In one exemplary embodiment, the target sequence may be one or more nucleotide sequences selected from the nucleotide sequences shown in Tables 7, 8 and 9.

The gRNA-CRISPR enzyme complex may consist of a gRNA and a CRISPR enzyme.

The gRNA may include a guide domain capable of partially or completely complementarily binding to the guide nucleic acid-binding sequence of the target sequence located upstream and/or downstream of the transcriptional regulartory region of the duplicate gene.

The guide domain may be at least 70%, 75%, 80%, 85%, 95% or more complementary, or completely complementary to the guide nucleic acid-binding sequence.

The guide domain may include a nucleotide sequence complementary to the guide nucleic acid-binding sequence of the target sequence located upstream and/or downstream of the transcriptional regulartory region of the duplicate gene. Here, the complementary nucleotide sequence may include 0 to 5, 0 to 4, 0 to 3, or 0 to 2 mismatches.

The gRNA may include one or more domains selected from the group consisting of a first complementary domain, a linker domain, a second complementary domain, a proximal domain and a tail domain.

The CRISPR enzyme may be one or more selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein. In one example, the editor protein may be a *Campylobacter jejuni*-derived Cas9 protein or a *Staphylococcus aureus*-derived Cas9 protein.

The gRNA-CRISPR enzyme complex may add an artificial manipulation or modification to delete the transcriptional regulartory region of a duplicate gene.

The artificial manipulation or modification may include the cleavage of a 1 to 50-bp contiguous nucleotide sequence, which is located in each of the target sequences located upstream and downstream of the artificially manipulated or modified transcriptional regulartory region of the duplicate gene or adjacent to the 5' end and/or 3' end of each target sequence.

Here, the cleavage may be double strand or single strand cleavage, which is generated by the gRNA-CRISPR enzyme complex.

The cleavage may occur upstream and downstream of the transcriptional regulartory region of a duplicate gene by the two types of gRNA-CRISPR enzyme complexes.

Here, one of the two types of gRNA-CRISPR enzyme complexes may be a first gRNA-CRISPR enzyme complex specifically recognizing the target sequence located upstream of the transcriptional regulartory region of the duplicate gene.

The other one of gRNA-CRISPR enzyme complexes may be a second gRNA-CRISPR enzyme complex specifically recognizing the target sequence located downstream of the transcriptional regulartory region of the duplicate gene.

Here, the first cleavage may take place upstream of the transcriptional regulartory region of the duplicate gene by the first gRNA-CRISPR enzyme complex.

The second cleavage may take place downstream of the transcriptional regulartory region of the duplicate gene by the second gRNA-CRISPR enzyme complex.

Here, the first cleavage and the second cleavage may take place simultaneously.

Here, the first cleavage and the second cleavage may take place sequentially.

Here, the first cleavage and the second cleavage may take place in reverse order.

The first cleavage and the second cleavage may take place upstream and downstream of the transcriptional regulartory region of the duplicate gene, and due to these cleavages, a fragment of the transcriptional regulartory region may be generated.

The fragment of the transcriptional regulartory region, which is generated by the first and second cleavages may be deleted or lost in DNA repairing.

Cleavage positions made by the two types of gRNA-CRISPR enzyme complexes, that is, a first cleavage part (a cleavage position upstream of the transcriptional regulartory region) and a second cleavage part (a cleavage position downstream of the transcriptional regulartory region), may be repaired through DNA repairing.

Here, the repairing may be repairing for linking the first cleavage part (3' end) and the second cleavage part (5' end).

Figure 39:
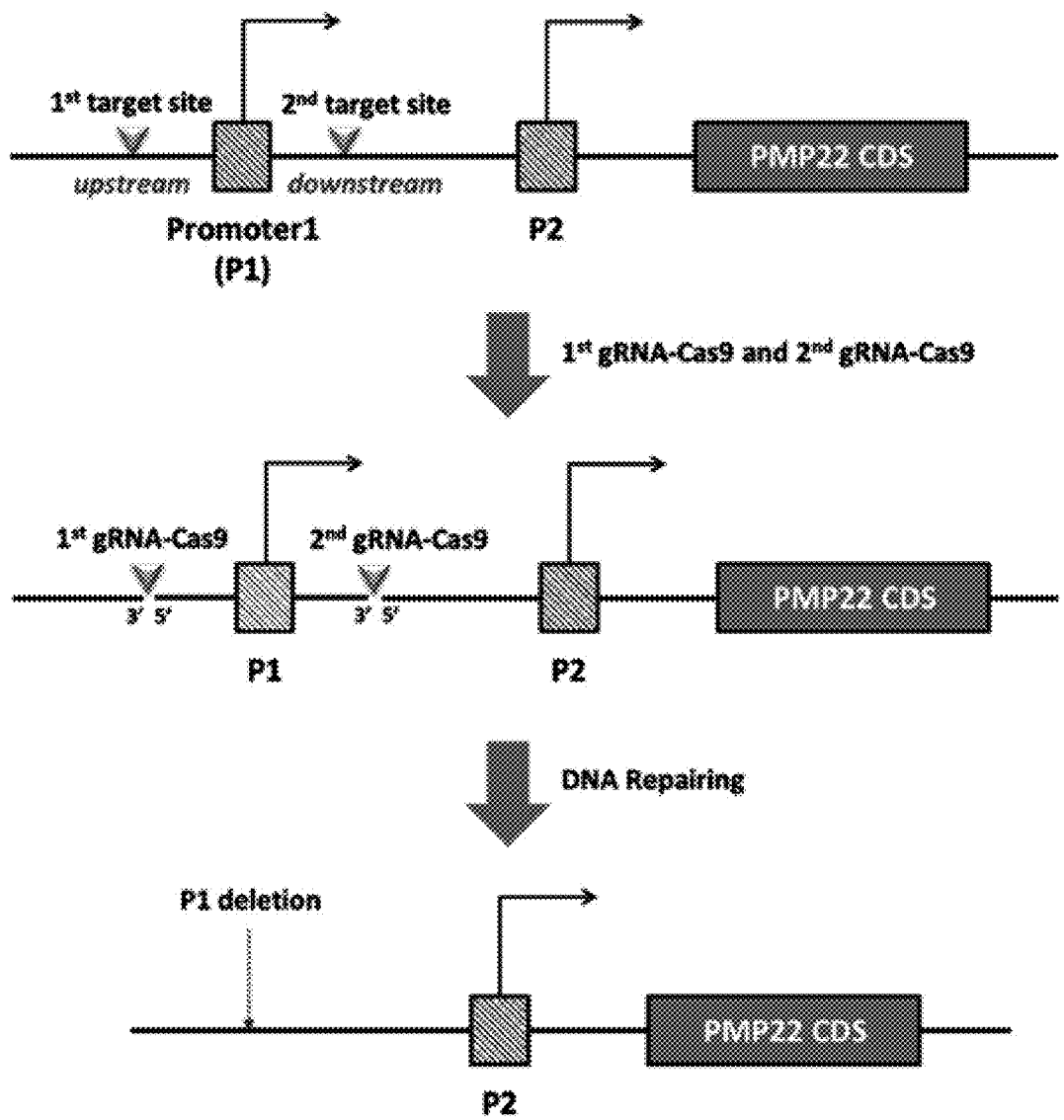
FIG. 39 illustrates the deletion of the transcriptional regulartory region of a duplicate gene using Cas9-sgRNA.

For example, a promoter of a duplicate gene may be deleted using a first gRNA-CRISPR enzyme complex targeting upstream of the promoter (e.g., P1 promoter, P2 promoter or both thereof) of the duplicate gene (e.g., PMP22) and a second gRNA-CRISPR enzyme complex targeting downstream of the promoter. Here, a part upstream of the promoter of the duplicate gene may be cleaved by the first gRNA-CRISPR enzyme complex, and a part downstream of the promoter of the duplicate gene may be cleaved by the second gRNA-CRISPR enzyme complex. Here, the first cleavage part (3' end) and the second cleavage part (5' end) are generated by the cleavages, and a nucleic acid fragment, that is, a promoter fragment (5'-promoter-3'), between the first cleavage part and the second cleavage part may be generated. The cleavage by the gRNA-CRISPR enzyme complex may be repaired through DNA repairing. Here, the repairing may be repairing for linking the first cleavage part (3' end) and the second cleavage part (5' end). A nucleic acid fragment, that is, the promoter fragment (5'-promoter-3') between the first cleavage part and the second cleavage part may be deleted through the repairing (FIG. 39). The deletion of the nucleic acid fragment, that is, the promoter fragment (5'-promoter-3'), may induce a knockdown effect of reducing the expression of the duplicate gene or a knockout effect of inhibiting or suppressing the expression.

One Aspect Disclosed in the Specification Relates to a Method of Controlling Expression.

One exemplary embodiment disclosed in the specification relates to a method of controlling the expression of a duplicate gene, which may be performed in vivo, ex vivo or in vitro.

In some embodiments, the method may include sampling a cell or a colony of cells from a human or non-human animal, and modifying the cell or cells. Culturing may occur in any step ex vivo. The cell or cells may be even reintroduced into a non-human animal or plant.

The method may be a method of artificially engineering eukaryotic cells, which includes introducing an expression control composition into a eukaryotic cell having a duplicate gene.

A description of the expression control composition is as described above.

In one embodiment, the expression control composition may include the following:

(a) a guide nucleic acid capable of targeting a target sequence located in the transcriptional regulatory region of a duplicate gene or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The guide nucleic acid and the editor protein may be present in one or more vectors in the form of individual nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

The guide nucleic acid, the editor protein and/or a donor may be present in one or more vectors in the form of individual nucleic acid sequence.

The introduction step may be performed in vivo or ex vivo.

For example, the introduction step may be performed by one or more methods selected from electroporation, liposomes, plasmids, viral vectors, nanoparticles and a protein translocation domain (PTD) fusion protein method.

For example, the viral vector may be one or more selected from the group consisting of a retrovirus, a lentivirus, an adenovirus, an adeno-associated virus (AAV), a vaccinia virus, a poxvirus and a herpes virus.

In another exemplary embodiment, the expression control composition may include:

i) a first guide nucleic acid capable of targeting a target sequence located upstream of the transcriptional regulartory region of a duplicate gene or a nucleic acid sequence encoding the same;

ii) a second guide nucleic acid capable of targeting a target sequence located downstream of the transcriptional regulartory region of a duplicate gene or a nucleic acid sequence encoding the same; and iii) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

The first guide nucleic acid, the second guide nucleic acid and the editor protein may be present in one or more vectors in the form of a nucleic acid sequence, or present by forming a complex by coupling of the guide nucleic acid and the editor protein.

Optionally, the expression control composition may further include a donor including a nucleic acid sequence desired to be inserted or a nucleic acid sequence encoding the same.

The first guide nucleic acid, the second guide nucleic acid and the editor protein, and/or a donor may be present in one or more vectors in the form of a nucleic acid sequence.

The introduction step may be performed in vivo or ex vivo.

For example, the introduction step may be performed by one or more methods selected from electroporation, liposomes, plasmids, viral vectors, nanoparticles and a protein translocation domain (PTD) fusion protein method.

For example, the viral vector may be one or more selected from the group consisting of a retrovirus, a lentivirus, an adenovirus, an adeno-associated virus (AAV), a vaccinia virus, a poxvirus and a herpes virus.

One Aspect Disclosed in the Specification Relates to a Method of Treating a Gene Duplication Disease Using a Composition for Controlling Expression to Treat a Gene Duplication Disease.

One exemplary embodiment disclosed in the specification relates to a use for treating a gene duplication disease using a method including administration of an expression control composition for artificially manipulating the transcriptional regulatory region of a duplicate gene into a subject to be treated.

Here, the subject to be treated may include mammals including a human, a primate such as monkey, and a rodent such as a mouse and a rat.

A description of the gene duplication disease is as described above.

In one exemplary embodiment, a gene duplication disease may be a disease generated by the duplication of a PMP22 gene.

In one example, a disease generated by the duplication of the PMP22 gene may be Charcot-Marie-Tooth Type 1A (CMT1A), Dejerine-Sottas disease (Dejerine-Sottas syndrome, DSS), congenital hypomyelination neuropathy (CHN), or Roussy-Levy syndrome (RLS).

Charcot-Marie-Tooth Disease (CMT)

CMT disease is a hereditary disease caused by gene duplication that occurs in human chromosomes, and genes involved in the development of peripheral nerves in the hands and feet are duplicated by mutations, thereby causing a deformation such as a shape like an inverted champagne bottle. The CMT disease is a relatively common neurological genetic disease that occurs in 36 out of 100,000 people in the United States, and the number of patients is 2.8 million worldwide and estimated to be around 17,000 even in Korea. The CMT disease is largely classified into a total of 5 types of CMT1, CMT2, CMT3, CMT4, and CMTX according to the inherited aspect, CMT1, CMT2 and CMT3 are dominant and inherited with a 50% probability in children, and CMT4 is recessive and inherited with a probability of 25%. CMT1 and CMT2 are dominantly inherited in most domestic patients (80% and 20 to 40%, respectively), and CMT3 and CMT4 are extremely rare. CMTX is inherited through the maternal line along X chromosomes, but the frequency thereof is 10 to 20%. CMT1 is a disease caused by the inability to perform the normal process of gene expression due to gene duplication involved in the formation of proteins of the myelin sheath surrounding the neuronal axon. CMT1 is classified into 3 types. CMT1A is an autosomal dominant genetic disease, caused by duplication of the PMP22 gene located on chromosome No. 17 17p11.2-p12, resulting in the structural and functional abnormalities of the myelin sheath caused by the overexpression of the PMP22, which is an important component of the myelin sheath.

CMT2 is associated with axonal abnormalities, and is a neuropathy with a considerably reduced action potential of motor sensory nerves while the nerve conduction velocity is close to the normal state, and CMT3 occurs in early childhood as an extremely rare autosomal recessive genetic disease and is a type in which clinical symptoms and a decrease in nerve conduction velocity are very severe. CMT4 is also a type in which the onset age is early and clinical symptoms are severe, is autosomal recessive inherited, and CMTX occurs while being associated with X chromosomes and the symptoms thereof in men are more severe than those in women.

Dejerine-Sottas Disease (Dejerine-Sottas Syndrome, DSS)

DSS is a demyelinating motor sensory neuropathy occurring at an early age and is a disease which is usually autosomal dominantly inherited but is also autosomal recessively inherited, exhibits a severe demyelinating neuropathy, exhibits abnormalities of motor nerves from infancy, and is characterized by exhibiting very slow nerve conduction and an increase in specific proteins in cerebrospinal fluid. Dejerine-Sottas disease has a very rapid rate of progression, and is characterized in that gait disturbance starts from an early age and is also inherited, but also occurs sporadically. Similarly to CMT1A, PMP22 duplication is found among some patients with DSS, and in addition, it was confirmed that a missense mutation of the corresponding gene was present.

Congenital Hypomyelination Neuropathy (CHN)

CHN is a nervous system disease whose symptoms appear immediately after birth, and as the main symptoms thereof, respiratory failure, muscle weakness, muscle movement dissonance, a decrease in muscle tonicity, areflexia, motor incoordination (kinesioneurosis; ataxia), paralysis or dysesthesia appear, and affect men and women at the same rate. CHN is a genetic disease, in which a disorder occurs in motor and sensory nerves, and is characterized by a reduction in myelin sheath formation while demyelination and remyelination of the myelin sheath are repeated.

Roussy-Levy Syndrome (RLS)

RLS is a rare type of hereditary motor sensory neuropathy and was first described by Roussy and Levy, et al., in 1926, and is a case where tremors of limbs, gait loss, and the like are more severe than other hereditary motor sensory neuropathies, but the same symptoms were later found in various hereditary motor sensory neuropathy subtypes, so that RLS is currently regarded as one symptom that appears in the hereditary motor sensory neuropathy. For RLS, a mutation of an MPZ gene as a myelin protein zero gene was found in a genetic test of patients who were first reported to have RLS, and in other patients, a case where there is a duplication of the PMP22 gene as a gene of myelin protein 22 of the peripheral nerves has been reported.

In one exemplary embodiment, the gene duplication disease may be a disease generated by the duplication of a PLP1 gene.

In one example, the disease generated by the duplication of the PLP1 gene may be Pelizaeus-Merzbacher disease (PMD).

Pelizaeus-Merzbacher Disease (PMD)

Pelizaeus-Merzbacher disease (PMD) is a very rare sudanophilic leukodystrophy exhibiting various neurological symptoms due to dysmyelination of the white matter of the central nervous system. The prevalence thereof is estimated to be approximately 1/400,000. In 1885, Pelizaeus first reported one family having developmental cerebral diplegia, which is inherited chromosome X-dependently, and characterized by nystagmus, ataxia, stiffness, and acquired microcephaly, shown at the beginning of the disease. The clinical signs of PMD appear early in infancy and childhood, and the characteristic clinical symptoms of PMD are pendular nystagmus, wheezing, psychomotor development disorder or degeneration, ataxia, irregular movement, involuntary movement, oral dysfunction, and mental retardation.

PMD is a neurodegenerative disease or leukodystrophy caused by the dysmyelination of the white matter of the central nervous system due to the decrease in oligodendrocytes and the synthetic disorder of proteolipid protein (PLP). Proteolipid protein (PLP) is a protein most abundantly present in the myelin sheath of the central nervous system, and is abnormally expressed or produced due to the mutation of the PLP1 gene (Xq22) located on the long arm of chromosome X, causing dysmyelination in the central nervous system. PMD has affinity to Sudan Red in brain tissue pathology, which is caused by some azo compounds reacting with lipids, refers to the breakdown of the myelin sheath, and is observed in the centrum semiovale, the cerebellum, and the brain stem. However, since breakdown products are not found, the cause of PMD is considered to be dysmyelination or hypomyelination, rather than demyelination. Generally, the connate form of PMD is characterized by total dysmyelination, and the classic form of PMD is characterized by partial dysmyelination. When partial dysmyelination occurs, the normal medullated white matter shows a tigroid appearance. Axons and neurons of lesions with dysmyelination are generally well preserved, the number of rare oligodendrocytes is reduced, increases in astrocytes and fibrous gliosis are found in the white matter, and atrophy is found in the micropolygyria and the granular layer of the cerebellum. In 80% or more of male patients, the mutation of the PLP1 gene (Xq22) located on the long arm of chromosome X is found. Among these patients, 10 to 30% have a point mutation in the gene, and in this case, are known to exhibit more severe clinical symptoms. A phenomenon of duplicating an entire PLP1 gene is more frequently found in 60 to 70% or more of PMD patients. Recently, since PLP1 gene is located on chromosome X, generally, PMD is chromosome X-dependently inherited, has a family history, and mostly occurs in males. However, the pathogenesis of PMD may not be explained only with the PLP1 gene, and sometimes, the connate form of PMD is autosomal recessive, the adult form of PMD is autosomal dominant, or PMD sporadically occurs without a family history. Rarely, it has been reported that the symptoms of PMD are rarely expressed even in females.

In one exemplary embodiment, a gene duplication disease may be a disease that occurs due to the duplication of an MECP2 gene.

In one example, the disease caused by the duplication of the MECP2 gene may be an MECP2 duplication syndrome.

MECP2 Duplication Syndrome

A brain disease, called MECP2 duplication syndrome, is caused by the duplication of genetic material, which occurs in a specific region of chromosome X having the MECP2 gene. This disease is accompanied by a variety of symptoms, and includes symptoms such as low muscle tone, developmental delays, respiratory infection, speech abnormalities, seizures, autistic behaviors and serious intellectual disability.

This disease is a genetic disorder, but even occurs without a family history. MECP2 duplication syndrome mainly occurs in males, and Rett Syndrome occurring due to the MECP2 gene deficiency mainly occurs in females.

In one exemplary embodiment, the gene duplication disease may be a disease caused by the duplication of an RAI1 gene.

In one example, a disease caused by the RAI1 gene duplication may be Potocki-Lupski syndrome (PTLS).

Potocki-Lupski Syndrome (PTLS)

PTLS is a contiguous gene syndrome having microduplication of 11.2 region (17p11.2) on the short arm of chromosome 17, and the first study case for PTLS was reported in 1996. PTLS is known to occur due to 1.3-3.7 Mb duplication at 17p11.2 having a retinoic acid induced-1 (RAI1) gene. PTLS is considered a rare disease, and its incidence is expected to be one in 20,000 newborn babies. PTLS is characterized by various connate abnormalities and mental retardation, and 80% of the cases of PTLS have autism spectrum disorder. In addition, other unique characteristics of PTLS include sleep apnea, structural cardiovascular abnormalities, abnormal social behavior, learning disability, attention deficit disorder, obsessive behavior, and a small height.

In one exemplary embodiment, the gene duplication disease may be a disease caused by the duplication of an ELN gene.

In one example, a disease caused by the ELN gene duplication may be Williams Beuren syndrome (WBS).

Williams Beuren Syndrome (WBS)

WBS is a proximal gene syndrome associated with the abnormality of chromosome 7 having characteristic clinical findings, and the incidence of WBS is one out of 20,000 newborn babies. As the cause of microdeletion of the proximal part of the long arm of chromosome 7 (7q11.23), in this region, various genes including an elastin gene associated with the production of an elastin protein forming elastic tissue such as blood vessel walls and an LIMK1 gene associated with cognitive ability are located. Due to the deletion of such genes, various and characteristic appearances and clinical symptoms are shown. The microdeletion of 7q11.23 naturally occurs in most cases, and a family history of the microdeletion is rarely shown. Children with WBS have characteristic appearances such as a slightly raised, small nose tip, a long philtrum, a wide mouth, full lips, small cheeks (Malar hypoplasia), puffy eyes, failure of nail formation, and hallux valgus.

In one exemplary embodiment, the gene duplication disease may be a disease caused by the duplication of a JAGGED1 gene.

In one example, the disease caused by the JAGGED1 gene duplication may be Alagille syndrome (AS).

Alagille Syndrome (AS)

AS is a syndrome in which the number of bile ducts in the liver is considerably reduced, induces cholestasis, and is accompanied with abnormalities in the cardiovascular system, skeletal system, eye balls, face, pancreas, and nerve development. According to foreign reports, the incidence of AS is $1/100,000$, and due to the characteristic of the disease, if including patients with minor symptoms, the incidence thereof is expected to be higher. AS occurs due to the abnormality of the JAGGED1 gene located on the short arm of chromosome 20. It is currently known that causative mutation or duplication can be found in 50 to 70% of cases through genetic testing.

The clinical symptoms of AS are generally expressed within three months after birth. AS is commonly found in the neonatal period because of contiguous jaundice and cholestasis, and found in the childhood because of chronic liver disease, and even found in the late adulthood. Since AS has various clinical symptoms and can be inherited incompletely, it may be difficult to be diagnosed. Most patients have symptoms of jaundice and cholestasis, itching resulting therefrom and progressive liver failure in infancy. Jaundice is observed in most patients, and lasts until late childhood in more than half of the patients. Itching resulting from cholestasis occurs, and some children have xanthoma in subcutaneous tissue. While the synthesis function in the liver is relatively well preserved, approximately 20% of the patients develop cirrhosis and liver failure.

In one exemplary embodiment, the gene duplication disease may be a disease caused by the duplication of a SNCA gene.

In one example, the disease caused by the SNCA gene duplication may be Parkinson's disease.

Parkinson's Disease

Parkinson's disease is a disease commonly exhibiting tremors, muscle stiffness, and movement disorders such as slowness of movement. If Parkinson's disease is not properly treated, movement disorders gradually progress, resulting in difficulty in walking and daily activity. Parkinson's disease is a disease that occurs mainly in the elderly, and with age, the risk of the onset of the disease may increase gradually. Although there is no accurate statistical data in Korea, it is estimated that Parkinson's disease occurs at a rate of 1 to 2 out of 1,000 people. Most cases of Parkinson's disease, which occur in the elderly, have been known to be less influenced by genetic factors through various studies. However, some cases of Parkinson's disease, which occur at younger ages under 40, have been known to be associated with genetic factors.

Parkinson's disease is a disease caused by a lowered dopamine concentration as dopamine neurons present in the substantia nigra gradually die. Another pathological characteristic of Parkinson's disease is the formation of a protein aggregate, which is called a Lewy body, observed in brain autopsies. The Lewy body has a protein called α-synuclein, which is the major component, and the Lewy body and α-synuclein are also associated with other diseases such as Lewy body dementia and synucleinopathy. The α-synuclein aggregation begins in the vagus nerve and anterior olfactory nucleus, rather than the midbrain, and then spreads to the cerebral cortex at the last stage via the midbrain. The hypothesis in which α-synuclein widely spreads to various regions of the brain according to the progression of Parkinson's disease is supported by recent reports in which α-synuclein is released from one cell and then transmitted to another cell.

The heritability of Parkinson's disease was first suggested by the report in which mutants (A53T and A30P) of α-synuclein, which is the major component of the Lewy body, induce Parkinson's disease. Afterward, duplication and triplication of an α-synuclein gene (SNCA) had been reported to be other causes of Parkinson's disease. This means that overexpression of a normal protein, in addition to the mutation of an α-synuclein protein, leads to accumulation of α-synuclein in cells and formation of an aggregate, resulting in the onset of Parkinson's disease.

In one exemplary embodiment, the gene duplication disease may be a disease caused by the duplication of an APP gene.

In one example, the disease caused by the APP gene duplication may be Alzheimer's disease.

Alzheimer's Disease

Alzheimer's disease is a disease caused by a brain abnormality leading to progressive degeneration of memory. In addition, Alzheimer's disease leads to dementia, which brings serious loss of intellectual functions (thinking, memory and reasoning) which is enough to interfere with daily life. In most cases, Alzheimer's disease occurs at ages beyond 65, but may rarely occur before 65. In the United States, approximately 3% of people at the age of 65 to 74, approximately 19% of people at the age of 75 to 84, and approximately 50% of people at the age of 85 or more suffer from Alzheimer's disease. In Korea, according to a recent study based on rural areas, it has been reported that approximately 21% of people at the age of 60 or more have dementia, and approximately 63% of the affected people have Alzheimer's dementia. In 2006, 266,000 people suffered from Alzheimer's disease in the world. It is anticipated that Alzheimer's disease will affect one out of 85 people by 2050.

The characteristics of the disease vary from person to person, but some of them are common in all affected people. Early symptoms tend to be mistaken for simple symptoms caused by aging or symptoms caused by stress. In the early stages of the illness, the affected people undergo common short-term memory loss, in which names, dates and places disappear from memory. If the disease becomes worse, symptoms of confusion, intensive behavior, a bipolar disorder, a speech disorder, and long-term memory loss are shown. Consequently, physical functions are lost, leading to death. Because of different symptoms per individual, it is difficult to predict how the disease will affect a person. When Alzheimer's disease is suspected, diagnosis in which thinking or acting ability is tested is usually performed, and if necessary, a brain test is performed. However, for accurate diagnosis, it is necessary to investigate cranial nerves. Although Alzheimer's disease occurs, it generally takes much time until the disease is completely diagnosed, and therefore the disease may progress for several years without diagnosis. When the disease occurs, average life expectancy is 7 years, and less than 3% of the affected people live 14 years after diagnosis.

Alzheimer's disease is classified as a neurodegenerative disease. The cause of the disease has not been fully understood, but is estimated that amyloid plaques modify a normal Alzheimer's disease protein to form a plaque mass, resulting in the loss of an intrinsic function. Alzheimer's disease has histopathological features including overall brain atrophy, ventricular enlargement, neurofibrillary tangle and neuritic plaques.

In one exemplary embodiment, the gene duplication disease may be a disease caused by the duplication of a SOX3 gene, TBX1 gene, NSD1 gene, MMP23 gene or LMB1 gene.

In one example, the gene duplication disease may be X-linked hypopituitarism (XLHP), velocardiofacial syndrome (VCFS), growth retardation syndrome, premature closure cranial sutures or autosomal dominant leukodystrophy (ADLD).

In one exemplary embodiment, the gene duplication disease may be a cancer generated by the duplication of an oncogene.

Here, the cancer gene may be an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene or an AKT2 gene.

In one example, the cancer may be breast cancer, cervical cancer, colorectal cancer, esophageal cancer, gastric cancer, glioblastoma, head and neck cancer, hepatocellular cancer, neuroblastoma, ovarian cancer, sarcoma or small cell lung cancer.

One exemplary embodiment disclosed in the specification provides a pharmaceutical composition including an expression control composition that may artificially manipulate or delete the transcriptional regulartory region of a duplicate gene.

A description of the expression control composition is as described above.

In one exemplary embodiment, the expression control composition may include the following:

(a) a guide nucleic acid capable of targeting a target sequence located in the transcriptional regulatory region of a duplicate gene or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

Each of the guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the guide nucleic acid, the editor protein and/or a donor may be present in one or more vectors in the form of a nucleic acid sequence.

The pharmaceutical composition may further include an additional element.

The additional element may include a suitable carrier for the delivery into the body of a subject.

In one exemplary embodiment, the expression control composition may include the following:

i) a first guide nucleic acid capable of targeting a target sequence located upstream of the transcriptional regulartory region of a duplicate gene or a nucleic acid sequence encoding the same;

ii) a second guide nucleic acid capable of targeting a target sequence located downstream of the transcriptional regulartory region of a duplicate gene or a nucleic acid sequence encoding the same; and iii) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulartory region is as described above.

Each of the first guide nucleic acid, the second guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the first guide nucleic acid, the second guide nucleic acid and the editor protein, and/or a donor may be present in one or more vectors in the form of a nucleic acid sequence.

The pharmaceutical composition may further include an additional element.

The additional element may include a suitable carrier for the delivery into the body of a subject.

One exemplary embodiment disclosed in the specification provides a method of treating a gene duplication disease, which includes administering a composition for gene engineering to an organism having a gene duplication disease to treat the gene duplication disease.

The treatment method may be a treatment method for controlling the expression of a duplicate gene by manipulating or deleting the transcriptional regulartory region of a duplicate gene present in the living body. Such a treatment method may be performed by directly injecting the expression control composition for manipulating or deleting the transcriptional regulartory region of a duplication gene present in the living body.

A description of the expression control composition is as described above.

In one exemplary embodiment, the expression control composition may include the following:

(a) a guide nucleic acid capable of targeting a target sequence located in the transcriptional regulatory region of a duplicate gene or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulatory region is as described above.

Each of the guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the guide nucleic acid, the editor protein and/or a donor may be present in one or more vectors in the form of a nucleic acid sequence.

Here, the vector may be a plasmid or viral vector.

Here, the viral vector may be one or more selected from the group consisting of a retrovirus, a lentivirus, an adenovirus, an adeno-associated virus (AAV), a vaccinia virus, a poxvirus and a herpes virus.

In another exemplary embodiment, the expression control composition may include the following:

i) a first guide nucleic acid capable of targeting a target sequence located upstream of the transcriptional regulatory region of a duplicate gene or a nucleic acid sequence encoding the same;

ii) a second guide nucleic acid capable of targeting a target sequence located downstream of the transcriptional regulartory region of a duplicate gene or a nucleic acid sequence encoding the same; and iii) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same.

Here, the duplicate gene may be one or more genes selected from the group consisting of a PMP22 gene, a PLP1 gene, an MECP2 gene, a SOX3 gene, an RAI1 gene, a TBX1 gene, an ELN gene, a JAGGED1 gene, an NSD1 gene, an MMP23 gene, an LMB1 gene, a SNCA gene and an APP gene.

Alternatively, the duplicate gene may be one or more genes selected from the group consisting of an MYC gene, an ERBB2 (HER2) gene, a CCND1 (Cyclin D1) gene, an FGFR1 gene, an FGFR2 gene, a HRAS gene, a KRAS gene, an MYB gene, an MDM2 gene, a CCNE (Cyclin E) gene, an MET gene, a CDK4 gene, an ERBB1 gene, an MYCN gene and an AKT2 gene.

A description of the transcriptional regulartory region is as described above.

Each of the first guide nucleic acid, the second guide nucleic acid and the editor protein may be present in one or more vectors in the form of a nucleic acid sequence, or by forming a complex through coupling of the guide nucleic acid and the editor protein.

Optionally, the expression control composition may further include a donor including a nucleic acid sequence desired to be inserted or a nucleic acid sequence encoding the same.

Each of the first guide nucleic acid, the second guide nucleic acid and the editor protein, and/or a donor may be present in one or more vectors in the form of a nucleic acid sequence.

Here, the vector may be a plasmid or viral vector.

Here, the viral vector may be one or more selected from the group consisting of a retrovirus, a lentivirus, an adenovirus, an adeno-associated virus (AAV), a vaccinia virus, a poxvirus and a herpes virus.

A description of the gene duplication disease is as described above.

The gene duplication disease may be Charcot-Marie-Tooth Type 1A (CMT1A), Dejerine-Sottas disease (DSD), congenital hypomyelination neuropathy (CHN), Roussy-Levy syndrome (RLS), Pelizaeus-Merzbacher disease (PMD), MECP2 duplication syndrome, X-linked hypopituitarism (XLHP), Potocki-Lupski syndrome (PTLS), velocardiofacial syndrome (VCFS), Williams Beuren syndrome (WBS), Alagille syndrome (AS), growth retardation syndrome, premature closure cranial sutures, autosomal dominant leukodystrophy (ADLD), Parkinson's disease or Alzheimer's disease.

In addition, the gene duplication disease may be breast cancer, cervical cancer, colorectal cancer, esophageal cancer, gastric cancer, glioblastoma, head and neck cancer, hepatocellular cancer, neuroblastoma, ovarian cancer, a sarcoma or small cell lung cancer.

The expression control composition may be administered to a treatment subject with a gene duplication disease.

The treatment subject may include mammals including a human, a primate such as monkey, and a rodent such as a mouse and a rat.

The expression control composition may be administered to the treatment subject.

The administration may be performed by injection, transfusion, implantation or transplantation.

The administration may be performed via an administration route selected from intraneural, subretinal, subcutaneously, intradermal, intraocular, intravitreal, intratumoral, intranodal, intramedullary, intramuscular, intravenous, intralymphatic, and intraperitoneal routes.

A dose of the expression control composition (a pharmaceutically effective amount to obtain a predetermined, desired effect) is approximately $10^4$ to $10^9$ cells/kg (body weight of an administration subject), for example, approximately $10^5$ to $10^6$ cells/kg (body weight), and may be selected from all integers in the numerical range, but the present invention is not limited thereto. The composition may be suitably prescribed in consideration of an age, health condition and body weight of an administration subject, the type of concurrent treatment, and if possible, the frequency of treatment and a desired effect.

When the transcriptional regulartory region of a duplicate gene is artificially manipulated or deleted by the method and composition according to some exemplary embodiments disclosed in the specification, the expression of mRNA and/or a protein of the duplicate gene may be controlled, thereby achieving an effect of normally controlling the expression of a duplicate gene abnormally expressed.

EXAMPLES

Hereinafter, the present invention will be described in further detail with reference to examples.

These examples are merely provided to describe the present invention in further detail, and it might be obvious to those of ordinary skill in the art that the scope of the present invention is not limited to the following examples.

Experimental Method 1. gRNA Design

CRISPR/Cas9 target regions of a human PMP22 gene, human PLP1 gene and mouse PLP1 gene were screened using CRISPR RGEN Tools (www.rgenome.net). The target regions of the PMP22 gene and the PLP1 gene may vary according to the type of CRISPR enzyme. Target sequences of a promoter region (TATA-box) and an enhancer region (for example, EGR2-, SOX10- or TEAD1-binding region); or a distal enhancer region B or C of the human PMP22 gene for SpCas9 are summarized in Table 1 above, and target sequences of a promoter region (TATA-box) and an enhancer region (for example, EGR2- or SOX10-binding region) of the human PMP22 gene for CjCas9 are summarized in Table 2. In addition, target sequences of a promoter region (TATA-box region) and an enhancer region (for example, wmN1 enhancer) of the human PLP1 gene for SpCas9 are summarized in Table 3 above, and target sequences of a promoter region (TATA-box region) and an enhancer region (For example, wmN1 enhancer) of the human PLP1 gene for CjCas9 are summarized in Table 4 above. Target sequences of a promoter region (TATA-box region) and an enhancer region (for example, wmN1 enhancer) of the mouse PLP1 gene for SpCas9 are summarized in Table 5 above, and target sequences of a promoter region (TATA-box region) and an enhancer region (for example, wmN1 enhancer) of the mouse PLP1 gene for CjCas9 are summarized in Table 6 above.

Moreover, target sequences located upstream and downstream of the promoter 1 (P1) of the human PMP22 gene and the mouse PMP22 gene are summarized in Tables 7, 8 and 9 above.

All gRNAs was generated in the form of chimeric single stranded RNA (sgRNA). The backbone sequences of Cj- and Sp-specific sgRNAs, excluding the target sequences, are 5'-GUUUUAGUCCCUGAAAAGGGAC-UAAAAUAAAGAGUUUGCGGGACUCUGCGGGG UUACAAUCCCCUAAAACCGCUUUU-3' (SEQ ID NO: 328) and 5'-GUUUUAGAGCUA-GAAAUAGCAAGUUAAAAUAAGGCUAGU-CCGUUAUCAACUUGA AAAAGUGGCACCGAGUCG-GUGC-3' (SEQ ID NO: 329).

2. Construction and Synthesis of gRNA sgRNA was packed into an AAV vector or synthesized with RNA. In order to insert the sgRNA into a viral vector, a DNA oligonucleotide corresponding to 20 to 22 base sequences of the sgRNA was designed and annealed, and ligated into a pRGEN-CAS9 (developed in-house) vector using a BsmBI site. Cas9 and the sgRNA including a variable target sequence at the 5' end were expressed through the CMV and U6 promoters, respectively.

Furthermore, for a delivery system by RNP, the sgRNA was transcribed by T7 RNA polymerase after a template was produced by annealing two partially complementary oligonucleotides produced by Phusion Taq-mediated polymerization. The transcribed sgRNA was purified and quantified using spectrometry.

3. Purification of Cas9 Protein

Codon-optimized Cas9 DNA sequences including NLS and HA epitopes were subcloned into a pET28 vector and expressed in BL21 (DE3) using IPTG under optimal culture conditions. The expressed Cas9 protein was purified using Ni-NTA agarose beads and dialyzed with an appropriate buffer. The activity of Cas9 was confirmed through an in vitro cleavage test using a well-known effective sgRNA.

4. Cell Culture

A human Schwann-like cell line (ATCC) and human primary Schwann cells (ScienCell) were cultured according to the manufacturer's manual. The human Schwann-like cells were cultured in Dulbecco's modified Eagle's medium (DMEM) (WelGene) containing a high concentration of glucose supplemented with 1× penicillin/streptomycin (WelGene) and 10% fetal calf serum (WelGene).

The human primary Schwann cells were maintained in a Schwann cell culture solution (ScienCell) provided by a vendor. For differentiation, the cells were cultured in DMEM (WelGene) containing a low concentration of glucose supplemented with a 1% fetal calf serum (WelGene), 100 ng/mL Nrg1 (Peprotech) for myelin sheath formation (myelination) signals, and 100 µM dbcAMP (Sigma-Aldrich) for 7 days.

5. Transduction (Transfection)

For transduction (transfection), an RNP complex containing 4 µg of the Cas9 protein (ToolGen) and 1 µg of sgRNA was incubated at room temperature for 15 minutes. Thereafter, the RNP complex was electroporated by using a 10 µl electroporation tip and a Neon electroporator (ThermoFisher) and delivered to $2×10^5$ cells. For targeted deep sequencing, genomic DNA (gDNA) was collected from transduced cells 72 hours after transduction.

6. In Vitro Real Time PCR (qRT-PCR)

mRNA was extracted from human primary Schwann cells according to the manufacturer's protocol using an RNeasy minikit (Qiagen). Thereafter, 100 ng mRNA was reverse transcribed using a high-capacity cDNA reverse transcription kit (ThermoFisher). qRT-PCR was performed with 100 ng of Taqman Gene expression master mix according to the manufacturer's protocol using QuantStudio 3 (ThermoFisher). PMP22 expression levels were calculated using Ct values, and GAPDH was used as an endogenous control. The Taqman probes (ThermoFisher) used in the present study are summarized in Table 16 below.

TABLE 16

| Target Gene | Taqman Gene Experssion Assay | Accession number |
|---|---|---|
| PMP22 | Hs00165556_m1 | NM_000304.3 |
| GAPDH | HS02786624_g1 | NM_001256799.2 |

7. Targeted Deep Sequencing

An on-target site was amplified by PCR from gDNA extracted from transduced cells using Phusion polymerase taq (New England BioLabs). Thereafter, paired-end deep sequencing was performed using Mi-Seq (Illumina) as the PCR amplification product. The deep sequencing results were analyzed using an online Cas-Analyzer tool (www.rgenome.net). It was confirmed whether a mutation occurred at 3 bp upstream from a PAM sequence as a result of indels by Cas9. The primers used in the present study are summarized in Table 17 below.

TABLE 17

|  | Target site | Primer-F (5' to 3') |  | Primer-R (5' to 3') |  |
|---|---|---|---|---|---|
| On-Target | hPMP22-TATA | CACAGGGCAGTCAGAGACCC | SEQ ID NO: 185 | GCAAACAAAGTTGGACACTG | SEQ ID NO: 186 |
|  | mRosa26 | AGACTCCCGCCCATCTTCTAGAAA | SEQ ID NO: 187 | AAGTCGCTCTGAGTTGTTATCAGT | SEQ ID NO: 188 |
|  | AAVS1 | CAGTGAAACGCACCAGACG | SEQ ID NO: 189 | AATCTGCCTAACAGGAGGTG | SEQ ID NO: 190 |
| Off-target (In silico, in vitro) | hPMP22-TATA Off1 | GAGGGAATGGGGACCAAAGGCATT | SEQ ID NO: 191 | TCATGTGGGGTGATGTTCAGGAAG | SEQ ID NO: 192 |
|  | hPMP22-TATA Off2 | AGAGCAGCTGACCTGAGGTCCAA | SEQ ID NO: 193 | CCCAAGGGTAGAGTGCAAGTAAAC | SEQ ID NO: 194 |
|  | hPMP22-TATA Off3 | GCATCCTAGCTCATTTGGTCTGCT | SEQ ID NO: 195 | GAGAGGATTCCTCATGAATGGGAT | SEQ ID NO: 196 |
|  | hPMP22-TATA Off4 | ACCAAACACTACACTTGGTTACTG | SEQ ID NO: 197 | CTCCCACTAGCAATTTTAAAGTCT | SEQ ID NO: 198 |
|  | hPMP22-TATA Off5 | GAATGTTCAGCACAGGTTTCCTTG | SEQ ID NO: 199 | GGTCAAAAGGAGCTCCATATTTGA | SEQ ID NO: 200 |
|  | hPMP22-TATA Off6 | CAGGACACCCATGGCCAAATCCAG | SEQ ID NO: 201 | CAGAGCCTCCTGCAGGGATGTCAA | SEQ ID NO: 202 |
|  | hPMP22-TATA Off7 | GCCTGCCAAGGTGACTCTCATCTA | SEQ ID NO: 203 | TGCCCAGGCTGATCTTGAACTCCT | SEQ ID NO: 204 |
|  | hPMP22-TATA Off8 | CCCAGAGTTAAGAGGTTCTTTCCT | SEQ ID NO: 205 | GAAGCTACTCCAGTGCAACTAGCT | SEQ ID NO: 206 |
|  | hPMP22-TATA Off9 | ACGCAGTCTGTTCTGTGCAGTGT | SEQ ID NO: 207 | AGGCCTTCCCAAGGAAGACCCTGA | SEQ ID NO: 208 |
|  | hPMP22-TATA Off10 | GCTGATCACTGGCCAAATCCAGCT | SEQ ID NO: 209 | GGGAAACAATGGGATCAAGCTGCA | SEQ ID NO: 210 |
|  | hPMP22-TATA Off11 | GCCCCTTTGTAAGTTGAGGAGCAT | SEQ ID NO: 211 | CCCTCTACCTCTCTCAATGGGCTT | SEQ ID NO: 212 |
|  | hPMP22-TATA Off12 | CAGACAAGCAAATGCTGAGAGATT | SEQ ID NO: 213 | CCTGTCATTATGATGTTCGCTAGT | SEQ ID NO: 214 |
|  | hPMP22-TATA Off13 | CCAGAGTTGGCCTCCTACAGAGAT | SEQ ID NO: 215 | GTGGATGCCCCACTACTGTTCATT | SEQ ID NO: 216 |
|  | hPMP22-TATA Off14 | TACCCAATTTGCCAGTCTGTGTCT | SEQ ID NO: 217 | ACCACCAGGCCTGCCCTACAAGA | SEQ ID NO: 218 |
|  | hPMP22-TATA Off15 | TGTGAATTTGATCCTGGCATTATG | SEQ ID NO: 219 | TACAGACAAGCAGATGCTGAGAGA | SEQ ID NO: 220 |
|  | hPMP22-TATA Off16 | CAGTCAACAGAGCTCTAACCTCCT | SEQ ID NO: 221 | AGCACCTGGTTGCACATCAACTT | SEQ ID NO: 222 |
|  | hPMP22-TATA Off17 | CATGTGGTCCCTGAACGTGAATGA | SEQ ID NO: 223 | GTCTGTCGCTTGCCCTCTTCTCT | SEQ ID NO: 224 |
|  | hPMP22-TATA Off18 | ATGCAGGGCCTCTAGACCATTTCA | SEQ ID NO: 225 | CTCAGCCCTTTGTGCACTCACCT | SEQ ID NO: 226 |
| Off-target (Digenome-seq, in vitro) | hPMP22-TATA Off1 | TGCACATCGCAAACATTTCG | SEQ ID NO: 227 | TGGGTATCGCACTGTGTCAG | SEQ ID NO: 228 |
|  | hPMP22-TATA Off2 | AGGTTCACATGGCTTGTGGT | SEQ ID NO: 229 | ATATCTGAAATGCCCGCAGG | SEQ ID NO: 230 |
|  | hPMP22-TATA Off3 | TGCACATCGCAAACATTTCG | SEQ ID NO: 231 | TGGGTATCGCACTGTGTCAG | SEQ ID NO: 232 |
|  | hPMP22-TATA Off4 | TCTTTAAAGGCCTTATCTCC | SEQ ID NO: 233 | TTCTGCTTGAGAATTCATCC | SEQ ID NO: 234 |
|  | hPMP22-TATA Off5 | CTCCTAATCTTTCACTTAGG | SEQ ID NO: 235 | CAAAGCCTGGTATAACATAG | SEQ ID NO: 236 |
|  | hPMP22-TATA Off6 | TCACTTCGAGCATCTGTGG | SEQ ID NO: 237 | CCAAATGACAGGCTGAGCT | SEQ ID NO: 238 |
|  | hPMP22-TATA Off7 | AGCAGGAAGTGAAGGCTAAG | SEQ ID NO: 239 | ATGTAACGTGGCAACTCTGG | SEQ ID NO: 240 |
|  | hPMP22-TATA Off8 | GTGTTGCTCTCGTCAATTAG | SEQ ID NO: 241 | AGGTGTTGTACATGGAGAAG | SEQ ID NO: 242 |
|  | hPMP22-TATA Off9 | TGTGAGCCACCATACCCAGC | SEQ ID NO: 243 | CCTGCAGTCCTTTGCGGATC | SEQ ID NO: 244 |
| Off-target (In silico, In vivo) | hPMP22-TATA Off1 | TCGCTGCCAGTATAACATGC | SEQ ID NO: 245 | AACTCCAGTCTCTAGACTCG | SEQ ID NO: 246 |
|  | hPMP22-TATA Off2 | AATAGTTTGACGTTGGAGCC | SEQ ID NO: 247 | ACTCCCAACATGTTCTCCTG | SEQ ID NO: 248 |
|  | hPMP22-TATA Off3 | ATCATCGCTCACAGAGTCC | SEQ ID NO: 249 | ACGACTGCAGGATCTTAATG | SEQ ID NO: 250 |
|  | hPMP22-TATA Off4 | TGGATGGAGGTTGGGAATCC | SEQ ID NO: 251 | TTGAGGCAGCAGCACTCTCC | SEQ ID NO: 252 |
|  | hPMP22-TATA Off5 | AGTCTATCCTAGCAGCTCC | SEQ ID NO: 253 | ACTGAGACCAGATAATGCAG | SEQ ID NO: 254 |

TABLE 17-continued

| Target site | Primer-F (5' to 3') | | Primer-R (5' to 3') | |
|---|---|---|---|---|
| hPMP22-TATA Off6 | AAGAGATGCGAGTTGTTCC | SEQ ID NO: 255 | CCTCTTCTACTCTGAGTGG | SEQ ID NO: 256 |
| hPMP22-TATA Off7 | ACCTGGTTTATCACAAGCTA | SEQ ID NO: 257 | AACGTGAACAGAAGGATTTC | SEQ ID NO: 258 |
| hPMP22-TATA Off8 | ATCACTCCATCAGAGTCAGG | SEQ ID NO: 259 | TGGCTCCTTCTATTCTCTCC | SEQ ID NO: 260 |

8. Design of In Silico Off-Target Site

An off-target potential site was designed in silico using an online tool (www.rgenome.net). A maximum of a 3 bp mismatch was considered as an off-target site.

9. Digenome-seq

Genomic DNA of HeLa cells was purified according to the vendor's protocol using a DNeasy Blood & Tissue Kit (Qiagen). The Cas9 protein (100 nM) and the sgRNA (300 nM) incubated in advance were mixed with genomic DNA (10 µg) in 1 mL of a reaction solution (100 mM NaCl, 50 mM Tris-HCl, 10 mM MgCl2, 100 µg/ml BSA, pH 7.9) at 37° C. for 8 hours. Cleaved genomic DNA was treated with RNase A (50 µg/mL), and purified again using a DNeasy Tissue Kit (Qiagen). 1 µg of the cleaved genomic DNA was split into fragments using a Covaris system, and an adaptor for producing a library was connected to the DNA fragments. Thereafter, the library was subjected to whole genome sequencing (WGS) using a HiSeq×Ten Sequencer (Illumina) at a sequencing depth of 30 to 40× (Macrogen). In vitro cleavage scores were calculated by a DNA cleavage scoring system at the positions of each base sequence cleaved in the genome.

10. Mice and Intraneural Injection

C22 mouse lines (B6; CBACa-Tg(PMP22)C22Clh/H) used in the present study were purchased from MRC Harwell (Oxfordshire, UK). C22 mice (4 males and 7 females) were treated with PMP22-TATA RNP. Intraneural injection was performed in the same manner as a previous study (Daisuke Ino., J Vis Exp., (2016) 115). 6-day old mice were anesthetized, and the mouse sciatic nerves were exposed by surgery. In order to minimize nerve damage, intraneural injection was immediately performed at the end of the sciatic notch was immediately using a pulled glass micropipettes attached to a microinjector. An RNP complex of 11 µg of the Cas9 protein and 2.75 µg of sgRNA per mouse was injected into the mice along with Lipofectamine 3000 (Invitrogen, Carlsbad, Calif., USA). The management, use, and treatment of all animals used in the present study were performed under the guidelines prepared by the Samsung Animal Management and Use Committee (SMC-20170206001) in accordance with the Association for Assessment and Accreditation of Laboratory Animal Care International.

11. Rotarod Experiment (Rotarod Test)

Motor coordination was evaluated using a rotarod device (B.S. Technolab INC., Korea). This experiment was performed to evaluate the balance and motor coordination of the mice. Prior to the experiment, mice went through a 3-day training period. In the experiment, a horizontal rotating rod (21 rpm) was used for the rotarod experiment. The retention time on the rotating rod of the mouse was measured, and the mouse was allowed to stay on the rod for up to 300 seconds.

12. Electrophysiological Test

In order to evaluate the electrophysiological state, a nerve conduction test (NCS) was performed in the same manner as in a previous study (Jinho Lee., J Biomed Sci., (2015) 22, 43). In summary, mice were anesthetized with carbon dioxide gas, and the anesthesia was maintained using a nose cone to supply 1.5% isoflurane during the experiment. Hair was completely removed from the end to the hind paw. The NCS was performed using a Nicolet VikingQuest device (Natus Medical). For a motor nerve conduction test of the sciatic nerve, responses from a distal part and a proximal part were each determined by placing an activity recording needle electrode on the gastrocnemius muscle with a reference electrode attached to the tendon, and disposing a stimulating negative electrode at a position close to a recording electrode at a distance of 6 mm toward the body center inside the hip and the center line of the post-orbital portion thigh. The distal latency (DL), the motor nerve conduction velocity (MNCV), and the amplitude of the compound muscle action potential (CMAP) were measured. The CMAP was measured at the maximal overstimulation.

13. Nerve Histology and Images

The sciatic nerves of the mice were biopsied and a pathological examination of the affected sample was performed by analysis with a microscope. The samples were respectively fixed using a 25 mM cacodylate buffer containing 2% glutaraldehyde. Semi-thin sections were stained with toluidine blue. After incubation in 1% OsO4 for 1 hour, the samples were dehydrated in an ethanol series, and then allowed to pass through propylene oxide and embedded in an epoxy resin (Epon 812, Oken, Nagano, Japan). The cells were sliced to a certain thickness (1 µm) using Leica ultra-microtome (Leica Microsystems), and stained with toluidine blue for 30 to 45 seconds. The g-ratio (axon diameter/fiber diameter) was calculated by measuring the inner diameter and the outer diameter of myelin using the Zeiss Zen 2 program (Carl Zeiss, Oberkochen, Germany).

14. Statistical Analysis

The statistical significance of data associated with mRNA expression levels was evaluated by a one-way ANOVA using multiple comparisons of post-hoc Tukey's. Other types of presented data were calculated using a Mann-Whitney U test (http://www.socscistatistics.com/tests/mann-whitney/Default2.aspx). Data and graphs produced from the present study were analyzed using GraphPad Prism. The significance level was set at 0.05.

15. sgRNA Screening for Plp1 Gene Targeting

Figure 30:
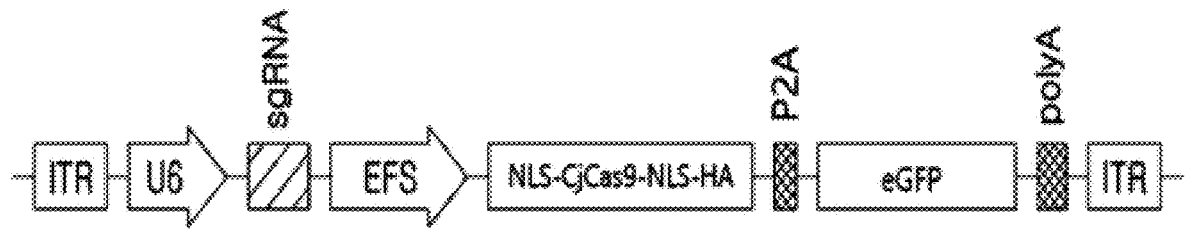
FIG. 30 illustrates a CjCas9 plasmid used in an exemplary embodiment.
Figure 31A:
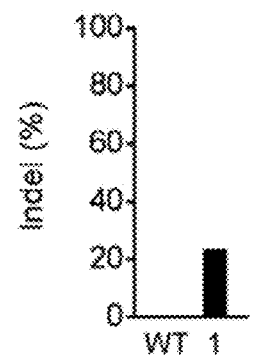
FIGS. 31A and 31B are a set of graphs showing screening results of SpCas9-sgRNAs targeting the TATA box region of mPlp1. (a) shows the indel frequency (%) confirmed in NIH-3T3 cells, and (b) shows the indel frequency (%) confirmed in N20.1 cells. Here, the used sgRNA are sgRNA targeting mPlp1-TATA-Sp-01, and distinguished by the numbers represented in target sequences on the graphs.
Figure 31B:
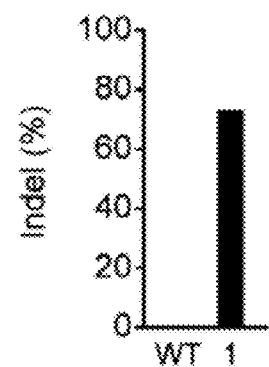
Figure 32A:
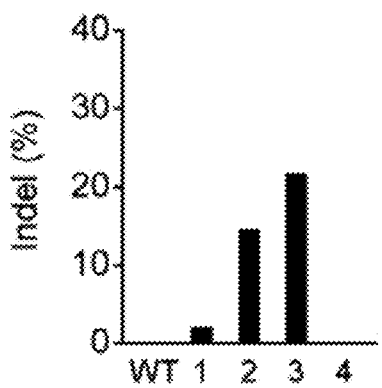
FIGS. 32A and 32B are a set of graphs showing screening results of CjCas9-sgRNAs targeting the TATA box region of mPlp1. (a) shows the indel frequency (%) confirmed in NIH-3T3 cells, and (b) shows the indel frequency (%) confirmed in N20.1 cells. Here, the used sgRNAs were mPlp1-TATA-Cj-01 to mPlp1-TATA-Cj-04, and distinguished by the numbers represented in target sequences on the graphs.
Figure 32B:
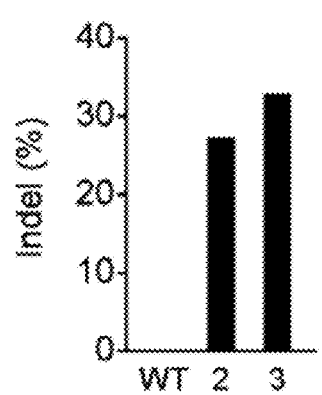
Figure 33A:
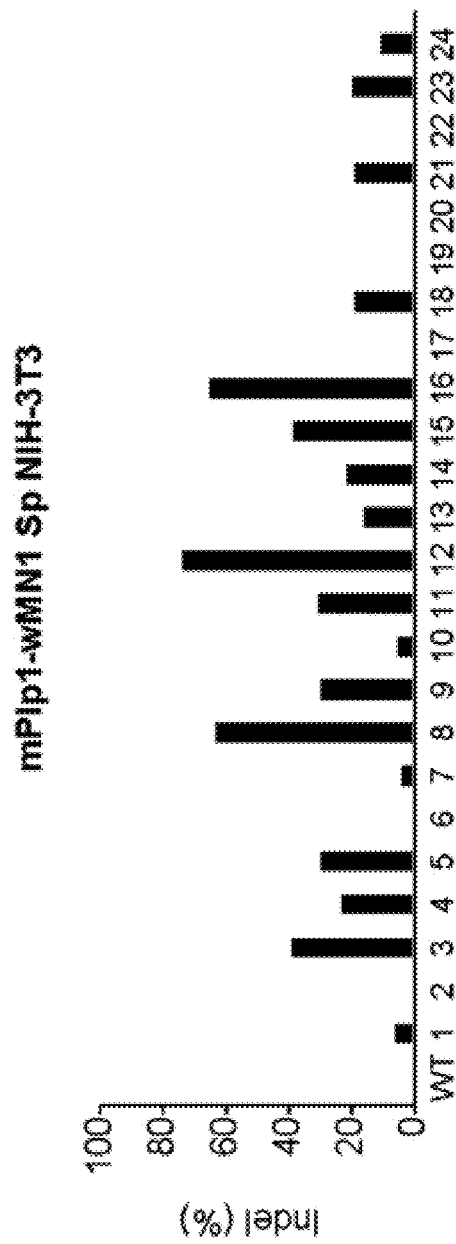
FIGS. 33A and 33B are a set of graphs showing screening results of SpCas9-sgRNAs targeting an enhancer (wMN1 enhancer) region of mPlp1. (a) shows the indel frequency (%) confirmed in NIH-3T3 cells, and (b) shows the indel frequency (%) confirmed in N20.1 cells. Here, the used sgRNAs were mPlp1-wMN1-Sp-01 to mPlp1-wMN1-Sp-36, and distinguished by the numbers represented in target sequences on the graphs.
Figure 33B:
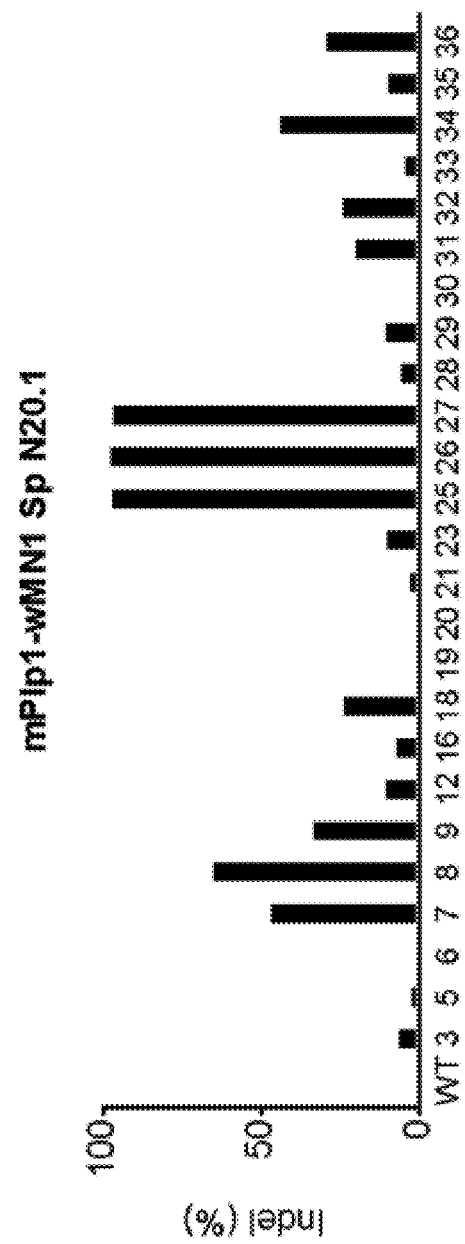
Figure 34A:
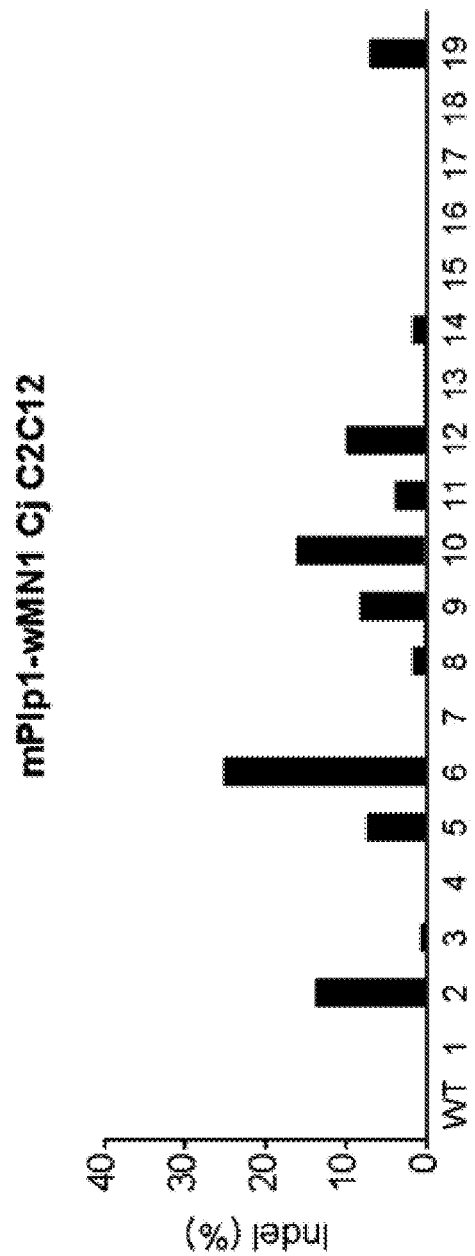
FIGS. 34A and 34B are a graph showing a screening result of CjCas9-sgRNAs targeting an enhancer (wMN1 enhancer) region of mPlp1. (a) shows the indel frequency (%) confirmed in NIH-3T3 cells, and (b) shows the indel frequency (%) confirmed in N20.1 cells. Here, the used sgRNAs were mPlp1-wMN1-Cj-01 to mPlp1-wMN1-Cj-28, and distinguished by the numbers represented in target sequences on the graph.
Figure 34B:

Mouse fibroblast cells, NIH-3T3 (ATCC, CRL-1658), myoblast cells, that is, a C2C12 line, (ATCC, CRL-1772) and oligodendrocyte cells, N20.1 (Cedarlane Laboratories, CLU108-P) were cultured according to the manuals of the manufacturers. The cells were cultured in a high-concentration glucose-containing Dulbecco's modified Eagle's medium (DMEM) supplemented with 1× penicillin/streptomycin (WelGene) and 10% fetus bovine serum (WelGene) at 37° C. and 5% $CO_2$. For transfection of a CRISPR/Cas9 composition, an RNP complex (SpCas9) consisting of 4 µg of a Cas9 protein and 1 µg of sgRNA or a CjCas9 plasmid (FIG. 30) was prepared. Afterward, the RNP complex or CjCas9 plasmid was delivered to $2 \times 10^5$ cells by electroporation using a 10 µl electroporation tip and a Neon electroporator (ThermoFisher). For targeted deep sequencing, 72 hours after transfection, genomic DNA (gDNA) was collected from the transfected cells.

16. Downregulation Assay for Plp1 Gene mRNAs were extracted from the N20.1 cell line using a RNeasy mini kit (Qiagen) according to the protocol of the manufacturer. Afterward, 1 µg of mRNA was reverse-transcribed using a high-capacity cDNA reverse transcription kit (ThermoFisher). Real-time quantitative reverse transcription polymerase chain reaction (qRT-PCR) was performed with 100 ng of a Taqman Gene expression master mix using QuantStudio 3 (ThermoFisher) according to the protocol of the manufacturer. A Plp1 expression level was calculated using a $C_T$ value, and Gapdh was used as an endogenous control. Taqman probes (ThermoFisher) used in this study are summarized in Table 18 below.

TABLE 18

| Target Gene | Taqman Gene Experssion Assay | Accession number |
|---|---|---|
| Plp1 | Mm01297210_m1 | NM_001290561.1 |
| Gapdh | Mm99999915_g1 | NM_001289726.1 |

17. sgRNA Screening for PLP1 Gene Targeting

A human lymphoblast Jurkat cell line (ATCC, TIB-152) and a human epithelial 293T cell line (ATCC, CRL-3216) were cultured according to the manual of the manufacturer. The cells were cultured in a high-concentration glucose-containing Dulbecco's modified Eagle's medium (DMEM) supplemented with 1× penicillin/streptomycin (WelGene) and 10% fetus bovine serum (WelGene) at 37° C. and 5% $CO_2$. For transfection of a CRISPR/Cas9 composition, an RNP complex (SpCas9) consisting of 4 µg of a Cas9 protein and 1 µg of sgRNA or a CjCas9 plasmid (FIG. 30) was prepared. Afterward, the RNP complex or CjCas9 plasmid was delivered to $2 \times 10^5$ cells by electroporation using a 10 µl electroporation tip and a Neon electroporator (ThermoFisher). For targeted deep sequencing, 72 hours after transfection, genomic DNA (gDNA) was collected from the transfected cells.

18. In Vitro Primary Schwann Cell Culture, CRISPR/Cas9 Transfection and DNA/RNA Analysis 18-1. Preparation of sgRNA sgRNAs were generated by in vitro transcription using T7 polymerase (New England BioLabs) according to the manufacturer's protocol.

18-2. In Vitro Primary Schwann Cell Culture and CRISPR/Cas9 Transfection

About 3-4 weeks old C22 mice (6-10 mice/preparation) were sacrificed by a CO2 gas chamber. The accompanying procedure requires a sterile environment, equipment and cell culture tools. Both sciatic nerves were exposed, dissected out. Then, the surrounding membranes and muscular tissue of isolated nerves were carefully removed under a stereomicroscope. The epineurium was stripped off with fine forceps. The remaining nerves were then transferred to tube containing ice-cold phosphate-buffered saline (PBS) and centrifuged at 1500 rpm for 10 min. For single cell dissociation, enzymatic digestion was performed with 0.05% collagenase-A solution (Sigma) for 30 min at 37° C. Enzymatic activity was stopped by fetal bovine serum (Welgene) and centrifuged for 5 min at 1500 rpm. Dissociated cells were then seeded onto poly-L-ornithine-(Sigma) and laminin (ThermoFisher) coated dishes and allowed to adhere overnight. To eliminate contaminating fibroblasts, 10 µM AraC (Sigma) was added to the medium. After 48 h, the medium was replaced by DMEM (Welgene) containing 3% FBS with 3 µM forskolin (Sigma) and 20 ng/ml neuregulin (R&D systems) to expand the cells. For transfection of CRISPR/Cas9 components, $2 \times 10^5$ cells were electroporated with the RNP complexes using a Neon electroporator (ThermoFisher).

18-3. Real Time PCR (qRT-PCR)

For gene expression analysis, total RNA of the primary Schwann cells were extracted using RNeasy Mini Kit (QIAGEN) according to manufacturer's protocol, 5 days post transfection. cDNA was obtained using SuperScript II according to the manufacturer's protocol (Thermo Fisher) as total mRNA extracted. qRT-PCR was performed using Power SYBR® Green Master Mix (Thermo Fisher) protocol with the following primers: Human P1-PMP22-F, 5'-CTTAGTCTGTCGGCTGCGGG-3' (SEQ ID NO: 364); Human P1-PMP22-R: 5'-GGCCAAACAGCGTAACCCCT-3' (SEQ ID NO: 365); Human P2-PMP22-F: 5'-CGTTAAAGGGGAACGCCAGGA-3' (SEQ ID NO: 366); Human P2-PMP22-R: 5'-CAGGGTGGCCTCAAACACAA-3' (SEQ ID NO: 367); Mouse Mpz-F: 5'-CGGACAGGGAAATCTATGGTGC-3' (SEQ ID NO: 368); Mouse Mpz-R: 5'-GCGCCAGGTAAAAGAGATGTCA-3' (SEQ ID NO: 369); Mouse P1-Pmp22-F: 5'-AGCTCCACCAGAGAACCTCTCA-3' (SEQ ID NO: 370); Mouse P1-Pmp22-R: 5'-TGAGGAGTAGCAGTGTTGGACGG-3' (SEQ ID NO: 371); Mouse P2-Pmp22-F: 5'-TGACCCGCAGCACAGCTGTCTTTG-3' (SEQ ID NO: 372); Mouse P2-Pmp22-R: 5'-TGAG-GAGTAGCAGTGTTGGACGG-3' (SEQ ID NO: 373).

18-4. Targeted Deep Sequencing

The on-target region was PCR amplified from gDNA extracted from transfected cells using Phusion polymerase (New England BioLabs). The resulting PCR amplicons were then subjected to paired-end deep sequencing using Mi-Seq (Illumina). Data from deep sequencing were analysed using the online Cas-Analyzer tool (www.rgenome.net). Indels in the region 3 bp upstream of the protospacer-adjacent motif (PAM) sequence were considered to be mutations resulting from Cas9.

Example 1. sgRNA Screening for PMP22 Gene

In order to screen for therapeutically effective sgRNA sequences which may reduce the expression of human PMP22 to a normal range, human cell lines were transduced with various sgRNAs and Cas9s designed to target the promoter (TATA-box) and intronic enhancer binding site of a PMP gene. In brief, Jurkat human T cells were used for SpCas9 screening, and HEK293T cells were used for CjCas9. gDNA was collected from the cells and subjected to targeted deep sequencing. Various patterns of mutations induced by the sgRNA sequences were identified by an NHEJ-mediated indel. Several SpCas9-sgRNAs strongly induced indels in two regulatory sites (FIGS. 1 and 2). It was confirmed that 30 to 40% of indels were induced in a specific CjCas9-sgRNA (FIGS. 3 and 4).

Example 2. Gene Manipulation of Schwann-Like Cells

Although effective indel mutations caused by sgRNA were identified in human cells, it is uncertain whether the effect would also be possible in Schwann cells. Thus, in order to investigate the effects of PMP22 expression inhibition and gene manipulation in Schwann cells, the SpCas9-sgRNA effect was confirmed using sNF2.0 cells, which are Schwann-like cells. The effective SpCas9-sgRNA identified in Jurkat cells was repeatedly tested in sNF02.0 cells. After transduction, it was confirmed through deep sequencing analysis that the same high indel frequency was obtained by the same sgRNA. Transduction of a single sgRNA targeting the promoter (TATA-box) site and enhancer-binding site induced indels of 31% and 59%, respectively (FIG. 7). Interestingly, a 40 to 50 bp small deletion containing a main controlling factor (for example, EGR or SOX10-binding site) of a myelin gene, or an important TATA-box was found in a very large number of cells of cells treated with dual sgRNA (FIG. 7).

Example 3. Expression Control of PMP22 by Gene Manipulation

Figure 8:
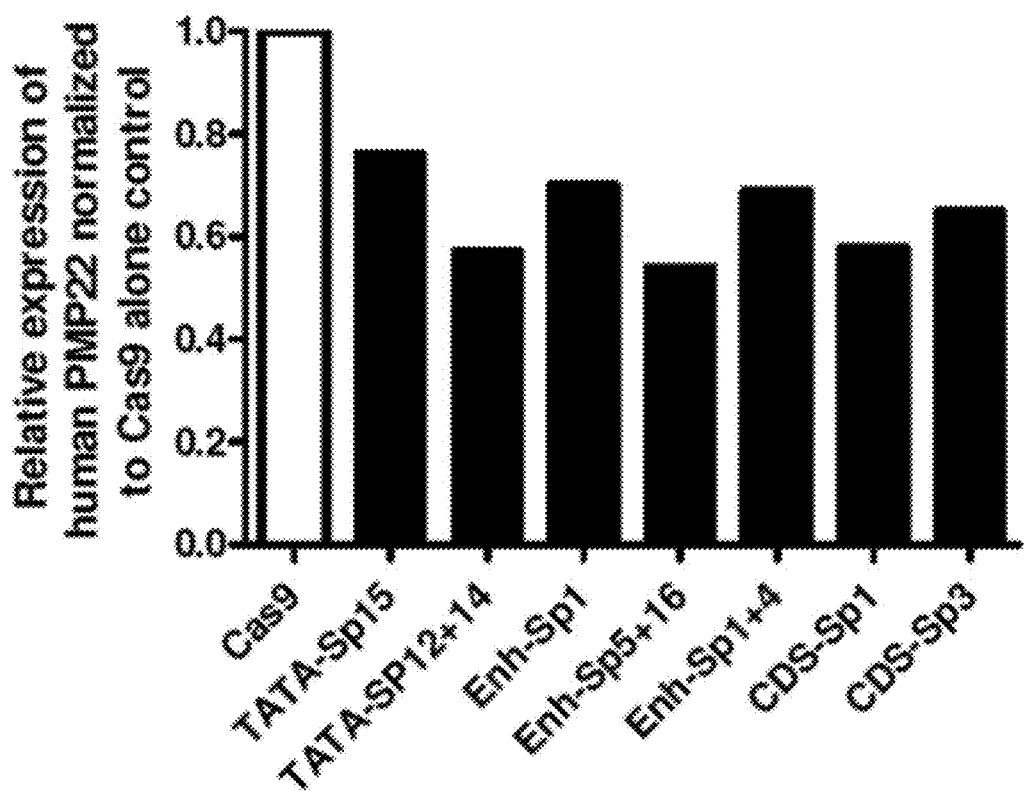
FIG. 8 is a graph illustrating a decrease in mRNA expression of human PMP22 by SpCas9-sgRNA in human Schwann-like cells.

In order to evaluate the change in expression of PMP22 by an effective sgRNA, Schwann-like cells were differentiated, and qRT-PCR was performed. As a result, most of the sgRNAs targeting PMP22 effectively inhibited the expression of PMP22 (FIG. 8). When single sgRNA was used, the expression of PMP22 was decreased by about 30% as compared to a control treated with only Cas9, and when dual sgRNA was used, the expression of PMP22 was decreased by about 50% as compared to the control treated with only Cas9.

Example 4. Gene Manipulation of Schwann Cells

Figure 9:
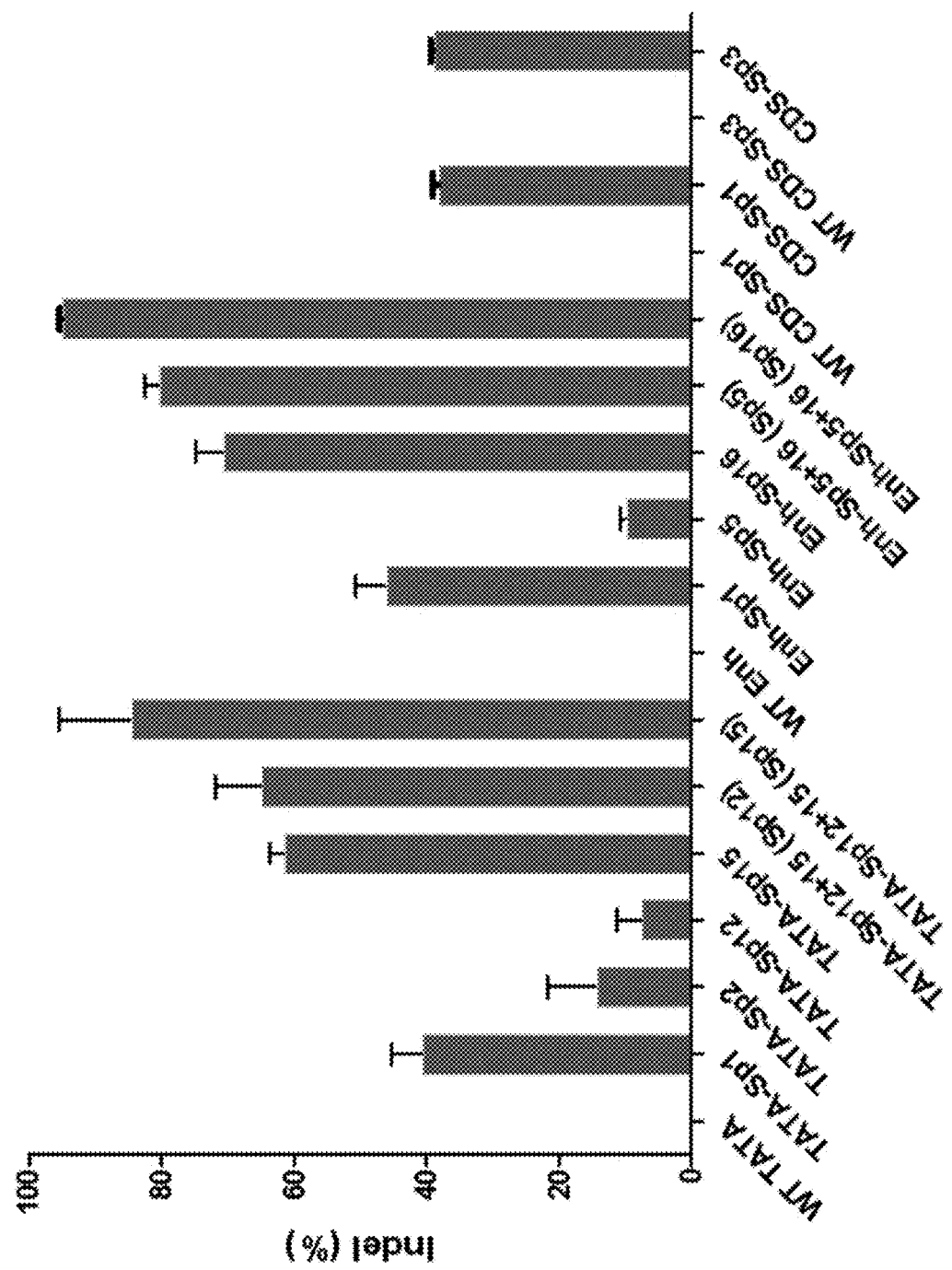
FIG. 9 illustrates indel frequency measurement results by SpCas9-sgRNA at each target site of a human PMP22 gene in human primary Schwann cells.
Figure 11:
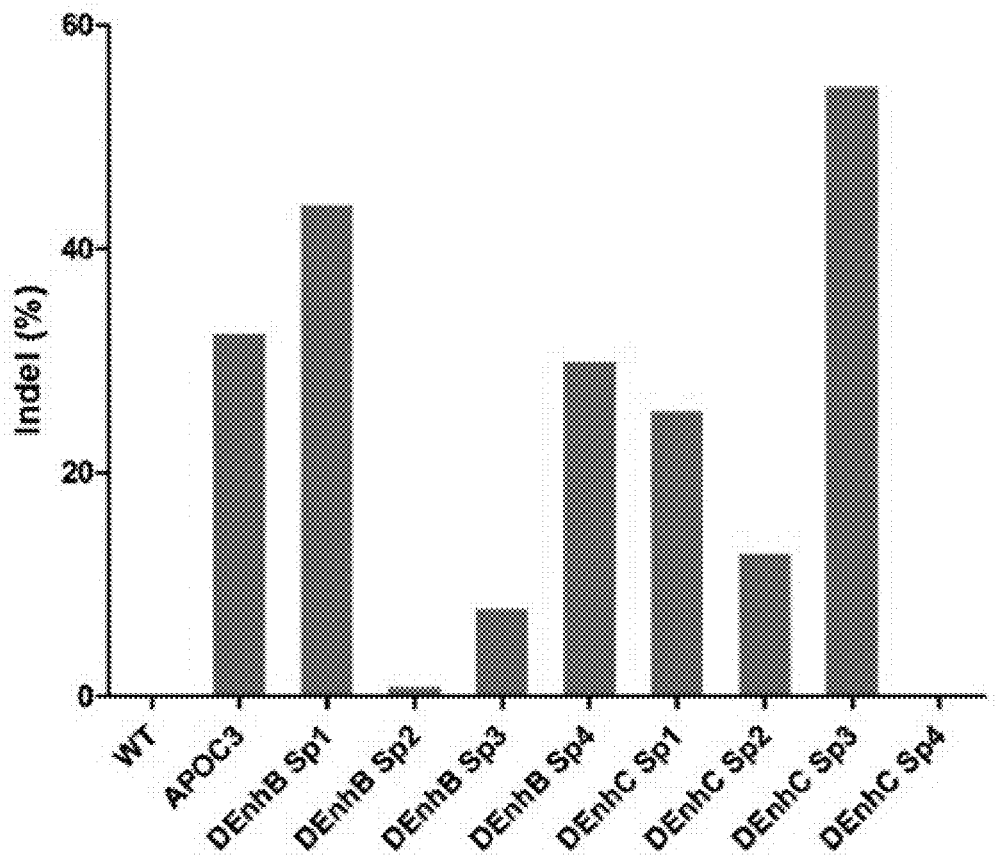
FIG. 11 illustrates indel frequency measurement results by SpCas9-sgRNA targeting distal enhancer sites (distal enhancer regions) B and C of a human PMP22 gene in human primary Schwann cells.
Figure 12:
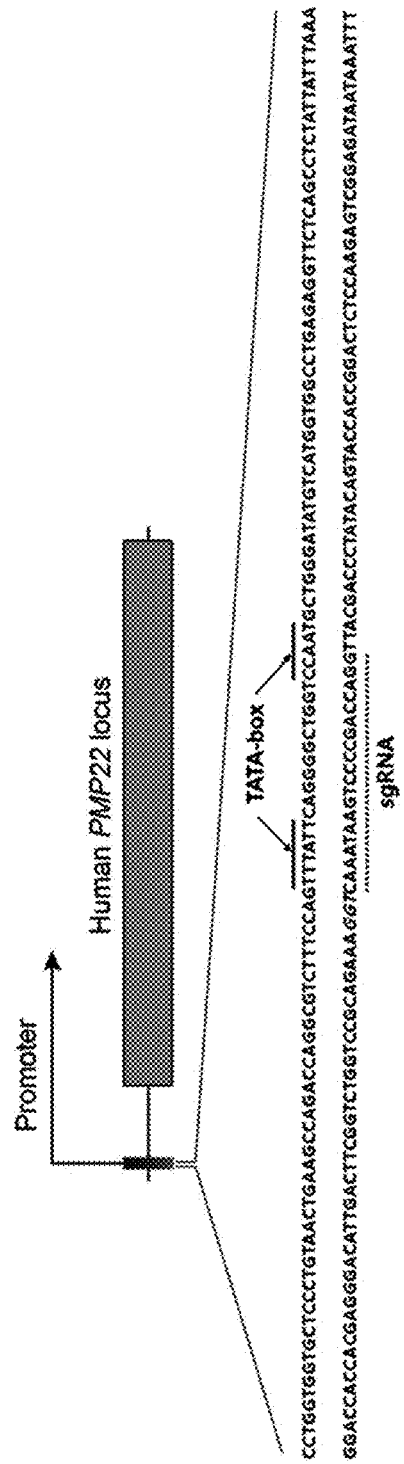
FIG. 12 illustrates a target sequence targeting a promoter region including a TATA-box site of a human PMP22 position. The sequences of a part of the promoter region are SEQ ID NOs: 590 (top strand) and 591 (bottom strand).

After expression inhibition and gene manipulation effects of PMP22 were previously confirmed in Schwann-like cells, it was confirmed whether the previous result exhibited a similar effect in human primary Schwann cells. The indel frequency according to the target site was observed using the SpCas9-sgRNA at each target site of the human PMP22 gene in human primary Schwann cells. As a result, it was confirmed that the indel frequency was high at the target site in most of the sgRNAs targeting TATA-box, enhancer, and coding sequences of the PMP22 gene (FIG. 9). Further, even when dual sgRNAs each targeting TATA-box and an enhancer was used, a high indel frequency was exhibited. It was confirmed that an indel occurred at the target site additionally using an sgRNA targeting sequences encoding distal enhancer sites B and C (FIG. 11), and in this case, an sgRNA targeting APOC3 was used as a control.

Figure 10:
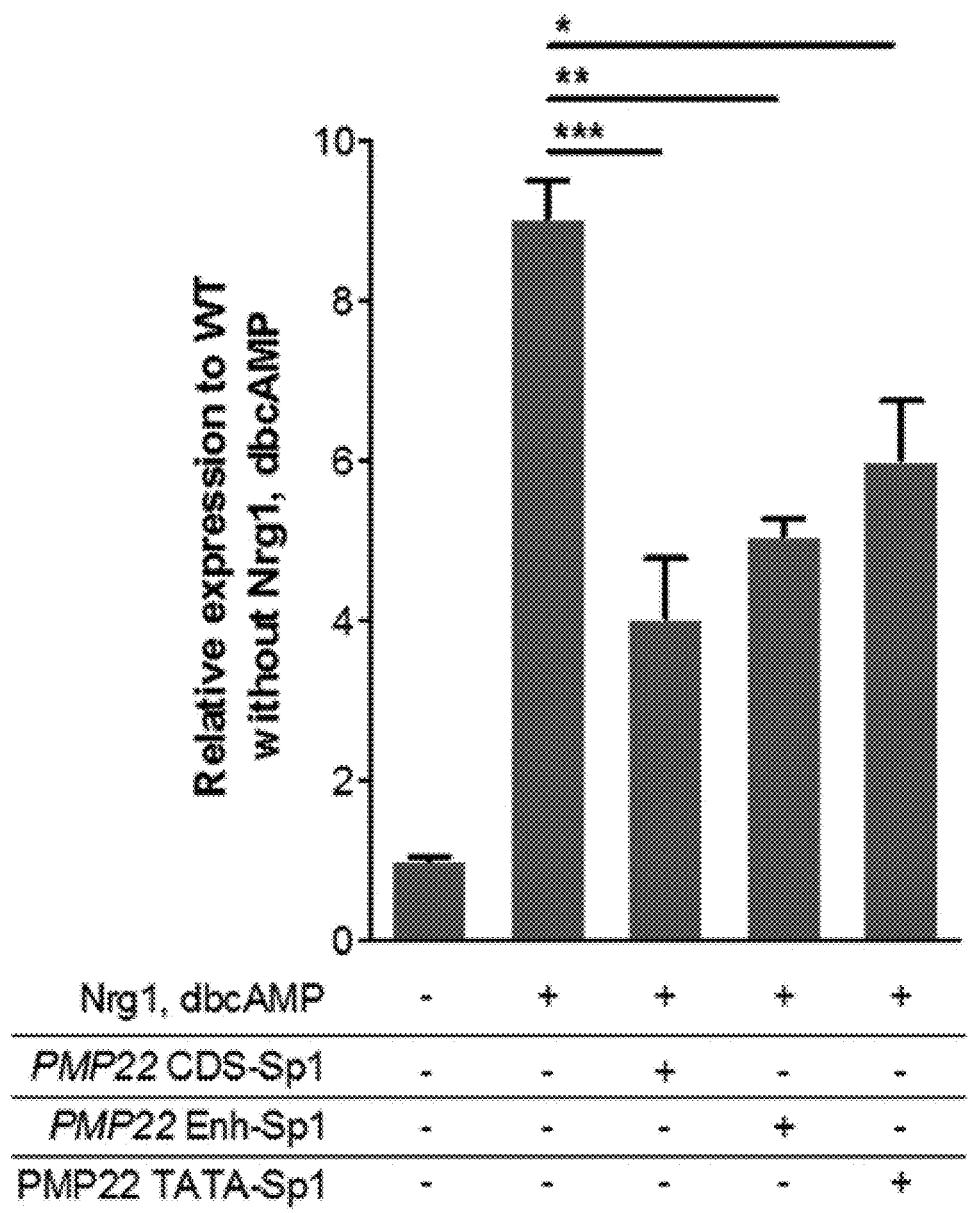
FIG. 10 is a graph illustrating effective and specific expression decreases of PMP22 by SpCas9-sgRNA at each target site of a human PMP22 gene in human primary Schwann cells, and illustrates relative mRNA expression comparison results of PMP22, which are measured by qRT-PCR with or without a treatment of a myelination signal factor and an RNP complex for each target site (n=3, One-way ANOVA and Tukey post-hoc tests: *$p<0.05$).

In addition, in order to confirm whether the SpCas9-sgRNA at each target site causes a decrease in expression of the PMP22 gene, a qRT-PCR analysis was performed. Since PMP22 is transcribed at the final stage of differentiation of Schwann cells, human primary Schwann cells were treated with a well-known differentiation signal factor including Neuregulin-1 (Nrg1) and dibutryral cyclic AMP (dbcAMP) for 7 days. As a result, it was confirmed that the expression of PMP22 was increased by 9 times in cells treated with Nrg1 and dbcAMP as compared to cells which were not treated with Nrg1 nor dbcAMP. In contrast, when cells were treated with SpCas9-sgRNA at each target site, it was confirmed that the expression of PMP22 was induced 4 to 6-fold. This is determined to be due to the expression inhibition of PMP22 due to each target site modification of PMP22 by SpCas9-sgRNA at each target site (FIG. 10).

Figure 13A:
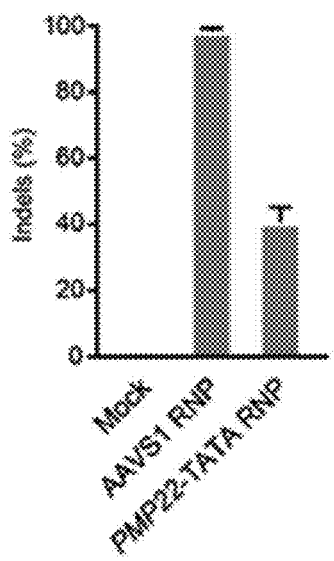
FIGS. 13A, 13B and 13C are graphs illustrating effective and specific expression decreases of PMP22 through CRISPR-Cas9 targeting a TATA-box site of a human PMP22 gene in vitro, and the leftmost graph (a), the middle graph (b), and the rightmost graph (c) illustrate indel frequency measurement results using targeted deep sequencing in human primary Schwann cells, TATA-box 1 mutation frequency measurement results (n=3) among the total indel frequencies, and relative mRNA expression comparison results of PMP22, which are measured by qRT-PCR with or without a treatment of a myelination signal factor and an RNP complex in human primary Schwann cells (n=3, One-way ANOVA and Tukey post-hoc tests: *p<0.05), respectively.
Figure 13B:
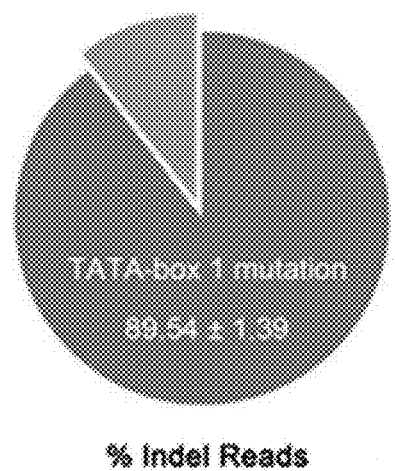
Figure 13C:
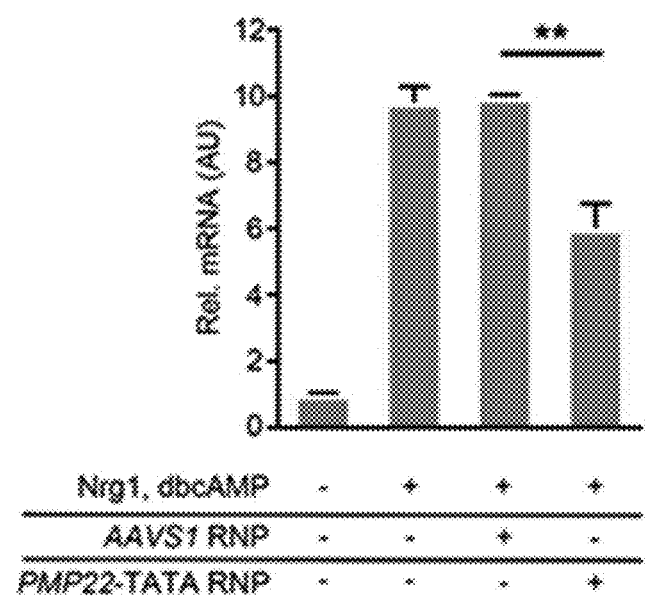

Example 5. Effects of Decrease in Effective and Specific Expression of PMP22 Using CRISPR/Cas9 Targeting TATA-Box Site of Human PMP22 Gene An experiment was performed in human primary Schwann cells by selecting sgRNA_TATA_Sp #1 (hereinafter, described as PMP22-TATA sgRNA) which exhibits a high indel efficiency among sgRNAs targeting a TATA-box site previously screened and may target the TATA-box. An indel was induced by transducing human primary Schwann cells with an RNP complex including an sgRNA and Cas9 protein (FIG. 13), and it was confirmed through a targeted deep sequencing analysis that 89.54±1.39% of the total indels were generated at the TATA-box site of human PMP22 (FIG. 13).

In addition, to confirm whether a mutation formed at the TATA-box of PMP22 caused a decrease in expression of the PMP22 gene, a qRT-PCR analysis was performed. Since PMP22 is transcribed at the final stage of differentiation of Schwann cells, human primary Schwann cells were treated with a well-known differentiation signal factor including Neuregulin-1 (Nrg1) and dibutryral cyclic AMP (dbcAMP) for 7 days. As a result, it was confirmed that the expression of PMP22 was increased by 9 times in cells treated with Nrg1 and dbcAMP as compared to cells which were not treated with Nrg1 nor dbcAMP. In contrast, it was confirmed that when cells were treated together with PMP22-TATA RNP, the expression of PMP22 was induced 6-fold. This is determined to be due to expression inhibition of PMP22 by TATA modification of PMP22 by CRISPR/Cas9 (FIG. 13). In a control treated with both the differentiation signal factor and the AAVS1 target RNP, no difference in expression of the PMP22 gene could be confirmed.

Figure 14:
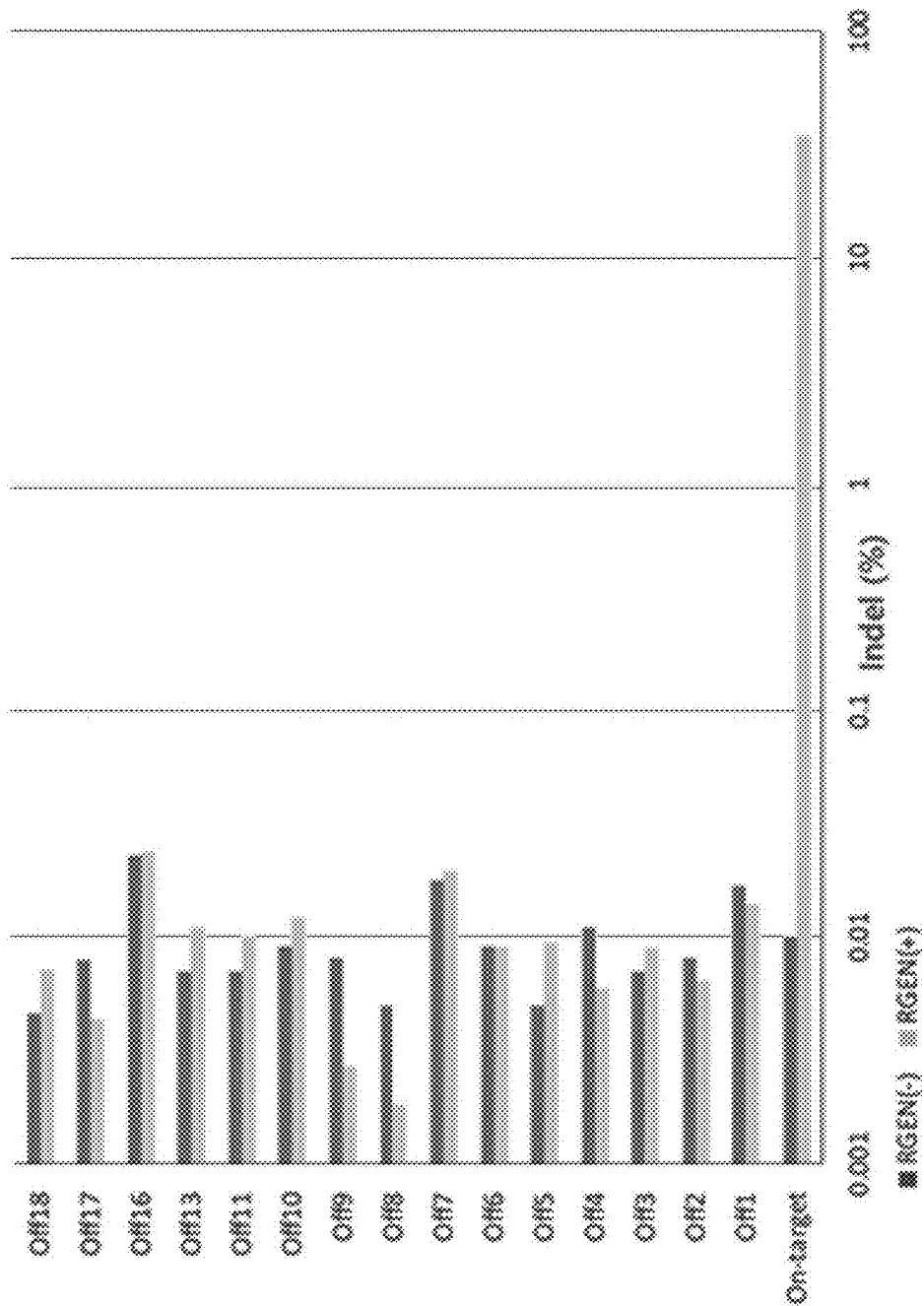
FIG. 14 illustrates indel frequencies by PMP22-TATA RNP in off-targets and on-targets found through an in silico off-target analysis by target deep sequencing in human primary Schwann cells.
Figure 17:
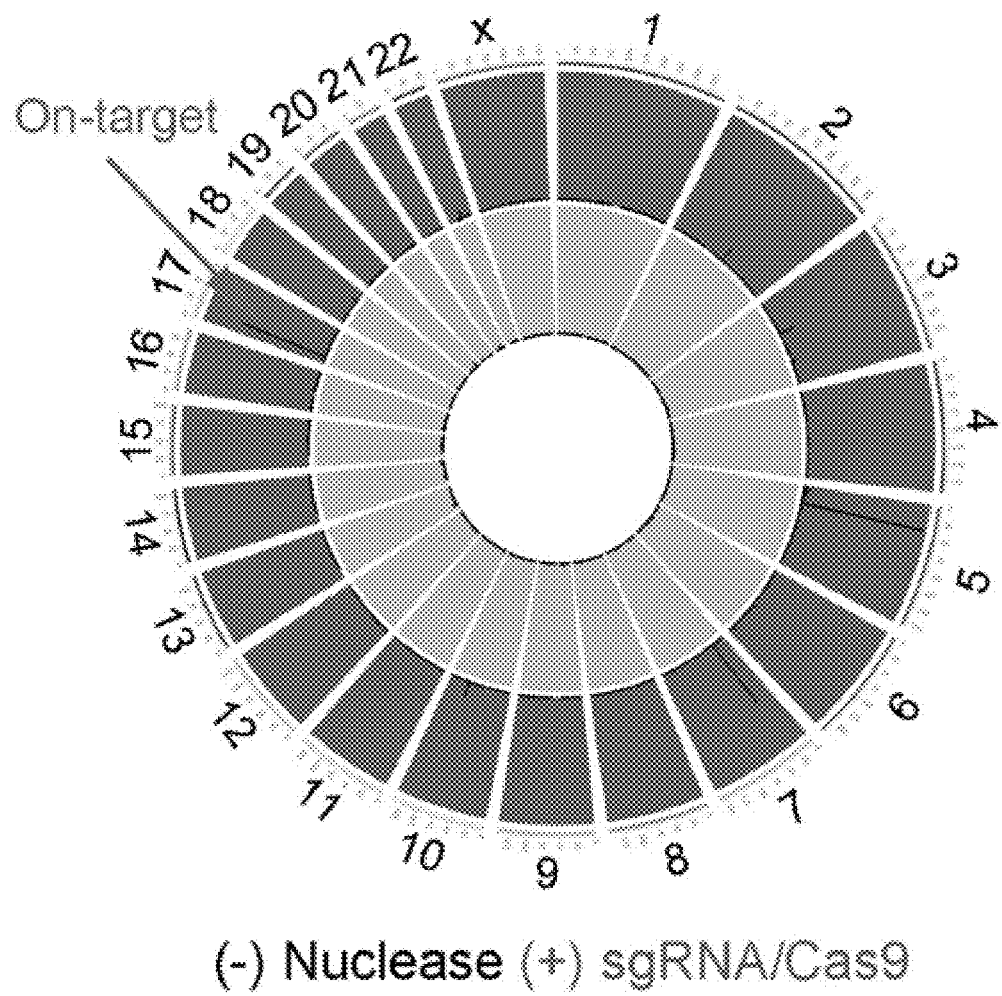
FIG. 17 is a Genome-wide Circos plot illustrating on-target site for PMP22-TATA RNP in a human's entire genome.
Figure 19:
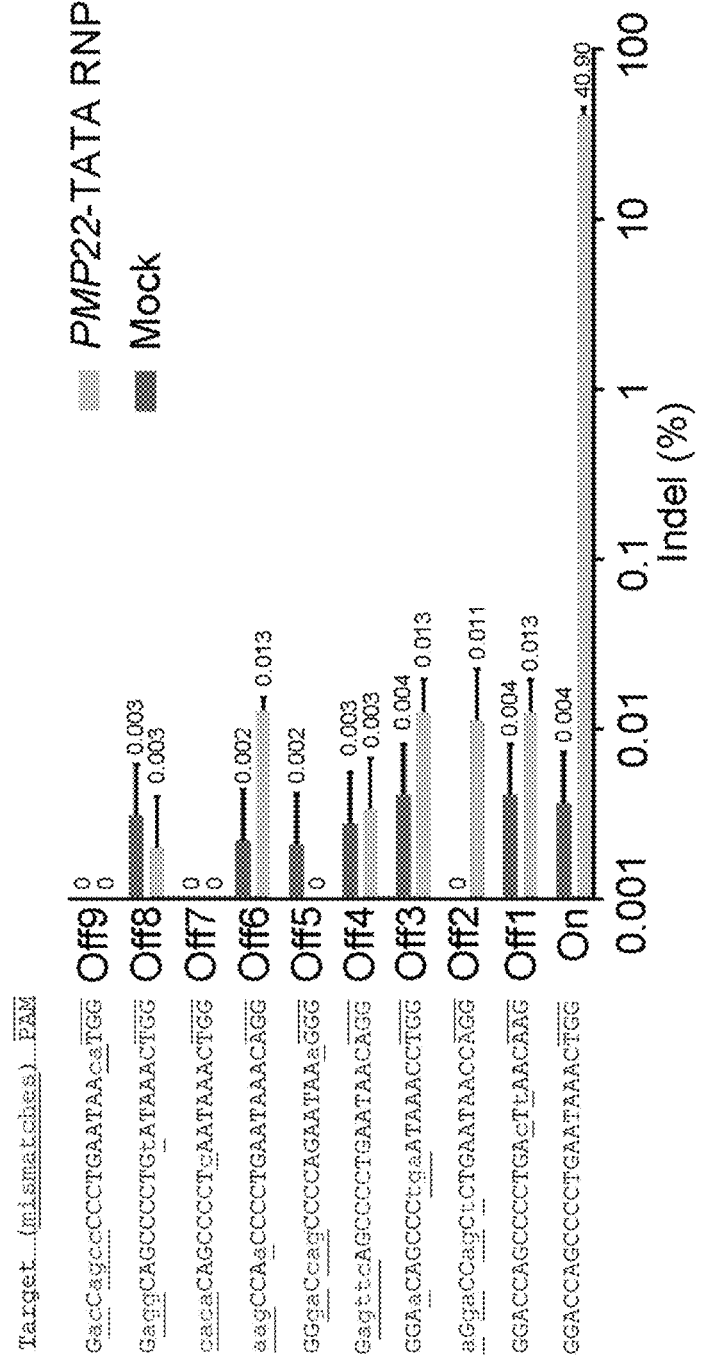
FIG. 19 is a graph illustrating indel frequencies in off-target sites by PMP22-TATA RNP. The on-target sequence is a SEQ ID NO: 598, and the off-target sequences are SEQ ID NOs: 617 to 625 (Off1 to Off9 order).

In order to confirm the specificity of PMP22-TATA RNP, an in silico-based off-target analysis was performed. Through the targeted deep sequencing, no indel mutation exceeding a sequencing error ratio (0.1% on average) was confirmed at the off-target site confirmed by an in silico analysis (FIG. 14). Since the in silico-based off-target analysis may be a biased approach, Digenome-seq (a whole sequencing-based off-target analysis which is not biased) was also performed. As a result, it was possible to confirm nine off-target sites cleaved by PMP22-TATA RNP in vitro (FIG. 17, FIG. 18). However, as a result of a re-analysis through the targeted deep sequencing, an abnormal indel mutation was not found at the off-target sites (FIG. 19).

These results show that the effective and specific modification of the TATA-box of PMP22 by PMP22-TATA RNP may control the transcription level of PMP22 in human primary Schwann cells.

Figure 20:
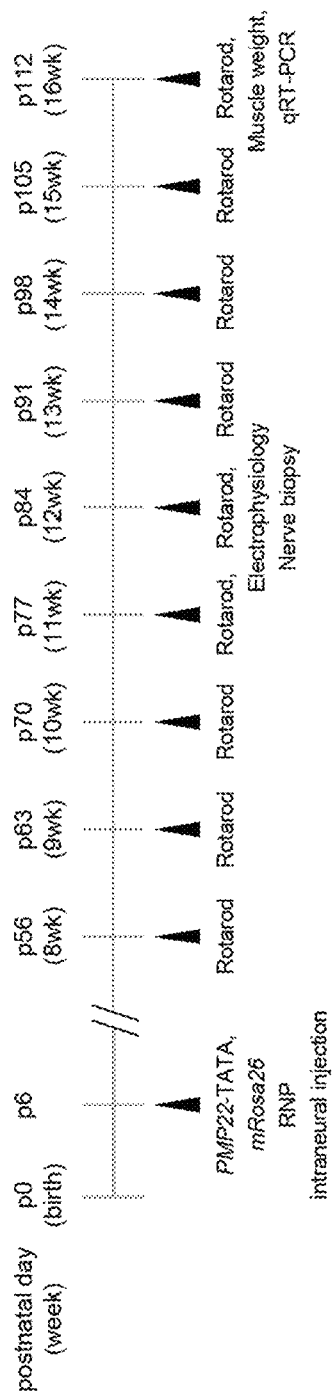
FIG. 20 schematically illustrates a therapeutic approach using PMP22-TATA RNA therapy in C22 mice.
Figure 21A:
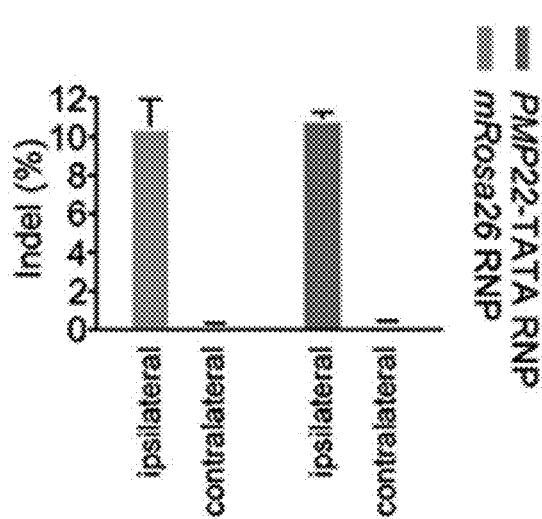
FIGS. 21A, 21B and 21C are a set of results illustrating the alleviation of a disease phenotype through expression inhibition of PMP22 by CRISPR/Cas9 in CMT1A mice, and (a) is a graph illustrating indel frequencies using targeted deep sequencing in a sciatic nerve treated with mRosa26 or a PMP22-TATA RNP complex (n=3), (b) is a TATA-box 1 mutation frequency measurement result (n=3) among the total indel frequencies, and (c) is a graph comparing the relative amounts of mRNA expressed of PMP22 using qRT-PCR from the sciatic nerve treated with mRosa26 or a PMP22-TATA RNP complex.
Figure 21B:
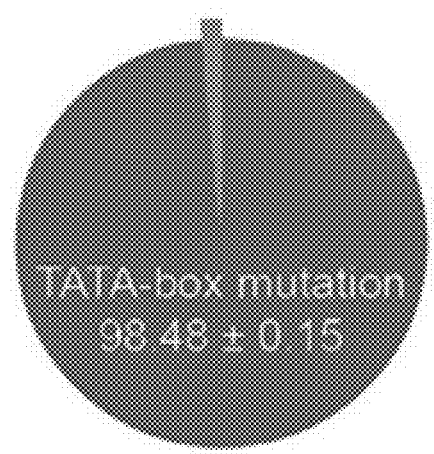
Figure 21C:
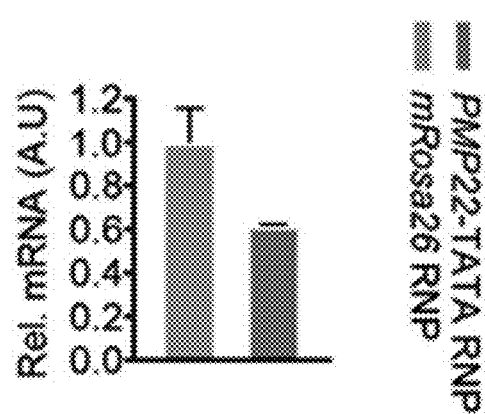

Example 6. Alleviation Effects of Disease Phenotype by Expression Inhibition of CRISPR/Cas9-Mediated PMP22 in CMT1A Mice In order to test the PMP22 transcription control by PMP22-TATA RNP in vivo, PMP22-TATA RNP enclosed by liposomes was directly injected into the sciatic nerve of the C22 mouse (FIG. 20). In this case, an RNP complex targeting Rosa26 (mRosa26) was used as a control. mRosa26 RNP or PMP22-TATA RNP was injected intraneurally into and delivered to the left sciatic nerve (ipsilateral) of a 6-day old (p6) mouse, and the right sciatic nerve was used as an internal control (contralateral). Four weeks after injection, the intraneural delivery efficiency of the RNP complex was confirmed through targeted deep sequencing by collecting genomic DNA from the sciatic nerve. As a result, all the sciatic nerves respectively treated with mRosa26 RNP and PMP22-TATA RNP showed indel efficiencies of about 11% (FIG. 21). Further, a TATA-box mutation of 98.48±0.15% was confirmed in the overall indel sequencing read consistent with the in vitro results (FIG. 21).

In addition, in order to confirm the expression inhibition of PMP22 by the TATA-box mutation in vivo, a qRT-PCR analysis of mRNA extracted from the whole sciatic nerve was performed on the RNP-treated sciatic nerve. Similar to the in vitro results, it was confirmed that the expression of the PMP22 gene was reduced by 38% as compared to the control (FIG. 21).

Figure 23:
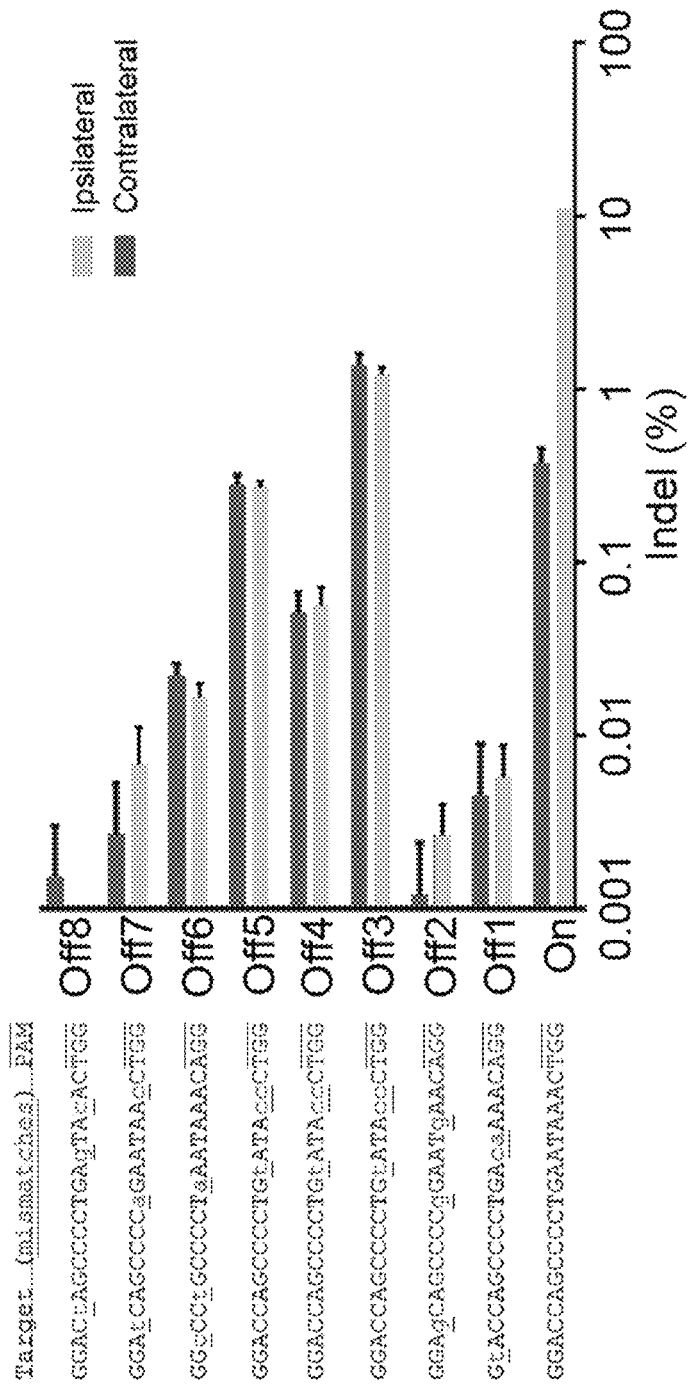
FIG. 23 is a graph illustrating an indel frequency at each off-target site of PMP22-TATA sgRNA in a mouse genome by an in silico analysis. The on-target sequence is a SEQ ID NO: 598, and the off-target sequences are SEQ ID NOs: 626 to 633 (Off1 to Off8 order).

In order to confirm whether the off-target mutation occurred in the sciatic nerve by PMP22-TATA RNP, an in silico-based off-target analysis was performed. As a result, eight off-targets including 3 bp or more mismatches were confirmed from the mouse genome (FIG. 22), and as a result of performing targeted deep sequencing, no indel mutation exceeding the sequencing error ratio was confirmed from the nerve (ipsilateral) treated with PMP22-TATA RNP (FIG. 23).

Figure 24:
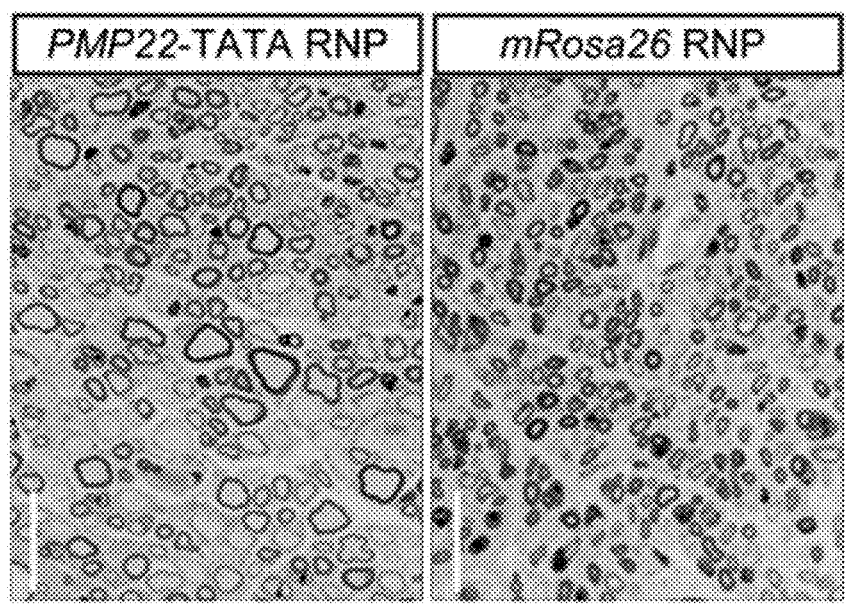
FIG. 24 is a set of images of a semithin section of the sciatic nerve tissue treated with mRosa26 or a PMP22-TATA RNP complex, shows the alleviation of a disease phenotype through expression inhibition of PMP22 by CRISPR/Cas9 in CMT1A mice.
Figure 25A:
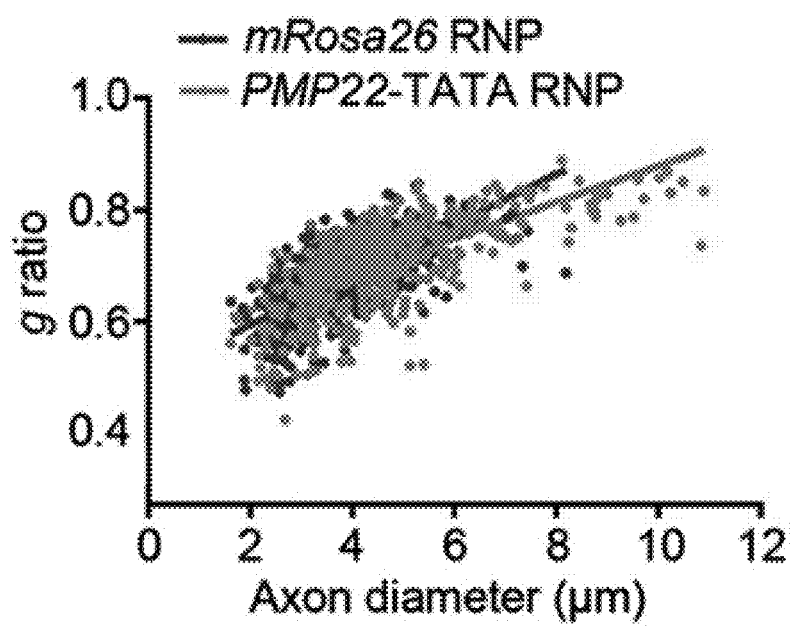
FIGS. 25A and 25B are a set of results illustrating the alleviation of a disease phenotype through expression inhibition of PMP22 by CRISPR/Cas9 in CMT1A mice, and the upper graph (a) and the low graph (b) are a scatter plot illustrating that the g-ratio is increased in mice treated with PMP22-TATA RNP and a graph illustrating that the diameter of the myelinated axon is increased in mice treated with PMP22-TATA RNP, respectively.
Figure 25B:
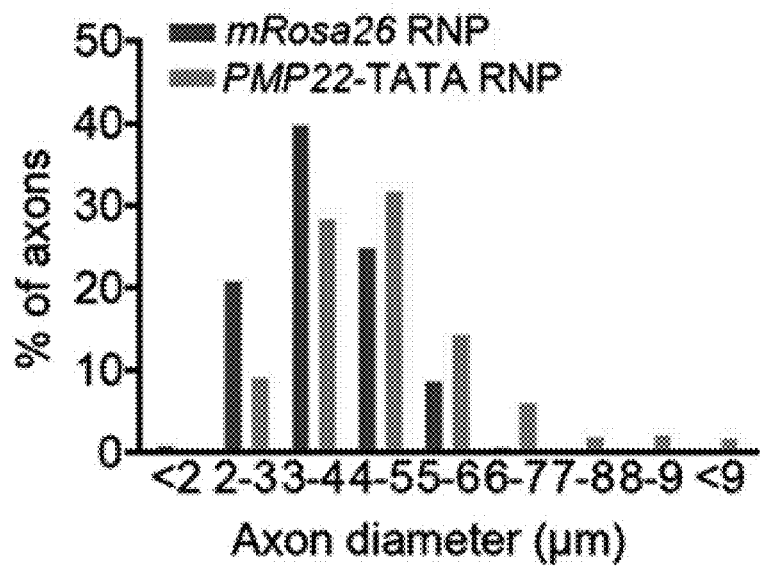

In order to test whether a decrease in transcription of PMP22 caused by PMP22-TATA RNA could prevent demyelination, the sciatic nerve of the C22 mouse treated with PMP22-TATA RNP or mRosa26 RNP was obtained, and the semi-thin cross sections thereof were stained with toluidine-blue (myelin staining). Furthermore, in order to measure the g-ratio, the axon diameter and the fiber (axon including myelin) diameter were measured. As a result, it could be confirmed that a thicker myelin sheet was formed in an experimental group treated with PMP22-TATA RNP (FIG. 24, FIG. 25). In addition, when the experimental group was treated with PMP22-TATA RNP, as compared to a control treated with mRosa26 RNP, it was found that the number of axons having a large diameter was increased (FIG. 24, FIG. 25). A result of measuring the number of large myelinated fibers having a diameter of 6 μm or more in an experimental group (16.5%) treated with PMP22-TATA RNP exhibits a clearer therapeutic effect than that in the control (2.6%, p<0.01).

Figure 26A:
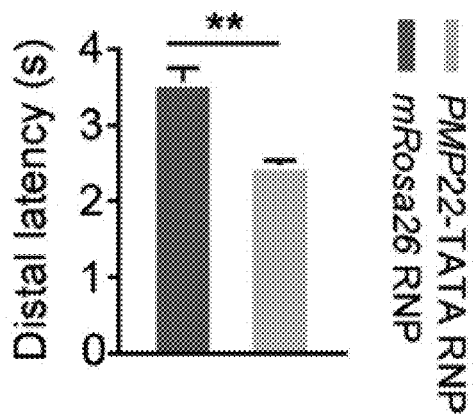
FIGS. 26A, 26B and 26C are a set of results illustrating electrophysiological changes through expression inhibition of PMP22 by CRISPR/Cas9 in CMT1A mice, and (a) is a graph illustrating the change in distal latency (DL), (b) is a graph illustrating the change in motor nerve conduction velocity (NCV), and (c) is a graph illustrating the change in compound muscle action potential (CMAP) (n=7 for mRosa26 RNP; n=10 for PMP22-TATA).
Figure 26B:
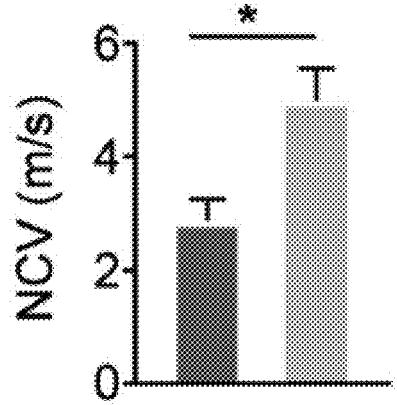
Figure 26C:
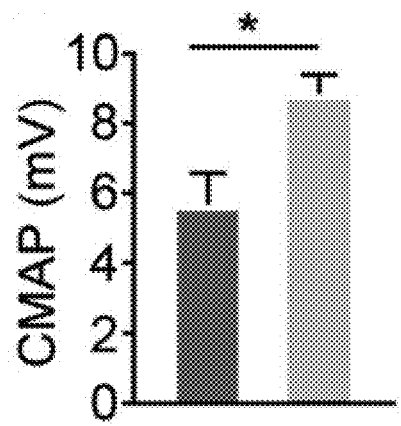

In consideration of a considerable improvement in myelination histological analysis, electrophysiological profiles of the two groups were investigated. As a result, it was confirmed that the distal latency (DL) was decreased and the motor nerve conduction velocity (NCV) was increased in the sciatic nerve of the experimental group treated with PMP22-TATA RNP as compared to a control treated with mRosa26 RNP (FIG. 26), and the results correspond to the increases in myelin thickness and axon diameter in the nerve treated with PMP22-TATA RNP. Further, it was confirmed that the amplitude of the compound muscle action potential (CMAP) was considerably increased in the nerve treated with PMP22-TATA RNP (FIG. 26), which corresponds to the previous result.

Figure 27A:
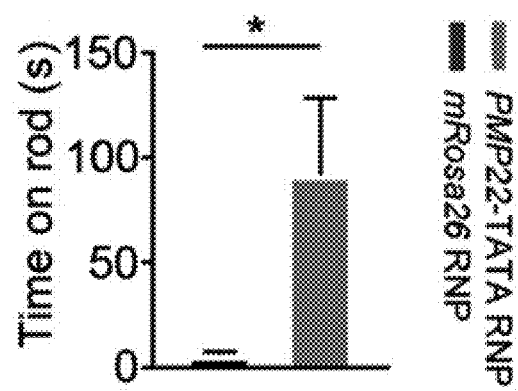
FIGS. 27A and 27B are a set of analysis results of locomotor behavior due to the expression inhibition of PMP22 by CRISPR/Cas9 in CMT1A mice, and the upper graph (a) and the lower graph (b) are a rotarod test result (n=7 for mRosa26 RNP, n=11 for PMP22-TATA) and a rotarod test result measured weekly until the mice became 8 weeks old to 16 weeks old (n=7 for mRosa26 RNP, n=11 for PMP22-TATA), respectively.
Figure 27B:
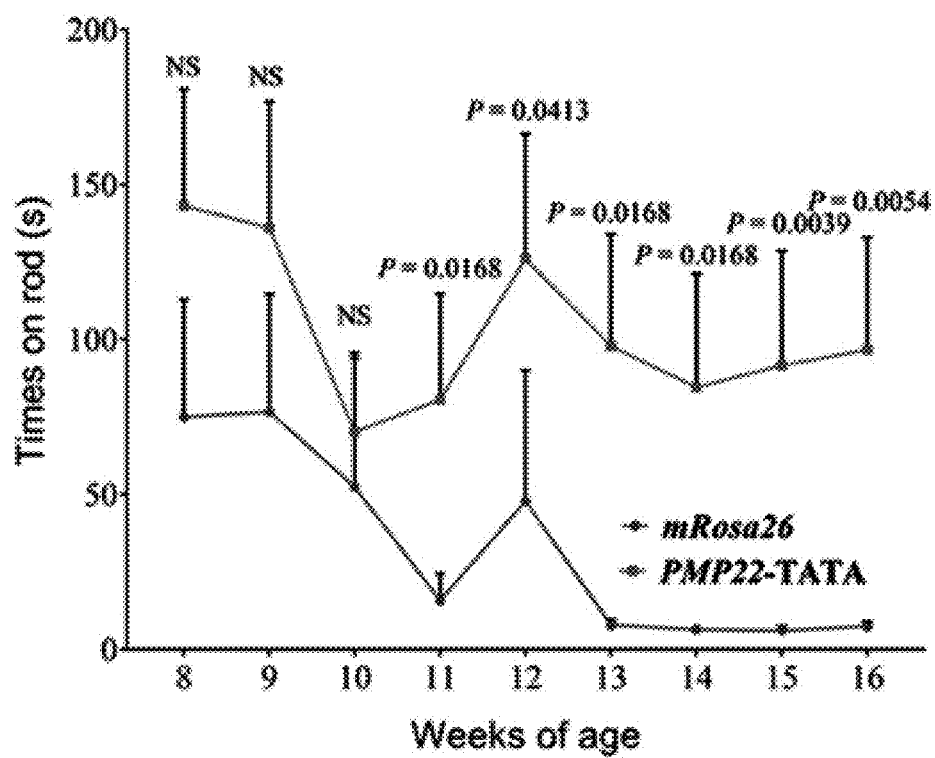
Figure 28A:
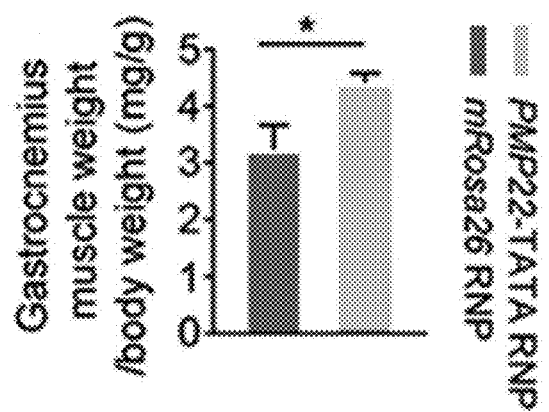
FIGS. 28A and 28B are a set of analysis results of locomotor behavior due to the expression inhibition of PMP22 by CRISPR/Cas9 in CMT1A mice, and the upper graph (a) and the lower image (b) are a graph illustrating the ratio of gastrocnemius muscle weight/body weight of a C22 mouse treated with mRosa26 or a PMP22-TATA RNP complex and a set of gastrocnemius muscle images of a C22 mouse treated with mRosa26 or a PMP22-TATA RNP complex, respectively.
Figure 28B:
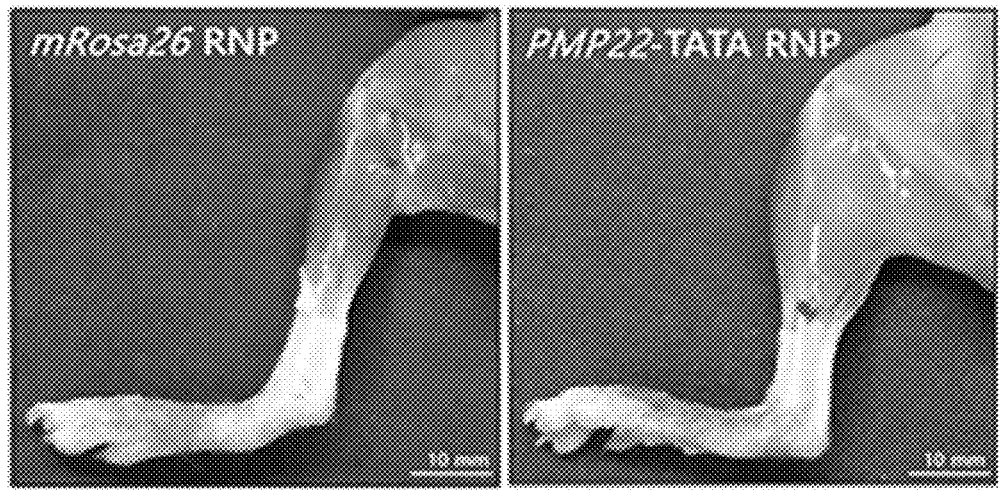

In consideration of the histologically and electrophysiologically improved effects by PMP22-TATA RNP, the locomotor behavior of mice was analyzed by a rotarod experiment. As a result, it was confirmed that mice (11 to 16 week old) treated with PMP22-TATA RNP remained longer on the rod than mice (11 to 16 week old) treated with mRosa26 RNP (FIG. 27). Further, it was confirmed that mice treated with MP22-TATA RNP were increased in muscle as compared to mice treated with mRosa26 RNP (FIG. 28).

These results show a therapeutic effect of PMP22-TATA RNP for alleviating or treating demyelination by overexpression of PMP22, such as CMT1A.

Accordingly, the aforementioned results show the expression inhibition effect of PMP22 using CRISPR/Cas9 targeting the promoter site of PMP22. Furthermore, the results show that a direct non-viral delivery of PMP22-TATA RNP to the sciatic nerve of the C22 mouse may improve the clinical and neuropathological phenotypes associated with the demyelination caused by the overexpression of PMP22. Therefore, it is believed that the CRISPR/Cas9-mediated modification of the transcriptional regulatory region of PMP22 may be a good strategy for the treatment of CMT1A and other diseases that exhibit demyelinating neuropathies.

Example 7. PLP Gene Expression Regulatory Effect

When a PLP1 gene is duplicated, the PLP1 gene is overexpressed, which becomes the major cause of a PMD disease. Therefore, to control PLP1 transcription for the treatment of the PMD disease, the transcriptional regulatory region of the PLP gene was artificially modified using CRISPR/Cas9 to confirm its effect.

Figure 29:
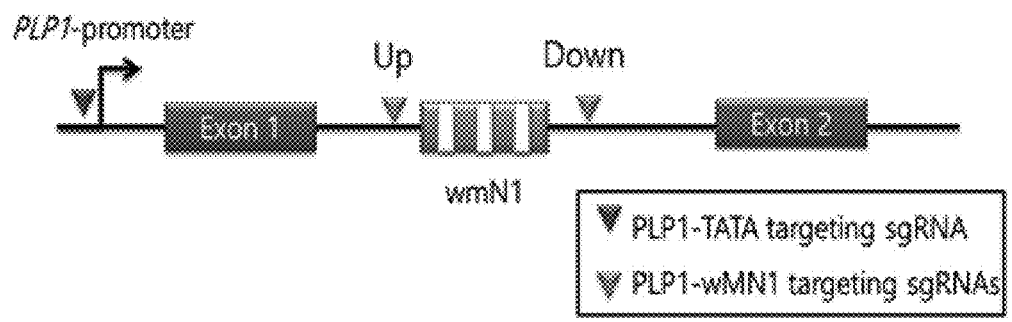
FIG. 29 is a schematic diagram illustrating a PMD therapeutic strategy, in which sgRNA targeting a TATA box region and an enhancer region of a PLP1 gene was designed. In the case of sgRNAs targeting the enhancer region, a strategy of removing an enhancer using two sgRNAs is shown. Here, sgRNA targeting the upstream of the enhancer region was represented as Up, and sgRNA targeting the downstream thereof was represented as down, and Up and Down are also represented according to locations in Tables 5 and 6.

To this end, SpCas9 and CjCas9 screening was performed for a TATA-box of the promoter sequence and the enhancer (wMN1) of mouse Plp1, sgRNA with the highest activity was selected, and then Plp1 downregulation was confirmed by qRT-PCR (FIG. 29). Here, the enhancer of Plp1 may be an ASE (Hamdan et al., 2015; Meng et al., 2005; Wight, 2017) or wMN1 (Hamdan et al., 2018; Tuason et al., 2008) region.

Based on the sgRNA screening result, each of sgRNAs for SpCas9 and CjCas9 with high indel ratios was selected (FIGS. 31 to 34 and Table 19), when the TATA-box and wMN1 enhancer regions of Plp1 were targeted using oligodendrocytes, that is, an N20.1 cell line expressing a Plp1 gene, a study on what could lead to the downregulation of the Plp1 gene was performed by qRT-PCR.

TABLE 19

Screened sgRNA list (mPlp1-TATA, mPlp1-wmN1 SpCas9 and CjCas9 lead sgRNA list)

| | mPlp1-TATA-SpCas9 | |
| --- | --- | --- |
| No. | #RGEN Target (5' to 3') | Indel ratio (%) |
| 1 | TGTTTGGTAGTATAGTAAGTAGG (SEQ ID NO: 116) | 74.6 |

| | mPlp1-WmN1-SpCas9 | | |
| --- | --- | --- | --- |
| No. | #RGEN Target (5' to 3') | Indel ratio (%) | location |
| 26 | CTCCCACTGCCTTATTAGGCAGG (SEQ ID NO: 141) | 98.9 | Up |
| 27 | AGAGCTCAAATGGGTTCTAAAGG (SEQ ID NO: 142) | 99.1 | Up |

TABLE 19-continued

Screened sgRNA list (mPlp1-TATA, mPlp1-wmN1 SpCas9 and CjCas9 lead sgRNA list)

| 28 | ACCACATTCAAGAGCTCAAATGG (SEQ ID NO: 143) | 98.6 | Up |
| --- | --- | --- | --- |
| 8 | ATCACAGTTTATACTTAGCTGGG (SEQ ID NO: 123) | 48.4 | Down |
| 9 | GGAATACCTCAGGCTCAACAGGG (SEQ ID NO: 124) | 66.6 | Down | mPlp1-TATA-CjCas9

| No. | #RGEN Target (5' to 3') | Indel ratio (%) |
| --- | --- | --- |
| 2 | AAAGCCTACTTACTATACTACCAAACACAC (SEQ ID NO: 154) | 27.9 |
| 3 | CAAAAGCCTACTTACTATACTACCAAACAC (SEQ ID NO: 155) | 33.6 | mPlp1-wMN1-CjCas9

| No. | #RGEN Target (5' to 3') | Indel ratio (%) | location |
| --- | --- | --- | --- |
| 10 | GACATACAGAGAGGGGCGGAGAGAAATAC (SEQ ID NO: 162) | 28.5 | Up |
| 25 | TTGAATGTGGTATAAGTGCTAATATCATAC (SEQ ID NO: 177) | 33.7 | Up |
| 13 | TCATCAAAGTAGTCGACAGTCAAAGCATAC (SEQ ID NO: 165) | 13.8 | Down |
| 14 | TGAATTCTAACAGGAAAACTCAGAACATAC (SEQ ID NO: 166) | 15.7 | Down |
| 23 | TTCCAAAGTTCTGTCACCCAGTAAAAACAC (SEQ ID NO: 175) | 5.4 | Down |

Figure 35A:
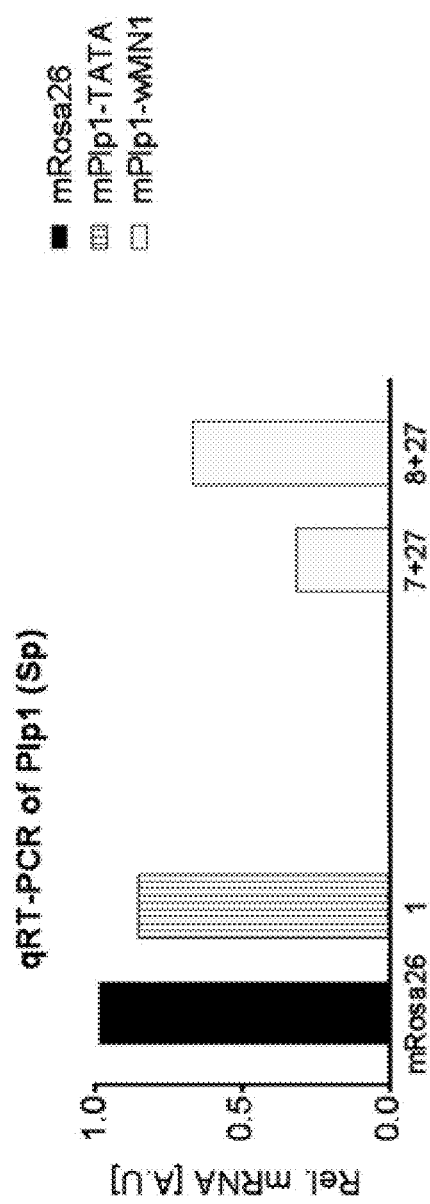
FIGS. 35A and 35B are a set of graphs showing the mRNA expression levels of Plp according to SpCas9-sgRNA and CjCas9-sgRNA targeting the TATA box and enhancer (wMN1 enhancer) regions of mPlp1. (a) shows the mRNA expression level of Plp according to SpCas9-sgRNA, and here, mPlp1-TATA-Sp-01 targeting the TATA box region and mPlp1-wMN1-Sp-07+mPlp1-wMN1-Sp-27 and mPlp1-wMN1-Sp-08+mPlp1-wMN1-Sp-27 targeting the enhancer were used as sgRNAs. (b) shows the mRNA expression level of Plp according to CjCas9-sgRNA, and here, mPlp1-TATA-Cj-02 and mPlp1-TATA-Cj-03 targeting the TATA box region; and mPlp1-wMN1-Cj-06+mPlp1-wMN1-Cj-09, mPlp1-wMN1-Cj-06+mPlp1-wMN1-Cj-10 and mPlp1-wMN1-Cj-06+mPlp1-wMN1-Cj-19 targeting the enhancer were used as sgRNAs. The mRosa26 was used as a control.
Figure 35B:
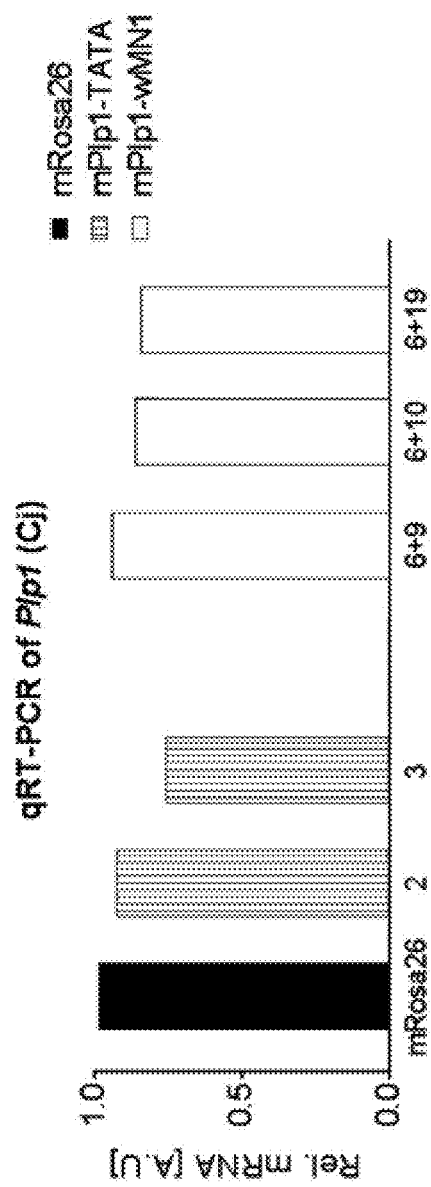
Figure 36:
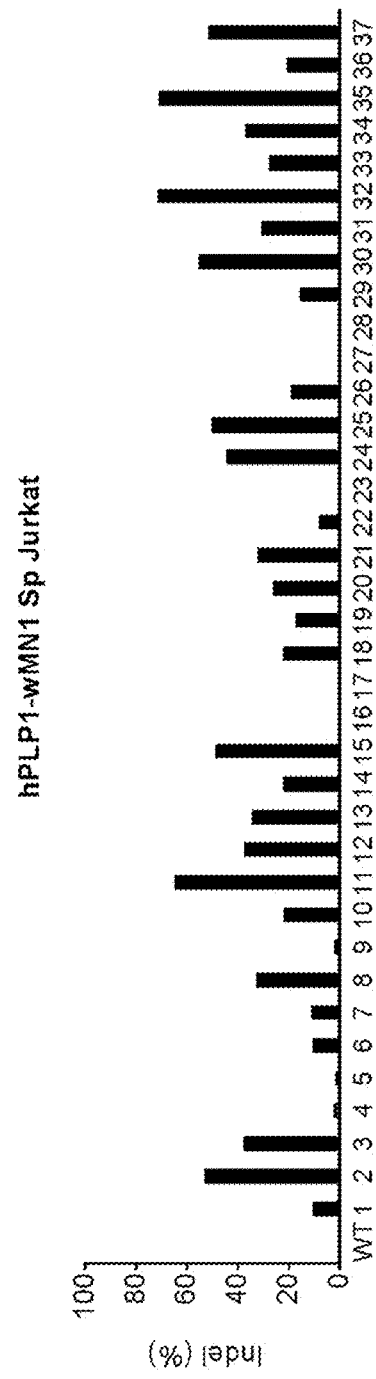
FIG. 36 is a graph showing a screening result of SpCas9-sgRNAs targeting the enhancer (wMN1 enhancer) region of hPLP1, showing indel frequencies (%) confirmed in Jurkat cells, and the used sgRNAs were hPLP1-wMN1-Sp-01 to hPLP1-wMN1-Sp-36, and distinguished by the numbers represented in target sequences on the graph.
Figure 37:
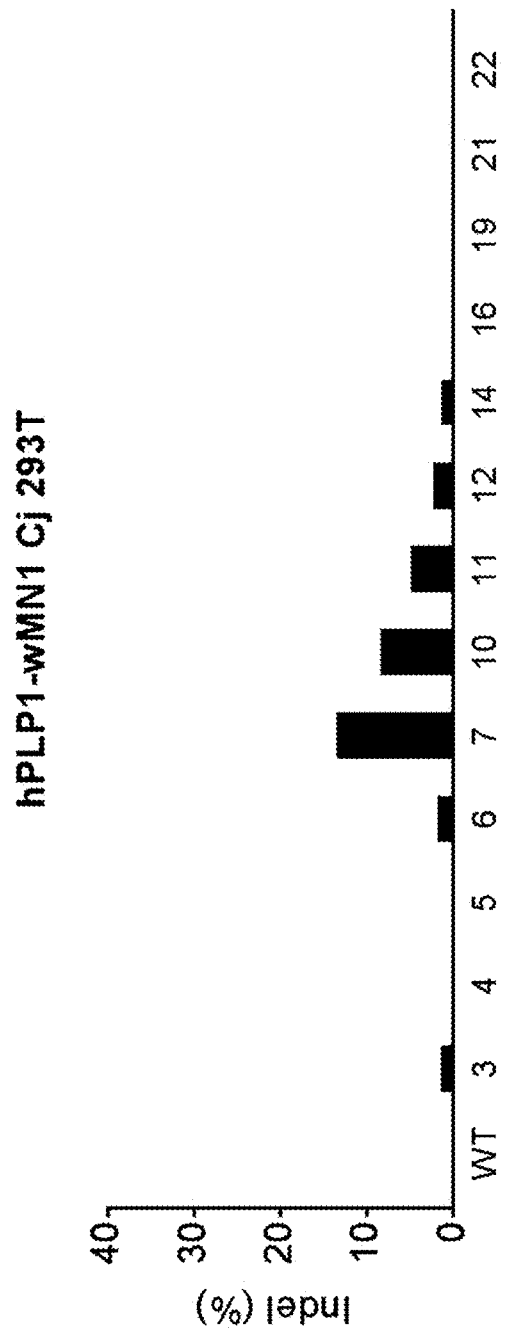
FIG. 37 is a graph showing a screening result of CjCas9-sgRNAs targeting the enhancer (wMN1 enhancer) region of hPLP1, showing indel frequencies (%) confirmed in 293T cells, and the used sgRNAs were hPLP1-wMN1-Cj-01 to hPLP1-wMN1-Cj-36, and distinguished by the numbers represented in target sequences on the graph.

As a result, it was confirmed that the targeting of the TATA box or wmN1 enhancer region of Plp1 using SpCas9 and CjCas9 leads to the significant downregulation of Plp1 (FIG. 35). In addition, SpCas9 and CjCas9 screening for the wmN1 enhancer region of a human PLP1 gene was performed to confirm an indel ratio (%) (FIGS. 36 and 37).

Therefore, it is considered that CRISPR/Cas9-mediated artificial modification of the transcriptional regulatory region of PLP1 can be a good strategy for PMD treatment.

Example 8. Manipulation of Promoter (P1) of PMP22 Gene Using SpCas9-sgRNAs and Effect of Controlling PMP22 Expression Mouse (C22 mice) primary Schwann cells overexpressing human PMP22 were treated with SpCas9-sgRNA targeting each of a P1 promoter and a P2 promoter of a human PMP22 gene, thereby confirming the expression level of PMP22.

Figure 38A:
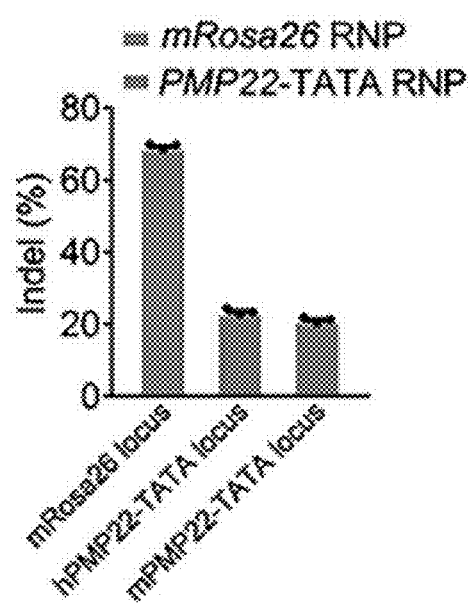
FIGS. 38A, 38B and 38C are a graph of comparing mRNA expression of human PMP22 by SpCas9-sgRNA-mediated gene manipulation, where (a) is a graph showing indel frequencies measurement results by SpCas9-sgRNA at TATA locus of human PMP22 gene and mouse PMP22 gene, (b) is a graph showing the mRNA expression of human PMP22 by SpCas9-sgRNA targeting a P1 promoter of a human PMP22 gene, and (c) is a graph showing the mRNA expression of human PMP22 by SpCas9-sgRNA targeting a P2 promoter of a human PMP22 gene.
Figures 38B, 38C:
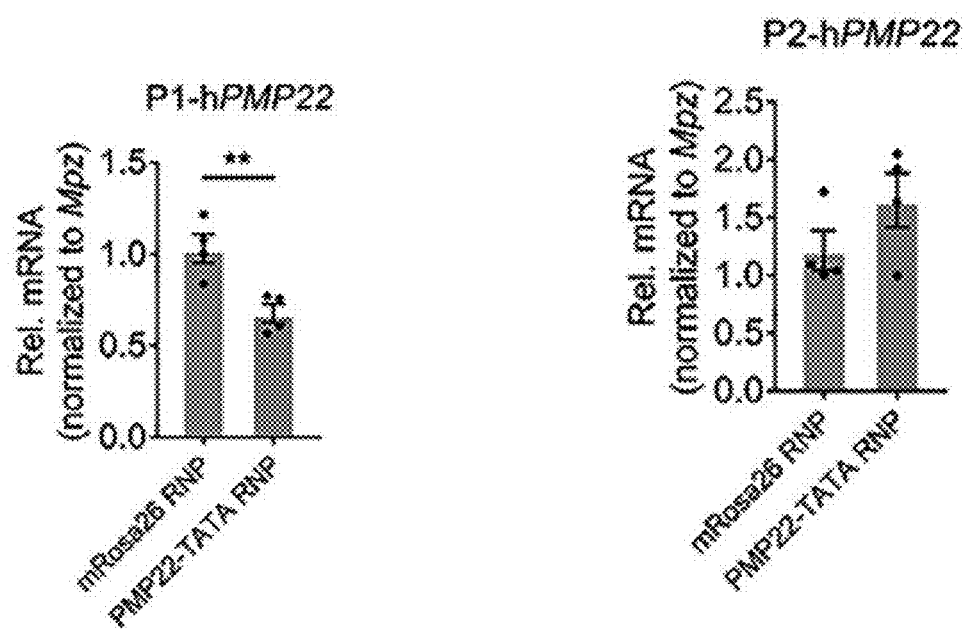

As a result, it was confirmed that, when SpCas9-sgRNA targeting the P1 promoter of the PMP22 is treated, a PMP22 expression level is reduced (FIG. 38). Contrarily, it was confirmed that, when SpCas9-sgRNA targeting the P2 promoter of the human PMP22 gene is treated, there is no significant change in a PMP22 expression level. Therefore, it can be confirmed that, since the P1 promoter plays a pivotal role in the control of the PMP22 expression, it can be an important target for controlling the PMP22 expression.

Example 9. sgRNA Screening for Deleting Promoter 1 (P1) of PMP22 Gene

Figure 40:
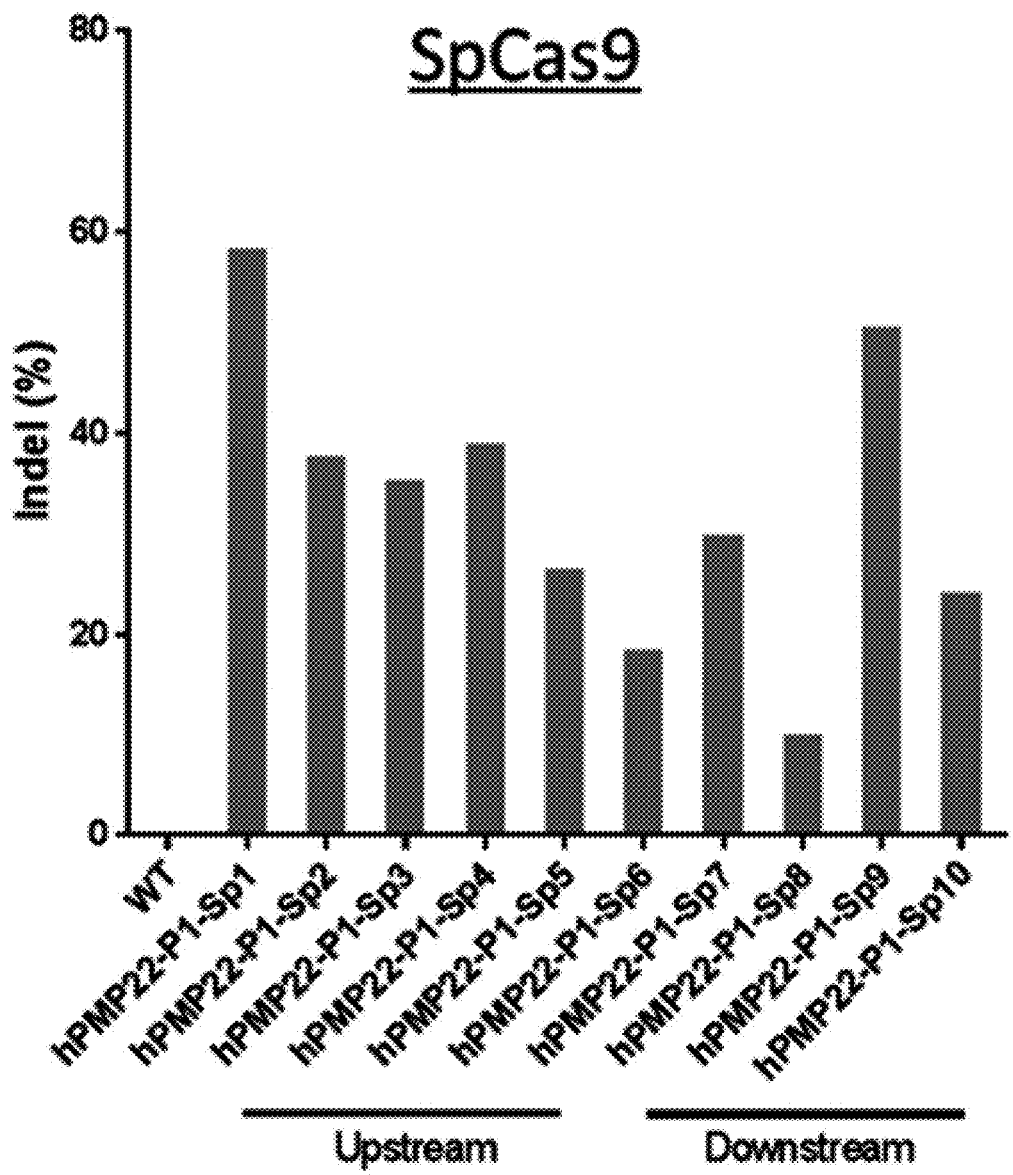
FIG. 40 illustrates indel frequencies (%) according to SpCas9-sgRNA-mediated gene manipulation, which are obtained by dividing a target site of sgRNA upstream and downstream.
Figure 41:
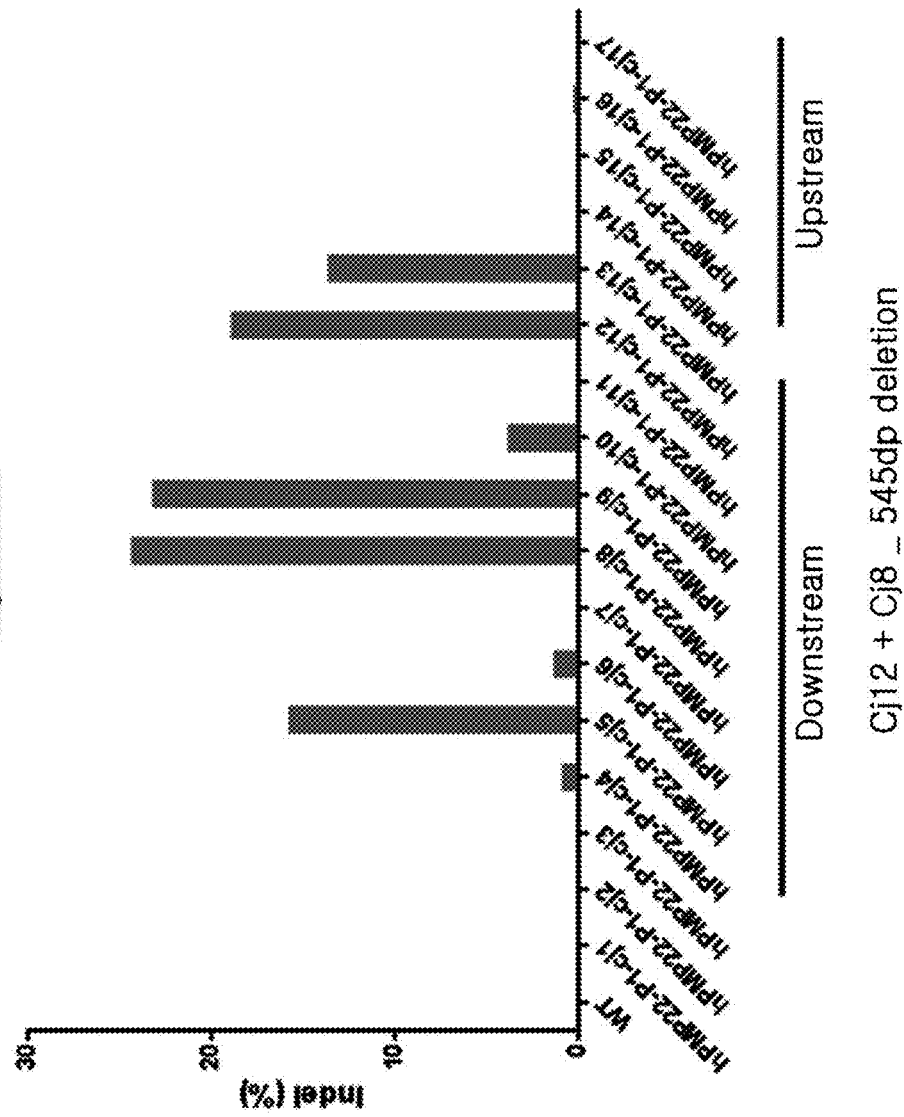
FIG. 41 illustrates indel frequencies (%) according to CjCas9-sgRNA-mediated gene manipulation, which are obtained by dividing a target site of sgRNA upstream and downstream.

To screen a therapeutically effective sgRNA sequence for reducing human PMP22 expression to a normal range, a human cell line was transduced with various sgRNAs and Cas9s, which are designed to target upstream and downstream of the promoter 1 (P1) of the PMP22 gene. gDNA was collected from the cells, and then subjected to targeted deep sequencing. Mutations with various patterns induced by the sgRNA sequence were identified by NHEJ-mediated indels. Some SpCas9-sgRNAs and CjCas9-sgRNAs highly induced indels in all regions upstream and downstream of promoter1 (P1) (FIGS. 40 and 41). SpCas9-sgRNAs (hPMP22-P1-Sp1 targeting an upstream region and hPMP22-P1-5p9 targeting a downstream region) and CjCas9-sgRNAs (hPMP22-P1-Cj12 targeting an upstream region and hPMP22-P1-Cj8 targeting a downstream region), which highly generate indels, were selected, and then a subsequent experiment was conducted.

Figure 42:
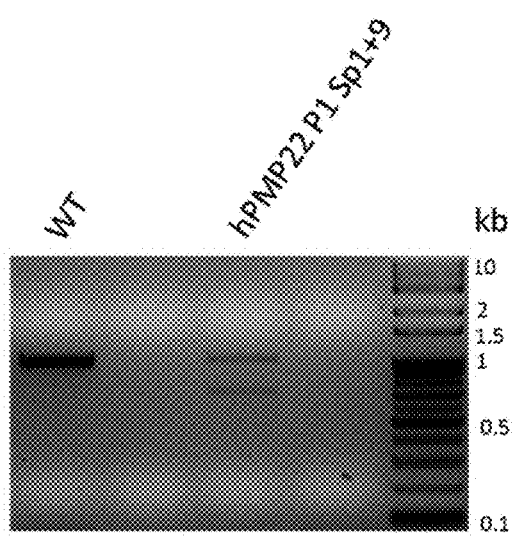
FIG. 42 illustrates the deletion of a PMP22 promoter1 using SpCas9-first sgRNA and SpCas9-second sgRNA.
Figure 43:
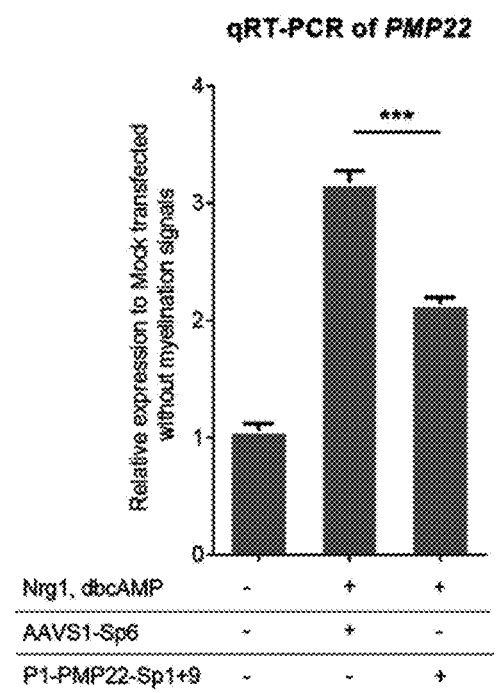
FIG. 43 illustrates the effect of reducing the PMP22 expression level by the deletion of PMP22 promoter1 using SpCas9-first sgRNA and SpCas9-second sgRNA.

Example 10. Deletion of Promoter of PMP22 Gene Using SpCas9-sgRNAs and Effect of Controlling PMP22 Expression To confirm whether the promoter of the PMP22 gene in human cells can be deleted using the selected SpCas9-sgRNAs, a promoter deleting effect was confirmed by the selected SpCas9-sgRNAs using Schwann-like cells (sNF02.0 cells). The sizes of products obtained by amplifying target genes using PCR of gDNAs of the cells collected after transduction were compared by electrophoresis. As a result, when the selected SpCas9-sgRNAs were introduced, it can be confirmed that approximately 310 bp was deleted by the selected SpCas9-sgRNAs, compared to the wild-type PMP22 gene (FIG. 42). Therefore, it can be seen that the promoter region of the PMP22 gene was deleted by the selected SpCas9-sgRNAs. In addition, as a result of comparing mRNA expression levels of the PMP22 gene, it can be confirmed that, when the promoter was deleted using the selected SpCas9-sgRNAs, the mRNA expression level of the PMP22 gene was considerably reduced (FIG. 43). Therefore, it was confirmed that the deletion of the promoter using the selected SpCas9-sgRNAs leads to knockdown of the expression of the PMP22 gene.

This result shows that, when an expression level increases due to a duplicate gene, since the expression level of the duplicate gene can be controlled by deleting or losing the transcriptional regulartory region, for example, a promoter, of the corresponding duplicate gene, the deletion of the transcriptional regulartory region may be utilized as one strategy to treat a disease caused by a duplicate gene.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for regulating an expression of PLP1 gene present in a eukaryotic cell, comprising introducing of an expression control composition into the eukaryotic cell,
wherein the expression control composition comprises the following:
a *Campylobacter jejuni*-derived Cas9 protein, or a nucleic acid encoding the Cas9 protein; and
a guide RNA comprising a crRNA and a tracrRNA, or a nucleic acid encoding the guide RNA,
wherein the crRNA comprises a guide domain, and a first complementary domain,
wherein the guide domain and the first complementary domain are linked sequentially from 5' to 3' end,
wherein the guide domain is capable of targeting a target sequence of a wmN1 enhancer region of the PLP1 gene,
wherein the target sequence is selected from the group consisting of SEQ ID NOs: 99, 100, 103, 104, 105, and 107, and
wherein the first complementary domain and the tracrRNA are capable of interacting with the Cas9 protein.

2. The method of claim 1, wherein the guide RNA is a single guide RNA.

3. The method of claim 1,
wherein the first complementary domain of the crRNA has a sequence of SEQ ID NO: 297,
wherein the tracrRNA has a sequence that SEQ ID NO: 300, SEQ ID NO: 303, and SEQ ID NO: 305 are linked sequentially from 5' to 3' end.

4. The method of claim 1, wherein the expression control composition includes the guide RNA and the Cas9 protein in a form of a ribonucleoprotein.

5. The method of claim 1, wherein the expression control composition is in a form of a vector comprising the nucleic acid encoding the guide RNA and the nucleic acid encoding the Cas9 protein.

6. The method of claim 1, wherein the introducing of the expression control composition is performed by one or more methods selected from electroporation, liposomes, plasmids, viral vectors, nanoparticles and a protein translocation domain (PTD) fusion protein method.

7. A guide RNA for targeting a target sequence of a wmN1 enhancer region of a PLP1 gene comprising:
crRNA comprising a guide domain and a first complementary domain,
wherein the guide domain and the first complementary domain are linked sequentially from 5' to 3' end,
wherein the guide domain is capable of targeting the target sequence of the wmN1 enhancer region of the PLP1 gene, wherein the target sequence is selected from the group consisting of SEQ ID NOs: 99, 100, 103, 104, 105, and 107; and
a tracrRNA,
wherein the first complementary domain and the tracrRNA are capable of interacting with a *Campylobacter jejuni*-derived Cas9 protein.

8. The guide RNA of claim 7, wherein the guide RNA is a single guide RNA.

9. The guide RNA of claim 7,
wherein the first complementary domain of the crRNA has a sequence of SEQ ID NO: 297,
wherein the tracrRNA has a sequence that SEQ ID NO: 300, SEQ ID NO: 303, and SEQ ID NO: 305 are linked sequentially from 5' to 3' end.

10. A DNA encoding the guide RNA of claim 7.

11. A composition for regulating an expression of a PLP1 gene, comprising:
a *Campylobacter jejuni*-derived Cas9 protein, or a nucleic acid encoding the Cas9 protein; and
a guide RNA comprising a crRNA and a tracrRNA, or a nucleic acid encoding the guide RNA,
wherein the crRNA comprises a guide domain, and a first complementary domain,
wherein the guide domain and the first complementary domain are linked sequentially from 5' to 3' end,
wherein the guide domain is capable of targeting a target sequence of a wmN1 enhancer region of the PLP1 gene,
wherein the target sequence is selected from the group consisting of SEQ ID NOs: 99, 100, 103, 104, 105, and 107,
wherein the first complementary domain and the tracrRNA are capable of interacting with the Cas9 protein.

12. The composition of claim 11, wherein the guide RNA is a single guide RNA.

13. The composition of claim 11,
wherein the first complementary domain of the crRNA has a sequence of SEQ ID NO: 297,
wherein the tracrRNA has a sequence that SEQ ID NO: 300, SEQ ID NO: 303, and SEQ ID NO: 305 are linked sequentially from 5' to 3' end.

14. The composition of claim 11, wherein the expression control composition includes the guide RNA and the Cas9 protein in a form of a ribonucleoprotein.

15. The composition of claim 11, wherein the expression control composition is in a form of a vector comprising the nucleic acid encoding the guide RNA and the nucleic acid encoding the Cas9 protein.

\* \* \* \* \*

```
                           SEQUENCE LISTING

<160> NUMBER OF SEQ ID NOS: 633

<210> SEQ ID NO 1
<211> LENGTH: 20
<212> TYPE: DNA
<213> ORGANISM: Homo sapiens

<400> SEQUENCE: 1
ggaccagccc ctgaataaac                                                    20

<210> SEQ ID NO 2
<211> LENGTH: 20
<212> TYPE: DNA
<213> ORGANISM: Homo sapiens

<400> SEQUENCE: 2
ggcgtctttc cagtttattc                                                    20

<210> SEQ ID NO 3
<211> LENGTH: 20
<212> TYPE: DNA
<213> ORGANISM: Homo sapiens

<400> SEQUENCE: 3
gcgtctttcc agtttattca                                                    20

<210> SEQ ID NO 4
<211> LENGTH: 20
<212> TYPE: DNA
<213> ORGANISM: Homo sapiens

<400> SEQUENCE: 4
cgtctttcca gtttattcag                                                    20

<210> SEQ ID NO 5
<211> LENGTH: 20
<212> TYPE: DNA
<213> ORGANISM: Homo sapiens

<400> SEQUENCE: 5
ttcaggggct ggtccaatgc                                                    20

<210> SEQ ID NO 6
<211> LENGTH: 20
<212> TYPE: DNA
<213> ORGANISM: Homo sapiens

<400> SEQUENCE: 6
tcaggggctg gtccaatgct                                                    20

<210> SEQ ID NO 7
<211> LENGTH: 20
<212> TYPE: DNA
<213> ORGANISM: Homo sapiens
```

```
<400> SEQUENCE: 7
accatgacat atcccagcat                                          20

<210> SEQ ID NO 8
<211> LENGTH: 20
<212> TYPE: DNA
<213> ORGANISM: Homo sapiens

<400> SEQUENCE: 8
tttccagttt attcaggggc                                          20

<210> SEQ ID NO 9
<211> LENGTH: 20
<212> TYPE: DNA
<213> ORGANISM: Homo sapiens

<400> SEQUENCE: 9
cagttacagg gagcaccacc                                          20

<210> SEQ ID NO 10
<211> LENGTH: 20
<212> TYPE: DNA
<213> ORGANISM: Homo sapiens

<400> SEQUENCE: 10
ctggtctggc ttcagttaca                                          20

<210> SEQ ID NO 11
<211> LENGTH: 20
<212> TYPE: DNA
<213> ORGANISM: Homo sapiens

<400> SEQUENCE: 11
cctggtctgg cttcagttac                                          20

<210> SEQ ID NO 12
<211> LENGTH: 20
<212> TYPE: DNA
<213> ORGANISM: Homo sapiens

<400> SEQUENCE: 12
aactggaaag acgcctggtc                                          20

<210> SEQ ID NO 13
<211> LENGTH: 20
<212> TYPE: DNA
<213> ORGANISM: Homo sapiens

<400> SEQUENCE: 13
gaataaactg gaaagacgcc                                          20

<210> SEQ ID NO 14
<211> LENGTH: 20
<212> TYPE: DNA
<213> ORGANISM: Homo sapiens

<400> SEQUENCE: 14
tccaatgctg ggatatgtca                                          20

<210> SEQ ID NO 15
<211> LENGTH: 20
<212> TYPE: DNA
```

```
<213> ORGANISM: Homo sapiens

<400> SEQUENCE: 15
aatgctggga tatgtcatgg                                               20

<210> SEQ ID NO 16
<211> LENGTH: 20
<212> TYPE: DNA
<213> ORGANISM: Homo sapiens

<400> SEQUENCE: 16
atagaggctg agaacctctc                                               20

<210> SEQ ID NO 17
<211> LENGTH: 20
<212> TYPE: DNA
<213> ORGANISM: Homo sapiens

<400> SEQUENCE: 17
ttgggcatgt ttgagctggt                                               20

<210> SEQ ID NO 18
<211> LENGTH: 20
<212> TYPE: DNA
<213> ORGANISM: Homo sapiens

<400> SEQUENCE: 18
tttgggcatg tttgagctgg                                               20

<210> SEQ ID NO 19
<211> LENGTH: 20
<212> TYPE: DNA
<213> ORGANISM: Homo sapiens

<400> SEQUENCE: 19
gagctggtgg gcgaagcata                                               20

<210> SEQ ID NO 20
<211> LENGTH: 20
<212> TYPE: DNA
<213> ORGANISM: Homo sapiens

<400> SEQUENCE: 20
agctggtggg cgaagcatat                                               20

<210> SEQ ID NO 21
<211> LENGTH: 20
<212> TYPE: DNA
<213> ORGANISM: Homo sapiens

<400> SEQUENCE: 21
tgggcgaagc atatgggcaa                                               20

<210> SEQ ID NO 22
<211> LENGTH: 20
<212> TYPE: DNA
<213> ORGANISM: Homo sapiens

<400> SEQUENCE: 22
ggcctccatc ctaaacaatg                                               20

<210> SEQ ID NO 23
<211> LENGTH: 20
```

```
<212> TYPE: DNA
<213> ORGANISM: Homo sapiens

<400> SEQUENCE: 23
gggttgggag gtttgggcgt                                              20

<210> SEQ ID NO 24
<211> LENGTH: 20
<212> TYPE: DNA
<213> ORGANISM: Homo sapiens

<400> SEQUENCE: 24
aggtttgggc gtgggagtcc                                              20

<210> SEQ ID NO 25
<211> LENGTH: 19
<212> TYPE: DNA
<213> ORGANISM: Homo sapiens

<400> SEQUENCE: 25
ttcagagact cagctattt                                               19

<210> SEQ ID NO 26
<211> LENGTH: 19
<212> TYPE: DNA
<213> ORGANISM: Homo sapiens

<400> SEQUENCE: 26
ggccacattg tttaggatg                                               19

<210> SEQ ID NO 27
<211> LENGTH: 19
<212> TYPE: DNA
<213> ORGANISM: Homo sapiens

<400> SEQUENCE: 27
ggctttgggc atgtttgag                                               19

<210> SEQ ID NO 28
<211> LENGTH: 19
<212> TYPE: DNA
<213> ORGANISM: Homo sapiens

<400> SEQUENCE: 28
aacatgccca agcccagc                                                19

<210> SEQ ID NO 29
<211> LENGTH: 19
<212> TYPE: DNA
<213> ORGANISM: Homo sapiens

<400> SEQUENCE: 29
acatgcccaa agcccagcg                                               19

<210> SEQ ID NO 30
<211> LENGTH: 20
<212> TYPE: DNA
<213> ORGANISM: Homo sapiens

<400> SEQUENCE: 30
cgatgatact cagcaacagg                                              20

<210> SEQ ID NO 31
```

-continued

```
<211> LENGTH: 20
<212> TYPE: DNA
<213> ORGANISM: Homo sapiens

<400> SEQUENCE: 31
atggacacgc aactgatctc                                              20

<210> SEQ ID NO 32
<211> LENGTH: 22
<212> TYPE: DNA
<213> ORGANISM: Homo sapiens

<400> SEQUENCE: 32
gccctctgaa tctccagtca at                                           22

<210> SEQ ID NO 33
<211> LENGTH: 22
<212> TYPE: DNA
<213> ORGANISM: Homo sapiens

<400> SEQUENCE: 33
aatctccagt caattccaac ac                                           22

<210> SEQ ID NO 34
<211> LENGTH: 22
<212> TYPE: DNA
<213> ORGANISM: Homo sapiens

<400> SEQUENCE: 34
aattaggcaa ttcttgtaaa gc                                           22

<210> SEQ ID NO 35
<211> LENGTH: 22
<212> TYPE: DNA
<213> ORGANISM: Homo sapiens

<400> SEQUENCE: 35
ttaggcaatt cttgtaaagc at                                           22

<210> SEQ ID NO 36
<211> LENGTH: 22
<212> TYPE: DNA
<213> ORGANISM: Homo sapiens

<400> SEQUENCE: 36
aaagcatagg cacacatcac cc                                           22

<210> SEQ ID NO 37
<211> LENGTH: 22
<212> TYPE: DNA
<213> ORGANISM: Homo sapiens

<400> SEQUENCE: 37
gcctggtctg gcttcagtta ca                                           22

<210> SEQ ID NO 38
<211> LENGTH: 22
<212> TYPE: DNA
<213> ORGANISM: Homo sapiens

<400> SEQUENCE: 38
gtgtccaact ttgtttgctt tc                                           22
```

```
<210> SEQ ID NO 39
<211> LENGTH: 22
<212> TYPE: DNA
<213> ORGANISM: Homo sapiens

<400> SEQUENCE: 39
gtattctgga aagcaaacaa ag                                              22

<210> SEQ ID NO 40
<211> LENGTH: 22
<212> TYPE: DNA
<213> ORGANISM: Homo sapiens

<400> SEQUENCE: 40
cagtcttggc atcacaggct tc                                              22

<210> SEQ ID NO 41
<211> LENGTH: 22
<212> TYPE: DNA
<213> ORGANISM: Homo sapiens

<400> SEQUENCE: 41
ggacctcttg gctattacac ag                                              22

<210> SEQ ID NO 42
<211> LENGTH: 22
<212> TYPE: DNA
<213> ORGANISM: Homo sapiens

<400> SEQUENCE: 42
ggagccagtg ggacctcttg gc                                              22

<210> SEQ ID NO 43
<211> LENGTH: 22
<212> TYPE: DNA
<213> ORGANISM: Homo sapiens

<400> SEQUENCE: 43
taaatcacag aggcaaagag tt                                              22

<210> SEQ ID NO 44
<211> LENGTH: 22
<212> TYPE: DNA
<213> ORGANISM: Homo sapiens

<400> SEQUENCE: 44
ttgcatagtg ctagactgtt tt                                              22

<210> SEQ ID NO 45
<211> LENGTH: 22
<212> TYPE: DNA
<213> ORGANISM: Homo sapiens

<400> SEQUENCE: 45
gggtcatgtg ttttgaaaac ag                                              22

<210> SEQ ID NO 46
<211> LENGTH: 22
<212> TYPE: DNA
<213> ORGANISM: Homo sapiens

<400> SEQUENCE: 46
cccaaacctc ccaacccaca ac                                              22
```

```
<210> SEQ ID NO 47
<211> LENGTH: 22
<212> TYPE: DNA
<213> ORGANISM: Homo sapiens

<400> SEQUENCE: 47
actcagctat ttctggaatg ac                                              22

<210> SEQ ID NO 48
<211> LENGTH: 22
<212> TYPE: DNA
<213> ORGANISM: Homo sapiens

<400> SEQUENCE: 48
tcatcgcctt tgtgagctcc at                                              22

<210> SEQ ID NO 49
<211> LENGTH: 22
<212> TYPE: DNA
<213> ORGANISM: Homo sapiens

<400> SEQUENCE: 49
cagacacagg ctttgctcta gc                                              22

<210> SEQ ID NO 50
<211> LENGTH: 22
<212> TYPE: DNA
<213> ORGANISM: Homo sapiens

<400> SEQUENCE: 50
caaagcctgt gtctggccac ta                                              22

<210> SEQ ID NO 51
<211> LENGTH: 22
<212> TYPE: DNA
<213> ORGANISM: Homo sapiens

<400> SEQUENCE: 51
agcagtttgt gcccactagt gg                                              22

<210> SEQ ID NO 52
<211> LENGTH: 22
<212> TYPE: DNA
<213> ORGANISM: Homo sapiens

<400> SEQUENCE: 52
atgtcaaggt attccagcta ac                                              22

<210> SEQ ID NO 53
<211> LENGTH: 22
<212> TYPE: DNA
<213> ORGANISM: Homo sapiens

<400> SEQUENCE: 53
gaataactgt atcaaagtta gc                                              22

<210> SEQ ID NO 54
<211> LENGTH: 22
<212> TYPE: DNA
<213> ORGANISM: Homo sapiens

<400> SEQUENCE: 54
ttcctaatta agaggctttg tg                                              22
```

<210> SEQ ID NO 55
<211> LENGTH: 22
<212> TYPE: DNA
<213> ORGANISM: Homo sapiens

<400> SEQUENCE: 55
gagctagttt gtcagggtct ag                                              22

<210> SEQ ID NO 56
<211> LENGTH: 23
<212> TYPE: DNA
<213> ORGANISM: Homo sapiens

<400> SEQUENCE: 56
gactttggga gctaatatct agg                                             23

<210> SEQ ID NO 57
<211> LENGTH: 23
<212> TYPE: DNA
<213> ORGANISM: Homo sapiens

<400> SEQUENCE: 57
ccctttcatc ttcccattcg tgg                                             23

<210> SEQ ID NO 58
<211> LENGTH: 23
<212> TYPE: DNA
<213> ORGANISM: Homo sapiens

<400> SEQUENCE: 58
cctttcatct tcccattcgt ggg                                             23

<210> SEQ ID NO 59
<211> LENGTH: 23
<212> TYPE: DNA
<213> ORGANISM: Homo sapiens

<400> SEQUENCE: 59
cccacgaatg ggaagatgaa agg                                             23

<210> SEQ ID NO 60
<211> LENGTH: 23
<212> TYPE: DNA
<213> ORGANISM: Homo sapiens

<400> SEQUENCE: 60
catcttccca ttcgtgggca agg                                             23

<210> SEQ ID NO 61
<211> LENGTH: 23
<212> TYPE: DNA
<213> ORGANISM: Homo sapiens

<400> SEQUENCE: 61
tctccacctt gcccacgaat ggg                                             23

<210> SEQ ID NO 62
<211> LENGTH: 23
<212> TYPE: DNA
<213> ORGANISM: Homo sapiens

<400> SEQUENCE: 62
gtctccacct tgcccacgaa tgg                                                23

<210> SEQ ID NO 63
<211> LENGTH: 23
<212> TYPE: DNA
<213> ORGANISM: Homo sapiens

<400> SEQUENCE: 63
cccaatgctt gcacataaat tgg                                                23

<210> SEQ ID NO 64
<211> LENGTH: 23
<212> TYPE: DNA
<213> ORGANISM: Homo sapiens

<400> SEQUENCE: 64
ccaatttatg tgcaagcatt ggg                                                23

<210> SEQ ID NO 65
<211> LENGTH: 23
<212> TYPE: DNA
<213> ORGANISM: Homo sapiens

<400> SEQUENCE: 65
tccaatttat gtgcaagcat tgg                                                23

<210> SEQ ID NO 66
<211> LENGTH: 23
<212> TYPE: DNA
<213> ORGANISM: Homo sapiens

<400> SEQUENCE: 66
tgtgcgcgtc tgaagaggag tgg                                                23

<210> SEQ ID NO 67
<211> LENGTH: 23
<212> TYPE: DNA
<213> ORGANISM: Homo sapiens

<400> SEQUENCE: 67
gtgcgcgtct gaagaggagt ggg                                                23

<210> SEQ ID NO 68
<211> LENGTH: 23
<212> TYPE: DNA
<213> ORGANISM: Homo sapiens

<400> SEQUENCE: 68
tgcgcgtctg aagaggagtg ggg                                                23

<210> SEQ ID NO 69
<211> LENGTH: 23
<212> TYPE: DNA
<213> ORGANISM: Homo sapiens

<400> SEQUENCE: 69
tagtccagat gctgttgccg tgg                                                23

<210> SEQ ID NO 70
<211> LENGTH: 23
<212> TYPE: DNA
<213> ORGANISM: Homo sapiens

<400> SEQUENCE: 70

-continued attaccacgg caacagcatc tgg 23

<210> SEQ ID NO 71
<211> LENGTH: 23
<212> TYPE: DNA
<213> ORGANISM: Homo sapiens

<400> SEQUENCE: 71
gacacgattt agtattacca cgg 23

<210> SEQ ID NO 72
<211> LENGTH: 23
<212> TYPE: DNA
<213> ORGANISM: Homo sapiens

<400> SEQUENCE: 72
ctaaatcgtg tccaaagagg agg 23

<210> SEQ ID NO 73
<211> LENGTH: 23
<212> TYPE: DNA
<213> ORGANISM: Homo sapiens

<400> SEQUENCE: 73
aggaatctca gcctcctctt tgg 23

<210> SEQ ID NO 74
<211> LENGTH: 23
<212> TYPE: DNA
<213> ORGANISM: Homo sapiens

<400> SEQUENCE: 74
gtggacaagg ttaactaaaa agg 23

<210> SEQ ID NO 75
<211> LENGTH: 23
<212> TYPE: DNA
<213> ORGANISM: Homo sapiens

<400> SEQUENCE: 75
atagtcaaat catgtggaca agg 23

<210> SEQ ID NO 76
<211> LENGTH: 23
<212> TYPE: DNA
<213> ORGANISM: Homo sapiens

<400> SEQUENCE: 76
tgctggatag tcaaatcatg tgg 23

<210> SEQ ID NO 77
<211> LENGTH: 23
<212> TYPE: DNA
<213> ORGANISM: Homo sapiens

<400> SEQUENCE: 77
acatgatttg actatccagc agg 23

<210> SEQ ID NO 78
<211> LENGTH: 23
<212> TYPE: DNA
<213> ORGANISM: Homo sapiens

<400> SEQUENCE: 78
atttgactat ccagcaggct tgg                                              23

<210> SEQ ID NO 79
<211> LENGTH: 23
<212> TYPE: DNA
<213> ORGANISM: Homo sapiens

<400> SEQUENCE: 79
gtcccgaagt ctctggggcc tgg                                              23

<210> SEQ ID NO 80
<211> LENGTH: 23
<212> TYPE: DNA
<213> ORGANISM: Homo sapiens

<400> SEQUENCE: 80
aaaacagtcc cgaagtctct ggg                                              23

<210> SEQ ID NO 81
<211> LENGTH: 23
<212> TYPE: DNA
<213> ORGANISM: Homo sapiens

<400> SEQUENCE: 81
gaaaacagtc ccgaagtctc tgg                                              23

<210> SEQ ID NO 82
<211> LENGTH: 23
<212> TYPE: DNA
<213> ORGANISM: Homo sapiens

<400> SEQUENCE: 82
tatataccac attcaagtgc tgg                                              23

<210> SEQ ID NO 83
<211> LENGTH: 23
<212> TYPE: DNA
<213> ORGANISM: Homo sapiens

<400> SEQUENCE: 83
tggatataac gaagttgtgt ggg                                              23

<210> SEQ ID NO 84
<211> LENGTH: 23
<212> TYPE: DNA
<213> ORGANISM: Homo sapiens

<400> SEQUENCE: 84
atggatataa cgaagttgtg tgg                                              23

<210> SEQ ID NO 85
<211> LENGTH: 23
<212> TYPE: DNA
<213> ORGANISM: Homo sapiens

<400> SEQUENCE: 85
atatgtttgt tcaccccaac agg                                              23

<210> SEQ ID NO 86
<211> LENGTH: 23
<212> TYPE: DNA
<213> ORGANISM: Homo sapiens

```
<400> SEQUENCE: 86
gaaaacttga aatcctgttg ggg                                              23

<210> SEQ ID NO 87
<211> LENGTH: 23
<212> TYPE: DNA
<213> ORGANISM: Homo sapiens

<400> SEQUENCE: 87
tagacattag gagaaacaga agg                                              23

<210> SEQ ID NO 88
<211> LENGTH: 23
<212> TYPE: DNA
<213> ORGANISM: Homo sapiens

<400> SEQUENCE: 88
ctagcagtga catagacatt agg                                              23

<210> SEQ ID NO 89
<211> LENGTH: 23
<212> TYPE: DNA
<213> ORGANISM: Homo sapiens

<400> SEQUENCE: 89
agccacctga ctttgatgaa agg                                              23

<210> SEQ ID NO 90
<211> LENGTH: 23
<212> TYPE: DNA
<213> ORGANISM: Homo sapiens

<400> SEQUENCE: 90
tgagaaatgt tattactata tgg                                              23

<210> SEQ ID NO 91
<211> LENGTH: 23
<212> TYPE: DNA
<213> ORGANISM: Homo sapiens

<400> SEQUENCE: 91
agactgcgag atgagagagt tgg                                              23

<210> SEQ ID NO 92
<211> LENGTH: 23
<212> TYPE: DNA
<213> ORGANISM: Homo sapiens

<400> SEQUENCE: 92
ctcgcagtct gtacttagac tgg                                              23

<210> SEQ ID NO 93
<211> LENGTH: 23
<212> TYPE: DNA
<213> ORGANISM: Homo sapiens

<400> SEQUENCE: 93
aatgtctctt gagagagcca agg                                              23

<210> SEQ ID NO 94
<211> LENGTH: 30
<212> TYPE: DNA
```

```
<213> ORGANISM: Homo sapiens

<400> SEQUENCE: 94
atgggaagat gaaagggaag taactggtac                                      30

<210> SEQ ID NO 95
<211> LENGTH: 30
<212> TYPE: DNA
<213> ORGANISM: Homo sapiens

<400> SEQUENCE: 95
actttgattg ttaaaactta tccttggcac                                      30

<210> SEQ ID NO 96
<211> LENGTH: 30
<212> TYPE: DNA
<213> ORGANISM: Homo sapiens

<400> SEQUENCE: 96
agtcctacct cagcttccca atgcttgcac                                      30

<210> SEQ ID NO 97
<211> LENGTH: 30
<212> TYPE: DNA
<213> ORGANISM: Homo sapiens

<400> SEQUENCE: 97
caatgcttgc acataaattg gaatgtgtac                                      30

<210> SEQ ID NO 98
<211> LENGTH: 30
<212> TYPE: DNA
<213> ORGANISM: Homo sapiens

<400> SEQUENCE: 98
acacagagag agacagaatg aatgatgtac                                      30

<210> SEQ ID NO 99
<211> LENGTH: 30
<212> TYPE: DNA
<213> ORGANISM: Homo sapiens

<400> SEQUENCE: 99
tcctcttcag acgcgcacac acacacacac                                      30

<210> SEQ ID NO 100
<211> LENGTH: 30
<212> TYPE: DNA
<213> ORGANISM: Homo sapiens

<400> SEQUENCE: 100
actcctcttc agacgcgcac acacacacac                                      30

<210> SEQ ID NO 101
<211> LENGTH: 30
<212> TYPE: DNA
<213> ORGANISM: Homo sapiens

<400> SEQUENCE: 101
ccactcctct tcagacgcgc acacacacac                                      30

<210> SEQ ID NO 102
<211> LENGTH: 30
```

```
<212> TYPE: DNA
<213> ORGANISM: Homo sapiens

<400> SEQUENCE: 102
ccccactcct cttcagacgc gcacacacac                                        30

<210> SEQ ID NO 103
<211> LENGTH: 30
<212> TYPE: DNA
<213> ORGANISM: Homo sapiens

<400> SEQUENCE: 103
ctccccactc ctcttcagac gcgcacacac                                        30

<210> SEQ ID NO 104
<211> LENGTH: 30
<212> TYPE: DNA
<213> ORGANISM: Homo sapiens

<400> SEQUENCE: 104
tactccccac tcctcttcag acgcgcacac                                        30

<210> SEQ ID NO 105
<211> LENGTH: 30
<212> TYPE: DNA
<213> ORGANISM: Homo sapiens

<400> SEQUENCE: 105
tatactcccc actcctcttc agacgcgcac                                        30

<210> SEQ ID NO 106
<211> LENGTH: 30
<212> TYPE: DNA
<213> ORGANISM: Homo sapiens

<400> SEQUENCE: 106
acagcatctg gactatcttg tttcctatac                                        30

<210> SEQ ID NO 107
<211> LENGTH: 30
<212> TYPE: DNA
<213> ORGANISM: Homo sapiens

<400> SEQUENCE: 107
atagtccaga tgctgttgcc gtggtaatac                                        30

<210> SEQ ID NO 108
<211> LENGTH: 30
<212> TYPE: DNA
<213> ORGANISM: Homo sapiens

<400> SEQUENCE: 108
aaaaggaatc tcagcctcct ctttggacac                                        30

<210> SEQ ID NO 109
<211> LENGTH: 30
<212> TYPE: DNA
<213> ORGANISM: Homo sapiens

<400> SEQUENCE: 109
tgtcactgct agtgtgctta attcttgtac                                        30

<210> SEQ ID NO 110
```

```
<211> LENGTH: 30
<212> TYPE: DNA
<213> ORGANISM: Homo sapiens

<400> SEQUENCE: 110
atgtgaattc agtacaagaa ttaagcacac                                    30

<210> SEQ ID NO 111
<211> LENGTH: 30
<212> TYPE: DNA
<213> ORGANISM: Homo sapiens

<400> SEQUENCE: 111
ttatgtgaat tcagtacaag aattaagcac                                    30

<210> SEQ ID NO 112
<211> LENGTH: 30
<212> TYPE: DNA
<213> ORGANISM: Homo sapiens

<400> SEQUENCE: 112
ctttcatttc tgtttatgtg aattcagtac                                    30

<210> SEQ ID NO 113
<211> LENGTH: 30
<212> TYPE: DNA
<213> ORGANISM: Homo sapiens

<400> SEQUENCE: 113
ttcacataaa cagaaatgaa agaaaaacac                                    30

<210> SEQ ID NO 114
<211> LENGTH: 30
<212> TYPE: DNA
<213> ORGANISM: Homo sapiens

<400> SEQUENCE: 114
atgccaactc tctcatctcg cagtctgtac                                    30

<210> SEQ ID NO 115
<211> LENGTH: 30
<212> TYPE: DNA
<213> ORGANISM: Homo sapiens

<400> SEQUENCE: 115
gagacattct cacatttcca gtctaagtac                                    30

<210> SEQ ID NO 116
<211> LENGTH: 23
<212> TYPE: DNA
<213> ORGANISM: Mus musculus

<400> SEQUENCE: 116
tgtttggtag tatagtaagt agg                                           23

<210> SEQ ID NO 117
<211> LENGTH: 23
<212> TYPE: DNA
<213> ORGANISM: Mus musculus

<400> SEQUENCE: 117
ggtctagaaa agatcaagcc agg                                           23
```

```
<210> SEQ ID NO 118
<211> LENGTH: 23
<212> TYPE: DNA
<213> ORGANISM: Mus musculus

<400> SEQUENCE: 118
gccaggactg tgacctgata agg                                            23

<210> SEQ ID NO 119
<211> LENGTH: 23
<212> TYPE: DNA
<213> ORGANISM: Mus musculus

<400> SEQUENCE: 119
tcaccttcac actttaacca agg                                            23

<210> SEQ ID NO 120
<211> LENGTH: 23
<212> TYPE: DNA
<213> ORGANISM: Mus musculus

<400> SEQUENCE: 120
caaggttgag acaatgttcc agg                                            23

<210> SEQ ID NO 121
<211> LENGTH: 23
<212> TYPE: DNA
<213> ORGANISM: Mus musculus

<400> SEQUENCE: 121
ccaattcatg tgcaaacatt tgg                                            23

<210> SEQ ID NO 122
<211> LENGTH: 23
<212> TYPE: DNA
<213> ORGANISM: Mus musculus

<400> SEQUENCE: 122
catcacagtt tatacttagc tgg                                            23

<210> SEQ ID NO 123
<211> LENGTH: 23
<212> TYPE: DNA
<213> ORGANISM: Mus musculus

<400> SEQUENCE: 123
atcacagttt atacttagct ggg                                            23

<210> SEQ ID NO 124
<211> LENGTH: 23
<212> TYPE: DNA
<213> ORGANISM: Mus musculus

<400> SEQUENCE: 124 ggaataccte aggctcaaca ggg                                            23

<210> SEQ ID NO 125
<211> LENGTH: 23
<212> TYPE: DNA
<213> ORGANISM: Mus musculus

<400> SEQUENCE: 125
tctctgtttc ggaataccte agg                                            23
```

```
<210> SEQ ID NO 126
<211> LENGTH: 23
<212> TYPE: DNA
<213> ORGANISM: Mus musculus

<400> SEQUENCE: 126
ctgtcgacta ctttgatgaa agg                                              23

<210> SEQ ID NO 127
<211> LENGTH: 23
<212> TYPE: DNA
<213> ORGANISM: Mus musculus

<400> SEQUENCE: 127
tgaaccaaga tgattatttg tgg                                              23

<210> SEQ ID NO 128
<211> LENGTH: 23
<212> TYPE: DNA
<213> ORGANISM: Mus musculus

<400> SEQUENCE: 128
atcttggttc atagaaattt ggg                                              23

<210> SEQ ID NO 129
<211> LENGTH: 23
<212> TYPE: DNA
<213> ORGANISM: Mus musculus

<400> SEQUENCE: 129
agccttgcat ggcagagctt ggg                                              23

<210> SEQ ID NO 130
<211> LENGTH: 23
<212> TYPE: DNA
<213> ORGANISM: Mus musculus

<400> SEQUENCE: 130
acactttaac caaggaaaga ggg                                              23

<210> SEQ ID NO 131
<211> LENGTH: 23
<212> TYPE: DNA
<213> ORGANISM: Mus musculus

<400> SEQUENCE: 131
taccagatcc cctctttcct tgg                                              23

<210> SEQ ID NO 132
<211> LENGTH: 23
<212> TYPE: DNA
<213> ORGANISM: Mus musculus

<400> SEQUENCE: 132
catttggagg ccaaaataca agg                                              23

<210> SEQ ID NO 133
<211> LENGTH: 23
<212> TYPE: DNA
<213> ORGANISM: Mus musculus

<400> SEQUENCE: 133
ccaaatgttt gcacatgaat tgg                                              23
```

<210> SEQ ID NO 134
<211> LENGTH: 23
<212> TYPE: DNA
<213> ORGANISM: Mus musculus

<400> SEQUENCE: 134
agtccagatg ctgtccctga agg                                      23

<210> SEQ ID NO 135
<211> LENGTH: 23
<212> TYPE: DNA
<213> ORGANISM: Mus musculus

<400> SEQUENCE: 135
cgcaagccat tcaaacacaa agg                                      23

<210> SEQ ID NO 136
<211> LENGTH: 23
<212> TYPE: DNA
<213> ORGANISM: Mus musculus

<400> SEQUENCE: 136
tcaaaaccct gttgagcctg agg                                      23

<210> SEQ ID NO 137
<211> LENGTH: 23
<212> TYPE: DNA
<213> ORGANISM: Mus musculus

<400> SEQUENCE: 137
cggaatacct caggctcaac agg                                      23

<210> SEQ ID NO 138
<211> LENGTH: 23
<212> TYPE: DNA
<213> ORGANISM: Mus musculus

<400> SEQUENCE: 138
gtcaaaatgt gaattctaac agg                                      23

<210> SEQ ID NO 139
<211> LENGTH: 23
<212> TYPE: DNA
<213> ORGANISM: Mus musculus

<400> SEQUENCE: 139
ttatctattc tattagagct cgg                                      23

<210> SEQ ID NO 140
<211> LENGTH: 23
<212> TYPE: DNA
<213> ORGANISM: Mus musculus

<400> SEQUENCE: 140
atcaagtaat gaaatggaca agg                                      23

<210> SEQ ID NO 141
<211> LENGTH: 23
<212> TYPE: DNA
<213> ORGANISM: Mus musculus

<400> SEQUENCE: 141
ctcccactgc cttattaggc agg                                               23

<210> SEQ ID NO 142
<211> LENGTH: 23
<212> TYPE: DNA
<213> ORGANISM: Mus musculus

<400> SEQUENCE: 142
agagctcaaa tgggttctaa agg                                               23

<210> SEQ ID NO 143
<211> LENGTH: 23
<212> TYPE: DNA
<213> ORGANISM: Mus musculus

<400> SEQUENCE: 143
accacattca agagctcaaa tgg                                               23

<210> SEQ ID NO 144
<211> LENGTH: 23
<212> TYPE: DNA
<213> ORGANISM: Mus musculus

<400> SEQUENCE: 144
ttacagattg gttacacttg ggg                                               23

<210> SEQ ID NO 145
<211> LENGTH: 23
<212> TYPE: DNA
<213> ORGANISM: Mus musculus

<400> SEQUENCE: 145
atcactgctg ctactactta tgg                                               23

<210> SEQ ID NO 146
<211> LENGTH: 23
<212> TYPE: DNA
<213> ORGANISM: Mus musculus

<400> SEQUENCE: 146
atacctgcct aataaggcag tgg                                               23

<210> SEQ ID NO 147
<211> LENGTH: 23
<212> TYPE: DNA
<213> ORGANISM: Mus musculus

<400> SEQUENCE: 147
gatcaggaga gtcagtggga tgg                                               23

<210> SEQ ID NO 148
<211> LENGTH: 23
<212> TYPE: DNA
<213> ORGANISM: Mus musculus

<400> SEQUENCE: 148
ctattgtgag tctcagatta agg                                               23

<210> SEQ ID NO 149
<211> LENGTH: 23
<212> TYPE: DNA
<213> ORGANISM: Mus musculus

<400> SEQUENCE: 149
tattacagat tggttacact tgg                                            23

<210> SEQ ID NO 150
<211> LENGTH: 23
<212> TYPE: DNA
<213> ORGANISM: Mus musculus

<400> SEQUENCE: 150
attacagatt ggttacactt ggg                                            23

<210> SEQ ID NO 151
<211> LENGTH: 23
<212> TYPE: DNA
<213> ORGANISM: Mus musculus

<400> SEQUENCE: 151
tacagattgg ttacacttgg ggg                                            23

<210> SEQ ID NO 152
<211> LENGTH: 23
<212> TYPE: DNA
<213> ORGANISM: Mus musculus

<400> SEQUENCE: 152
acagattggt tacacttggg ggg                                            23

<210> SEQ ID NO 153
<211> LENGTH: 30
<212> TYPE: DNA
<213> ORGANISM: Mus musculus

<400> SEQUENCE: 153
ctacttacta tactaccaaa cacaccgcac                                     30

<210> SEQ ID NO 154
<211> LENGTH: 30
<212> TYPE: DNA
<213> ORGANISM: Mus musculus

<400> SEQUENCE: 154
aaagcctact tactatacta ccaaacacac                                     30

<210> SEQ ID NO 155
<211> LENGTH: 30
<212> TYPE: DNA
<213> ORGANISM: Mus musculus

<400> SEQUENCE: 155
caaaagccta cttactatac taccaaacac                                     30

<210> SEQ ID NO 156
<211> LENGTH: 30
<212> TYPE: DNA
<213> ORGANISM: Mus musculus

<400> SEQUENCE: 156
gggtctgaat caaaagccta cttactatac                                     30

<210> SEQ ID NO 157
<211> LENGTH: 30
<212> TYPE: DNA
<213> ORGANISM: Mus musculus

<400> SEQUENCE: 157
agagtgggat tctacaagtc accttcacac                                    30

<210> SEQ ID NO 158
<211> LENGTH: 30
<212> TYPE: DNA
<213> ORGANISM: Mus musculus

<400> SEQUENCE: 158
ggaaagaggg gatctggtag cataaagtac                                    30

<210> SEQ ID NO 159
<211> LENGTH: 30
<212> TYPE: DNA
<213> ORGANISM: Mus musculus

<400> SEQUENCE: 159
gggatctggt agcataaagt acagctacac                                    30

<210> SEQ ID NO 160
<211> LENGTH: 30
<212> TYPE: DNA
<213> ORGANISM: Mus musculus

<400> SEQUENCE: 160
atctgtcact agcgacaagt gtagctgtac                                    30

<210> SEQ ID NO 161
<211> LENGTH: 30
<212> TYPE: DNA
<213> ORGANISM: Mus musculus

<400> SEQUENCE: 161
tcatgtgcaa acatttggag gccaaaatac                                    30

<210> SEQ ID NO 162
<211> LENGTH: 30
<212> TYPE: DNA
<213> ORGANISM: Mus musculus

<400> SEQUENCE: 162
gacatacaga gaggggcgg agagaaatac                                     30

<210> SEQ ID NO 163
<211> LENGTH: 30
<212> TYPE: DNA
<213> ORGANISM: Mus musculus

<400> SEQUENCE: 163
atactgacgc catcacatca cagtttatac                                    30

<210> SEQ ID NO 164
<211> LENGTH: 30
<212> TYPE: DNA
<213> ORGANISM: Mus musculus

<400> SEQUENCE: 164
taaaactata agctctctgt ttcggaatac                                    30

<210> SEQ ID NO 165
<211> LENGTH: 30
<212> TYPE: DNA
<213> ORGANISM: Mus musculus

<400> SEQUENCE: 165
tcatcaaagt agtcgacagt caaagcatac                                    30

<210> SEQ ID NO 166
<211> LENGTH: 30
<212> TYPE: DNA
<213> ORGANISM: Mus musculus

<400> SEQUENCE: 166
tgaattctaa caggaaaact cagaacatac                                    30

<210> SEQ ID NO 167
<211> LENGTH: 30
<212> TYPE: DNA
<213> ORGANISM: Mus musculus

<400> SEQUENCE: 167
actgctgcta ctacttatgg tgactagtac                                    30

<210> SEQ ID NO 168
<211> LENGTH: 30
<212> TYPE: DNA
<213> ORGANISM: Mus musculus

<400> SEQUENCE: 168
agtcaccata agtagtagca gcagtgatac                                    30

<210> SEQ ID NO 169
<211> LENGTH: 30
<212> TYPE: DNA
<213> ORGANISM: Mus musculus

<400> SEQUENCE: 169
cataagtagt agcagcagtg atactaatac                                    30

<210> SEQ ID NO 170
<211> LENGTH: 30
<212> TYPE: DNA
<213> ORGANISM: Mus musculus

<400> SEQUENCE: 170
ttgaatggct tgcgaacaaa gattaaacac                                    30

<210> SEQ ID NO 171
<211> LENGTH: 30
<212> TYPE: DNA
<213> ORGANISM: Mus musculus

<400> SEQUENCE: 171
ttaatctttg ttcgcaagcc attcaaacac                                    30

<210> SEQ ID NO 172
<211> LENGTH: 30
<212> TYPE: DNA
<213> ORGANISM: Mus musculus

<400> SEQUENCE: 172
ttgctgcatc tctaacgtga actctaacac                                    30

<210> SEQ ID NO 173
<211> LENGTH: 30
<212> TYPE: DNA

<213> ORGANISM: Mus musculus

<400> SEQUENCE: 173
ttcacgttag agatgcagca aagtctatac                                30

<210> SEQ ID NO 174
<211> LENGTH: 30
<212> TYPE: DNA
<213> ORGANISM: Mus musculus

<400> SEQUENCE: 174
tggaagcaac tctaaatcac cacccgatac                                30

<210> SEQ ID NO 175
<211> LENGTH: 30
<212> TYPE: DNA
<213> ORGANISM: Mus musculus

<400> SEQUENCE: 175
ttccaaagtt ctgtcaccca gtaaaaacac                                30

<210> SEQ ID NO 176
<211> LENGTH: 30
<212> TYPE: DNA
<213> ORGANISM: Mus musculus

<400> SEQUENCE: 176
ttcaagagct caaatgggtt ctaaaggcac                                30

<210> SEQ ID NO 177
<211> LENGTH: 30
<212> TYPE: DNA
<213> ORGANISM: Mus musculus

<400> SEQUENCE: 177
ttgaatgtgg tataagtgct aatatcatac                                30

<210> SEQ ID NO 178
<211> LENGTH: 30
<212> TYPE: DNA
<213> ORGANISM: Mus musculus

<400> SEQUENCE: 178
gtataagtgc taatatcata caggaaacac                                30

<210> SEQ ID NO 179
<211> LENGTH: 30
<212> TYPE: DNA
<213> ORGANISM: Mus musculus

<400> SEQUENCE: 179
gtgtttcctg tatgatatta gcacttatac                                30

<210> SEQ ID NO 180
<211> LENGTH: 30
<212> TYPE: DNA
<213> ORGANISM: Mus musculus

<400> SEQUENCE: 180
gactttgtgt ttcctgtatg atattagcac                                30

<210> SEQ ID NO 181
<211> LENGTH: 30

```
<212> TYPE: DNA
<213> ORGANISM: Mus musculus

<400> SEQUENCE: 181
aaaacaatta tcaggcagtg acagagacac                                        30

<210> SEQ ID NO 182
<211> LENGTH: 30
<212> TYPE: DNA
<213> ORGANISM: Mus musculus

<400> SEQUENCE: 182
ccaagatact agagtagctg tgactggcac                                        30

<210> SEQ ID NO 183
<211> LENGTH: 30
<212> TYPE: DNA
<213> ORGANISM: Mus musculus

<400> SEQUENCE: 183
ggcctatagc cattcaaatg gccaagatac                                        30

<210> SEQ ID NO 184
<211> LENGTH: 30
<212> TYPE: DNA
<213> ORGANISM: Mus musculus

<400> SEQUENCE: 184
gtcccatctc cctaagtctc gaatctgcac                                        30

<210> SEQ ID NO 185
<211> LENGTH: 20
<212> TYPE: DNA
<213> ORGANISM: Artificial Sequence
<220> FEATURE:
<223> OTHER INFORMATION: Primer

<400> SEQUENCE: 185
cacagggcag tcagagaccc                                                   20

<210> SEQ ID NO 186
<211> LENGTH: 20
<212> TYPE: DNA
<213> ORGANISM: Artificial Sequence
<220> FEATURE:
<223> OTHER INFORMATION: Primer

<400> SEQUENCE: 186
gcaaacaaag ttggacactg                                                   20

<210> SEQ ID NO 187
<211> LENGTH: 24
<212> TYPE: DNA
<213> ORGANISM: Artificial Sequence
<220> FEATURE:
<223> OTHER INFORMATION: Primer

<400> SEQUENCE: 187
agactcccgc ccatcttcta gaaa                                              24

<210> SEQ ID NO 188
<211> LENGTH: 24
<212> TYPE: DNA
<213> ORGANISM: Artificial Sequence
<220> FEATURE:
```

```
<223> OTHER INFORMATION: Primer

<400> SEQUENCE: 188
aagtcgctct gagttgttat cagt                                            24

<210> SEQ ID NO 189
<211> LENGTH: 19
<212> TYPE: DNA
<213> ORGANISM: Artificial Sequence
<220> FEATURE:
<223> OTHER INFORMATION: Primer

<400> SEQUENCE: 189
cagtgaaacg caccagacg                                                  19

<210> SEQ ID NO 190
<211> LENGTH: 20
<212> TYPE: DNA
<213> ORGANISM: Artificial Sequence
<220> FEATURE:
<223> OTHER INFORMATION: Primer

<400> SEQUENCE: 190
aatctgccta acaggaggtg                                                 20

<210> SEQ ID NO 191
<211> LENGTH: 24
<212> TYPE: DNA
<213> ORGANISM: Artificial Sequence
<220> FEATURE:
<223> OTHER INFORMATION: Primer

<400> SEQUENCE: 191
gagggaatgg ggaccaaagg catt                                            24

<210> SEQ ID NO 192
<211> LENGTH: 24
<212> TYPE: DNA
<213> ORGANISM: Artificial Sequence
<220> FEATURE:
<223> OTHER INFORMATION: Primer

<400> SEQUENCE: 192
tcatgtgggg tgatgttcag gaag                                            24

<210> SEQ ID NO 193
<211> LENGTH: 23
<212> TYPE: DNA
<213> ORGANISM: Artificial Sequence
<220> FEATURE:
<223> OTHER INFORMATION: Primer

<400> SEQUENCE: 193
agagcagctg acctgaggtc caa                                             23

<210> SEQ ID NO 194
<211> LENGTH: 24
<212> TYPE: DNA
<213> ORGANISM: Artificial Sequence
<220> FEATURE:
<223> OTHER INFORMATION: Primer

<400> SEQUENCE: 194
cccaagggta gagtgcaagt aaac                                            24
```

```
<210> SEQ ID NO 195
<211> LENGTH: 24
<212> TYPE: DNA
<213> ORGANISM: Artificial Sequence
<220> FEATURE:
<223> OTHER INFORMATION: Primer

<400> SEQUENCE: 195
gcatcctagc tcatttggtc tgct                                          24

<210> SEQ ID NO 196
<211> LENGTH: 24
<212> TYPE: DNA
<213> ORGANISM: Artificial Sequence
<220> FEATURE:
<223> OTHER INFORMATION: Primer

<400> SEQUENCE: 196
gagaggattc ctcatgaatg ggat                                          24

<210> SEQ ID NO 197
<211> LENGTH: 24
<212> TYPE: DNA
<213> ORGANISM: Artificial Sequence
<220> FEATURE:
<223> OTHER INFORMATION: Primer

<400> SEQUENCE: 197
accaaacact acacttggtt actg                                          24

<210> SEQ ID NO 198
<211> LENGTH: 24
<212> TYPE: DNA
<213> ORGANISM: Artificial Sequence
<220> FEATURE:
<223> OTHER INFORMATION: Primer

<400> SEQUENCE: 198
ctcccactag caattttaaa gtct                                          24

<210> SEQ ID NO 199
<211> LENGTH: 24
<212> TYPE: DNA
<213> ORGANISM: Artificial Sequence
<220> FEATURE:
<223> OTHER INFORMATION: Primer

<400> SEQUENCE: 199
gaatgttcag cacaggtttc cttg                                          24

<210> SEQ ID NO 200
<211> LENGTH: 24
<212> TYPE: DNA
<213> ORGANISM: Artificial Sequence
<220> FEATURE:
<223> OTHER INFORMATION: Primer

<400> SEQUENCE: 200
ggtcaaaagg agctccatat ttga                                          24

<210> SEQ ID NO 201
<211> LENGTH: 24
<212> TYPE: DNA
<213> ORGANISM: Artificial Sequence
<220> FEATURE:
<223> OTHER INFORMATION: Primer
```

```
<400> SEQUENCE: 201
caggacaccc atggccaaat ccag                                            24

<210> SEQ ID NO 202
<211> LENGTH: 24
<212> TYPE: DNA
<213> ORGANISM: Artificial Sequence
<220> FEATURE:
<223> OTHER INFORMATION: Primer

<400> SEQUENCE: 202
cagagcctcc tgcagggatg tcaa                                            24

<210> SEQ ID NO 203
<211> LENGTH: 24
<212> TYPE: DNA
<213> ORGANISM: Artificial Sequence
<220> FEATURE:
<223> OTHER INFORMATION: Primer

<400> SEQUENCE: 203
gcctgccaag gtgactctca tcta                                            24

<210> SEQ ID NO 204
<211> LENGTH: 24
<212> TYPE: DNA
<213> ORGANISM: Artificial Sequence
<220> FEATURE:
<223> OTHER INFORMATION: Primer

<400> SEQUENCE: 204
tgcccaggct gatcttgaac tcct                                            24

<210> SEQ ID NO 205
<211> LENGTH: 24
<212> TYPE: DNA
<213> ORGANISM: Artificial Sequence
<220> FEATURE:
<223> OTHER INFORMATION: Primer

<400> SEQUENCE: 205
cccagagtta agaggttctt tcct                                            24

<210> SEQ ID NO 206
<211> LENGTH: 24
<212> TYPE: DNA
<213> ORGANISM: Artificial Sequence
<220> FEATURE:
<223> OTHER INFORMATION: Primer

<400> SEQUENCE: 206
gaagctactc cagtgcaact agct                                            24

<210> SEQ ID NO 207
<211> LENGTH: 23
<212> TYPE: DNA
<213> ORGANISM: Artificial Sequence
<220> FEATURE:
<223> OTHER INFORMATION: Primer

<400> SEQUENCE: 207
acgcagtctg ttctgtgcag tgt                                             23

<210> SEQ ID NO 208
<211> LENGTH: 24
```

```
<212> TYPE: DNA
<213> ORGANISM: Artificial Sequence
<220> FEATURE:
<223> OTHER INFORMATION: Primer

<400> SEQUENCE: 208
aggccttccc aaggaagacc ctga                                          24

<210> SEQ ID NO 209
<211> LENGTH: 24
<212> TYPE: DNA
<213> ORGANISM: Artificial Sequence
<220> FEATURE:
<223> OTHER INFORMATION: Primer

<400> SEQUENCE: 209
gctgatcact ggccaaatcc agct                                          24

<210> SEQ ID NO 210
<211> LENGTH: 24
<212> TYPE: DNA
<213> ORGANISM: Artificial Sequence
<220> FEATURE:
<223> OTHER INFORMATION: Primer

<400> SEQUENCE: 210
gggaaacaat gggatcaagc tgca                                          24

<210> SEQ ID NO 211
<211> LENGTH: 24
<212> TYPE: DNA
<213> ORGANISM: Artificial Sequence
<220> FEATURE:
<223> OTHER INFORMATION: Primer

<400> SEQUENCE: 211
gcccctttgt aagttgagga gcat                                          24

<210> SEQ ID NO 212
<211> LENGTH: 24
<212> TYPE: DNA
<213> ORGANISM: Artificial Sequence
<220> FEATURE:
<223> OTHER INFORMATION: Primer

<400> SEQUENCE: 212
ccctctacct ctctcaatgg gctt                                          24

<210> SEQ ID NO 213
<211> LENGTH: 24
<212> TYPE: DNA
<213> ORGANISM: Artificial Sequence
<220> FEATURE:
<223> OTHER INFORMATION: Primer

<400> SEQUENCE: 213
cagacaagca aatgctgaga gatt                                          24

<210> SEQ ID NO 214
<211> LENGTH: 24
<212> TYPE: DNA
<213> ORGANISM: Artificial Sequence
<220> FEATURE:
<223> OTHER INFORMATION: Primer

<400> SEQUENCE: 214
```
cctgtcatta tgatgttcgc tagt                                          24

<210> SEQ ID NO 215
<211> LENGTH: 24
<212> TYPE: DNA
<213> ORGANISM: Artificial Sequence
<220> FEATURE:
<223> OTHER INFORMATION: Primer

<400> SEQUENCE: 215
ccagagttgg cctcctacag agat                                          24

<210> SEQ ID NO 216
<211> LENGTH: 24
<212> TYPE: DNA
<213> ORGANISM: Artificial Sequence
<220> FEATURE:
<223> OTHER INFORMATION: Primer

<400> SEQUENCE: 216
gtggatgccc cactactgtt catt                                          24

<210> SEQ ID NO 217
<211> LENGTH: 24
<212> TYPE: DNA
<213> ORGANISM: Artificial Sequence
<220> FEATURE:
<223> OTHER INFORMATION: Primer

<400> SEQUENCE: 217
tacccaattt gccagtctgt gtct                                          24

<210> SEQ ID NO 218
<211> LENGTH: 23
<212> TYPE: DNA
<213> ORGANISM: Artificial Sequence
<220> FEATURE:
<223> OTHER INFORMATION: Primer

<400> SEQUENCE: 218
accaccaggc ctgccctaca aga                                           23

<210> SEQ ID NO 219
<211> LENGTH: 24
<212> TYPE: DNA
<213> ORGANISM: Artificial Sequence
<220> FEATURE:
<223> OTHER INFORMATION: Primer

<400> SEQUENCE: 219
tgtgaatttg atcctggcat tatg                                          24

<210> SEQ ID NO 220
<211> LENGTH: 24
<212> TYPE: DNA
<213> ORGANISM: Artificial Sequence
<220> FEATURE:
<223> OTHER INFORMATION: Primer

<400> SEQUENCE: 220
tacagacaag cagatgctga gaga                                          24

<210> SEQ ID NO 221
<211> LENGTH: 24
<212> TYPE: DNA
<213> ORGANISM: Artificial Sequence

```
<220> FEATURE:
<223> OTHER INFORMATION: Primer

<400> SEQUENCE: 221
cagtcaacag agctctaacc tcct                                          24

<210> SEQ ID NO 222
<211> LENGTH: 23
<212> TYPE: DNA
<213> ORGANISM: Artificial Sequence
<220> FEATURE:
<223> OTHER INFORMATION: Primer

<400> SEQUENCE: 222
agcacctggt tgcacatcaa ctt                                           23

<210> SEQ ID NO 223
<211> LENGTH: 24
<212> TYPE: DNA
<213> ORGANISM: Artificial Sequence
<220> FEATURE:
<223> OTHER INFORMATION: Primer

<400> SEQUENCE: 223
catgtggtcc ctgaacgtga atga                                          24

<210> SEQ ID NO 224
<211> LENGTH: 23
<212> TYPE: DNA
<213> ORGANISM: Artificial Sequence
<220> FEATURE:
<223> OTHER INFORMATION: Primer

<400> SEQUENCE: 224
gtctgtcgct tgccctcttc tct                                           23

<210> SEQ ID NO 225
<211> LENGTH: 24
<212> TYPE: DNA
<213> ORGANISM: Artificial Sequence
<220> FEATURE:
<223> OTHER INFORMATION: Primer

<400> SEQUENCE: 225
atgcagggcc tctagaccat ttca                                          24

<210> SEQ ID NO 226
<211> LENGTH: 23
<212> TYPE: DNA
<213> ORGANISM: Artificial Sequence
<220> FEATURE:
<223> OTHER INFORMATION: Primer

<400> SEQUENCE: 226
ctcagcccct tgtgcactca cct                                           23

<210> SEQ ID NO 227
<211> LENGTH: 20
<212> TYPE: DNA
<213> ORGANISM: Artificial Sequence
<220> FEATURE:
<223> OTHER INFORMATION: Primer

<400> SEQUENCE: 227
tgcacatcgc aaacatttcg                                               20
```

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228
tgggtatcgc actgtgtcag                                                   20

<210> SEQ ID NO 229
<211> LENGTH: 20
<212> TYPE: DNA
<213> ORGANISM: Artificial Sequence
<220> FEATURE:
<223> OTHER INFORMATION: Primer

<400> SEQUENCE: 229
aggttcacat ggcttgtggt                                                   20

<210> SEQ ID NO 230
<211> LENGTH: 20
<212> TYPE: DNA
<213> ORGANISM: Artificial Sequence
<220> FEATURE:
<223> OTHER INFORMATION: Primer

<400> SEQUENCE: 230
atatctgaaa tgcccgcagg                                                   20

<210> SEQ ID NO 231
<211> LENGTH: 20
<212> TYPE: DNA
<213> ORGANISM: Artificial Sequence
<220> FEATURE:
<223> OTHER INFORMATION: Primer

<400> SEQUENCE: 231
tgcacatcgc aaacatttcg                                                   20

<210> SEQ ID NO 232
<211> LENGTH: 20
<212> TYPE: DNA
<213> ORGANISM: Artificial Sequence
<220> FEATURE:
<223> OTHER INFORMATION: Primer

<400> SEQUENCE: 232
tgggtatcgc actgtgtcag                                                   20

<210> SEQ ID NO 233
<211> LENGTH: 20
<212> TYPE: DNA
<213> ORGANISM: Artificial Sequence
<220> FEATURE:
<223> OTHER INFORMATION: Primer

<400> SEQUENCE: 233
tctttaaagg ccttatctcc                                                   20

<210> SEQ ID NO 234
<211> LENGTH: 20
<212> TYPE: DNA
<213> ORGANISM: Artificial Sequence
<220> FEATURE:
<223> OTHER INFORMATION: Primer -continued

```
<400> SEQUENCE: 234
ttctgcttga gaattcatcc                                                 20

<210> SEQ ID NO 235
<211> LENGTH: 20
<212> TYPE: DNA
<213> ORGANISM: Artificial Sequence
<220> FEATURE:
<223> OTHER INFORMATION: Primer

<400> SEQUENCE: 235
ctcctaatct ttcacttagg                                                 20

<210> SEQ ID NO 236
<211> LENGTH: 20
<212> TYPE: DNA
<213> ORGANISM: Artificial Sequence
<220> FEATURE:
<223> OTHER INFORMATION: Primer

<400> SEQUENCE: 236
caaagcctgg tataacatag                                                 20

<210> SEQ ID NO 237
<211> LENGTH: 19
<212> TYPE: DNA
<213> ORGANISM: Artificial Sequence
<220> FEATURE:
<223> OTHER INFORMATION: Primer

<400> SEQUENCE: 237
tcacttcgag catctgtgg                                                  19

<210> SEQ ID NO 238
<211> LENGTH: 19
<212> TYPE: DNA
<213> ORGANISM: Artificial Sequence
<220> FEATURE:
<223> OTHER INFORMATION: Primer

<400> SEQUENCE: 238
ccaaatgaca ggctgagct                                                  19

<210> SEQ ID NO 239
<211> LENGTH: 20
<212> TYPE: DNA
<213> ORGANISM: Artificial Sequence
<220> FEATURE:
<223> OTHER INFORMATION: Primer

<400> SEQUENCE: 239
agcaggaagt gaaggctaag                                                 20

<210> SEQ ID NO 240
<211> LENGTH: 20
<212> TYPE: DNA
<213> ORGANISM: Artificial Sequence
<220> FEATURE:
<223> OTHER INFORMATION: Primer

<400> SEQUENCE: 240
atgtaacgtg gcaactctgg                                                 20

<210> SEQ ID NO 241
```

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 241
gtgttgctct cgtcaattag                                                  20

<210> SEQ ID NO 242
<211> LENGTH: 20
<212> TYPE: DNA
<213> ORGANISM: Artificial Sequence
<220> FEATURE:
<223> OTHER INFORMATION: Primer

<400> SEQUENCE: 242
aggtgttgta catggagaag                                                  20

<210> SEQ ID NO 243
<211> LENGTH: 20
<212> TYPE: DNA
<213> ORGANISM: Artificial Sequence
<220> FEATURE:
<223> OTHER INFORMATION: Primer

<400> SEQUENCE: 243
tgtgagccac catacccagc                                                  20

<210> SEQ ID NO 244
<211> LENGTH: 20
<212> TYPE: DNA
<213> ORGANISM: Artificial Sequence
<220> FEATURE:
<223> OTHER INFORMATION: Primer

<400> SEQUENCE: 244
cctgcagtcc tttgcggatc                                                  20

<210> SEQ ID NO 245
<211> LENGTH: 20
<212> TYPE: DNA
<213> ORGANISM: Artificial Sequence
<220> FEATURE:
<223> OTHER INFORMATION: Primer

<400> SEQUENCE: 245
tcgctgccag tataacatgc                                                  20

<210> SEQ ID NO 246
<211> LENGTH: 20
<212> TYPE: DNA
<213> ORGANISM: Artificial Sequence
<220> FEATURE:
<223> OTHER INFORMATION: Primer

<400> SEQUENCE: 246
aactccagtc tctagactcg                                                  20

<210> SEQ ID NO 247
<211> LENGTH: 20
<212> TYPE: DNA
<213> ORGANISM: Artificial Sequence
<220> FEATURE:
<223> OTHER INFORMATION: Primer

<400> SEQUENCE: 247
```

-continued

```
aatagtttga cgttggagcc                                              20

<210> SEQ ID NO 248
<211> LENGTH: 20
<212> TYPE: DNA
<213> ORGANISM: Artificial Sequence
<220> FEATURE:
<223> OTHER INFORMATION: Primer

<400> SEQUENCE: 248
actcccaaca tgttctcctg                                              20

<210> SEQ ID NO 249
<211> LENGTH: 19
<212> TYPE: DNA
<213> ORGANISM: Artificial Sequence
<220> FEATURE:
<223> OTHER INFORMATION: Primer

<400> SEQUENCE: 249
atcatcgctc acagagtcc                                               19

<210> SEQ ID NO 250
<211> LENGTH: 20
<212> TYPE: DNA
<213> ORGANISM: Artificial Sequence
<220> FEATURE:
<223> OTHER INFORMATION: Primer

<400> SEQUENCE: 250
acgactgcag gatcttaatg                                              20

<210> SEQ ID NO 251
<211> LENGTH: 20
<212> TYPE: DNA
<213> ORGANISM: Artificial Sequence
<220> FEATURE:
<223> OTHER INFORMATION: Primer

<400> SEQUENCE: 251
tggatggagg ttgggaatcc                                              20

<210> SEQ ID NO 252
<211> LENGTH: 20
<212> TYPE: DNA
<213> ORGANISM: Artificial Sequence
<220> FEATURE:
<223> OTHER INFORMATION: Primer

<400> SEQUENCE: 252
ttgaggcagc agcactctcc                                              20

<210> SEQ ID NO 253
<211> LENGTH: 19
<212> TYPE: DNA
<213> ORGANISM: Artificial Sequence
<220> FEATURE:
<223> OTHER INFORMATION: Primer

<400> SEQUENCE: 253
agtctatcct agcagctcc                                               19

<210> SEQ ID NO 254
<211> LENGTH: 20
<212> TYPE: DNA
```

```
<213> ORGANISM: Artificial Sequence
<220> FEATURE:
<223> OTHER INFORMATION: Primer

<400> SEQUENCE: 254
actgagacca gataatgcag                                                   20

<210> SEQ ID NO 255
<211> LENGTH: 19
<212> TYPE: DNA
<213> ORGANISM: Artificial Sequence
<220> FEATURE:
<223> OTHER INFORMATION: Primer

<400> SEQUENCE: 255
aagagatgcg agttgttcc                                                    19

<210> SEQ ID NO 256
<211> LENGTH: 19
<212> TYPE: DNA
<213> ORGANISM: Artificial Sequence
<220> FEATURE:
<223> OTHER INFORMATION: Primer

<400> SEQUENCE: 256
cctcttctac tctgagtgg                                                    19

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
acctggttta tcacaagcta                                                   20

<210> SEQ ID NO 258
<211> LENGTH: 20
<212> TYPE: DNA
<213> ORGANISM: Artificial Sequence
<220> FEATURE:
<223> OTHER INFORMATION: Primer

<400> SEQUENCE: 258
aacgtgaaca gaaggatttc                                                   20

<210> SEQ ID NO 259
<211> LENGTH: 20
<212> TYPE: DNA
<213> ORGANISM: Artificial Sequence
<220> FEATURE:
<223> OTHER INFORMATION: Primer

<400> SEQUENCE: 259
atcactccat cagagtcagg                                                   20

<210> SEQ ID NO 260
<211> LENGTH: 20
<212> TYPE: DNA
<213> ORGANISM: Artificial Sequence
<220> FEATURE:
<223> OTHER INFORMATION: Primer

<400> SEQUENCE: 260
tggctccttc tattctctcc                                                   20
```

```
<210> SEQ ID NO 261
<211> LENGTH: 4
<212> TYPE: DNA
<213> ORGANISM: Homo sapiens

<400> SEQUENCE: 261 tata                                                                   4

<210> SEQ ID NO 262
<211> LENGTH: 7
<212> TYPE: DNA
<213> ORGANISM: Homo sapiens

<400> SEQUENCE: 262 tatawaw                                                                7

<210> SEQ ID NO 263
<211> LENGTH: 8
<212> TYPE: DNA
<213> ORGANISM: Homo sapiens

<400> SEQUENCE: 263 tatawawr                                                               8

<210> SEQ ID NO 264
<211> LENGTH: 7
<212> TYPE: DNA
<213> ORGANISM: Homo sapiens

<400> SEQUENCE: 264 cataaaa                                                                7

<210> SEQ ID NO 265
<211> LENGTH: 5
<212> TYPE: DNA
<213> ORGANISM: Homo sapiens

<400> SEQUENCE: 265 tataa                                                                  5

<210> SEQ ID NO 266
<211> LENGTH: 7
<212> TYPE: DNA
<213> ORGANISM: Homo sapiens

<400> SEQUENCE: 266 tataaaa                                                                7

<210> SEQ ID NO 267
<211> LENGTH: 8
<212> TYPE: DNA
<213> ORGANISM: Homo sapiens

<400> SEQUENCE: 267 cataaata                                                               8

<210> SEQ ID NO 268
<211> LENGTH: 7
<212> TYPE: DNA
<213> ORGANISM: Homo sapiens

<400> SEQUENCE: 268
```

```
tatataa                                                      7

<210> SEQ ID NO 269
<211> LENGTH: 15
<212> TYPE: DNA
<213> ORGANISM: Homo sapiens

<400> SEQUENCE: 269
tatatatata tataa                                            15

<210> SEQ ID NO 270
<211> LENGTH: 9
<212> TYPE: DNA
<213> ORGANISM: Homo sapiens

<400> SEQUENCE: 270 tatattata                                                    9

<210> SEQ ID NO 271
<211> LENGTH: 6
<212> TYPE: DNA
<213> ORGANISM: Homo sapiens

<400> SEQUENCE: 271 tataaa                                                       6

<210> SEQ ID NO 272
<211> LENGTH: 9
<212> TYPE: DNA
<213> ORGANISM: Homo sapiens

<400> SEQUENCE: 272 tataaaata                                                    9

<210> SEQ ID NO 273
<211> LENGTH: 6
<212> TYPE: DNA
<213> ORGANISM: Homo sapiens

<400> SEQUENCE: 273 tatata                                                       6

<210> SEQ ID NO 274
<211> LENGTH: 9
<212> TYPE: DNA
<213> ORGANISM: Homo sapiens

<400> SEQUENCE: 274 gattaaaaa                                                    9

<210> SEQ ID NO 275
<211> LENGTH: 8
<212> TYPE: DNA
<213> ORGANISM: Homo sapiens

<400> SEQUENCE: 275 tataaaaa                                                     8

<210> SEQ ID NO 276
<211> LENGTH: 6
<212> TYPE: DNA
<213> ORGANISM: Homo sapiens

<400> SEQUENCE: 276
```

```
ttataa                                                          6

<210> SEQ ID NO 277
<211> LENGTH: 8
<212> TYPE: DNA
<213> ORGANISM: Homo sapiens

<400> SEQUENCE: 277 ttttaaaa                                                        8

<210> SEQ ID NO 278
<211> LENGTH: 9
<212> TYPE: DNA
<213> ORGANISM: Homo sapiens

<400> SEQUENCE: 278 tctttaaaa                                                       9

<210> SEQ ID NO 279
<211> LENGTH: 9
<212> TYPE: DNA
<213> ORGANISM: Homo sapiens

<400> SEQUENCE: 279 gacatttaa                                                       9

<210> SEQ ID NO 280
<211> LENGTH: 9
<212> TYPE: DNA
<213> ORGANISM: Homo sapiens

<400> SEQUENCE: 280 tgatatcaa                                                       9

<210> SEQ ID NO 281
<211> LENGTH: 8
<212> TYPE: DNA
<213> ORGANISM: Homo sapiens

<400> SEQUENCE: 281 tataaata                                                        8

<210> SEQ ID NO 282
<211> LENGTH: 7
<212> TYPE: DNA
<213> ORGANISM: Homo sapiens

<400> SEQUENCE: 282 tataaga                                                         7

<210> SEQ ID NO 283
<211> LENGTH: 6
<212> TYPE: DNA
<213> ORGANISM: Homo sapiens

<400> SEQUENCE: 283 aataaa                                                          6

<210> SEQ ID NO 284
<211> LENGTH: 6
<212> TYPE: DNA
<213> ORGANISM: Homo sapiens
```

-continued

```
<400> SEQUENCE: 284 tttata                                                                    6

<210> SEQ ID NO 285
<211> LENGTH: 8
<212> TYPE: DNA
<213> ORGANISM: Homo sapiens

<400> SEQUENCE: 285 cataaaaa                                                                  8

<210> SEQ ID NO 286
<211> LENGTH: 6
<212> TYPE: DNA
<213> ORGANISM: Homo sapiens

<400> SEQUENCE: 286 tataca                                                                    6

<210> SEQ ID NO 287
<211> LENGTH: 7
<212> TYPE: DNA
<213> ORGANISM: Homo sapiens

<400> SEQUENCE: 287 tttaaga                                                                   7

<210> SEQ ID NO 288
<211> LENGTH: 7
<212> TYPE: DNA
<213> ORGANISM: Homo sapiens

<400> SEQUENCE: 288 gataaag                                                                   7

<210> SEQ ID NO 289
<211> LENGTH: 7
<212> TYPE: DNA
<213> ORGANISM: Homo sapiens

<400> SEQUENCE: 289 tataaca                                                                   7

<210> SEQ ID NO 290
<211> LENGTH: 9
<212> TYPE: DNA
<213> ORGANISM: Homo sapiens

<400> SEQUENCE: 290 tcttatctt                                                                 9

<210> SEQ ID NO 291
<211> LENGTH: 9
<212> TYPE: DNA
<213> ORGANISM: Homo sapiens

<400> SEQUENCE: 291 ttgtacttt                                                                 9

<210> SEQ ID NO 292
<211> LENGTH: 7
<212> TYPE: DNA
<213> ORGANISM: Homo sapiens
```

```
<400> SEQUENCE: 292 cataaa                                                               7

<210> SEQ ID NO 293
<211> LENGTH: 7
<212> TYPE: DNA
<213> ORGANISM: Homo sapiens

<400> SEQUENCE: 293 tataaat                                                              7

<210> SEQ ID NO 294
<211> LENGTH: 15
<212> TYPE: DNA
<213> ORGANISM: Homo sapiens

<400> SEQUENCE: 294
tatatataaa aaaaa                                                    15

<210> SEQ ID NO 295
<211> LENGTH: 18
<212> TYPE: DNA
<213> ORGANISM: Homo sapiens

<400> SEQUENCE: 295
cataaataaa aaaaatta                                                 18

<210> SEQ ID NO 296
<211> LENGTH: 12
<212> TYPE: RNA
<213> ORGANISM: Streptococcus pyogenes

<400> SEQUENCE: 296
guuuuagagc ua                                                       12

<210> SEQ ID NO 297
<211> LENGTH: 25
<212> TYPE: RNA
<213> ORGANISM: Campylobacter jejuni

<400> SEQUENCE: 297
guuuuagucc cuuuuuaaau uucuu                                         25

<210> SEQ ID NO 298
<211> LENGTH: 9
<212> TYPE: RNA
<213> ORGANISM: Unknown
<220> FEATURE:
<223> OTHER INFORMATION: Parcubacteria bacterium

<400> SEQUENCE: 298 uuuguagau                                                            9

<210> SEQ ID NO 299
<211> LENGTH: 14
<212> TYPE: RNA
<213> ORGANISM: Streptococcus pyogenes

<400> SEQUENCE: 299
uagcaaguua aaau                                                     14

<210> SEQ ID NO 300
```

```
<211> LENGTH: 25
<212> TYPE: RNA
<213> ORGANISM: Campylobacter jejuni

<400> SEQUENCE: 300
aagaaauuua aaagggacu aaaau                                              25

<210> SEQ ID NO 301
<211> LENGTH: 11
<212> TYPE: RNA
<213> ORGANISM: Unknown
<220> FEATURE:
<223> OTHER INFORMATION: Parcubacteria bacterium

<400> SEQUENCE: 301
aaauuucuac u                                                            11

<210> SEQ ID NO 302
<211> LENGTH: 12
<212> TYPE: RNA
<213> ORGANISM: Streptococcus pyogenes

<400> SEQUENCE: 302
aaggcuaguc cg                                                           12

<210> SEQ ID NO 303
<211> LENGTH: 11
<212> TYPE: RNA
<213> ORGANISM: Campylobacter jejuni

<400> SEQUENCE: 303
aaagaguuug c                                                            11

<210> SEQ ID NO 304
<211> LENGTH: 34
<212> TYPE: RNA
<213> ORGANISM: Streptococcus pyogenes

<400> SEQUENCE: 304
uuaucaacuu gaaaaagugg caccgagucg gugc                                   34

<210> SEQ ID NO 305
<211> LENGTH: 38
<212> TYPE: RNA
<213> ORGANISM: Campylobacter jejuni

<400> SEQUENCE: 305
gggacucugc gggguuacaa uccccuaaaa ccgcuuuu                               38

<210> SEQ ID NO 306
<211> LENGTH: 22
<212> TYPE: RNA
<213> ORGANISM: Streptococcus thermophilus

<400> SEQUENCE: 306
guuuuagagc uguguuguuu cg                                                22

<210> SEQ ID NO 307
<211> LENGTH: 24
<212> TYPE: RNA
<213> ORGANISM: Streptococcus thermophilus

<400> SEQUENCE: 307
cgaaacaaca cagcgaguua aaau                                              24
```

<210> SEQ ID NO 308
<211> LENGTH: 13
<212> TYPE: RNA
<213> ORGANISM: Streptococcus thermophilus

<400> SEQUENCE: 308
aaggcuuagu ccg                                                          13

<210> SEQ ID NO 309
<211> LENGTH: 38
<212> TYPE: RNA
<213> ORGANISM: Streptococcus thermophilus

<400> SEQUENCE: 309
uacucaacuu gaaaaggugg caccgauucg guguuuuu                               38

<210> SEQ ID NO 310
<211> LENGTH: 20
<212> TYPE: DNA
<213> ORGANISM: Artificial Sequence
<220> FEATURE:
<223> OTHER INFORMATION: target sequence

<400> SEQUENCE: 310
atcattggca gactagttcg                                                   20

<210> SEQ ID NO 311
<211> LENGTH: 20
<212> TYPE: DNA
<213> ORGANISM: Artificial Sequence
<220> FEATURE:
<223> OTHER INFORMATION: target sequence

<400> SEQUENCE: 311
cgaactagtc tgccaatgat                                                   20

<210> SEQ ID NO 312
<211> LENGTH: 7
<212> TYPE: PRT
<213> ORGANISM: Artificial Sequence
<220> FEATURE:
<223> OTHER INFORMATION: Nuclear localization sequence

<400> SEQUENCE: 312

Pro Lys Lys Lys Arg Lys Val
1               5

<210> SEQ ID NO 313
<211> LENGTH: 16
<212> TYPE: PRT
<213> ORGANISM: Artificial Sequence
<220> FEATURE:
<223> OTHER INFORMATION: Nuclear localization sequence

<400> SEQUENCE: 313

Lys Arg Pro Ala Ala Thr Lys Lys Ala Gly Gln Ala Lys Lys Lys Lys
1               5                   10                  15

<210> SEQ ID NO 314
<211> LENGTH: 9
<212> TYPE: PRT
<213> ORGANISM: Artificial Sequence
<220> FEATURE:
<223> OTHER INFORMATION: Nuclear localization sequence

```
<400> SEQUENCE: 314

Pro Ala Ala Lys Arg Val Lys Leu Asp
1               5

<210> SEQ ID NO 315
<211> LENGTH: 11
<212> TYPE: PRT
<213> ORGANISM: Artificial Sequence
<220> FEATURE:
<223> OTHER INFORMATION: Nuclear localization sequence

<400> SEQUENCE: 315

Arg Gln Arg Arg Asn Glu Leu Lys Arg Ser Pro
1               5                   10

<210> SEQ ID NO 316
<211> LENGTH: 38
<212> TYPE: PRT
<213> ORGANISM: Artificial Sequence
<220> FEATURE:
<223> OTHER INFORMATION: Nuclear localization sequence

<400> SEQUENCE: 316

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 317
<211> LENGTH: 42
<212> TYPE: PRT
<213> ORGANISM: Artificial Sequence
<220> FEATURE:
<223> OTHER INFORMATION: Nuclear localization sequence

<400> SEQUENCE: 317

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 318
<211> LENGTH: 8
<212> TYPE: PRT
<213> ORGANISM: Artificial Sequence
<220> FEATURE:
<223> OTHER INFORMATION: Nuclear localization sequence

<400> SEQUENCE: 318

Val Ser Arg Lys Arg Pro Arg Pro
1               5

<210> SEQ ID NO 319
<211> LENGTH: 8
<212> TYPE: PRT
<213> ORGANISM: Artificial Sequence
<220> FEATURE:
<223> OTHER INFORMATION: Nuclear localization sequence

<400> SEQUENCE: 319
```

```
Pro Pro Lys Lys Ala Arg Glu Asp
1               5

<210> SEQ ID NO 320
<211> LENGTH: 8
<212> TYPE: PRT
<213> ORGANISM: Artificial Sequence
<220> FEATURE:
<223> OTHER INFORMATION: Nuclear localization sequence

<400> SEQUENCE: 320

Pro Gln Pro Lys Lys Lys Pro Leu
1               5

<210> SEQ ID NO 321
<211> LENGTH: 12
<212> TYPE: PRT
<213> ORGANISM: Artificial Sequence
<220> FEATURE:
<223> OTHER INFORMATION: Nuclear localization sequence

<400> SEQUENCE: 321

Ser Ala Leu Ile Lys Lys Lys Lys Lys Met Ala Pro
1               5                   10

<210> SEQ ID NO 322
<211> LENGTH: 5
<212> TYPE: PRT
<213> ORGANISM: Artificial Sequence
<220> FEATURE:
<223> OTHER INFORMATION: Nuclear localization sequence

<400> SEQUENCE: 322

Asp Arg Leu Arg Arg
1               5

<210> SEQ ID NO 323
<211> LENGTH: 7
<212> TYPE: PRT
<213> ORGANISM: Artificial Sequence
<220> FEATURE:
<223> OTHER INFORMATION: Nuclear localization sequence

<400> SEQUENCE: 323

Pro Lys Gln Lys Lys Arg Lys
1               5

<210> SEQ ID NO 324
<211> LENGTH: 10
<212> TYPE: PRT
<213> ORGANISM: Artificial Sequence
<220> FEATURE:
<223> OTHER INFORMATION: Nuclear localization sequence

<400> SEQUENCE: 324

Arg Lys Leu Lys Lys Lys Ile Lys Lys Leu
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Nuclear localization sequence

<400> SEQUENCE: 325

Arg Glu Lys Lys Lys Phe Leu Lys Arg Arg
```

```
<210> SEQ ID NO 326
<211> LENGTH: 20
<212> TYPE: PRT
<213> ORGANISM: Artificial Sequence
<220> FEATURE:
<223> OTHER INFORMATION: Nuclear localization sequence

<400> SEQUENCE: 326

Lys Arg Lys Gly Asp Glu Val Asp Gly Val Asp Glu Val Ala Lys Lys
1               5                   10                  15

Lys Ser Lys Lys
            20

<210> SEQ ID NO 327
<211> LENGTH: 17
<212> TYPE: PRT
<213> ORGANISM: Artificial Sequence
<220> FEATURE:
<223> OTHER INFORMATION: Nuclear localization sequence

<400> SEQUENCE: 327

Arg Lys Cys Leu Gln Ala Gly Met Asn Leu Glu Ala Arg Lys Thr Lys
1               5                   10                  15

Lys

<210> SEQ ID NO 328
<211> LENGTH: 77
<212> TYPE: RNA
<213> ORGANISM: Artificial Sequence
<220> FEATURE:
<223> OTHER INFORMATION: Backbone sequence of chimeric single stranded
      RNA

<400> SEQUENCE: 328 guuuuaguccc cugaaaaggg acuaaaauaa agaguuugcg ggacucugcg ggguuacaau    60
ccccuaaaac cgcuuuu                                                    77

<210> SEQ ID NO 329
<211> LENGTH: 76
<212> TYPE: RNA
<213> ORGANISM: Artificial Sequence
<220> FEATURE:
<223> OTHER INFORMATION: Backbone sequence of chimeric single stranded
      RNA

<400> SEQUENCE: 329
guuuuagagc uagaaauagc aaguuaaaau aaggcuaguc cguuaucaac uugaaaaagu    60
ggcaccgagu cggugc                                                    76

<210> SEQ ID NO 330
<211> LENGTH: 23
<212> TYPE: DNA
<213> ORGANISM: Homo sapiens

<400> SEQUENCE: 330
agttacaggg agcaccacca ggg                                            23

<210> SEQ ID NO 331
<211> LENGTH: 23
<212> TYPE: DNA
<213> ORGANISM: Homo sapiens
```

<400> SEQUENCE: 331
cagttacagg gagcaccacc agg                                              23

<210> SEQ ID NO 332
<211> LENGTH: 23
<212> TYPE: DNA
<213> ORGANISM: Homo sapiens

<400> SEQUENCE: 332
ctggtctggc ttcagttaca ggg                                              23

<210> SEQ ID NO 333
<211> LENGTH: 23
<212> TYPE: DNA
<213> ORGANISM: Homo sapiens

<400> SEQUENCE: 333
cctggtctgg cttcagttac agg                                              23

<210> SEQ ID NO 334
<211> LENGTH: 23
<212> TYPE: DNA
<213> ORGANISM: Homo sapiens

<400> SEQUENCE: 334
cctggtctgg cttcagttac agg                                              23

<210> SEQ ID NO 335
<211> LENGTH: 23
<212> TYPE: DNA
<213> ORGANISM: Homo sapiens

<400> SEQUENCE: 335
tctgcagaat tcactgggag ggg                                              23

<210> SEQ ID NO 336
<211> LENGTH: 23
<212> TYPE: DNA
<213> ORGANISM: Homo sapiens

<400> SEQUENCE: 336
ctctgcagaa ttcactggga ggg                                              23

<210> SEQ ID NO 337
<211> LENGTH: 23
<212> TYPE: DNA
<213> ORGANISM: Homo sapiens

<400> SEQUENCE: 337
tctctgcaga attcactggg agg                                              23

<210> SEQ ID NO 338
<211> LENGTH: 23
<212> TYPE: DNA
<213> ORGANISM: Homo sapiens

<400> SEQUENCE: 338
taatctctgc agaattcact ggg                                              23

<210> SEQ ID NO 339
<211> LENGTH: 23
<212> TYPE: DNA
<213> ORGANISM: Homo sapiens

```
<400> SEQUENCE: 339
ttaatctctg cagaattcac tgg                                    23

<210> SEQ ID NO 340
<211> LENGTH: 30
<212> TYPE: DNA
<213> ORGANISM: Homo sapiens

<400> SEQUENCE: 340
gcctggtctg gcttcagtta cagggagcac                             30

<210> SEQ ID NO 341
<211> LENGTH: 30
<212> TYPE: DNA
<213> ORGANISM: Homo sapiens

<400> SEQUENCE: 341
gtgtccaact ttgtttgctt tccagaatac                             30

<210> SEQ ID NO 342
<211> LENGTH: 30
<212> TYPE: DNA
<213> ORGANISM: Homo sapiens

<400> SEQUENCE: 342
gtattctgga aagcaaacaa agttggacac                             30

<210> SEQ ID NO 343
<211> LENGTH: 30
<212> TYPE: DNA
<213> ORGANISM: Homo sapiens

<400> SEQUENCE: 343
cagtcttggc atcacaggct tcaggcatac                             30

<210> SEQ ID NO 344
<211> LENGTH: 30
<212> TYPE: DNA
<213> ORGANISM: Homo sapiens

<400> SEQUENCE: 344
ggacctcttg gctattacac aggttggcac                             30

<210> SEQ ID NO 345
<211> LENGTH: 30
<212> TYPE: DNA
<213> ORGANISM: Homo sapiens

<400> SEQUENCE: 345
ggagccagtg ggacctcttg gctattacac                             30

<210> SEQ ID NO 346
<211> LENGTH: 30
<212> TYPE: DNA
<213> ORGANISM: Homo sapiens

<400> SEQUENCE: 346
cccagtgaat tctgcagaga ttaaatatac                             30

<210> SEQ ID NO 347
<211> LENGTH: 30
<212> TYPE: DNA
```

<213> ORGANISM: Homo sapiens

<400> SEQUENCE: 347
ggaaggatct gtgtctacag tgttacatac					30

<210> SEQ ID NO 348
<211> LENGTH: 30
<212> TYPE: DNA
<213> ORGANISM: Homo sapiens

<400> SEQUENCE: 348
ttacctgcac gtatgtaaca ctgtagacac					30

<210> SEQ ID NO 349
<211> LENGTH: 30
<212> TYPE: DNA
<213> ORGANISM: Homo sapiens

<400> SEQUENCE: 349
aaataaaact tacctgcacg tatgtaacac					30

<210> SEQ ID NO 350
<211> LENGTH: 30
<212> TYPE: DNA
<213> ORGANISM: Homo sapiens

<400> SEQUENCE: 350
aagtttattt aaaataaaac ttacctgcac					30

<210> SEQ ID NO 351
<211> LENGTH: 30
<212> TYPE: DNA
<213> ORGANISM: Homo sapiens

<400> SEQUENCE: 351
aaagcatagg cacacatcac ccagaggcac					30

<210> SEQ ID NO 352
<211> LENGTH: 30
<212> TYPE: DNA
<213> ORGANISM: Homo sapiens

<400> SEQUENCE: 352
ttaggcaatt cttgtaaagc ataggcacac					30

<210> SEQ ID NO 353
<211> LENGTH: 30
<212> TYPE: DNA
<213> ORGANISM: Homo sapiens

<400> SEQUENCE: 353
aattaggcaa ttcttgtaaa gcataggcac					30

<210> SEQ ID NO 354
<211> LENGTH: 30
<212> TYPE: DNA
<213> ORGANISM: Homo sapiens

<400> SEQUENCE: 354
aatctccagt caattccaac acaaatgcac					30

<210> SEQ ID NO 355
<211> LENGTH: 30

<212> TYPE: DNA
<213> ORGANISM: Homo sapiens

<400> SEQUENCE: 355
gccctctgaa tctccagtca attccaacac                                    30

<210> SEQ ID NO 356
<211> LENGTH: 30
<212> TYPE: DNA
<213> ORGANISM: Homo sapiens

<400> SEQUENCE: 356
tatatccttg gttaaaaggt ggatatatac                                    30

<210> SEQ ID NO 357
<211> LENGTH: 30
<212> TYPE: DNA
<213> ORGANISM: Mus musculus

<400> SEQUENCE: 357
ctcttgggat cactctatcc tggaagatac                                    30

<210> SEQ ID NO 358
<211> LENGTH: 30
<212> TYPE: DNA
<213> ORGANISM: Mus musculus

<400> SEQUENCE: 358
cttgggatca ctctatcctg gaagatacac                                    30

<210> SEQ ID NO 359
<211> LENGTH: 30
<212> TYPE: DNA
<213> ORGANISM: Mus musculus

<400> SEQUENCE: 359
tctatcctgg aagatacaca agctggacac                                    30

<210> SEQ ID NO 360
<211> LENGTH: 30
<212> TYPE: DNA
<213> ORGANISM: Mus musculus

<400> SEQUENCE: 360
gagacatcca agtggaggaa ggggttacac                                    30

<210> SEQ ID NO 361
<211> LENGTH: 30
<212> TYPE: DNA
<213> ORGANISM: Mus musculus

<400> SEQUENCE: 361
ctctataaag cacaccctac ccagagatac                                    30

<210> SEQ ID NO 362
<211> LENGTH: 30
<212> TYPE: DNA
<213> ORGANISM: Mus musculus

<400> SEQUENCE: 362
acaaaaactg agccactcta taaagcacac                                    30

<210> SEQ ID NO 363

-continued

```
<211> LENGTH: 30
<212> TYPE: DNA
<213> ORGANISM: Mus musculus

<400> SEQUENCE: 363
ggacaaaaac tgagccactc tataaagcac                                        30

<210> SEQ ID NO 364
<211> LENGTH: 20
<212> TYPE: DNA
<213> ORGANISM: Artificial Sequence
<220> FEATURE:
<223> OTHER INFORMATION: Primer

<400> SEQUENCE: 364
cttagtctgt cggctgcggg                                                   20

<210> SEQ ID NO 365
<211> LENGTH: 20
<212> TYPE: DNA
<213> ORGANISM: Artificial Sequence
<220> FEATURE:
<223> OTHER INFORMATION: Primer

<400> SEQUENCE: 365
ggccaaacag cgtaacccct                                                   20

<210> SEQ ID NO 366
<211> LENGTH: 21
<212> TYPE: DNA
<213> ORGANISM: Artificial Sequence
<220> FEATURE:
<223> OTHER INFORMATION: Primer

<400> SEQUENCE: 366
cgttaaaggg gaacgccagg a                                                 21

<210> SEQ ID NO 367
<211> LENGTH: 20
<212> TYPE: DNA
<213> ORGANISM: Artificial Sequence
<220> FEATURE:
<223> OTHER INFORMATION: Primer

<400> SEQUENCE: 367
cagggtggcc tcaaacacaa                                                   20

<210> SEQ ID NO 368
<211> LENGTH: 22
<212> TYPE: DNA
<213> ORGANISM: Artificial Sequence
<220> FEATURE:
<223> OTHER INFORMATION: Primer

<400> SEQUENCE: 368
cggacaggga aatctatggt gc                                                22

<210> SEQ ID NO 369
<211> LENGTH: 22
<212> TYPE: DNA
<213> ORGANISM: Artificial Sequence
<220> FEATURE:
<223> OTHER INFORMATION: Primer

<400> SEQUENCE: 369
gcgccaggta aaagagatgt ca                                                22
```

```
<210> SEQ ID NO 370
<211> LENGTH: 22
<212> TYPE: DNA
<213> ORGANISM: Artificial Sequence
<220> FEATURE:
<223> OTHER INFORMATION: Primer

<400> SEQUENCE: 370
agctccacca gagaacctct ca                                              22

<210> SEQ ID NO 371
<211> LENGTH: 23
<212> TYPE: DNA
<213> ORGANISM: Artificial Sequence
<220> FEATURE:
<223> OTHER INFORMATION: Primer

<400> SEQUENCE: 371
tgaggagtag cagtgttgga cgg                                             23

<210> SEQ ID NO 372
<211> LENGTH: 24
<212> TYPE: DNA
<213> ORGANISM: Artificial Sequence
<220> FEATURE:
<223> OTHER INFORMATION: Primer

<400> SEQUENCE: 372
tgacccgcag cacagctgtc tttg                                            24

<210> SEQ ID NO 373
<211> LENGTH: 23
<212> TYPE: DNA
<213> ORGANISM: Artificial Sequence
<220> FEATURE:
<223> OTHER INFORMATION: Primer

<400> SEQUENCE: 373
tgaggagtag cagtgttgga cgg                                             23

<210> SEQ ID NO 374
<211> LENGTH: 4
<212> TYPE: RNA
<213> ORGANISM: Artificial Sequence
<220> FEATURE:
<223> OTHER INFORMATION: Guide sequence

<400> SEQUENCE: 374 uaua                                                                   4

<210> SEQ ID NO 375
<211> LENGTH: 7
<212> TYPE: RNA
<213> ORGANISM: Artificial Sequence
<220> FEATURE:
<223> OTHER INFORMATION: Guide sequence

<400> SEQUENCE: 375 uauawaw                                                                7

<210> SEQ ID NO 376
<211> LENGTH: 7
<212> TYPE: RNA
<213> ORGANISM: Artificial Sequence
<220> FEATURE:
```

-continued

```
<223> OTHER INFORMATION: Guide sequence

<400> SEQUENCE: 376 wuwuaua                                                              7

<210> SEQ ID NO 377
<211> LENGTH: 8
<212> TYPE: RNA
<213> ORGANISM: Artificial Sequence
<220> FEATURE:
<223> OTHER INFORMATION: Guide sequence

<400> SEQUENCE: 377 uauawawr                                                             8

<210> SEQ ID NO 378
<211> LENGTH: 8
<212> TYPE: RNA
<213> ORGANISM: Artificial Sequence
<220> FEATURE:
<223> OTHER INFORMATION: Guide sequence

<400> SEQUENCE: 378 rwuwuaua                                                             8

<210> SEQ ID NO 379
<211> LENGTH: 7
<212> TYPE: RNA
<213> ORGANISM: Artificial Sequence
<220> FEATURE:
<223> OTHER INFORMATION: Guide sequence

<400> SEQUENCE: 379 cauaaaa                                                              7

<210> SEQ ID NO 380
<211> LENGTH: 5
<212> TYPE: RNA
<213> ORGANISM: Artificial Sequence
<220> FEATURE:
<223> OTHER INFORMATION: Guide sequence

<400> SEQUENCE: 380 uauaa                                                                5

<210> SEQ ID NO 381
<211> LENGTH: 7
<212> TYPE: RNA
<213> ORGANISM: Artificial Sequence
<220> FEATURE:
<223> OTHER INFORMATION: Guide sequence

<400> SEQUENCE: 381 uauaaaa                                                              7

<210> SEQ ID NO 382
<211> LENGTH: 8
<212> TYPE: RNA
<213> ORGANISM: Artificial Sequence
<220> FEATURE:
<223> OTHER INFORMATION: Guide sequence

<400> SEQUENCE: 382 cauaaaua                                                             8
```

```
<210> SEQ ID NO 383
<211> LENGTH: 7
<212> TYPE: RNA
<213> ORGANISM: Artificial Sequence
<220> FEATURE:
<223> OTHER INFORMATION: Guide sequence

<400> SEQUENCE: 383 uauauaa                                                                    7

<210> SEQ ID NO 384
<211> LENGTH: 15
<212> TYPE: RNA
<213> ORGANISM: Artificial Sequence
<220> FEATURE:
<223> OTHER INFORMATION: Guide sequence

<400> SEQUENCE: 384
uauauauaua uauaa                                                          15

<210> SEQ ID NO 385
<211> LENGTH: 9
<212> TYPE: RNA
<213> ORGANISM: Artificial Sequence
<220> FEATURE:
<223> OTHER INFORMATION: Guide sequence

<400> SEQUENCE: 385 uauauuaua                                                                  9

<210> SEQ ID NO 386
<211> LENGTH: 6
<212> TYPE: RNA
<213> ORGANISM: Artificial Sequence
<220> FEATURE:
<223> OTHER INFORMATION: Guide sequence

<400> SEQUENCE: 386 uauaaa                                                                     6

<210> SEQ ID NO 387
<211> LENGTH: 9
<212> TYPE: RNA
<213> ORGANISM: Artificial Sequence
<220> FEATURE:
<223> OTHER INFORMATION: Guide sequence

<400> SEQUENCE: 387 uauaaaaua                                                                  9

<210> SEQ ID NO 388
<211> LENGTH: 6
<212> TYPE: RNA
<213> ORGANISM: Artificial Sequence
<220> FEATURE:
<223> OTHER INFORMATION: Guide sequence

<400> SEQUENCE: 388 uauaua                                                                     6

<210> SEQ ID NO 389
<211> LENGTH: 9
<212> TYPE: RNA
<213> ORGANISM: Artificial Sequence
<220> FEATURE:
<223> OTHER INFORMATION: Guide sequence
```

```
<400> SEQUENCE: 389 gauuaaaaa                                                            9

<210> SEQ ID NO 390
<211> LENGTH: 8
<212> TYPE: RNA
<213> ORGANISM: Artificial Sequence
<220> FEATURE:
<223> OTHER INFORMATION: Guide sequence

<400> SEQUENCE: 390 uauaaaaa                                                             8

<210> SEQ ID NO 391
<211> LENGTH: 6
<212> TYPE: RNA
<213> ORGANISM: Artificial Sequence
<220> FEATURE:
<223> OTHER INFORMATION: Guide sequence

<400> SEQUENCE: 391 uuauaa                                                               6

<210> SEQ ID NO 392
<211> LENGTH: 8
<212> TYPE: RNA
<213> ORGANISM: Artificial Sequence
<220> FEATURE:
<223> OTHER INFORMATION: Guide sequence

<400> SEQUENCE: 392 uuuuaaaa                                                             8

<210> SEQ ID NO 393
<211> LENGTH: 9
<212> TYPE: RNA
<213> ORGANISM: Artificial Sequence
<220> FEATURE:
<223> OTHER INFORMATION: Guide sequence

<400> SEQUENCE: 393 ucuuuaaaa                                                            9

<210> SEQ ID NO 394
<211> LENGTH: 9
<212> TYPE: RNA
<213> ORGANISM: Artificial Sequence
<220> FEATURE:
<223> OTHER INFORMATION: Guide sequence

<400> SEQUENCE: 394 gacauuuaa                                                            9

<210> SEQ ID NO 395
<211> LENGTH: 9
<212> TYPE: RNA
<213> ORGANISM: Artificial Sequence
<220> FEATURE:
<223> OTHER INFORMATION: Guide sequence

<400> SEQUENCE: 395 ugauaucaa                                                            9

<210> SEQ ID NO 396
<211> LENGTH: 8
```

```
<212> TYPE: RNA
<213> ORGANISM: Artificial Sequence
<220> FEATURE:
<223> OTHER INFORMATION: Guide sequence

<400> SEQUENCE: 396 uauaaaua                                                                8

<210> SEQ ID NO 397
<211> LENGTH: 7
<212> TYPE: RNA
<213> ORGANISM: Artificial Sequence
<220> FEATURE:
<223> OTHER INFORMATION: Guide sequence

<400> SEQUENCE: 397 uauaaga                                                                 7

<210> SEQ ID NO 398
<211> LENGTH: 6
<212> TYPE: RNA
<213> ORGANISM: Artificial Sequence
<220> FEATURE:
<223> OTHER INFORMATION: Guide sequence

<400> SEQUENCE: 398 aauaaa                                                                  6

<210> SEQ ID NO 399
<211> LENGTH: 6
<212> TYPE: RNA
<213> ORGANISM: Artificial Sequence
<220> FEATURE:
<223> OTHER INFORMATION: Guide sequence

<400> SEQUENCE: 399 uuuaua                                                                  6

<210> SEQ ID NO 400
<211> LENGTH: 8
<212> TYPE: RNA
<213> ORGANISM: Artificial Sequence
<220> FEATURE:
<223> OTHER INFORMATION: Guide sequence

<400> SEQUENCE: 400 cauaaaaa                                                                8

<210> SEQ ID NO 401
<211> LENGTH: 6
<212> TYPE: RNA
<213> ORGANISM: Artificial Sequence
<220> FEATURE:
<223> OTHER INFORMATION: Guide sequence

<400> SEQUENCE: 401 uauaca                                                                  6

<210> SEQ ID NO 402
<211> LENGTH: 7
<212> TYPE: RNA
<213> ORGANISM: Artificial Sequence
<220> FEATURE:
<223> OTHER INFORMATION: Guide sequence

<400> SEQUENCE: 402
``` uuuaaga 7

<210> SEQ ID NO 403
<211> LENGTH: 7
<212> TYPE: RNA
<213> ORGANISM: Artificial Sequence
<220> FEATURE:
<223> OTHER INFORMATION: Guide sequence

<400> SEQUENCE: 403 gauaaag 7

<210> SEQ ID NO 404
<211> LENGTH: 7
<212> TYPE: RNA
<213> ORGANISM: Artificial Sequence
<220> FEATURE:
<223> OTHER INFORMATION: Guide sequence

<400> SEQUENCE: 404 uauaaca 7

<210> SEQ ID NO 405
<211> LENGTH: 9
<212> TYPE: RNA
<213> ORGANISM: Artificial Sequence
<220> FEATURE:
<223> OTHER INFORMATION: Guide sequence

<400> SEQUENCE: 405 ucuuaucuu 9

<210> SEQ ID NO 406
<211> LENGTH: 9
<212> TYPE: RNA
<213> ORGANISM: Artificial Sequence
<220> FEATURE:
<223> OTHER INFORMATION: Guide sequence

<400> SEQUENCE: 406 uuguacuuu 9

<210> SEQ ID NO 407
<211> LENGTH: 7
<212> TYPE: RNA
<213> ORGANISM: Artificial Sequence
<220> FEATURE:
<223> OTHER INFORMATION: Guide sequence

<400> SEQUENCE: 407 cauauaa 7

<210> SEQ ID NO 408
<211> LENGTH: 7
<212> TYPE: RNA
<213> ORGANISM: Artificial Sequence
<220> FEATURE:
<223> OTHER INFORMATION: Guide sequence

<400> SEQUENCE: 408 uauaaau 7

<210> SEQ ID NO 409
<211> LENGTH: 15
<212> TYPE: RNA
<213> ORGANISM: Artificial Sequence

```
<220> FEATURE:
<223> OTHER INFORMATION: Guide sequence

<400> SEQUENCE: 409
uauauauaaa aaaaa                                                    15

<210> SEQ ID NO 410
<211> LENGTH: 18
<212> TYPE: RNA
<213> ORGANISM: Artificial Sequence
<220> FEATURE:
<223> OTHER INFORMATION: Guide sequence

<400> SEQUENCE: 410
cauaaauaaa aaaaauua                                                 18

<210> SEQ ID NO 411
<211> LENGTH: 7
<212> TYPE: RNA
<213> ORGANISM: Artificial Sequence
<220> FEATURE:
<223> OTHER INFORMATION: Guide sequence

<400> SEQUENCE: 411 uuuuaug                                                              7

<210> SEQ ID NO 412
<211> LENGTH: 5
<212> TYPE: RNA
<213> ORGANISM: Artificial Sequence
<220> FEATURE:
<223> OTHER INFORMATION: Guide sequence

<400> SEQUENCE: 412 uuaua                                                                5

<210> SEQ ID NO 413
<211> LENGTH: 7
<212> TYPE: RNA
<213> ORGANISM: Artificial Sequence
<220> FEATURE:
<223> OTHER INFORMATION: Guide sequence

<400> SEQUENCE: 413 uuuuaua                                                              7

<210> SEQ ID NO 414
<211> LENGTH: 8
<212> TYPE: RNA
<213> ORGANISM: Artificial Sequence
<220> FEATURE:
<223> OTHER INFORMATION: Guide sequence

<400> SEQUENCE: 414 uauuuaug                                                             8

<210> SEQ ID NO 415
<211> LENGTH: 7
<212> TYPE: RNA
<213> ORGANISM: Artificial Sequence
<220> FEATURE:
<223> OTHER INFORMATION: Guide sequence

<400> SEQUENCE: 415 uuauaua                                                              7
```

```
<210> SEQ ID NO 416
<211> LENGTH: 15
<212> TYPE: RNA
<213> ORGANISM: Artificial Sequence
<220> FEATURE:
<223> OTHER INFORMATION: Guide sequence

<400> SEQUENCE: 416
uuauauauau auaua                                                        15

<210> SEQ ID NO 417
<211> LENGTH: 9
<212> TYPE: RNA
<213> ORGANISM: Artificial Sequence
<220> FEATURE:
<223> OTHER INFORMATION: Guide sequence

<400> SEQUENCE: 417 uauaauaua                                                                9

<210> SEQ ID NO 418
<211> LENGTH: 6
<212> TYPE: RNA
<213> ORGANISM: Artificial Sequence
<220> FEATURE:
<223> OTHER INFORMATION: Guide sequence

<400> SEQUENCE: 418 uuuaua                                                                   6

<210> SEQ ID NO 419
<211> LENGTH: 9
<212> TYPE: RNA
<213> ORGANISM: Artificial Sequence
<220> FEATURE:
<223> OTHER INFORMATION: Guide sequence

<400> SEQUENCE: 419 uauuuuaua                                                                9

<210> SEQ ID NO 420
<211> LENGTH: 9
<212> TYPE: RNA
<213> ORGANISM: Artificial Sequence
<220> FEATURE:
<223> OTHER INFORMATION: Guide sequence

<400> SEQUENCE: 420 uuuuuaauc                                                                9

<210> SEQ ID NO 421
<211> LENGTH: 8
<212> TYPE: RNA
<213> ORGANISM: Artificial Sequence
<220> FEATURE:
<223> OTHER INFORMATION: Guide sequence

<400> SEQUENCE: 421 uuuuuaua                                                                 8

<210> SEQ ID NO 422
<211> LENGTH: 9
<212> TYPE: RNA
<213> ORGANISM: Artificial Sequence
<220> FEATURE:
<223> OTHER INFORMATION: Guide sequence
```

```
<400> SEQUENCE: 422 uuuuaaaga                                                                      9

<210> SEQ ID NO 423
<211> LENGTH: 9
<212> TYPE: RNA
<213> ORGANISM: Artificial Sequence
<220> FEATURE:
<223> OTHER INFORMATION: Guide sequence

<400> SEQUENCE: 423 uuaaauguc                                                                      9

<210> SEQ ID NO 424
<211> LENGTH: 9
<212> TYPE: RNA
<213> ORGANISM: Artificial Sequence
<220> FEATURE:
<223> OTHER INFORMATION: Guide sequence

<400> SEQUENCE: 424 uugauauca                                                                      9

<210> SEQ ID NO 425
<211> LENGTH: 8
<212> TYPE: RNA
<213> ORGANISM: Artificial Sequence
<220> FEATURE:
<223> OTHER INFORMATION: Guide sequence

<400> SEQUENCE: 425 uauuuaua                                                                       8

<210> SEQ ID NO 426
<211> LENGTH: 7
<212> TYPE: RNA
<213> ORGANISM: Artificial Sequence
<220> FEATURE:
<223> OTHER INFORMATION: Guide sequence

<400> SEQUENCE: 426 ucuuaua                                                                        7

<210> SEQ ID NO 427
<211> LENGTH: 6
<212> TYPE: RNA
<213> ORGANISM: Artificial Sequence
<220> FEATURE:
<223> OTHER INFORMATION: Guide sequence

<400> SEQUENCE: 427 uuuauu                                                                         6

<210> SEQ ID NO 428
<211> LENGTH: 6
<212> TYPE: RNA
<213> ORGANISM: Artificial Sequence
<220> FEATURE:
<223> OTHER INFORMATION: Guide sequence

<400> SEQUENCE: 428 uauaaa                                                                         6

<210> SEQ ID NO 429
```

```
<211> LENGTH: 8
<212> TYPE: RNA
<213> ORGANISM: Artificial Sequence
<220> FEATURE:
<223> OTHER INFORMATION: Guide sequence

<400> SEQUENCE: 429 uuuuuaug                                                                  8

<210> SEQ ID NO 430
<211> LENGTH: 6
<212> TYPE: RNA
<213> ORGANISM: Artificial Sequence
<220> FEATURE:
<223> OTHER INFORMATION: Guide sequence

<400> SEQUENCE: 430 uguaua                                                                    6

<210> SEQ ID NO 431
<211> LENGTH: 7
<212> TYPE: RNA
<213> ORGANISM: Artificial Sequence
<220> FEATURE:
<223> OTHER INFORMATION: Guide sequence

<400> SEQUENCE: 431 ucuuaaa                                                                   7

<210> SEQ ID NO 432
<211> LENGTH: 7
<212> TYPE: RNA
<213> ORGANISM: Artificial Sequence
<220> FEATURE:
<223> OTHER INFORMATION: Guide sequence

<400> SEQUENCE: 432 cuuuauc                                                                   7

<210> SEQ ID NO 433
<211> LENGTH: 7
<212> TYPE: RNA
<213> ORGANISM: Artificial Sequence
<220> FEATURE:
<223> OTHER INFORMATION: Guide sequence

<400> SEQUENCE: 433 uguuaua                                                                   7

<210> SEQ ID NO 434
<211> LENGTH: 9
<212> TYPE: RNA
<213> ORGANISM: Artificial Sequence
<220> FEATURE:
<223> OTHER INFORMATION: Guide sequence

<400> SEQUENCE: 434 aagauaaga                                                                 9

<210> SEQ ID NO 435
<211> LENGTH: 9
<212> TYPE: RNA
<213> ORGANISM: Artificial Sequence
<220> FEATURE:
<223> OTHER INFORMATION: Guide sequence

<400> SEQUENCE: 435
```

-continued

```
aaaguacaa                                                          9

<210> SEQ ID NO 436
<211> LENGTH: 7
<212> TYPE: RNA
<213> ORGANISM: Artificial Sequence
<220> FEATURE:
<223> OTHER INFORMATION: Guide sequence

<400> SEQUENCE: 436 uuauaug                                                            7

<210> SEQ ID NO 437
<211> LENGTH: 7
<212> TYPE: RNA
<213> ORGANISM: Artificial Sequence
<220> FEATURE:
<223> OTHER INFORMATION: Guide sequence

<400> SEQUENCE: 437 auuuaua                                                            7

<210> SEQ ID NO 438
<211> LENGTH: 15
<212> TYPE: RNA
<213> ORGANISM: Artificial Sequence
<220> FEATURE:
<223> OTHER INFORMATION: Guide sequence

<400> SEQUENCE: 438
uuuuuuuuau auaua                                                  15

<210> SEQ ID NO 439
<211> LENGTH: 18
<212> TYPE: RNA
<213> ORGANISM: Artificial Sequence
<220> FEATURE:
<223> OTHER INFORMATION: Guide sequence

<400> SEQUENCE: 439
uaauuuuuuu uauuuaug                                               18

<210> SEQ ID NO 440
<211> LENGTH: 20
<212> TYPE: RNA
<213> ORGANISM: Artificial Sequence
<220> FEATURE:
<223> OTHER INFORMATION: Guide Sequence

<400> SEQUENCE: 440
ggaccagccc cugaauaaac                                             20

<210> SEQ ID NO 441
<211> LENGTH: 20
<212> TYPE: RNA
<213> ORGANISM: Artificial Sequence
<220> FEATURE:
<223> OTHER INFORMATION: Guide Sequence

<400> SEQUENCE: 441
ggcgucuuuc caguuuauuc                                             20

<210> SEQ ID NO 442
<211> LENGTH: 20
<212> TYPE: RNA
```

```
<213> ORGANISM: Artificial Sequence
<220> FEATURE:
<223> OTHER INFORMATION: Guide Sequence

<400> SEQUENCE: 442
gcgucuuucc aguuuauuca                                              20

<210> SEQ ID NO 443
<211> LENGTH: 20
<212> TYPE: RNA
<213> ORGANISM: Artificial Sequence
<220> FEATURE:
<223> OTHER INFORMATION: Guide Sequence

<400> SEQUENCE: 443
cgucuuucca guuuauucag                                              20

<210> SEQ ID NO 444
<211> LENGTH: 20
<212> TYPE: RNA
<213> ORGANISM: Artificial Sequence
<220> FEATURE:
<223> OTHER INFORMATION: Guide Sequence

<400> SEQUENCE: 444
uucaggggcu gguccaaugc                                              20

<210> SEQ ID NO 445
<211> LENGTH: 20
<212> TYPE: RNA
<213> ORGANISM: Artificial Sequence
<220> FEATURE:
<223> OTHER INFORMATION: Guide Sequence

<400> SEQUENCE: 445 ucagggcug guccaaugcu                                               20

<210> SEQ ID NO 446
<211> LENGTH: 20
<212> TYPE: RNA
<213> ORGANISM: Artificial Sequence
<220> FEATURE:
<223> OTHER INFORMATION: Guide Sequence

<400> SEQUENCE: 446
accaugacau aucccagcau                                              20

<210> SEQ ID NO 447
<211> LENGTH: 20
<212> TYPE: RNA
<213> ORGANISM: Artificial Sequence
<220> FEATURE:
<223> OTHER INFORMATION: Guide Sequence

<400> SEQUENCE: 447
uuuccaguuu auucaggggc                                              20

<210> SEQ ID NO 448
<211> LENGTH: 20
<212> TYPE: RNA
<213> ORGANISM: Artificial Sequence
<220> FEATURE:
<223> OTHER INFORMATION: Guide Sequence

<400> SEQUENCE: 448
caguuacagg gagcaccacc                                              20
```

<210> SEQ ID NO 449
<211> LENGTH: 20
<212> TYPE: RNA
<213> ORGANISM: Artificial Sequence
<220> FEATURE:
<223> OTHER INFORMATION: Guide Sequence

<400> SEQUENCE: 449
cuggucuggc uucaguuaca                                               20

<210> SEQ ID NO 450
<211> LENGTH: 20
<212> TYPE: RNA
<213> ORGANISM: Artificial Sequence
<220> FEATURE:
<223> OTHER INFORMATION: Guide Sequence

<400> SEQUENCE: 450
ccuggucugg cuucaguuac                                               20

<210> SEQ ID NO 451
<211> LENGTH: 20
<212> TYPE: RNA
<213> ORGANISM: Artificial Sequence
<220> FEATURE:
<223> OTHER INFORMATION: Guide Sequence

<400> SEQUENCE: 451
aacuggaaag acgccugguc                                               20

<210> SEQ ID NO 452
<211> LENGTH: 20
<212> TYPE: RNA
<213> ORGANISM: Artificial Sequence
<220> FEATURE:
<223> OTHER INFORMATION: Guide Sequence

<400> SEQUENCE: 452
gaauaaacug gaaagacgcc                                               20

<210> SEQ ID NO 453
<211> LENGTH: 20
<212> TYPE: RNA
<213> ORGANISM: Artificial Sequence
<220> FEATURE:
<223> OTHER INFORMATION: Guide Sequence

<400> SEQUENCE: 453
uccaaugcug ggauauguca                                               20

<210> SEQ ID NO 454
<211> LENGTH: 20
<212> TYPE: RNA
<213> ORGANISM: Artificial Sequence
<220> FEATURE:
<223> OTHER INFORMATION: Guide Sequence

<400> SEQUENCE: 454
aaugcuggga uaugucaugg                                               20

<210> SEQ ID NO 455
<211> LENGTH: 20
<212> TYPE: RNA
<213> ORGANISM: Artificial Sequence
<220> FEATURE:

-continued

<223> OTHER INFORMATION: Guide Sequence

<400> SEQUENCE: 455
auagaggcug agaaccucuc                                              20

<210> SEQ ID NO 456
<211> LENGTH: 20
<212> TYPE: RNA
<213> ORGANISM: Artificial Sequence
<220> FEATURE:
<223> OTHER INFORMATION: Guide Sequence

<400> SEQUENCE: 456
uugggcaugu uugagcuggu                                              20

<210> SEQ ID NO 457
<211> LENGTH: 20
<212> TYPE: RNA
<213> ORGANISM: Artificial Sequence
<220> FEATURE:
<223> OTHER INFORMATION: Guide Sequence

<400> SEQUENCE: 457
uuugggcaug uuugagcugg                                              20

<210> SEQ ID NO 458
<211> LENGTH: 20
<212> TYPE: RNA
<213> ORGANISM: Artificial Sequence
<220> FEATURE:
<223> OTHER INFORMATION: Guide Sequence

<400> SEQUENCE: 458
gagcuggugg gcgaagcaua                                              20

<210> SEQ ID NO 459
<211> LENGTH: 20
<212> TYPE: RNA
<213> ORGANISM: Artificial Sequence
<220> FEATURE:
<223> OTHER INFORMATION: Guide Sequence

<400> SEQUENCE: 459
agcugguggg cgaagcauau                                              20

<210> SEQ ID NO 460
<211> LENGTH: 20
<212> TYPE: RNA
<213> ORGANISM: Artificial Sequence
<220> FEATURE:
<223> OTHER INFORMATION: Guide Sequence

<400> SEQUENCE: 460
ugggcgaagc auaugggcaa                                              20

<210> SEQ ID NO 461
<211> LENGTH: 20
<212> TYPE: RNA
<213> ORGANISM: Artificial Sequence
<220> FEATURE:
<223> OTHER INFORMATION: Guide Sequence

<400> SEQUENCE: 461
ggccuccauc cuaaacaaug                                              20

```
<210> SEQ ID NO 462
<211> LENGTH: 20
<212> TYPE: RNA
<213> ORGANISM: Artificial Sequence
<220> FEATURE:
<223> OTHER INFORMATION: Guide Sequence

<400> SEQUENCE: 462
ggguugggag guuugggcgu                                              20

<210> SEQ ID NO 463
<211> LENGTH: 20
<212> TYPE: RNA
<213> ORGANISM: Artificial Sequence
<220> FEATURE:
<223> OTHER INFORMATION: Guide Sequence

<400> SEQUENCE: 463
agguuugggc gugggagucc                                              20

<210> SEQ ID NO 464
<211> LENGTH: 19
<212> TYPE: RNA
<213> ORGANISM: Artificial Sequence
<220> FEATURE:
<223> OTHER INFORMATION: Guide Sequence

<400> SEQUENCE: 464
uucagagacu cagcuauuu                                               19

<210> SEQ ID NO 465
<211> LENGTH: 19
<212> TYPE: RNA
<213> ORGANISM: Artificial Sequence
<220> FEATURE:
<223> OTHER INFORMATION: Guide Sequence

<400> SEQUENCE: 465
ggccacauug uuuaggaug                                               19

<210> SEQ ID NO 466
<211> LENGTH: 19
<212> TYPE: RNA
<213> ORGANISM: Artificial Sequence
<220> FEATURE:
<223> OTHER INFORMATION: Guide Sequence

<400> SEQUENCE: 466
ggcuuugggc auguuugag                                               19

<210> SEQ ID NO 467
<211> LENGTH: 19
<212> TYPE: RNA
<213> ORGANISM: Artificial Sequence
<220> FEATURE:
<223> OTHER INFORMATION: Guide Sequence

<400> SEQUENCE: 467
aacaugccca aagcccagc                                               19

<210> SEQ ID NO 468
<211> LENGTH: 19
<212> TYPE: RNA
<213> ORGANISM: Artificial Sequence
<220> FEATURE:
<223> OTHER INFORMATION: Guide Sequence
```

```
<400> SEQUENCE: 468
acaugcccaa agcccagcg                                              19

<210> SEQ ID NO 469
<211> LENGTH: 20
<212> TYPE: RNA
<213> ORGANISM: Artificial Sequence
<220> FEATURE:
<223> OTHER INFORMATION: Guide Sequence

<400> SEQUENCE: 469
cgaugauacu cagcaacagg                                             20

<210> SEQ ID NO 470
<211> LENGTH: 20
<212> TYPE: RNA
<213> ORGANISM: Artificial Sequence
<220> FEATURE:
<223> OTHER INFORMATION: Guide Sequence

<400> SEQUENCE: 470
auggacacgc aacugaucuc                                             20

<210> SEQ ID NO 471
<211> LENGTH: 22
<212> TYPE: RNA
<213> ORGANISM: Artificial Sequence
<220> FEATURE:
<223> OTHER INFORMATION: Guide Sequence

<400> SEQUENCE: 471
gcccucugaa ucuccaguca au                                          22

<210> SEQ ID NO 472
<211> LENGTH: 22
<212> TYPE: RNA
<213> ORGANISM: Artificial Sequence
<220> FEATURE:
<223> OTHER INFORMATION: Guide Sequence

<400> SEQUENCE: 472
aaucuccagu caauuccaac ac                                          22

<210> SEQ ID NO 473
<211> LENGTH: 22
<212> TYPE: RNA
<213> ORGANISM: Artificial Sequence
<220> FEATURE:
<223> OTHER INFORMATION: Guide Sequence

<400> SEQUENCE: 473
aauuaggcaa uucuuguaaa gc                                          22

<210> SEQ ID NO 474
<211> LENGTH: 22
<212> TYPE: RNA
<213> ORGANISM: Artificial Sequence
<220> FEATURE:
<223> OTHER INFORMATION: Guide Sequence

<400> SEQUENCE: 474
uuaggcaauu cuuguaaagc au                                          22

<210> SEQ ID NO 475
<211> LENGTH: 22
```

```
<212> TYPE: RNA
<213> ORGANISM: Artificial Sequence
<220> FEATURE:
<223> OTHER INFORMATION: Guide Sequence

<400> SEQUENCE: 475
aaagcauagg cacacaucac cc                                           22

<210> SEQ ID NO 476
<211> LENGTH: 22
<212> TYPE: RNA
<213> ORGANISM: Artificial Sequence
<220> FEATURE:
<223> OTHER INFORMATION: Guide Sequence

<400> SEQUENCE: 476
gccuggucug gcuucaguua ca                                           22

<210> SEQ ID NO 477
<211> LENGTH: 22
<212> TYPE: RNA
<213> ORGANISM: Artificial Sequence
<220> FEATURE:
<223> OTHER INFORMATION: Guide Sequence

<400> SEQUENCE: 477
guguccaacu uuguuugcuu uc                                           22

<210> SEQ ID NO 478
<211> LENGTH: 22
<212> TYPE: RNA
<213> ORGANISM: Artificial Sequence
<220> FEATURE:
<223> OTHER INFORMATION: Guide Sequence

<400> SEQUENCE: 478
guauucugga aagcaaacaa ag                                           22

<210> SEQ ID NO 479
<211> LENGTH: 22
<212> TYPE: RNA
<213> ORGANISM: Artificial Sequence
<220> FEATURE:
<223> OTHER INFORMATION: Guide Sequence

<400> SEQUENCE: 479
cagucuuggc aucacaggcu uc                                           22

<210> SEQ ID NO 480
<211> LENGTH: 22
<212> TYPE: RNA
<213> ORGANISM: Artificial Sequence
<220> FEATURE:
<223> OTHER INFORMATION: Guide Sequence

<400> SEQUENCE: 480
ggaccucuug gcuauuacac ag                                           22

<210> SEQ ID NO 481
<211> LENGTH: 22
<212> TYPE: RNA
<213> ORGANISM: Artificial Sequence
<220> FEATURE:
<223> OTHER INFORMATION: Guide Sequence

<400> SEQUENCE: 481
```

```
ggagccagug ggaccucuug gc                                              22

<210> SEQ ID NO 482
<211> LENGTH: 22
<212> TYPE: RNA
<213> ORGANISM: Artificial Sequence
<220> FEATURE:
<223> OTHER INFORMATION: Guide Sequence

<400> SEQUENCE: 482
uaaaucacag aggcaaagag uu                                              22

<210> SEQ ID NO 483
<211> LENGTH: 22
<212> TYPE: RNA
<213> ORGANISM: Artificial Sequence
<220> FEATURE:
<223> OTHER INFORMATION: Guide Sequence

<400> SEQUENCE: 483
uugcauagug cuagacuguu uu                                              22

<210> SEQ ID NO 484
<211> LENGTH: 22
<212> TYPE: RNA
<213> ORGANISM: Artificial Sequence
<220> FEATURE:
<223> OTHER INFORMATION: Guide Sequence

<400> SEQUENCE: 484
gggucaugug uuuugaaaac ag                                              22

<210> SEQ ID NO 485
<211> LENGTH: 22
<212> TYPE: RNA
<213> ORGANISM: Artificial Sequence
<220> FEATURE:
<223> OTHER INFORMATION: Guide Sequence

<400> SEQUENCE: 485
cccaaaccuc ccaacccaca ac                                              22

<210> SEQ ID NO 486
<211> LENGTH: 22
<212> TYPE: RNA
<213> ORGANISM: Artificial Sequence
<220> FEATURE:
<223> OTHER INFORMATION: Guide Sequence

<400> SEQUENCE: 486
acucagcuau uucuggaaug ac                                              22

<210> SEQ ID NO 487
<211> LENGTH: 22
<212> TYPE: RNA
<213> ORGANISM: Artificial Sequence
<220> FEATURE:
<223> OTHER INFORMATION: Guide Sequence

<400> SEQUENCE: 487
ucaucgccuu ugugagcucc au                                              22

<210> SEQ ID NO 488
<211> LENGTH: 22
<212> TYPE: RNA
<213> ORGANISM: Artificial Sequence
```

```
<220> FEATURE:
<223> OTHER INFORMATION: Guide Sequence

<400> SEQUENCE: 488
cagacacagg cuuugcucua gc                                              22

<210> SEQ ID NO 489
<211> LENGTH: 22
<212> TYPE: RNA
<213> ORGANISM: Artificial Sequence
<220> FEATURE:
<223> OTHER INFORMATION: Guide Sequence

<400> SEQUENCE: 489
caaagccugu gucuggccac ua                                              22

<210> SEQ ID NO 490
<211> LENGTH: 22
<212> TYPE: RNA
<213> ORGANISM: Artificial Sequence
<220> FEATURE:
<223> OTHER INFORMATION: Guide Sequence

<400> SEQUENCE: 490
agcaguuugu gcccacuagu gg                                              22

<210> SEQ ID NO 491
<211> LENGTH: 22
<212> TYPE: RNA
<213> ORGANISM: Artificial Sequence
<220> FEATURE:
<223> OTHER INFORMATION: Guide Sequence

<400> SEQUENCE: 491
augucaaggu auuccagcua ac                                              22

<210> SEQ ID NO 492
<211> LENGTH: 22
<212> TYPE: RNA
<213> ORGANISM: Artificial Sequence
<220> FEATURE:
<223> OTHER INFORMATION: Guide Sequence

<400> SEQUENCE: 492
gaauaacugu aucaaaguua gc                                              22

<210> SEQ ID NO 493
<211> LENGTH: 22
<212> TYPE: RNA
<213> ORGANISM: Artificial Sequence
<220> FEATURE:
<223> OTHER INFORMATION: Guide Sequence

<400> SEQUENCE: 493
uuccuaauua agaggcuuug ug                                              22

<210> SEQ ID NO 494
<211> LENGTH: 22
<212> TYPE: RNA
<213> ORGANISM: Artificial Sequence
<220> FEATURE:
<223> OTHER INFORMATION: Guide Sequence

<400> SEQUENCE: 494
gagcuaguuu gucagggucu ag                                              22
```

```
<210> SEQ ID NO 495
<211> LENGTH: 20
<212> TYPE: RNA
<213> ORGANISM: Artificial Sequence
<220> FEATURE:
<223> OTHER INFORMATION: Guide Sequence

<400> SEQUENCE: 495
gacuuuggga gcuaauaucu                                               20

<210> SEQ ID NO 496
<211> LENGTH: 20
<212> TYPE: RNA
<213> ORGANISM: Artificial Sequence
<220> FEATURE:
<223> OTHER INFORMATION: Guide Sequence

<400> SEQUENCE: 496
cccuuucauc uucccauucg                                               20

<210> SEQ ID NO 497
<211> LENGTH: 20
<212> TYPE: RNA
<213> ORGANISM: Artificial Sequence
<220> FEATURE:
<223> OTHER INFORMATION: Guide Sequence

<400> SEQUENCE: 497
ccuuucaucu ucccauucgu                                               20

<210> SEQ ID NO 498
<211> LENGTH: 20
<212> TYPE: RNA
<213> ORGANISM: Artificial Sequence
<220> FEATURE:
<223> OTHER INFORMATION: Guide Sequence

<400> SEQUENCE: 498
cccacgaaug ggaagaugaa                                               20

<210> SEQ ID NO 499
<211> LENGTH: 20
<212> TYPE: RNA
<213> ORGANISM: Artificial Sequence
<220> FEATURE:
<223> OTHER INFORMATION: Guide Sequence

<400> SEQUENCE: 499
caucuuccca uucgugggca                                               20

<210> SEQ ID NO 500
<211> LENGTH: 20
<212> TYPE: RNA
<213> ORGANISM: Artificial Sequence
<220> FEATURE:
<223> OTHER INFORMATION: Guide Sequence

<400> SEQUENCE: 500
ucuccaccuu gcccacgaau                                               20

<210> SEQ ID NO 501
<211> LENGTH: 20
<212> TYPE: RNA
<213> ORGANISM: Artificial Sequence
<220> FEATURE:
<223> OTHER INFORMATION: Guide Sequence
```

```
<400> SEQUENCE: 501
gucuccaccu ugcccacgaa                                               20

<210> SEQ ID NO 502
<211> LENGTH: 20
<212> TYPE: RNA
<213> ORGANISM: Artificial Sequence
<220> FEATURE:
<223> OTHER INFORMATION: Guide Sequence

<400> SEQUENCE: 502
cccaaugcuu gcacauaaau                                               20

<210> SEQ ID NO 503
<211> LENGTH: 20
<212> TYPE: RNA
<213> ORGANISM: Artificial Sequence
<220> FEATURE:
<223> OTHER INFORMATION: Guide Sequence

<400> SEQUENCE: 503
ccaauuuaug ugcaagcauu                                               20

<210> SEQ ID NO 504
<211> LENGTH: 20
<212> TYPE: RNA
<213> ORGANISM: Artificial Sequence
<220> FEATURE:
<223> OTHER INFORMATION: Guide Sequence

<400> SEQUENCE: 504
uccaauuuau gugcaagcau                                               20

<210> SEQ ID NO 505
<211> LENGTH: 20
<212> TYPE: RNA
<213> ORGANISM: Artificial Sequence
<220> FEATURE:
<223> OTHER INFORMATION: Guide Sequence

<400> SEQUENCE: 505
ugugcgcguc ugaagaggag                                               20

<210> SEQ ID NO 506
<211> LENGTH: 20
<212> TYPE: RNA
<213> ORGANISM: Artificial Sequence
<220> FEATURE:
<223> OTHER INFORMATION: Guide Sequence

<400> SEQUENCE: 506
gugcgcgucu gaagaggagu                                               20

<210> SEQ ID NO 507
<211> LENGTH: 20
<212> TYPE: RNA
<213> ORGANISM: Artificial Sequence
<220> FEATURE:
<223> OTHER INFORMATION: Guide Sequence

<400> SEQUENCE: 507
ugcgcgucug aagaggagug                                               20

<210> SEQ ID NO 508
```

```
<211> LENGTH: 20
<212> TYPE: RNA
<213> ORGANISM: Artificial Sequence
<220> FEATURE:
<223> OTHER INFORMATION: Guide Sequence

<400> SEQUENCE: 508
uaguccagau gcuguugccg                                               20

<210> SEQ ID NO 509
<211> LENGTH: 20
<212> TYPE: RNA
<213> ORGANISM: Artificial Sequence
<220> FEATURE:
<223> OTHER INFORMATION: Guide Sequence

<400> SEQUENCE: 509
auuaccacgg caacagcauc                                               20

<210> SEQ ID NO 510
<211> LENGTH: 20
<212> TYPE: RNA
<213> ORGANISM: Artificial Sequence
<220> FEATURE:
<223> OTHER INFORMATION: Guide Sequence

<400> SEQUENCE: 510
gacacgauuu aguauuacca                                               20

<210> SEQ ID NO 511
<211> LENGTH: 20
<212> TYPE: RNA
<213> ORGANISM: Artificial Sequence
<220> FEATURE:
<223> OTHER INFORMATION: Guide Sequence

<400> SEQUENCE: 511
cuaaaucgug uccaaagagg                                               20

<210> SEQ ID NO 512
<211> LENGTH: 20
<212> TYPE: RNA
<213> ORGANISM: Artificial Sequence
<220> FEATURE:
<223> OTHER INFORMATION: Guide Sequence

<400> SEQUENCE: 512
aggaaucuca gccuccucuu                                               20

<210> SEQ ID NO 513
<211> LENGTH: 20
<212> TYPE: RNA
<213> ORGANISM: Artificial Sequence
<220> FEATURE:
<223> OTHER INFORMATION: Guide Sequence

<400> SEQUENCE: 513
guggacaagg uuaacuaaaa                                               20

<210> SEQ ID NO 514
<211> LENGTH: 20
<212> TYPE: RNA
<213> ORGANISM: Artificial Sequence
<220> FEATURE:
<223> OTHER INFORMATION: Guide Sequence

<400> SEQUENCE: 514
```

-continued auagucaaau cauguggaca                                              20

<210> SEQ ID NO 515
<211> LENGTH: 20
<212> TYPE: RNA
<213> ORGANISM: Artificial Sequence
<220> FEATURE:
<223> OTHER INFORMATION: Guide Sequence

<400> SEQUENCE: 515
ugcuggauag ucaaaucaug                                              20

<210> SEQ ID NO 516
<211> LENGTH: 20
<212> TYPE: RNA
<213> ORGANISM: Artificial Sequence
<220> FEATURE:
<223> OTHER INFORMATION: Guide Sequence

<400> SEQUENCE: 516
acaugauuug acuauccagc                                              20

<210> SEQ ID NO 517
<211> LENGTH: 20
<212> TYPE: RNA
<213> ORGANISM: Artificial Sequence
<220> FEATURE:
<223> OTHER INFORMATION: Guide Sequence

<400> SEQUENCE: 517
auuugacuau ccagcaggcu                                              20

<210> SEQ ID NO 518
<211> LENGTH: 20
<212> TYPE: RNA
<213> ORGANISM: Artificial Sequence
<220> FEATURE:
<223> OTHER INFORMATION: Guide Sequence

<400> SEQUENCE: 518
gucccgaagu cucuggggcc                                              20

<210> SEQ ID NO 519
<211> LENGTH: 20
<212> TYPE: RNA
<213> ORGANISM: Artificial Sequence
<220> FEATURE:
<223> OTHER INFORMATION: Guide Sequence

<400> SEQUENCE: 519
aaaacagucc cgaagucucu                                              20

<210> SEQ ID NO 520
<211> LENGTH: 20
<212> TYPE: RNA
<213> ORGANISM: Artificial Sequence
<220> FEATURE:
<223> OTHER INFORMATION: Guide Sequence

<400> SEQUENCE: 520
gaaaacaguc ccgaagucuc                                              20

<210> SEQ ID NO 521
<211> LENGTH: 20
<212> TYPE: RNA

```
<213> ORGANISM: Artificial Sequence
<220> FEATURE:
<223> OTHER INFORMATION: Guide Sequence

<400> SEQUENCE: 521
uauauaccac auucaagugc                                              20

<210> SEQ ID NO 522
<211> LENGTH: 20
<212> TYPE: RNA
<213> ORGANISM: Artificial Sequence
<220> FEATURE:
<223> OTHER INFORMATION: Guide Sequence

<400> SEQUENCE: 522
uggauauaac gaaguugugu                                              20

<210> SEQ ID NO 523
<211> LENGTH: 20
<212> TYPE: RNA
<213> ORGANISM: Artificial Sequence
<220> FEATURE:
<223> OTHER INFORMATION: Guide Sequence

<400> SEQUENCE: 523
auggauauaa cgaaguugug                                              20

<210> SEQ ID NO 524
<211> LENGTH: 20
<212> TYPE: RNA
<213> ORGANISM: Artificial Sequence
<220> FEATURE:
<223> OTHER INFORMATION: Guide Sequence

<400> SEQUENCE: 524
auauguuugu ucaccccaac                                              20

<210> SEQ ID NO 525
<211> LENGTH: 20
<212> TYPE: RNA
<213> ORGANISM: Artificial Sequence
<220> FEATURE:
<223> OTHER INFORMATION: Guide Sequence

<400> SEQUENCE: 525
gaaaacuuga aauccuguug                                              20

<210> SEQ ID NO 526
<211> LENGTH: 20
<212> TYPE: RNA
<213> ORGANISM: Artificial Sequence
<220> FEATURE:
<223> OTHER INFORMATION: Guide Sequence

<400> SEQUENCE: 526
uagacauuag gagaaacaga                                              20

<210> SEQ ID NO 527
<211> LENGTH: 20
<212> TYPE: RNA
<213> ORGANISM: Artificial Sequence
<220> FEATURE:
<223> OTHER INFORMATION: Guide Sequence

<400> SEQUENCE: 527
cuagcaguga cauagacauu                                              20
```

<210> SEQ ID NO 528
<211> LENGTH: 20
<212> TYPE: RNA
<213> ORGANISM: Artificial Sequence
<220> FEATURE:
<223> OTHER INFORMATION: Guide Sequence

<400> SEQUENCE: 528
agccaccuga cuuugaugaa                                               20

<210> SEQ ID NO 529
<211> LENGTH: 20
<212> TYPE: RNA
<213> ORGANISM: Artificial Sequence
<220> FEATURE:
<223> OTHER INFORMATION: Guide Sequence

<400> SEQUENCE: 529
ugagaaaugu uauuacuaua                                               20

<210> SEQ ID NO 530
<211> LENGTH: 20
<212> TYPE: RNA
<213> ORGANISM: Artificial Sequence
<220> FEATURE:
<223> OTHER INFORMATION: Guide Sequence

<400> SEQUENCE: 530
agacugcgag augagagagu                                               20

<210> SEQ ID NO 531
<211> LENGTH: 20
<212> TYPE: RNA
<213> ORGANISM: Artificial Sequence
<220> FEATURE:
<223> OTHER INFORMATION: Guide Sequence

<400> SEQUENCE: 531
cucgcagucu guacuuagac                                               20

<210> SEQ ID NO 532
<211> LENGTH: 20
<212> TYPE: RNA
<213> ORGANISM: Artificial Sequence
<220> FEATURE:
<223> OTHER INFORMATION: Guide Sequence

<400> SEQUENCE: 532
aaugucucuu gagagagcca                                               20

<210> SEQ ID NO 533
<211> LENGTH: 22
<212> TYPE: RNA
<213> ORGANISM: Artificial Sequence
<220> FEATURE:
<223> OTHER INFORMATION: Guide Sequence

<400> SEQUENCE: 533
augggaagau gaaagggaag ua                                            22

<210> SEQ ID NO 534
<211> LENGTH: 22
<212> TYPE: RNA
<213> ORGANISM: Artificial Sequence
<220> FEATURE:

```
<223> OTHER INFORMATION: Guide Sequence

<400> SEQUENCE: 534
acuuugauug uuaaaacuua uc                                                 22

<210> SEQ ID NO 535
<211> LENGTH: 22
<212> TYPE: RNA
<213> ORGANISM: Artificial Sequence
<220> FEATURE:
<223> OTHER INFORMATION: Guide Sequence

<400> SEQUENCE: 535
aguccuaccu cagcuuccca au                                                 22

<210> SEQ ID NO 536
<211> LENGTH: 22
<212> TYPE: RNA
<213> ORGANISM: Artificial Sequence
<220> FEATURE:
<223> OTHER INFORMATION: Guide Sequence

<400> SEQUENCE: 536
caaugcuugc acauaaauug ga                                                 22

<210> SEQ ID NO 537
<211> LENGTH: 22
<212> TYPE: RNA
<213> ORGANISM: Artificial Sequence
<220> FEATURE:
<223> OTHER INFORMATION: Guide Sequence

<400> SEQUENCE: 537
acacagagag agacagaaug aa                                                 22

<210> SEQ ID NO 538
<211> LENGTH: 22
<212> TYPE: RNA
<213> ORGANISM: Artificial Sequence
<220> FEATURE:
<223> OTHER INFORMATION: Guide Sequence

<400> SEQUENCE: 538
uccucuucag acgcgcacac ac                                                 22

<210> SEQ ID NO 539
<211> LENGTH: 22
<212> TYPE: RNA
<213> ORGANISM: Artificial Sequence
<220> FEATURE:
<223> OTHER INFORMATION: Guide Sequence

<400> SEQUENCE: 539
acuccucuuc agacgcgcac ac                                                 22

<210> SEQ ID NO 540
<211> LENGTH: 22
<212> TYPE: RNA
<213> ORGANISM: Artificial Sequence
<220> FEATURE:
<223> OTHER INFORMATION: Guide Sequence

<400> SEQUENCE: 540
ccacuccucu ucagacgcgc ac                                                 22
```

```
<210> SEQ ID NO 541
<211> LENGTH: 22
<212> TYPE: RNA
<213> ORGANISM: Artificial Sequence
<220> FEATURE:
<223> OTHER INFORMATION: Guide Sequence

<400> SEQUENCE: 541
ccccacuccu cuucagacgc gc                                              22

<210> SEQ ID NO 542
<211> LENGTH: 22
<212> TYPE: RNA
<213> ORGANISM: Artificial Sequence
<220> FEATURE:
<223> OTHER INFORMATION: Guide Sequence

<400> SEQUENCE: 542
cuccccacuc cucuucagac gc                                              22

<210> SEQ ID NO 543
<211> LENGTH: 22
<212> TYPE: RNA
<213> ORGANISM: Artificial Sequence
<220> FEATURE:
<223> OTHER INFORMATION: Guide Sequence

<400> SEQUENCE: 543
uacuccccac uccucuucag ac                                              22

<210> SEQ ID NO 544
<211> LENGTH: 22
<212> TYPE: RNA
<213> ORGANISM: Artificial Sequence
<220> FEATURE:
<223> OTHER INFORMATION: Guide Sequence

<400> SEQUENCE: 544 uauacuccccc acuccucuuc ag                                             22

<210> SEQ ID NO 545
<211> LENGTH: 22
<212> TYPE: RNA
<213> ORGANISM: Artificial Sequence
<220> FEATURE:
<223> OTHER INFORMATION: Guide Sequence

<400> SEQUENCE: 545
acagcaucug acuaucuug uu                                               22

<210> SEQ ID NO 546
<211> LENGTH: 22
<212> TYPE: RNA
<213> ORGANISM: Artificial Sequence
<220> FEATURE:
<223> OTHER INFORMATION: Guide Sequence

<400> SEQUENCE: 546
auaguccaga ugcuguugcc gu                                              22

<210> SEQ ID NO 547
<211> LENGTH: 22
<212> TYPE: RNA
<213> ORGANISM: Artificial Sequence
<220> FEATURE:
<223> OTHER INFORMATION: Guide Sequence
```

```
<400> SEQUENCE: 547
aaaaggaauc ucagccuccu cu                                              22

<210> SEQ ID NO 548
<211> LENGTH: 22
<212> TYPE: RNA
<213> ORGANISM: Artificial Sequence
<220> FEATURE:
<223> OTHER INFORMATION: Guide Sequence

<400> SEQUENCE: 548
ugucacugcu agugugcuua au                                              22

<210> SEQ ID NO 549
<211> LENGTH: 22
<212> TYPE: RNA
<213> ORGANISM: Artificial Sequence
<220> FEATURE:
<223> OTHER INFORMATION: Guide Sequence

<400> SEQUENCE: 549
augugaauuc aguacaagaa uu                                              22

<210> SEQ ID NO 550
<211> LENGTH: 22
<212> TYPE: RNA
<213> ORGANISM: Artificial Sequence
<220> FEATURE:
<223> OTHER INFORMATION: Guide Sequence

<400> SEQUENCE: 550
uuaugugaau ucaguacaag aa                                              22

<210> SEQ ID NO 551
<211> LENGTH: 22
<212> TYPE: RNA
<213> ORGANISM: Artificial Sequence
<220> FEATURE:
<223> OTHER INFORMATION: Guide Sequence

<400> SEQUENCE: 551
cuuucauuuc uguuuaugug aa                                              22

<210> SEQ ID NO 552
<211> LENGTH: 22
<212> TYPE: RNA
<213> ORGANISM: Artificial Sequence
<220> FEATURE:
<223> OTHER INFORMATION: Guide Sequence

<400> SEQUENCE: 552
uucacauaaa cagaaaugaa ag                                              22

<210> SEQ ID NO 553
<211> LENGTH: 22
<212> TYPE: RNA
<213> ORGANISM: Artificial Sequence
<220> FEATURE:
<223> OTHER INFORMATION: Guide Sequence

<400> SEQUENCE: 553
augccaacuc ucucaucucg ca                                              22

<210> SEQ ID NO 554
<211> LENGTH: 22
```

```
<212> TYPE: RNA
<213> ORGANISM: Artificial Sequence
<220> FEATURE:
<223> OTHER INFORMATION: Guide Sequence

<400> SEQUENCE: 554
gagacauucu cacauuucca gu                                              22

<210> SEQ ID NO 555
<211> LENGTH: 20
<212> TYPE: RNA
<213> ORGANISM: Artificial Sequence
<220> FEATURE:
<223> OTHER INFORMATION: Guide Sequence

<400> SEQUENCE: 555
aguuacaggg agcaccacca                                                 20

<210> SEQ ID NO 556
<211> LENGTH: 20
<212> TYPE: RNA
<213> ORGANISM: Artificial Sequence
<220> FEATURE:
<223> OTHER INFORMATION: Guide Sequence

<400> SEQUENCE: 556
caguuacagg gagcaccacc                                                 20

<210> SEQ ID NO 557
<211> LENGTH: 20
<212> TYPE: RNA
<213> ORGANISM: Artificial Sequence
<220> FEATURE:
<223> OTHER INFORMATION: Guide Sequence

<400> SEQUENCE: 557
cuggucuggc uucaguuaca                                                 20

<210> SEQ ID NO 558
<211> LENGTH: 20
<212> TYPE: RNA
<213> ORGANISM: Artificial Sequence
<220> FEATURE:
<223> OTHER INFORMATION: Guide Sequence

<400> SEQUENCE: 558
ccuggucugg cuucaguuac                                                 20

<210> SEQ ID NO 559
<211> LENGTH: 20
<212> TYPE: RNA
<213> ORGANISM: Artificial Sequence
<220> FEATURE:
<223> OTHER INFORMATION: Guide Sequence

<400> SEQUENCE: 559
ccuggucugg cuucaguuac                                                 20

<210> SEQ ID NO 560
<211> LENGTH: 20
<212> TYPE: RNA
<213> ORGANISM: Artificial Sequence
<220> FEATURE:
<223> OTHER INFORMATION: Guide Sequence

<400> SEQUENCE: 560
```
ucugcagaau ucacuggag                                          20

<210> SEQ ID NO 561
<211> LENGTH: 20
<212> TYPE: RNA
<213> ORGANISM: Artificial Sequence
<220> FEATURE:
<223> OTHER INFORMATION: Guide Sequence

<400> SEQUENCE: 561
cucugcagaa uucacuggga                                         20

<210> SEQ ID NO 562
<211> LENGTH: 20
<212> TYPE: RNA
<213> ORGANISM: Artificial Sequence
<220> FEATURE:
<223> OTHER INFORMATION: Guide Sequence

<400> SEQUENCE: 562
ucucugcaga auucacuggg                                         20

<210> SEQ ID NO 563
<211> LENGTH: 20
<212> TYPE: RNA
<213> ORGANISM: Artificial Sequence
<220> FEATURE:
<223> OTHER INFORMATION: Guide Sequence

<400> SEQUENCE: 563
uaaucucugc agaauucacu                                         20

<210> SEQ ID NO 564
<211> LENGTH: 20
<212> TYPE: RNA
<213> ORGANISM: Artificial Sequence
<220> FEATURE:
<223> OTHER INFORMATION: Guide Sequence

<400> SEQUENCE: 564
uuaaucucug cagaauucac                                         20

<210> SEQ ID NO 565
<211> LENGTH: 22
<212> TYPE: RNA
<213> ORGANISM: Artificial Sequence
<220> FEATURE:
<223> OTHER INFORMATION: Guide Sequence

<400> SEQUENCE: 565
gccuggucug gcuucaguua ca                                      22

<210> SEQ ID NO 566
<211> LENGTH: 22
<212> TYPE: RNA
<213> ORGANISM: Artificial Sequence
<220> FEATURE:
<223> OTHER INFORMATION: Guide Sequence

<400> SEQUENCE: 566
guguccaacu uuguuugcuu uc                                      22

<210> SEQ ID NO 567
<211> LENGTH: 22
<212> TYPE: RNA
<213> ORGANISM: Artificial Sequence

```
<220> FEATURE:
<223> OTHER INFORMATION: Guide Sequence

<400> SEQUENCE: 567
guauucugga aagcaaacaa ag                                          22

<210> SEQ ID NO 568
<211> LENGTH: 22
<212> TYPE: RNA
<213> ORGANISM: Artificial Sequence
<220> FEATURE:
<223> OTHER INFORMATION: Guide Sequence

<400> SEQUENCE: 568
cagucuuggc aucacaggcu uc                                          22

<210> SEQ ID NO 569
<211> LENGTH: 22
<212> TYPE: RNA
<213> ORGANISM: Artificial Sequence
<220> FEATURE:
<223> OTHER INFORMATION: Guide Sequence

<400> SEQUENCE: 569
ggaccucuug gcuauuacac ag                                          22

<210> SEQ ID NO 570
<211> LENGTH: 22
<212> TYPE: RNA
<213> ORGANISM: Artificial Sequence
<220> FEATURE:
<223> OTHER INFORMATION: Guide Sequence

<400> SEQUENCE: 570
ggagccagug ggaccucuug gc                                          22

<210> SEQ ID NO 571
<211> LENGTH: 22
<212> TYPE: RNA
<213> ORGANISM: Artificial Sequence
<220> FEATURE:
<223> OTHER INFORMATION: Guide Sequence

<400> SEQUENCE: 571
cccagugaau ucugcagaga uu                                          22

<210> SEQ ID NO 572
<211> LENGTH: 22
<212> TYPE: RNA
<213> ORGANISM: Artificial Sequence
<220> FEATURE:
<223> OTHER INFORMATION: Guide Sequence

<400> SEQUENCE: 572
ggaaggaucu gugucuacag ug                                          22

<210> SEQ ID NO 573
<211> LENGTH: 22
<212> TYPE: RNA
<213> ORGANISM: Artificial Sequence
<220> FEATURE:
<223> OTHER INFORMATION: Guide Sequence

<400> SEQUENCE: 573
uuaccugcac guauguaaca cu                                          22
```

```
<210> SEQ ID NO 574
<211> LENGTH: 22
<212> TYPE: RNA
<213> ORGANISM: Artificial Sequence
<220> FEATURE:
<223> OTHER INFORMATION: Guide Sequence

<400> SEQUENCE: 574
aaauaaaacu uaccugcacg ua                                                22

<210> SEQ ID NO 575
<211> LENGTH: 22
<212> TYPE: RNA
<213> ORGANISM: Artificial Sequence
<220> FEATURE:
<223> OTHER INFORMATION: Guide Sequence

<400> SEQUENCE: 575
aaguuuauuu aaauaaaac uu                                                 22

<210> SEQ ID NO 576
<211> LENGTH: 22
<212> TYPE: RNA
<213> ORGANISM: Artificial Sequence
<220> FEATURE:
<223> OTHER INFORMATION: Guide Sequence

<400> SEQUENCE: 576
aaagcauagg cacacaucac cc                                                22

<210> SEQ ID NO 577
<211> LENGTH: 22
<212> TYPE: RNA
<213> ORGANISM: Artificial Sequence
<220> FEATURE:
<223> OTHER INFORMATION: Guide Sequence

<400> SEQUENCE: 577
uuaggcaauu cuuguaaagc au                                                22

<210> SEQ ID NO 578
<211> LENGTH: 22
<212> TYPE: RNA
<213> ORGANISM: Artificial Sequence
<220> FEATURE:
<223> OTHER INFORMATION: Guide Sequence

<400> SEQUENCE: 578
aauuaggcaa uucuuguaaa gc                                                22

<210> SEQ ID NO 579
<211> LENGTH: 22
<212> TYPE: RNA
<213> ORGANISM: Artificial Sequence
<220> FEATURE:
<223> OTHER INFORMATION: Guide Sequence

<400> SEQUENCE: 579
aaucuccagu caauuccaac ac                                                22

<210> SEQ ID NO 580
<211> LENGTH: 22
<212> TYPE: RNA
<213> ORGANISM: Artificial Sequence
<220> FEATURE:
<223> OTHER INFORMATION: Guide Sequence
```

```
<400> SEQUENCE: 580
gcccucugaa ucuccaguca au                                              22

<210> SEQ ID NO 581
<211> LENGTH: 22
<212> TYPE: RNA
<213> ORGANISM: Artificial Sequence
<220> FEATURE:
<223> OTHER INFORMATION: Guide Sequence

<400> SEQUENCE: 581
uauauccuug guuaaaaggu gg                                              22

<210> SEQ ID NO 582
<211> LENGTH: 89
<212> TYPE: DNA
<213> ORGANISM: Homo sapiens

<400> SEQUENCE: 582
ggcctccatc ctaaacaatg tggcctttgc ccatatgctt cgcccaccag ctcaaacatg     60
cccaaagccc aaagcccagc gtgggtctt                                       89

<210> SEQ ID NO 583
<211> LENGTH: 39
<212> TYPE: DNA
<213> ORGANISM: Artificial Sequence
<220> FEATURE:
<223> OTHER INFORMATION: Modified sequence by targeting target sequences
      using Enh-Sp5 and Enh-Sp16

<400> SEQUENCE: 583
ggcctccatc ctaaacaatg tggcctttgc gtgggtctt                            39

<210> SEQ ID NO 584
<211> LENGTH: 23
<212> TYPE: DNA
<213> ORGANISM: Homo sapiens

<400> SEQUENCE: 584
cctttgccca tatgcttcgc cca                                             23

<210> SEQ ID NO 585
<211> LENGTH: 23
<212> TYPE: DNA
<213> ORGANISM: Homo sapiens

<400> SEQUENCE: 585
acatgcccaa agcccagcgt ggg                                             23

<210> SEQ ID NO 586
<211> LENGTH: 89
<212> TYPE: DNA
<213> ORGANISM: Homo sapiens

<400> SEQUENCE: 586
ggtgctccct gtaactgaag ccagaccagg cgtctttcca gtttattcag gggctggtcc     60
aatgctggga tatgtcatgg tggcctgag                                       89

<210> SEQ ID NO 587
<211> LENGTH: 41
<212> TYPE: DNA
<213> ORGANISM: Artificial Sequence
```

```
<220> FEATURE:
<223> OTHER INFORMATION: Modified sequence by targeting target sequences
      using TATA-Sp12 and TATA-Sp14

<400> SEQUENCE: 587
ggtgctccct gtaactgaag ccagactcat ggtggcctga g                           41

<210> SEQ ID NO 588
<211> LENGTH: 23
<212> TYPE: DNA
<213> ORGANISM: Homo sapiens

<400> SEQUENCE: 588
ccagaccagg cgtctttcca gtt                                               23

<210> SEQ ID NO 589
<211> LENGTH: 23
<212> TYPE: DNA
<213> ORGANISM: Homo sapiens

<400> SEQUENCE: 589
tccaatgctg ggatatgtca tgg                                               23

<210> SEQ ID NO 590
<211> LENGTH: 120
<212> TYPE: DNA
<213> ORGANISM: Homo sapiens

<400> SEQUENCE: 590
cctggtggtg ctccctgtaa ctgaagccag accaggcgtc tttccagttt attcaggggc       60
tggtccaatg ctgggatatg tcatggtggc ctgagaggtt ctcagcctct attatttaaa      120

<210> SEQ ID NO 591
<211> LENGTH: 120
<212> TYPE: DNA
<213> ORGANISM: Homo sapiens

<400> SEQUENCE: 591
tttaaataat agaggctgag aacctctcag gccaccatga catatcccag cattggacca       60 gccctgaat aaactggaaa gacgcctggt ctggcttcag ttacagggag caccaccagg       120

<210> SEQ ID NO 592
<211> LENGTH: 90
<212> TYPE: DNA
<213> ORGANISM: Homo sapiens

<400> SEQUENCE: 592
actgaagcca gaccaggcgt ctttccagtt tattcagggg ctggtccaat gctgggatat       60
gtcatggtgg cctgagaggt tctcagcctc                                        90

<210> SEQ ID NO 593
<211> LENGTH: 89
<212> TYPE: DNA
<213> ORGANISM: Artificial Sequence
<220> FEATURE:
<223> OTHER INFORMATION: Modified sequence by PMP22-TATA RNP

<400> SEQUENCE: 593
actgaagcca gaccaggcgt ctttccagtt attcaggggc tggtccaatg ctgggatatg       60
tcatggcggc ctgagaggtt ctcagcctc                                         89
```

-continued

```
<210> SEQ ID NO 594
<211> LENGTH: 88
<212> TYPE: DNA
<213> ORGANISM: Artificial Sequence
<220> FEATURE:
<223> OTHER INFORMATION: Modified sequence by PMP22-TATA RNP

<400> SEQUENCE: 594
actgaagcca gaccaggcgt ctttccagtt ttcagggggct ggtccaatgc tgggatatgt      60
catggtggcc tgagaggttc tcagcctc                                         88

<210> SEQ ID NO 595
<211> LENGTH: 91
<212> TYPE: DNA
<213> ORGANISM: Artificial Sequence
<220> FEATURE:
<223> OTHER INFORMATION: Modified sequence by PMP22-TATA RNP

<400> SEQUENCE: 595
actgaagcca gaccaggcgt ctttccagtt ttattcaggg gctggtccaa tgctgggata      60
tgtcatggcg gcctgagagg ttctcagcct c                                      91

<210> SEQ ID NO 596
<211> LENGTH: 87
<212> TYPE: DNA
<213> ORGANISM: Artificial Sequence
<220> FEATURE:
<223> OTHER INFORMATION: Modified sequence by PMP22-TATA RNP

<400> SEQUENCE: 596
actgaagcca gaccaggcgt ctttccagtt tcaggggctg gtccaatgct gggatatgtc      60
atggcggcct gagaggttct cagcctc                                          87

<210> SEQ ID NO 597
<211> LENGTH: 86
<212> TYPE: DNA
<213> ORGANISM: Artificial Sequence
<220> FEATURE:
<223> OTHER INFORMATION: Modified sequence by PMP22-TATA RNP

<400> SEQUENCE: 597
actgaagcca gaccaggcgt ctttccagtt caggggctgg tccaatgctg ggatatgtca      60
tggcggcctg agaggttctc agcctc                                           86

<210> SEQ ID NO 598
<211> LENGTH: 23
<212> TYPE: DNA
<213> ORGANISM: Homo sapiens

<400> SEQUENCE: 598
ggaccagccc ctgaataaac tgg                                              23

<210> SEQ ID NO 599
<211> LENGTH: 23
<212> TYPE: DNA
<213> ORGANISM: Homo sapiens

<400> SEQUENCE: 599
ggaccagcca cagaataaac aag                                              23

<210> SEQ ID NO 600
<211> LENGTH: 23
<212> TYPE: DNA
```

```
<213> ORGANISM: Homo sapiens

<400> SEQUENCE: 600
tgaccagtcc atgaataaac cag                                              23

<210> SEQ ID NO 601
<211> LENGTH: 23
<212> TYPE: DNA
<213> ORGANISM: Homo sapiens

<400> SEQUENCE: 601
ggaccagaca ctgaatatac cag                                              23

<210> SEQ ID NO 602
<211> LENGTH: 23
<212> TYPE: DNA
<213> ORGANISM: Homo sapiens

<400> SEQUENCE: 602
ggaccagcca cagaataaat tgg                                              23

<210> SEQ ID NO 603
<211> LENGTH: 23
<212> TYPE: DNA
<213> ORGANISM: Homo sapiens

<400> SEQUENCE: 603
ggatcagccc cagaataaat tag                                              23

<210> SEQ ID NO 604
<211> LENGTH: 23
<212> TYPE: DNA
<213> ORGANISM: Homo sapiens

<400> SEQUENCE: 604
ggagcatccc cagaataaac cag                                              23

<210> SEQ ID NO 605
<211> LENGTH: 23
<212> TYPE: DNA
<213> ORGANISM: Homo sapiens

<400> SEQUENCE: 605
ggatcagcgt ctgaataaac aag                                              23

<210> SEQ ID NO 606
<211> LENGTH: 23
<212> TYPE: DNA
<213> ORGANISM: Homo sapiens

<400> SEQUENCE: 606
agaccagccc cagaacaaac aag                                              23

<210> SEQ ID NO 607
<211> LENGTH: 23
<212> TYPE: DNA
<213> ORGANISM: Homo sapiens

<400> SEQUENCE: 607
gtacgagccc ctgaataaat agg                                              23

<210> SEQ ID NO 608
<211> LENGTH: 23
```

<212> TYPE: DNA
<213> ORGANISM: Homo sapiens

<400> SEQUENCE: 608
ggaccaaaca ctgaataaac cag                                          23

<210> SEQ ID NO 609
<211> LENGTH: 23
<212> TYPE: DNA
<213> ORGANISM: Homo sapiens

<400> SEQUENCE: 609
gcaccagcca ctgaattaac aag                                          23

<210> SEQ ID NO 610
<211> LENGTH: 23
<212> TYPE: DNA
<213> ORGANISM: Homo sapiens

<400> SEQUENCE: 610
gtaccagcca ctgaaaaaac agg                                          23

<210> SEQ ID NO 611
<211> LENGTH: 23
<212> TYPE: DNA
<213> ORGANISM: Homo sapiens

<400> SEQUENCE: 611
gaaccagccc ctgattagac cag                                          23

<210> SEQ ID NO 612
<211> LENGTH: 23
<212> TYPE: DNA
<213> ORGANISM: Homo sapiens

<400> SEQUENCE: 612
gtaccagcca ctgaaaaaac agg                                          23

<210> SEQ ID NO 613
<211> LENGTH: 23
<212> TYPE: DNA
<213> ORGANISM: Homo sapiens

<400> SEQUENCE: 613
gtaccagcca ctgaaaaaac agg                                          23

<210> SEQ ID NO 614
<211> LENGTH: 23
<212> TYPE: DNA
<213> ORGANISM: Homo sapiens

<400> SEQUENCE: 614
gcaccaggcc ttgaataaac aag                                          23

<210> SEQ ID NO 615
<211> LENGTH: 23
<212> TYPE: DNA
<213> ORGANISM: Homo sapiens

<400> SEQUENCE: 615
ggcccagcca ctgagtaaac tag                                          23

<210> SEQ ID NO 616

<211> LENGTH: 23
<212> TYPE: DNA
<213> ORGANISM: Homo sapiens

<400> SEQUENCE: 616
ggaattgccc ctgaataaac aag                                    23

<210> SEQ ID NO 617
<211> LENGTH: 23
<212> TYPE: DNA
<213> ORGANISM: Homo sapiens

<400> SEQUENCE: 617
gggaacagcc ctgaataaac ctg                                    23

<210> SEQ ID NO 618
<211> LENGTH: 23
<212> TYPE: DNA
<213> ORGANISM: Homo sapiens

<400> SEQUENCE: 618
aggaccagct ctgaataacc agg                                    23

<210> SEQ ID NO 619
<211> LENGTH: 23
<212> TYPE: DNA
<213> ORGANISM: Homo sapiens

<400> SEQUENCE: 619
ggaacagccc tgaataaacc tgg                                    23

<210> SEQ ID NO 620
<211> LENGTH: 23
<212> TYPE: DNA
<213> ORGANISM: Homo sapiens

<400> SEQUENCE: 620
gagttcagcc cctgaataac agg                                    23

<210> SEQ ID NO 621
<211> LENGTH: 23
<212> TYPE: DNA
<213> ORGANISM: Homo sapiens

<400> SEQUENCE: 621
gggaccagcc ccagaataaa ggg                                    23

<210> SEQ ID NO 622
<211> LENGTH: 23
<212> TYPE: DNA
<213> ORGANISM: Homo sapiens

<400> SEQUENCE: 622
aagccaaccc ctgaataaac agg                                    23

<210> SEQ ID NO 623
<211> LENGTH: 23
<212> TYPE: DNA
<213> ORGANISM: Homo sapiens

<400> SEQUENCE: 623
cacacagccc ctcaataaac tgg                                    23

```
<210> SEQ ID NO 624
<211> LENGTH: 23
<212> TYPE: DNA
<213> ORGANISM: Homo sapiens

<400> SEQUENCE: 624
gaggcagccc ctgtataaac tgg                                              23

<210> SEQ ID NO 625
<211> LENGTH: 23
<212> TYPE: DNA
<213> ORGANISM: Homo sapiens

<400> SEQUENCE: 625
gaccagcccc ctgaataaca tgg                                              23

<210> SEQ ID NO 626
<211> LENGTH: 23
<212> TYPE: DNA
<213> ORGANISM: Mus musculus

<400> SEQUENCE: 626
gtaccagccc ctgacaaaac agg                                              23

<210> SEQ ID NO 627
<211> LENGTH: 23
<212> TYPE: DNA
<213> ORGANISM: Mus musculus

<400> SEQUENCE: 627
ggagcagccc cggaatgaac agg                                              23

<210> SEQ ID NO 628
<211> LENGTH: 23
<212> TYPE: DNA
<213> ORGANISM: Mus musculus

<400> SEQUENCE: 628
ggaccagccc ctgtataccc tgg                                              23

<210> SEQ ID NO 629
<211> LENGTH: 23
<212> TYPE: DNA
<213> ORGANISM: Mus musculus

<400> SEQUENCE: 629
ggaccagccc ctgtataccc tgg                                              23

<210> SEQ ID NO 630
<211> LENGTH: 23
<212> TYPE: DNA
<213> ORGANISM: Mus musculus

<400> SEQUENCE: 630
ggaccagccc ctgtataccc tgg                                              23

<210> SEQ ID NO 631
<211> LENGTH: 23
<212> TYPE: DNA
<213> ORGANISM: Mus musculus

<400> SEQUENCE: 631
ggccctgccc ctaaataaac agg                                              23
```

```
<210> SEQ ID NO 632
<211> LENGTH: 23
<212> TYPE: DNA
<213> ORGANISM: Mus musculus

<400> SEQUENCE: 632
ggatcagccc cagaataacc tgg                                              23

<210> SEQ ID NO 633
<211> LENGTH: 23
<212> TYPE: DNA
<213> ORGANISM: Mus musculus

<400> SEQUENCE: 633
ggactagccc ctgagtacac tgg                                              23
```